(12) United States Patent
Hagel et al.

(10) Patent No.: US 11,858,895 B2
(45) Date of Patent: Jan. 2, 2024

(54) AMINATED PSILOCYBIN DERIVATIVES AND METHODS OF USING

(71) Applicant: Enveric Biosciences Canada Inc., Calgary (CA)

(72) Inventors: Jillian M. Hagel, Calgary (CA); Peter J. Facchini, Calgary (CA); Chang-Chun Ling, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

(21) Appl. No.: 17/946,457

(22) Filed: Sep. 16, 2022

(65) Prior Publication Data

US 2023/0135143 A1   May 4, 2023

Related U.S. Application Data

(63) Continuation of application No. PCT/CA2022/050007, filed on Jan. 5, 2022.

(60) Provisional application No. 63/248,009, filed on Sep. 24, 2021.

(51) Int. Cl.
C07D 209/16 (2006.01)

(52) U.S. Cl.
CPC .................. C07D 209/16 (2013.01)

(58) Field of Classification Search
CPC .................................. C07D 209/16
See application file for complete search history.

(56) References Cited

U.S. PATENT DOCUMENTS

| | | | | |
|---|---|---|---|---|
| 7,375,219 B2 * | 5/2008 | Maddaford | ............. | A61P 13/12 548/503 |
| 2004/0198803 A1 * | 10/2004 | Pintor | .................... | A61K 31/55 548/495 |
| 2007/0009597 A1 * | 1/2007 | Torrens Jover | ........... | A61P 3/10 424/468 |
| 2007/0213326 A1 * | 9/2007 | Merce Vidal | ........... | A61P 25/14 514/249 |
| 2011/0092540 A1 * | 4/2011 | Mas Prio | ................ | A61P 25/18 548/154 |

FOREIGN PATENT DOCUMENTS

| WO | WO1999064044 A1 | 12/1999 |
|---|---|---|
| WO | WO200209702 A2 | 2/2002 |
| WO | WO2006002421 A2 | 1/2006 |
| WO | WO 2008/092665 A1 * | 8/2008 |
| WO | WO 2008/092666 A1 * | 8/2008 |
| WO | WO 2009/036955 A1 * | 3/2009 |

OTHER PUBLICATIONS

Holenz, et al. Journal of Medicinal Chemistry, 2005, vol. 48, No. 6, 1781-1795.*
Saathoff, et al. Bioorg. Med. Chem. Lett. 43 (2021) 128081, pp. 1-6.*
Daniel, J. et al. Clinical potential of psilocybin as a treatment for mental health conditions. Mental Health Clin/, 2017;7 (1): 24-28.
Grob, C. et al. Pilot study of psilocybin treatment for anxiety in patients with advanced-stage cancerArch. Gen. Psychiatry, 2011, 68(1) 71-78.
Cathart-Harris, R.L. et al. Psilocybin with psychological support for treatment-resistant depression: an open-label feasibility study. Lancet Psychiatry, 2016, 3: 619-627.
Devereux et al., A comprehensive set of sequence analysis programs for the VAX. Nucleic Acids Res., 1984, 12: 387.
Altschul et al., Basic local alignment search tool. J Mol Biol. Oct. 5, 1990;215(3):403-10.
Thompson, J D, Higgines, D G and Gibson T J. Clustal W: improving the sensitivity of progressive multiple sequence alignment through sequence weighting, position-specific gap penalties and weight matrix choice. 1994, Nucleic Acid Res 22(22): 4673-4680.
Needleman and Wunsch. A general method applicable to the search for similarities in the amino acid sequence of two proteins J. Mol. Biol., 1970, 48: 443.
Smith and Waterman. Comparison of Biosciences. Adv. Appl. Math., 1981, 2: 482.
Carillo and Lipton. The Multiple Sequence Alignment Problem in Biology. SIAM J. Applied Math., 1988, 48:1073.
Jones et al. ePathOptimize: A Combinatorial Approach for Transcriptional Balancing of Metabolic Pathways. 2015, Sci Rep. 5: 11301.
Vinograd et al. '126.Substituted Nitrotryptamines', Khimiya Geterotsiklicheskikh Soedinenii, 1984, vol. 9, pp. 1206-1210.
S. Kawai et al., Transformation of *Saccharomyces cerevisiae* and other fungi: methods and possible underlying mechanism. Bioeng Bugs. Nov.-Dec. 2010;1(6):395-403.
Henikoff S & Henikoff, J G, Amino acid substitution matrices from protein blocks. Proc Natl Acad Sci U S A. Nov. 15, 1992,89(22):10915-9.
Chang et al.,Isolation and Characterization of O-methyltransferases Involved in the Biosynthesis of Glaucine in Glaucium flavum. 2015, Plant Physiol. 169: 1127-1140.
Inserra et al., 2020, Pharmacol Rev 73: 202.
Kim K. et al., Structure of a Hallucinogen-Activated Gq-Coupled 5-HT 2A Serotonin Receptor. 2020, Cell 182: 1574-1588.
Cregg et al., Recombinant protein expression in Pichia pastoris. Mol Biotechnol. (2000) 16(1): 23-52.
Maguire et al.,Radioligand binding assays and their analysis. 2012, Methods Mol Biol 897: 31.
Pyrgiotakis G. et al., Cell death discrimination with Raman spectroscopy and support vector machines. 2009, Ann. Biomed. Eng. 37: 1464-1473.
Schnepel C. et al. Enzymatic Halogenation: A Timely Strategy for Regioselective C-H Activation. Chemistry. Sep. 7, 2017;23(50):12064-12086.
Durak L.J. et al. Late-Stage Diversification of Biologically Active Molecules via Chemoenzymatic C-H Functionalization ACS Catal. Mar. 4, 2016; 6(3): 1451-1454.

(Continued)

*Primary Examiner* — Shawquia Jackson
(74) *Attorney, Agent, or Firm* — BERESKIN & PARR LLP/ S.E.N.C.R.L., s.r.l.; Michael Fenwick

(57) ABSTRACT

Disclosed are novel aminated psilocybin derivative compounds and pharmaceutical and recreational drug formulations containing the same. The aminated psilocybin derivative compounds may be chemically synthesized.

28 Claims, 38 Drawing Sheets

Specification includes a Sequence Listing.

(56) References Cited

OTHER PUBLICATIONS

Menéndez-Perdomo et al. Benzylisoquinoline alkaloid analysis using high-resolution Orbitrap LC-MS n2021, Mass Spectrom 56: 34683.

Corr M.J. et al. Sonogashira diversification of unprotected halotryptophans, halotryptophan containing tripeptides; and generation of a new to nature bromo-natural product and its diversification in water Chem Sci. Mar. 1, 2017;8 (3):2039-2046.

Petrunin et al. '130.Synthesis of Disubstituted Tryptamines by Nitration of 5-Methoxy-N-Phthalyltryptamine', Khimiya Geterotsiklicheskikh Soedinenii, Aug. 1987, vol. 8, pp. 839-842.

Núñez et al., Target-drug interactions: first principles and their application to drug discovery. 2012, Drug Disc Today 17: 10.

Donato et al., Culture and Functional Characterization of Human Hepatoma HepG2 Cells. 2015, Methods Mol Biol 1250: 77.

Terrasso et al., Human neuron-astrocyte 3D co-culture-based assay for evaluation of neuroprotective compounds. 2017, J Pharmacol Toxicol Methods 83: 72.

Weaver et al., Test systems in drug discovery for hazard identification and risk assessment of human drug-induced liver injury. 2017, Expert Opin Drug Metab Toxicol 13: 767.

Roy A.D. et al. Development of fluorescent aryltryptophans by Pd mediated cross-coupling of unprotected halotryptophans in water. Chem Commun (Camb). Oct. 21, 2008;(39):4831-3.

Runguphan W. et al. Diversification of monoterpene indole alkaloid analogs through cross-coupling. Org Lett. Jun. 7, 2013; 15(11):2850-3.

Mattanovich et al., Recombinant protein production in yeasts. Methods Mol. Biol., 2012, 824:329-58.

Finnin, B. and Morgan, T.M., Transdermal penetration enhancers: applications, limitations, and potential J Pharm Sci. Oct. 1999;88(10):955-8.

Romanos et al., Foreign gene expression in yeast: a review. Yeast. Jun. 1992;8(6):423-88.

Tarafder et al. The role of ion-pairing in peak deformations in overloaded reversed-phase chromatography of peptides. 2010, J Chromatogr A 1217:7065-7073.

Servillo L. et al.,Benzylisoquinoline alkaloid analysis using high-resolution Orbitrap LC-MS n J. Agric. Food Chem 61: 5156-5162.

* cited by examiner

AMINATED PSILOCYBIN DERIVATIVES AND METHODS OF USING

RELATED APPLICATION

This application is a continuation of PCT Application No. PCT/CA2022/050007 filed Jan. 5, 2022, which claims the benefit of U.S. Provisional Application No. 63/248,009 filed Sep. 24, 2021; the entire contents of Patent Application Nos. PCT/CA2022/050007 and 63/248,009 are hereby incorporated by reference.

INCORPORATION OF SEQUENCE LISTING

A computer readable form of the Sequence Listing "29664-P62652US03_SequenceListing.xml" (29,876 bytes), submitted via EFS-WEB and created on Sep. 15, 2022, is herein incorporated by reference.

FIELD OF THE DISCLOSURE

The compositions and methods disclosed herein relate to a chemical compound known as psilocybin. Furthermore, the compositions and methods disclosed herein relate in particular to aminated forms of psilocybin.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus *Psilocybe*, such as *Psilocybe azurescens, Psilocybe semilanceata, Psilocybe serbica, Psilocybe mexicana*, and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al. Mental Health Clin/, 2017; 7(1): 24-28), including to treat anxiety in terminal cancer patients (Grob, C. et al. Arch. Gen. Psychiatry, 2011, 68(1) 71-78) and to alleviate symptoms of treatment-resistant depression (Cathart-Harris, R. L. et al. Lancet Psychiatry, 2016, 3: 619-627).

Although the toxicity of psilocybin is low, adverse side effects, including, for example, panic attacks, paranoia, and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds.

In another aspect, the present disclosure relates to aminated psilocybin derivative compounds and methods of making and using these compounds.

Accordingly, in one aspect, the present disclosure provides, in at least one embodiment, in accordance with the teachings herein, a chemical compound or salt thereof having formula (I):

(I)

wherein at least one of $R_2$, $R_4$, $R_5$, $R_6$, or $R_7$ is an amino group or an N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group.

In at least one embodiment, in an aspect, $R_2$ can be an amino group or N-substituted amino group, $R_5$, $R_6$ and $R_7$ can each be a hydrogen atom or an alkyl group or O-alkyl group, and $R_4$ can be a phosphate group, a hydrogen atom, a hydroxy group, or an alkyl group or O-alkyl group.

In at least one embodiment, in an aspect, $R_4$ can be an amino group or N-substituted amino group and $R_2$, $R_5$, $R_6$ and $R_7$ can each be a hydrogen atom or an alkyl group or O-alkyl group.

In at least one embodiment, in an aspect, $R_5$ can be an amino group or N-substituted amino group, $R_2$, $R_6$ and $R_7$ can each be a hydrogen atom or an alkyl group or O-alkyl group, and $R_4$ can be a phosphate group, a hydrogen atom, a hydroxy group, or an alkyl group or O-alkyl group.

In at least one embodiment, in an aspect, $R_6$ can be an amino group or N-substituted amino group, $R_2$, $R_5$ and $R_7$ can each be a hydrogen atom or an alkyl group or O-alkyl group, and $R_4$ can be a phosphate group, a hydrogen atom, a hydroxy group, or an alkyl group or O-alkyl group.

In at least one embodiment, in an aspect, $R_7$ can be an amino group or N-substituted amino group, $R_2$, $R_5$ and $R_6$ can each be a hydrogen atom or an alkyl group or O-alkyl group, and $R_4$ can be a phosphate group, a hydrogen atom, a hydroxy group, or an alkyl group or O-alkyl group.

In at least one embodiment, in an aspect, at least two of $R_2$, $R_4$, $R_5$, $R_6$ or $R_7$ can be an amino group or N-substituted amino group.

In at least one embodiment, in an aspect, $R_2$ and $R_4$ can be an amino group or N-substituted amino group, and $R_5$, $R_6$ and $R_7$ can be a hydrogen atom or an alkyl group or O-alkyl group.

In at least one embodiment, in an aspect, $R_2$ and $R_5$ can be an amino group or N-substituted amino group, $R_6$ and $R_7$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_2$ and $R_6$ can be an amino group or N-substituted amino group, $R_5$ and $R_7$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_2$ and $R_7$ can be an amino group or N-substituted amino group, $R_5$ and $R_6$ can be a hydrogen atom or an alkyl group or O-alkyl group, and $R_4$ can be a hydrogen atom, an alkyl group an alkyl group, O-alkyl group, a hydroxy group, or a phosphate group.

In at least one embodiment, in an aspect, $R_4$ and $R_5$ can be an amino group or N-substituted amino group, and $R_2$, $R_6$ and $R_7$ can be a hydrogen atom or an alkyl group or O-alkyl group.

In at least one embodiment, in an aspect, $R_4$ and $R_6$ can be an amino group or N-substituted amino group, and $R_2$, $R_5$ and $R_7$ can be a hydrogen atom or an alkyl group or O-alkyl group.

In at least one embodiment, in an aspect, $R_4$ and $R_7$ can be an amino group or N-substituted amino group and $R_2$, $R_5$ and $R_6$ can be a hydrogen atom or an alkyl group or O-alkyl group.

In at least one embodiment, in an aspect, $R_5$ and $R_6$ can be an amino group or N-substituted amino group, $R_2$ and $R_7$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_5$ and $R_7$ can be an amino group or N-substituted amino group, $R_2$ and $R_6$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_6$ and $R_7$ can be an amino group or N-substituted amino group, $R_2$ and $R_5$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_4$, $R_5$, $R_6$ or $R_7$ can be an N-substituted amino group.

In at least one embodiment, in an aspect, $R_7$ can be an N-substituted amino group.

In at least one embodiment, in an aspect, $R_4$, $R_5$, $R_6$ or $R_7$ can be an N-substituted amino group, wherein the N-substituted group has the formula:

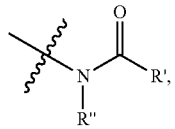

(XXII)

wherein R' and R" are each independently selected from a hydrogen atom, an alkyl group and an aryl group.

In at least one embodiment, in an aspect, $R_7$ can be an N-substituted amino group, wherein the N-substituted group has the formula:

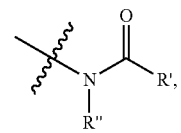

(XXII)

wherein R' and R" are each independently selected from a hydrogen atom, an alkyl group and an aryl group.

In at least one embodiment, in an aspect, $R_4$, $R_5$, $R_6$ or $R_7$ can be an N-substituted amino group, wherein the N-substituted group has the formula:

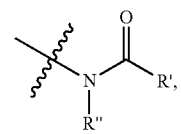

(XXII)

wherein R' and R" each are a hydrogen atom.

In at least one embodiment, in an aspect, $R_7$ can be an N-substituted amino group, wherein the N-substituted group has the formula:

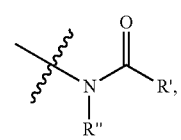

(XXII)

wherein R' and R" each are a hydrogen atom.

In at least one embodiment, in an aspect, $R_4$ when it is not aminated can be a hydrogen atom.

In at least one embodiment, in an aspect, $R_4$ when it is not aminated can be a hydroxy group.

In at least one embodiment, in an aspect, $R_4$ when it is not aminated can be an O-alkyl group.

In at least one embodiment, in an aspect, $R_4$ when it is not aminated can be a phosphate group.

In at least one embodiment, in an aspect, three, four or all five of $R_2$, $R_4$, $R_5$, $R_6$ or $R_7$ can be an amino group or N-substituted amino group.

In at least one embodiment, in an aspect, the chemical compound can be selected from the group consisting of compounds having formulas (III); (IV); (V); (VI); (VII); (VIII); (IX); (X); (XI); (XII); (XIII); (XIV); (XV); (XVI); and (XVII):

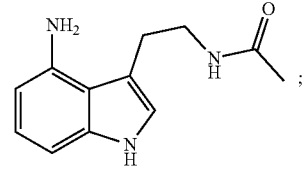

(III)

(IV) 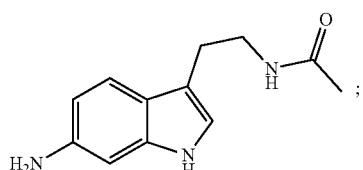

(V) 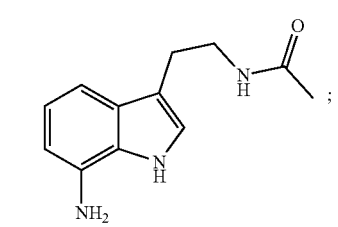

(VI) 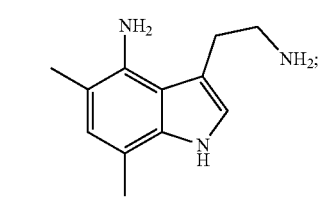

(VII) 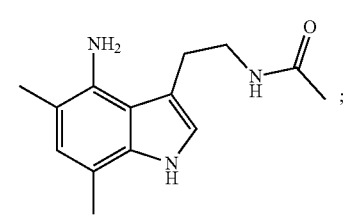

(VIII) 

(IX) 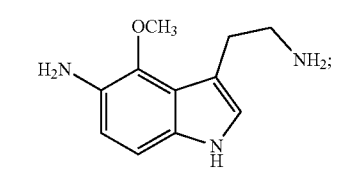

(X) 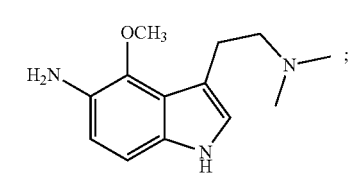

(XI) 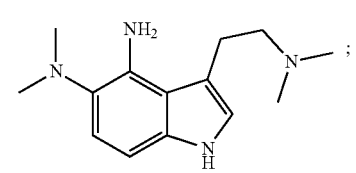

(XII) 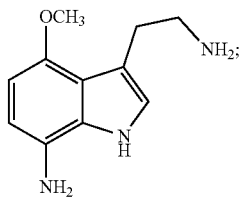

(XIII) 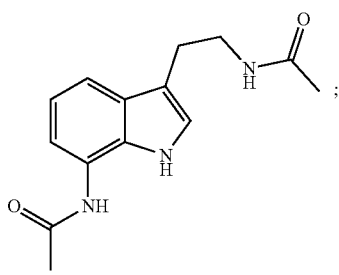

(XIV) 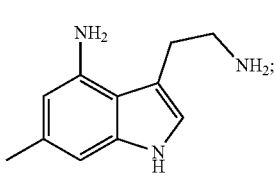

(XV) 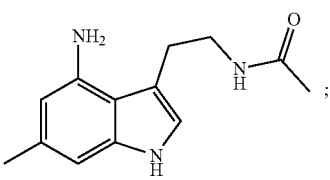

(XVI) 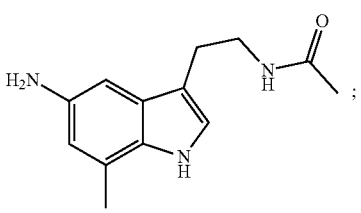

and (XVII) 

In at least one embodiment, in an aspect, the chemical compound can be at least about 95% (w/w) pure.

In another aspect, the present disclosure relates to pharmaceutical and recreational drug formulations comprising aminated psilocybin derivatives. Accordingly, in one aspect, the present disclosure provides, in at least one embodiment, a pharmaceutical or recreational drug formulation comprising an effective amount of a chemical compound or salt thereof having formula (I):

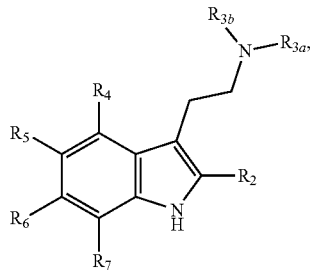

(I)

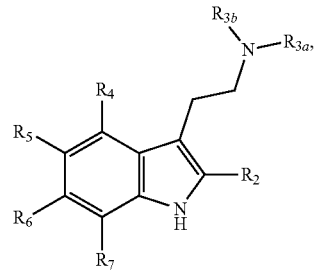

(II)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group, together with a pharmaceutically acceptable excipient, diluent or carrier.

In another aspect, the present disclosure relates to methods of treatment of psychiatric disorders. Accordingly, the present disclosure further provides, in at least one embodiment, a method for treating a psychiatric disorder, the method comprising administering to a subject in need thereof a pharmaceutical formulation comprising a chemical compound or salt thereof having formula (I):

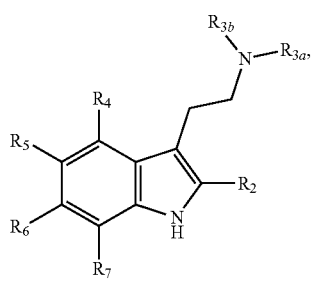

(I)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group, wherein the pharmaceutical formulation is administered in an effective amount to treat the psychiatric disorder in the subject.

In at least one embodiment, in an aspect, the disorder can be a 5-$HT_{2A}$ receptor mediated disorder or a 5-$HT_{1A}$ receptor mediated disorder.

In at least one embodiment, in an aspect, a dose can be administered of about 0.001 mg to about 5,000 mg.

In another aspect, the present disclosure relates to methods of making aminated psilocybin derivatives. Accordingly, in one aspect, the present disclosure provides, in at least one embodiment, a method of making an aminated psilocybin derivative the method comprising:

reacting a reactant psilocybin derivative compound or a salt thereof having the formula (II):

wherein at least one of $R_2$, $R_4$, $R_5$, $R_6$, or $R_7$ is a reactive group selected from a nitro group, an azido group, or a hydrogen atom, and wherein $R_2$, $R_4$, $R_5$, $R_6$, or $R_7$ which are not a reactive group, are a hydrogen atom, an alkyl group or O-alkyl group and wherein $R_{3A}$ and $R_{3B}$ are each independently a hydrogen atom, an alkyl group, and acyl group, or an aryl group under conditions sufficient to form a chemical compound having formula (I):

(I)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group.

In a least one embodiment, in an aspect, $R_2$, $R_4$, $R_5$, $R_6$, or $R_7$ in the reactant psilocybin derivative compound can be a hydrogen atom, and the conditions can comprise (i) reacting the reactant psilocybin compound with a nitrogenous compound selected from nitric acid ($HNO_3$); a nitrate salt; an acyl nitrate; trifluoromethansulfonyl nitrate; nitrosonium tetrafluoroborate ($NO_2BF_4$); and trifluoracetyl nitrate to form a nitrated compound having chemical formula (XXV):

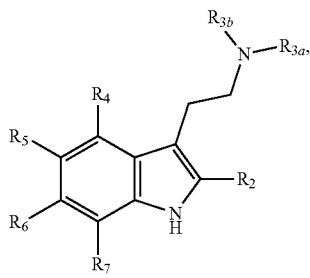

(XXV)

wherein at least one of $R_2$, $R_4$, $R_5$, $R_6$, or $R_7$ is a nitro group, and wherein each non-nitrated $R_2$, $R_5$, $R_6$, or $R_7$ is a hydrogen atom, an alkyl group or O-alkyl group, wherein $R_4$ when it is not nitrated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group, and then (ii) reacting the nitrated compound under reducing conditions to form an aminated compound having chemical formula (XXVI):

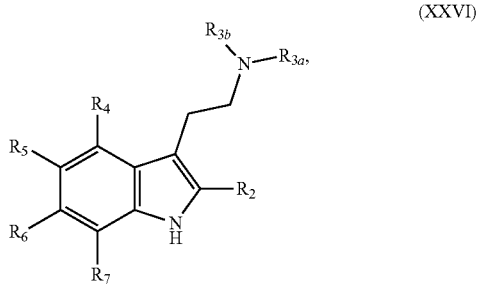

(XXVI)

wherein at least one of $R_2$, $R_4$, $R_5$, $R_6$, or $R_7$ is an amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group to thereby form a compound having chemical formula (I), wherein at least one of $R_2$, $R_4$, $R_5$, $R_6$, or $R_7$ is an amino group, and (iii) optionally substituting the at least one amino group to form at least one N-substituted group.

In at least one embodiment, in an aspect, $R_2$, $R_4$, $R_5$, $R_6$, or $R_7$ in the reactant psilocybin derivative compound can be a nitro group or an azide, and the reaction conditions can comprise reacting the reactant psilocybin compound under reducing conditions to form an aminated compound having chemical formula (XXVI):

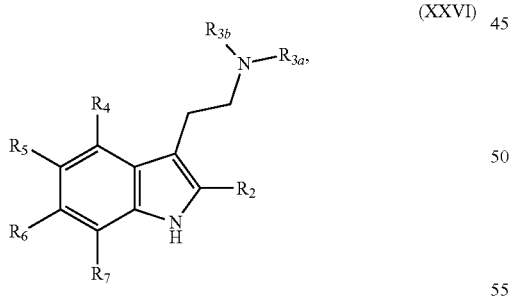

(XXVI)

wherein at least one of $R_2$, $R_4$, $R_5$, $R_6$, or $R_7$ is an amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group to thereby form a compound having chemical formula (I), wherein at least one of $R_2$, $R_4$, $R_5$, $R_6$, or $R_7$ is an amino group, and to then optionally substitute the at least one amino group to form at least one N-substituted group.

In at least one embodiment, in an aspect, at least one of $R_2$, $R_4$, $R_5$, $R_6$, or $R_7$ in the reactant psilocybin derivative compound can be a hydrogen atom, and the conditions can comprise reacting the reactant psilocybin compound with ammonia and hydrogen peroxide in the presence of a catalyst to form the chemical compound having formula (I) and to then optionally substitute the at least one amino group in the chemical compound having formula (I) to form at least one N-substituted group.

In the least one embodiment, in an aspect, the catalyst can be $Cu/SiO_2$.

In the least one embodiment, in an aspect, the method can comprise:
 (i) reacting the reactant psilocybin derivative compound to protect the side-chain amino groups $R_{3a}$ and $R_{3b}$, and, optionally, protect nitrogen atom $N_1$ of the reactant psilocybin derivative compound to obtain an amino-protected compound wherein $R_{3a}$ and $R_{3b}$ are each a protective group, and wherein, optionally, $N_1$ is protected by protective group,
 (ii) reacting the amino-protected compound with a nitrogenous compound selected from nitric acid ($HNO_3$), a nitrate salt, an acyl nitrate, benzoyl nitrate, nitrosonium tetrafluoroborate ($NO_2BF_4$), and trifluoracetyl nitrate to form a nitrated compound having chemical formula (XXXI):

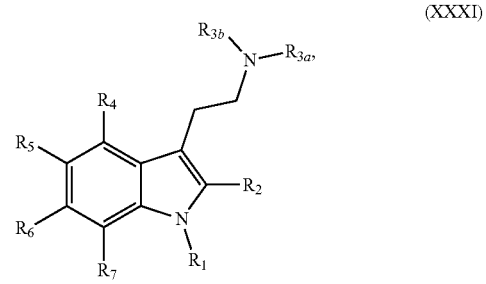

(XXXI)

wherein at least one of $R_2$, $R_4$, $R_5$, $R_6$, or $R_7$ is a nitro group, and wherein each non-nitrated $R_2$, $R_5$, $R_6$, or $R_7$ is a hydrogen atom, an alkyl group or O-alkyl group, wherein $R_4$ when it is not nitrated is a hydrogen atom, an alkyl group, O-alkyl group, a hydroxy group, or a phosphate group, and wherein $R_{3a}$ and $R_{3b}$ are a protective group, and wherein $R_1$ is a protective group or a hydrogen atom;
 (iii) reacting the compound having chemical formula (XXXI) under reducing conditions to form a compound having chemical formula (XXXII):

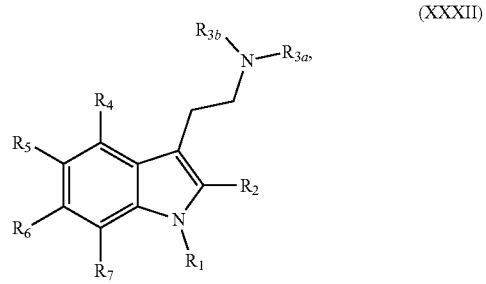

(XXXII)

wherein at least one of $R_2$, $R_4$, $R_5$, $R_6$, or $R_7$ is an amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group, O-alkyl group, a hydroxy group, or a phosphate group, wherein $R_{3a}$ and $R_{3b}$, are a protective group, and wherein $R_1$ is a protective group or a hydrogen atom; and (iv) reacting the compound having chemical formula (XXXII) to remove the protective groups to thereby form the aminated compound having chemical formula (I).

In the least one embodiment, in an aspect, the protective group can be an alkyl group, an acyl group, an acetyl group, a substituted acetyl group, or carbamate group.

In at least one embodiment, in an aspect, the carbamate group can be fluorenylmethyloxycarbonyl (Fmoc), benzyloxycarbonyl, or tert-butyloxycarbonyl (Boc).

In the least one embodiment, in an aspect, the method can comprise comprising performing an additional step following step (iii) and prior to step (iv), the additional step comprising substituting the amino group at the at least one $R_2$, $R_4$, $R_5$, $R_6$, or $R_7$ groups to form at least one N-substituted amino group.

In the least one embodiment, in an aspect, the method can comprise performing an additional step following step (iv), the additional step comprising, in a compound wherein $R_{3A}$ and $R_{3B}$ are each a hydrogen atom, substituting at least one of the hydrogen atoms by an alkyl group, an aryl group, or an acyl group form a N-substituted amino group.

In at least one embodiment, in an aspect, $R_2$ in the compound having formula (I) can be an amino group or N-substituted amino group, $R_5$, $R_6$ and $R_7$ can each be a hydrogen atom or an alkyl group or O-alkyl group, and $R_4$ can be a phosphate group, a hydrogen atom, a hydroxy group, or an alkyl group or O-alkyl group.

In at least one embodiment, in an aspect, $R_4$ in the compound having formula (I) can be an amino group or N-substituted amino group and $R_2$, $R_5$, $R_6$ and $R_7$ can each be a hydrogen atom or an alkyl group or O-alkyl group.

In at least one embodiment, in an aspect, $R_5$ in the compound having formula (I) can be an amino group or N-substituted amino group, $R_2$, $R_6$ and $R_7$ can each be a hydrogen atom or an alkyl group or O-alkyl group, and $R_4$ can be a phosphate group, a hydrogen atom, a hydroxy group, or an alkyl group or O-alkyl group.

In at least one embodiment, in an aspect, $R_6$ in the compound having formula (I) can be an amino group or N-substituted amino group atom, $R_2$, $R_5$ and $R_7$ can each be a hydrogen atom or an alkyl group or O-alkyl group, and $R_4$ can be a phosphate group, a hydrogen atom, a hydroxy group, or an alkyl group or O-alkyl group.

In at least one embodiment, in an aspect, $R_7$ in the compound having formula (I) can be an amino group or N-substituted amino group, $R_2$, $R_5$ and $R_6$ can each be a hydrogen atom or an alkyl group or O-alkyl group, and $R_4$ can be a phosphate group, a hydrogen atom, a hydroxy group, or an alkyl group or O-alkyl group.

In at least one embodiment, in an aspect, at least two of $R_2$, $R_4$, $R_5$, $R_6$ or $R_7$ in the compound formula (I) can be an amino group or N-substituted amino group.

In at least one embodiment, in an aspect, $R_2$ and $R_4$ in the compound having formula (I) can be an amino group or N-substituted amino group, and $R_5$, $R_6$ and $R_7$ can be a hydrogen atom or an alkyl group or O-alkyl group.

In at least one embodiment, in an aspect, $R_2$ and $R_5$ in the compound having formula (I) can be an amino group or N-substituted amino group, $R_6$ and $R_7$ can be a hydrogen atom, or an alkyl group or O-alkyl group, and $R_4$ can be a hydrogen atom, an alkyl group, O-alkyl group, a hydroxy group, or a phosphate group.

In at least one embodiment, in an aspect, $R_2$ and $R_6$ in the compound having formula (I) can be an amino group or N-substituted amino group, $R_5$ and $R_7$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_2$ and $R_7$ in the compound having formula (I) can be an amino group or N-substituted amino group, $R_5$ and $R_6$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_4$ and $R_5$ in the compound having formula (I) can be an amino group or N-substituted amino group, and $R_2$, $R_6$ and $R_7$ can be a hydrogen atom, or an alkyl group or O-alkyl group.

In at least one embodiment, in an aspect, $R_4$ and $R_6$ in the compound having formula (I) can be an amino group or N-substituted amino group, and $R_2$, $R_5$ and $R_7$ can be a hydrogen atom or an alkyl group or O-alkyl group.

In at least one embodiment, in an aspect, $R_4$ and $R_7$ in the compound having formula (I) can be an amino group or N-substituted amino group and $R_2$, $R_5$ and $R_6$ can be a hydrogen atom or an alkyl group or O-alkyl group.

In at least one embodiment, in an aspect, $R_5$ and $R_6$ in the compound having formula (I) can be an amino group or N-substituted amino group, $R_2$ and $R_7$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_5$ and $R_7$ in the compound having formula (I) can be an amino group or N-substituted amino group, $R_2$ and $R_6$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_6$ and $R_7$ in the compound having formula (I) can be an amino group or N-substituted amino group, $R_2$ and $R_5$ can be a hydrogen atom or an alkyl group or O-alkyl group, and $R_4$ can be a hydrogen atom, an alkyl group, O-alkyl group, a hydroxy group, or a phosphate group.

In at least one embodiment, in an aspect, $R_4$ in the compound having formula (I) when it is not aminated can be a hydrogen atom.

In at least one embodiment, in an aspect, $R_4$ in the compound having formula (I) when it is not aminated can be a hydroxy group.

In at least one embodiment, in an aspect, $R_4$ in the compound having formula (I) when it is not aminated can be an alkyl group.

In at least one embodiment, in an aspect, $R_4$ when it is not aminated can be an O-alkyl group.

In at least one embodiment, in an aspect, $R_4$ in the compound having formula (I) when it is not aminated can be a phosphate group.

In at least one embodiment, in an aspect, three, four or all five of $R_2$, $R_4$, $R_5$, $R_6$ or $R_7$ in the compound having formula (I) can be an amino group or N-substituted amino group.

In at least one embodiment, in an aspect, the compound having formula (I) can be selected from the group consisting of compounds having formulas (III); (IV); (V); (VI); (VII); (VIII); (IX); (X); (XI); (XII); (XIII); (XIV); (XV); (XVI); and (XVII):

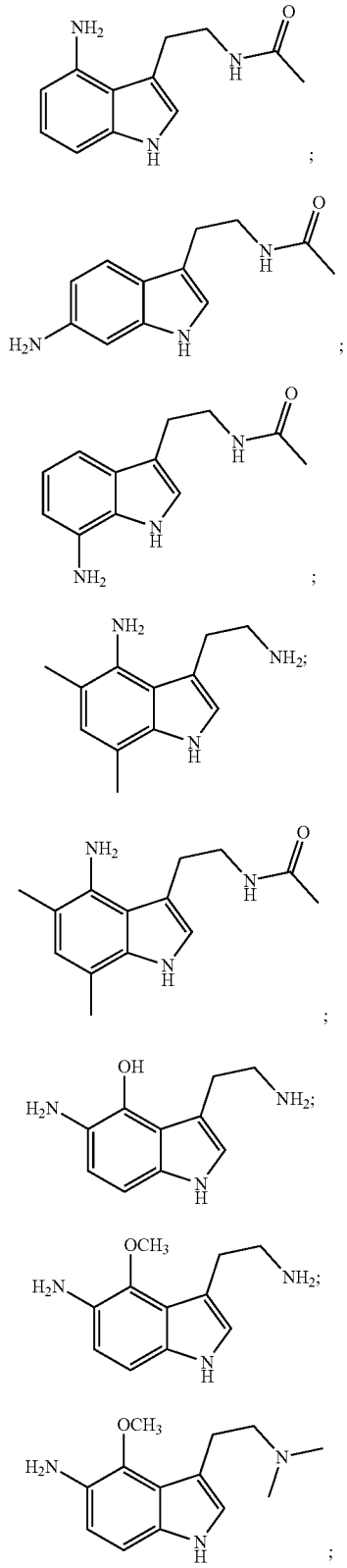

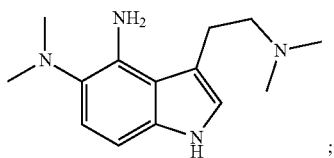

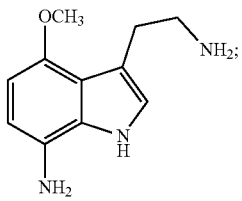

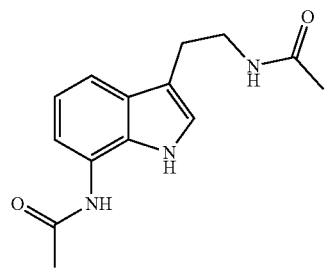

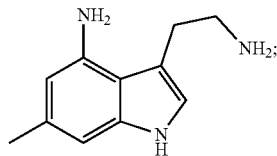

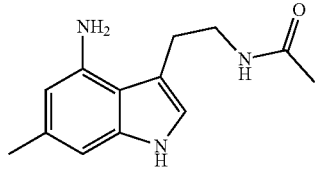

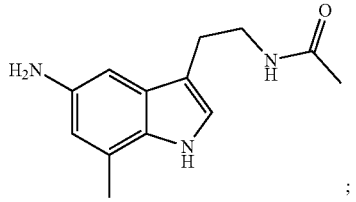

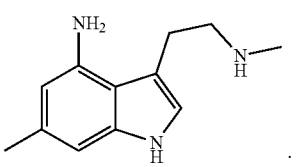

In another aspect, the present disclosure relates to further methods of making aminated psilocybin derivatives. Accordingly, in one aspect, the present disclosure provides in at least one aspect, a method of making an aminated psilocybin derivative the method comprising:
(a) contacting an aminated psilocybin precursor compound with a host cell comprising a psilocybin biosynthetic enzyme complement; and
(b) growing the host cell to produce an aminated psilocybin derivative or salts thereof having the formula (I):

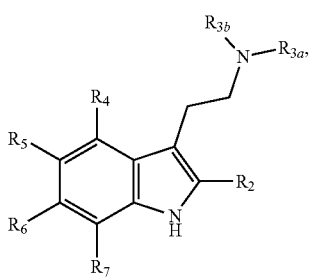

(I)

wherein at least one of $R_2$, $R_4$, $R_5$, $R_6$, or $R_7$ is an amino group or an N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group.

In at least one embodiment, in an aspect, the psilocybin biosynthetic enzyme complement can comprise at least one enzyme selected from a nucleic acid selected from:
(a) SEQ. ID NO: 4, SEQ. ID NO: 8, SEQ. ID NO: 11, and SEQ. ID NO: 13;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ. ID NO: 5, SEQ. ID NO: 9, SEQ. ID NO: 12, or SEQ. ID NO: 14;
(f) a nucleic acid sequence that encodes a functional variant of any one of the amino acid sequences set forth in SEQ. ID NO: 5, SEQ. ID NO:7, SEQ. ID NO: 12, or SEQ. ID NO: 14; and
(g) a nucleic acid sequence that hybridizes under stringent conditions to any one of the nucleic acid sequences set forth in (a), (b), (c), (d), (e) or (f).

In at least one embodiment, in an aspect, the aminated psilocybin precursor compound can be a compound, having the formula (XXVII):

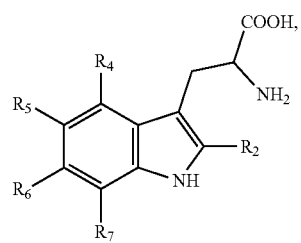

(XXVII)

wherein at least one of $R_2$, $R_4$, $R_5$, $R_6$ and $R_7$ is an amino group or N-substituted amino group, wherein $R_2$, $R_4$, $R_5$, $R_6$ and $R_7$ when they are not aminated are hydrogen atoms, an alkyl group or O-alkyl group, wherein $R_4$ when it is not aminated is a hydrogen atom, an alkyl group or O-alkyl group, a hydroxy group, or a phosphate group;

wherein the psilocybin biosynthetic enzyme complement can comprise:
a tryptophan decarboxylase encoded by a nucleic acid sequence selected from:
(a) SEQ. ID NO: 11;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 12;
(f) a nucleic acid sequence that encodes a functional variant of the amino acid sequence set forth in SEQ. ID NO: 12; and
(g) a nucleic acid sequence that hybridizes under stringent conditions to any one of the nucleic acid sequences set forth in (a), (b), (c), (d), (e) or (f); and the formed aminated psilocybin derivative can be a compound having formula (XXVIII):

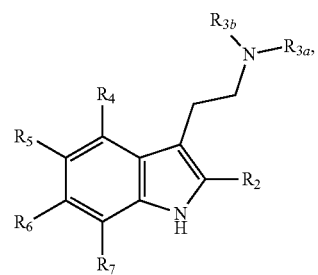

(XXVIII)

wherein at least one of $R_2$, $R_4$, $R_5$, $R_6$, or $R_7$ is an amino group or an N-substituted amino group, and wherein each non-aminated $R_2$, $R_5$, $R_6$, or $R_7$ is a hydrogen atom, an alkyl group, or O-alkyl group, wherein $R_4$ when it is not aminated is a hydrogen atom, an alkyl or O-alkyl group, a hydroxy group, or a phosphate group, and wherein at least one of $R_{3A}$ and $R_{3B}$ are each independently a hydrogen atom.

In at least one embodiment, in an aspect, the aminated psilocybin precursor compound can be an aminated indole compound having the formula (XXIX):

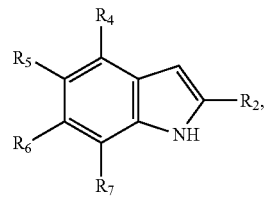

(XXIX)

wherein at least one of $R_2$, $R_4$, $R_5$, $R_6$ and $R_7$ is an amino group or N-substituted amino group, wherein $R_2$, $R_4$, $R_5$, $R_6$ and $R_7$ when they are not aminated are hydrogen atoms, an alkyl group or O-alkyl group, wherein $R_4$ when it is not aminated is a hydrogen atom, an alkyl group or O-alkyl group, a hydroxy group, or a phosphate group;

wherein the psilocybin biosynthetic enzyme complement can comprise:

(i) a tryptophan synthase subunit B polypeptide encoded by a nucleic acid selected from:
(a) SEQ. ID NO: 8;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 9;
(f) a nucleic acid sequence that encodes a functional variant of the amino acid sequence set forth in SEQ. ID NO: 9; and
(g) a nucleic acid sequence that hybridizes under stringent conditions to any one of the nucleic acid sequences set forth in (a), (b), (c), (d), (e) or (f); and (ii) a tryptophan decarboxylase encoded by a nucleic acid sequence selected from:
(a) SEQ. ID NO: 11;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 12;
(f) a nucleic acid sequence that encodes a functional variant of the amino acid sequence set forth in SEQ. ID NO: 12; and
(g) a nucleic acid sequence that hybridizes under stringent conditions to
any one of the nucleic acid sequences set forth in (a), (b), (c), (d), (e) or (f); and wherein the formed aminated psilocybin derivative can be a compound having formula (XXVIII):

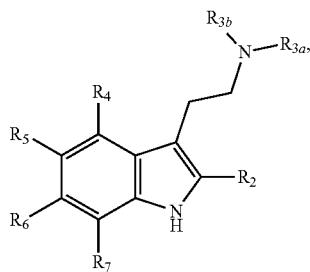

(XXVIII)

wherein at least one of $R_2$, $R_4$, $R_5$, $R_6$, or $R_7$ is an amino group or an N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein at least one of $R_{3A}$ and $R_{3B}$ are hydrogen atom.

In at least one embodiment, in an aspect, $R_{3A}$ and $R_{3B}$ in formula (XXVIII) can each be a hydrogen atom.

In at least one embodiment, in an aspect, the psilocybin biosynthetic enzyme complement can further comprise an N-acetyl transferase.

In at least one embodiment, in an aspect, the N-acetyl transferase can be an enzyme encoded by a nucleic acid sequence selected from:
(a) SEQ. ID NO: 4;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 5;
(f) a nucleic acid sequence that encodes a functional variant of the amino acid sequence set forth in SEQ. ID NO: 5; and
(g) a nucleic acid sequence that hybridizes under stringent conditions to any one of the nucleic acid sequences set forth in (a), (b), (c), (d), (e) or (f).

In at least one embodiment, in an aspect, the formed aminated psilocybin compound can have the formula (XXX):

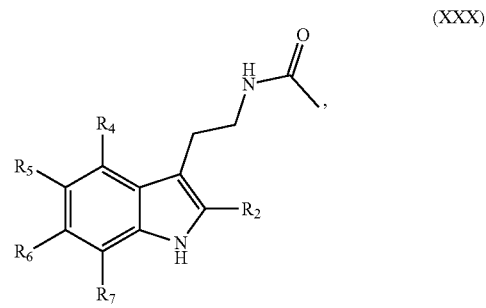

(XXX)

wherein at least one of $R_2$, $R_4$, $R_5$, $R_6$ or $R_7$ is an amino group or substituted amino group, wherein each non-aminated $R_2$, $R_5$, $R_6$, or $R_7$ is a hydrogen atom, or an alkyl group or O-alkyl group, wherein $R_4$ when it is not aminated is a phosphate group, a hydrogen atom or an alkyl group or O-alkyl group.

In at least one embodiment, in an aspect, the psilocybin biosynthetic enzyme complement can further comprise an N-methyl transferase.

In at least one embodiment, in an aspect, the N-methyl transferase can be an enzyme encoded by a nucleic acid sequence selected from:
(a) SEQ. ID NO: 13;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);

(e) a nucleic acid sequence encoding a polypeptide having any one of the amino acid sequences set forth in SEQ. ID NO: 14;

(f) a nucleic acid sequence that encodes a functional variant of the amino acid sequence set forth in SEQ. ID NO: 14; and (g) a nucleic acid sequence that hybridizes under stringent conditions to any one of the nucleic acid sequences set forth in (a), (b), (c), (d), (e) or (f).

In at least one embodiment, in an aspect, the formed aminated psilocybin compound can have the chemical formula (XXXIII):

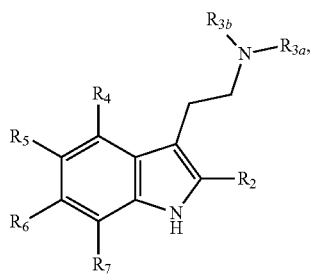
(XXXIII)

wherein at least one of $R_2$, $R_4$, $R_5$, $R_6$ or $R_7$ is an amino group or substituted amino group, wherein each non-aminated $R_2$, $R_5$, $R_6$, or $R_7$ is a hydrogen atom, or an alkyl group or O-alkyl group, wherein $R_4$ when it is not aminated is a phosphate group, a hydrogen atom or an alkyl group or O-alkyl group, and wherein at least one of $R_{3a}$ and $R_{3b}$ is an amino group, and wherein a non-aminated $R_{3a}$ and $R_{3b}$ is a hydrogen atom.

In at least one embodiment, in an aspect, the aminated psilocybin derivative compound having formula (I) can be selected from the group consisting of compounds having formulas (III); (IV); (V); (VI); (VII); (VIII); (IX); (X); (XI); (XII); (XIII); (XIV); (XV); (XVI); and (XVII):

(III)

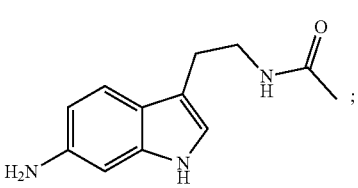
(IV)

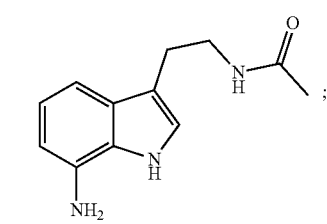
(V)

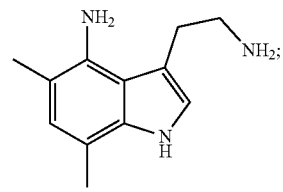
(VI)

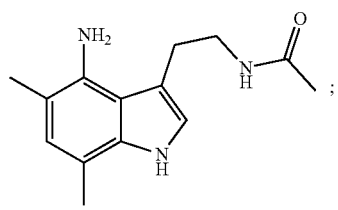
(VII)

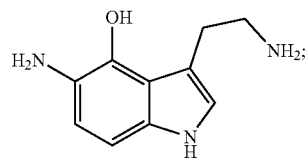
(VIII)

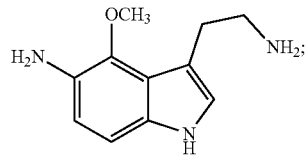
(IX)

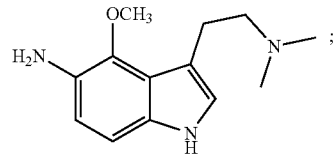
(X)

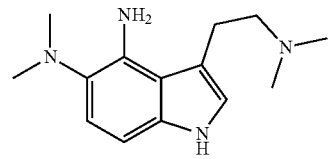
(XI)

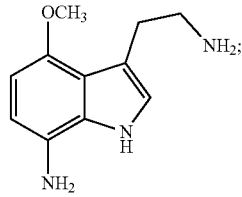
(XII)

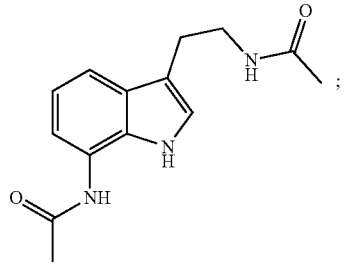
(XIII)

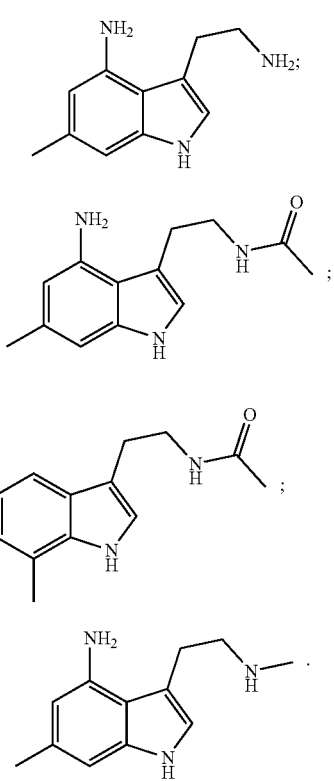

(XIV)

(XV)

(XVI)

and (XVII)

In at least one embodiment, in an aspect, the aminated psilocybin precursor compound can be contacted with the host cell by including the aminated psilocybin precursor compound in a growth medium for the host cell.

In at least one embodiment, in an aspect, the method can further include a step comprising isolating the aminated psilocybin derivative.

In at least one embodiment, in an aspect, the host cell can be a microbial cell.

In at least one embodiment, in an aspect, the host cell can be a bacterial cell or a yeast cell.

In another aspect, the present disclosure provides, in at least one embodiment, a method for modulating a 5-$HT_{2A}$ receptor or a 5-$HT_{1A}$ receptor, the method comprising contacting the 5-$HT_{2A}$ receptor or the 5-$HT_{1A}$ receptor with a chemical compound or salts thereof having the formula (I):

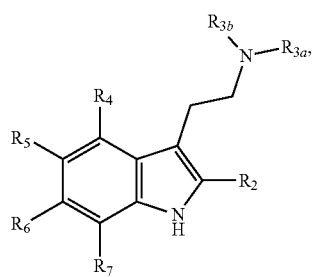

(I)

under conditions sufficient to modulate the 5-$HT_{2A}$ receptor or the 5-$HT_{1A}$ receptor, wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group, together with a pharmaceutically acceptable excipient, diluent or carrier.

In at least one embodiment, in an aspect, the reaction conditions can be in vitro reaction conditions.

In at least one embodiment, in an aspect, the reaction conditions can be in vivo reaction conditions.

In another aspect, the present disclosure provides, in at least one embodiment, a use of a chemical compound having the formula (I):

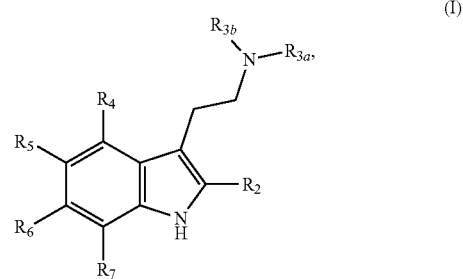

(I)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a phosphate group, a hydrogen atom, or a hydroxy group, an alkyl group or O-alkyl group and wherein $R_{3A}$ and $R_{3B}$ are a hydrogen atom, an alkyl group or O-alkyl group, in the manufacture of a pharmaceutical or recreational drug formulation.

In at least one embodiment, in an aspect, the manufacture can comprise formulating the chemical compound with an excipient, diluent or carrier.

In at least one embodiment, in an aspect, the manufacture can further include a step comprising derivatizing the chemical compound having the formula (I) by substituting the amino group or N-substituted amino group with another group or an atom.

In another aspect, the present disclosure provides, in at least one embodiment, a use of a chemical compound having the formula (I):

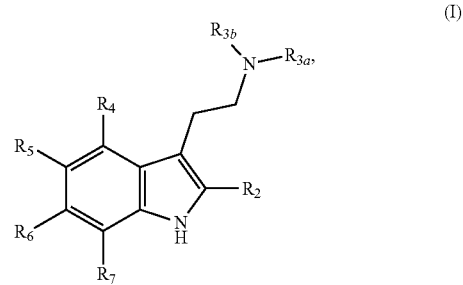

(I)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a phosphate group, a hydrogen atom, a hydroxy group, or an alkyl group or O-alkyl group, and wherein $R_{3A}$ and $R_{3B}$ are each independently a hydrogen atom, an alkyl group or O-alkyl group, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

FIG. 9C depicts a possible direction amination method with $H_2O_2$ and $NH_3 \cdot H_2O$ with the help of a catalyst. FIG. 9D further depicts a multistep synthesis of two 4-O-methyl-psilocybin derivatives respectively aminated at $C_5$ (compound 9D-8) and $C_7$ (compound 9D-10).

FIG. 10 depicts example biosynthesis processes for the synthesis of several example aminated psilocybin derivatives.

FIGS. 11A, 11B, 11C, 11D, 11E, 11F, 11G, 11H, 11I, 11J, 11K, 11L, and 11M depict various graphs, obtained in the performance of experimental assays to evaluate the efficacy of an example aminated psilocybin derivative having the chemical formulae (IX), (XII) and (XIII) set forth herein, notably a cell viability assay for an aminated psilocybin derivative having the chemical formulae (IX) (FIG. 11A), (XII) (FIG. 11B) and (XIII) (FIG. 11C); a saturation binding assay for [$^3$H]ketanserin at the 5-$HT_{2A}$ receptor (FIG. 11D); a competition assay for psilocin as a positive control (binding) (top panel), and a competition assay for tryptophan as a negative control (no binding) (bottom panel) (FIG. 11E); a competition assay for an aminated psilocybin derivative compound with formula (IX), designated "IX" (FIG. 11F); a competition assay for an aminated psilocybin derivative compound with formula (XII), designated "XII" (FIG. 11G); a competition assay for an aminated psilocybin derivative compound with formula (XIII), designated "XIII" (FIG. 11H); a luminescence assay in +5$HT_{1A}$ cell cultures at various forskolin concentrations (FIG. 11I), a luminescence assay in +5$HT_{1A}$ cell cultures in the presence of constant (4 μM) forskolin but with decreasing DMT concentration (FIG. 11J), a luminescence assay in +5$HT_{1A}$ cell cultures in the presence of constant (4 μM) forskolin but with decreasing tryptophan concentration (FIG. 14K), a cAMP assay in the presence of constant (4 μM) forskolin but with decreasing serotonin concentration in +5$HT_{1A}$ cells (FIG. 11L), a cAMP assay in the presence of constant (4 μM) forskolin but with increasing concentration of an aldehyde psilocybin compound having formula (IX), designated "IX" in +5$HT_{1A}$ cells and −5$HT_{1A}$ cells (FIG. 11M).

FIGS. 12A and 12B depict a representation of mass spectrometry data in the form of a chromatogram, notably a chromatogram obtained in the performance of an experiment to synthesize an example aminated psilocybin derivative compound having the chemical formula (VI) set forth herein (FIG. 12A); and a representation of mass spectrometry data in the form of a mass spectrometry spectrum obtained in the performance of an experiment to identify an aminated psilocybin derivative compound having the chemical formula (VI) set forth herein (FIG. 12B).

FIGS. 13A and 13B depict a representation of further mass spectrometry data in the form of a chromatogram, notably a chromatogram obtained in the performance of an experiment to synthesize an example aminated psilocybin derivative compound having the chemical formula (XIV) set forth herein (FIG. 13A); and a representation of mass spectrometry data in the form of a further mass spectrometry spectrum obtained in the performance of an experiment to identify an aminated psilocybin derivative compound having the chemical formula (XIV) set forth herein (FIG. 13B).

FIGS. 14A and 14B depict a representation of further mass spectrometry data in the form of a chromatogram, notably a chromatogram obtained in the performance of an experiment to synthesize an example aminated psilocybin derivative compound having the chemical formula (VII) set forth herein (FIG. 14A); and a representation of mass spectrometry data in the form of a further mass spectrometry spectrum obtained in the performance of an experiment to identify an aminated psilocybin derivative compound having the chemical formula (VII) set forth herein (FIG. 14B).

FIGS. 15A and 15B depict a representation of further mass spectrometry data in the form of a chromatogram, notably a chromatogram obtained in the performance of an experiment to synthesize an example aminated psilocybin derivative compound having the chemical formula (IV) set forth herein (FIG. 15A); and a representation of mass spectrometry data in the form of a further mass spectrometry spectrum obtained in the performance of an experiment to identify an aminated psilocybin derivative compound having the chemical formula (IV) set forth herein (FIG. 15B).

FIGS. 16A and 16B depict a representation of further mass spectrometry data in the form of a chromatogram, notably a chromatogram obtained in the performance of an experiment to synthesize an example aminated psilocybin derivative compound having the chemical formula (III) set forth herein (FIG. 16A); and a representation of mass spectrometry data in the form of a further mass spectrometry spectrum obtained in the performance of an experiment to identify an aminated psilocybin derivative compound having the chemical formula (III) set forth herein (FIG. 16B).

FIGS. 17A and 17B depict a representation of further mass spectrometry data in the form of a chromatogram, notably a chromatogram obtained in the performance of an experiment to synthesize an example aminated psilocybin derivative compound having the chemical formula (XV) set forth herein (FIG. 17A); and a representation of mass spectrometry data in the form of a further mass spectrometry spectrum obtained in the performance of an experiment to identify an aminated psilocybin derivative compound having the chemical formula (XV) set forth herein (FIG. 17B).

FIGS. 18A and 18B depict a representation of further mass spectrometry data in the form of a chromatogram, notably a chromatogram obtained in the performance of an experiment to synthesize an example aminated psilocybin derivative compound having the chemical formula (XVI) set forth herein (FIG. 18A); and a representation of mass spectrometry data in the form of a further mass spectrometry spectrum obtained in the performance of an experiment to identify an aminated psilocybin derivative compound having the chemical formula (XVI) set forth herein (FIG. 18B).

FIG. 19 depicts a representation of further mass spectrometry data in the form of a chromatogram, notably a chromatogram obtained in the performance of an experiment to synthesize an example aminated psilocybin derivative compound having the chemical formula (XVII) set forth herein (FIG. 19).

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

Figure 1:
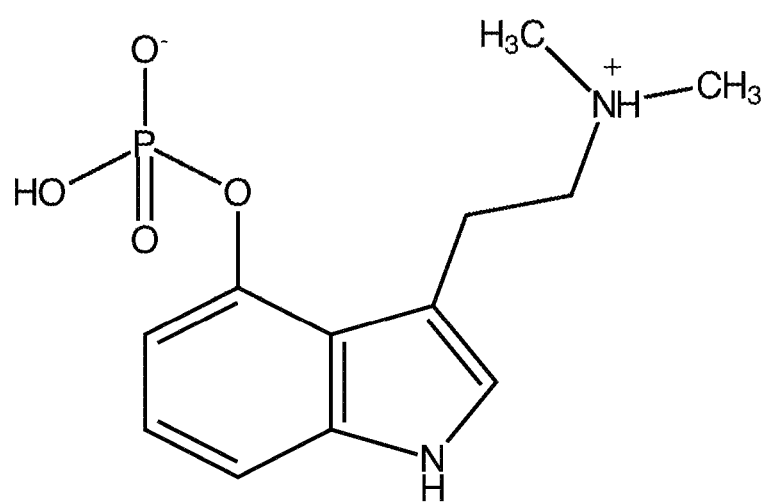
FIG. 1 depicts the chemical structure of psilocybin.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

The term "psilocybin", refers to a chemical compound having the structure set forth in FIG. 1.

Figure 2:
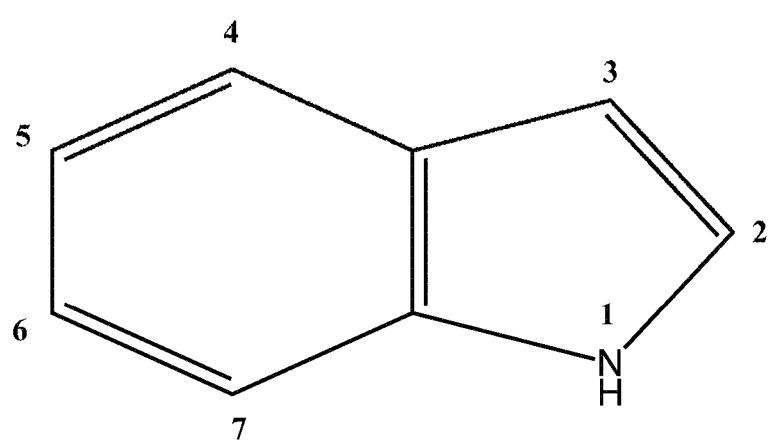
FIG. 2 depicts a certain prototype structure of psilocybin and psilocybin derivative compounds, namely an indole. Certain carbon and nitrogen atoms may be referred to herein by reference to their position within the indole structure, i.e., $N_1$, $C_2$, $C_3$ etc. The pertinent atom numbering is shown.

The term "indole prototype structure" refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example $R_4$ and $R_6$ reference chemical groups attached to the $C_4$ and $C_6$ atom, respectively. In addition, $R_{3A}$ and $R_{3B}$, in this respect, reference chemical groups extending from the ethyl-amino group extending in turn from the $C_3$ atom of the prototype indole structure.

The term "aminated psilocybin derivative" refers to a psilocybin derivative compound to which an amino group has been bonded to psilocybin or a psilocybin derivative. The nitrogen of the amino group may bear 1-3 substituents (i.e., be a N-substituted amino group). N-substituents can be an alkyl, aryl, acyl, sulfonyl groups or combinations thereof. Reference may be made to specific carbon atoms which may be aminated. For example, a 5-amino-psilocybin derivative refers to a psilocybin derivative in which carbon atom number 5 (as identified in the indole prototype structure) possesses an amino or N-substituted amino group, or, similarly, 7-amino-psilocybin derivative refers to a psilocybin derivative in which carbon atom number 7 (as identified in the indole prototype structure) possess an amino or N-substituted amino group. Thus, for example, aminated psilocybin derivatives include, single amino derivatives, 2-amino, 4-amino, 5-amino, 6-amino, and 7-amino psilocybin derivatives, for example, and multiple amino derivatives, such as, for example, 5,7-di-amino psilocybin derivatives, and 2,5,7-tri-amino psilocybin derivatives. The term aminated psilocybin derivatives further includes chemical compounds having the chemical formula (I):

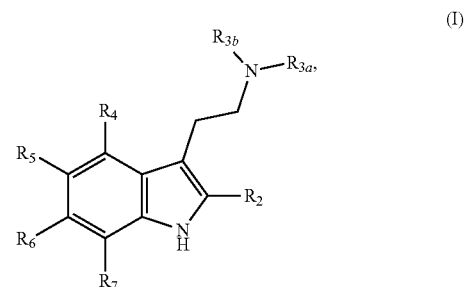

wherein at least one of $R_2$, $R_4$, $R_5$, $R_6$, or $R_7$ is an amino group or an N-substituted amino group, and wherein each non-aminated $R_2$, $R_5$, $R_6$, or $R_7$ is a hydrogen atom or an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are a hydrogen atom, an alkyl group, an aryl group, or an acyl group. Furthermore, it is noted that when $R_4$ is a phosphate group, the term aminated psilocybin derivatives includes compounds having the formula (XIX):

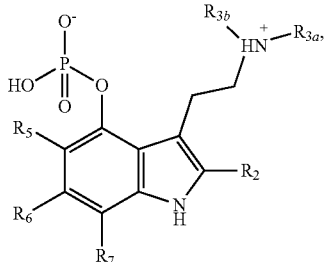
(XIX)

wherein at least one of $R_2$, $R_5$, $R_6$, or $R_7$ is a hydrogen atom, and wherein $R_2$, $R_5$, $R_6$, or $R_7$ which are not a hydrogen atom are an amino or N-substituted amino group, and wherein $R_{3A}$ and $R_{3B}$ are a hydrogen atom, an alkyl group or aryl group. The term further includes salts of aminated psilocybins, such as a sodium salt, a potassium salt etc.

The term "amino group" and "amino", as used herein refers to a molecule containing one atom of nitrogen bonded to hydrogen atoms and having the formula —$NH_2$. An amino group also may be protonated and having the formula —$NH_3^+$. An amino group through its nitrogen atom may be chemically bonded to another entity. Furthermore, it is noted that an entity attached to an amino group may be referred to herein as an "aminated" entity, e.g., an aminated psilocybin derivative is a psilocybin derivative possessing either an amino group or a N-substituted amino group.

The term "N-substituted amino group", as used herein, refers to an amino group wherein at least one of the hydrogen atoms has been substituted by another atom or group, such as, for example, an alkyl group, an acyl group, an aryl group a sulfonyl group etc., excluding, however, an amino group wherein both of the hydrogen atoms are substituted by oxygen atoms to thereby form a nitro group. An N-substituted amino group also may be protonated, and the amino group through its nitrogen atom may be chemically bonded to another entity. Thus, N-substituted amino group may be represented herein as:

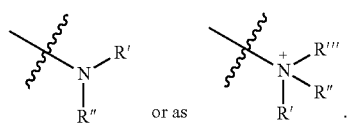

Furthermore N-substituted amino groups include:
(i) chemical group (XX) (an alkyl group, an aryl group):

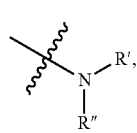
(XX)

wherein R' and R" are each independently selected from a hydrogen atom, an alkyl group, and an aryl group, provided however that at least one of R', and R" is not a hydrogen atom;

(ii) chemical group (XXI):

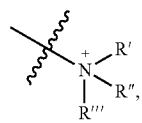
(XXI)

wherein R', R" and R'" are each independently selected from a hydrogen atom, an alkyl group, and an aryl group, provided however that at least one of R', R", and R'" is not a hydrogen atom;

(iii) chemical group (XXII) (an acyl group):

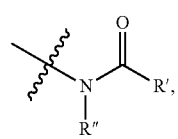
(XXII)

wherein R' and R" are each independently selected from a hydrogen atom, an alkyl group and an aryl group;

(iv) chemical group (XXIII) (a sulfonyl group):

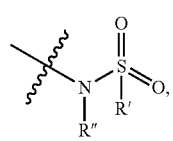
(XXIII)

wherein R', and R" are each independently selected from a hydrogen atom, an alkyl group and an aryl group; or (v) chemical group (XXIV) (a sulfonate group):

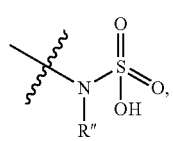
(XXIV)

wherein R" is selected from a hydrogen atom, an alkyl group, and an aryl group. The nitrogen atom of chemical groups (XXII), (XXIII) and (XXIV) can also be positively charged and be further substituted with H, or R'".

It is noted that R', R" and R'" can herein additionally include numerical subscripts, such as 5a, 6b, 7b etc., and be represented, for example, as $R'_{5a}$, $R''_{6b}$ or $R'''_{7a}$, respectively. Where such numerical values are included, they reference chemical entity extending from the amino group extending in turn from the thus numbered C atom of the prototype indole structure. Thus, for example, $R'_{5a}$ is a chemical entity extending from an aminated group attached to the $C_5$ atom of the indole ring structure, $R'_{2a}$ is a chemical entity extending from an aminated group attached to the $C_2$ atom of the indole ring structure, and so forth. Furthermore, it is noted that an entity attached to an N-substituted amino group may be referred to herein as an "aminated" entity, e.g., an aminated psilocybin derivative is a psilocybin derivative possessing either an amino group or a N-substituted amino group.

The term "sulfonyl", as used herein, refers to a molecule containing one sulfur atom bonded to two oxygen atoms, and one other entity and having the formula:

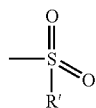

wherein R may be a variety of entities including a hydroxy group, an alkyl group, or an aryl group. A sulfonyl group through its sulfur atom may be chemically bonded to another entity. Furthermore, it is noted that an entity attached to a sulfonyl group may be referred to herein as a "sulfonylated".

The term "phosphate group", as used herein, is a molecule containing one atom of phosphorus, covalently bound to four oxygen atoms (three single bonds and one double bond). Of the four oxygen atoms, one oxygen atom may be a hydroxy, and one of the non-hydroxylated oxygen atom may be chemically bonded to another entity.

The terms "hydroxy group", and "hydroxy", as used herein, refer to a molecule containing one atom of oxygen bonded to one atom of hydrogen, and having the formula —OH. A hydroxy through its oxygen atom may be chemically bonded to another entity.

The terms "nitro" and "nitro group", as used herein, refer to a molecule containing one atom of nitrogen bonded to two atoms of oxygen and having the formula —$NO_2$. A nitro group through its nitrogen atom may be chemically bonded to another entity. Furthermore, it is noted that an entity attached to a nitro group may be referred to herein as a "nitrated" entity, e.g., a nitrated psilocybin derivative is a psilocybin derivative possessing a nitro group.

The term "alkyl", as used herein, refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical Alkyl groups further include hydrocarbon groups arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$).

The term "O-alkyl", as used herein, refers to a hydrocarbon group arranged in a chain having the chemical formula —O—$C_nH_{2n+1}$. O-alkyl groups include, without limitation, O-methyl groups (—O—$CH_3$), O-ethyl groups (—O—$C_2H_5$), O-propyl groups (—O—$C_3H_7$) and O-butyl groups (—O—$C_4H_9$).

The term "aryl", as used herein, refers to a monocyclic, bicyclic, or tricyclic aromatic ring system containing, depending on the number of atoms in the rings, for example, from 6 to 14 carbon atoms ($C_6$-$C_{14}$-aryl) or from 6 to 10 carbons ($C_6$-$C_{10}$-aryl), and at least 1 aromatic ring and includes phenyl, naphthyl, anthracenyl, 1,2-dihydronaphthyl, 1,2,3,4-tetrahydronaphthyl, fluorenyl, phenanthrenyl, biphenylenyl, indanyl, indenyl and the like.

The term "acyl", as used herein, refers to a carbon atom double bonded to an oxygen and single bonded to an alkyl group. The carbon atom further can be bonded to another entity. An acyl group can be described by the chemical formula: —C(═O)—$C_nH_{2n+1}$.

The term "O-acyl group" refers to an acyl group in which the carbon atom is single bonded to an additional oxygen atom. The additional oxygen atom can be bonded to another entity. An O-acyl group can be described by the chemical formula: —O—C(═O)—$C_nH_{2n+1}$. Furthermore, depending on the carbon chain, length specific O-acyl groups may be termed an acetyl group (n=1), a propanoyl group (n=2), propoxycarbonyl group (n=3), a butoxycarbonyl group (n=4) etc.

The term "azido", as used herein refers to a chemical group having the formula: —N═$N^+$═$N^-$.

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds.

The term "modulating 5-$HT_{2A}$ receptors", as used herein, refers to the ability of a compound disclosed herein to alter the function of 5-$HT_{2A}$ receptors. A 5-$HT_{2A}$ receptor modulator may activate the activity of a 5-$HT_{2A}$ receptor, may activate or inhibit the activity of a 5-$HT_{2A}$ receptor depending on the concentration of the compound exposed to the 5-$HT_{2A}$ receptor, or may inhibit the activity of a 5-$HT_{2A}$ receptor. Such activation or inhibition may be contingent on the occurrence of a specific event, such as activation of a signal transduction pathway, and/or maybe manifest only in particular cell types. The term "modulating 5-$HT_{2A}$ receptors," also refers to altering the function of a 5-$HT_{2A}$ receptor by increasing or decreasing the probability that a complex forms between a 5-$HT_{2A}$ receptor and a natural binding partner to form a multimer. A 5-$HT_{2A}$ receptor modulator may increase the probability that such a complex forms between the 5-$HT_{2A}$ receptor and the natural binding partner, may increase or decrease the probability that a complex forms between the 5-$HT_{2A}$ receptor and the natural binding partner depending on the concentration of the compound exposed to the 5-$HT_{2A}$ receptor, and or may decrease the probability that a complex forms between the 5-$HT_{2A}$ receptor and the natural binding partner. Furthermore, the term includes allosteric modulation of the receptor 5-$HT_{2A}$, i.e., modulation of the 5-$HT_{2A}$ receptor through interaction with the 5-$HT_{2A}$ receptor that is topographically different than the orthosteric site recognized by the cell's endogenous agonist, such modulation further including positive allosteric modulation (PAM), negative allosteric modulation (NAM) and silent allosteric modulation (SAM).

The term "5-$HT_{2A}$ receptor-mediated disorder", as used herein, refers to a disorder that is characterized by abnormal 5-$HT_{2A}$ receptor activity. A 5-$HT_{2A}$ receptor-mediated disorder may be completely or partially mediated by modulating 5-$HT_{2A}$ receptors. In particular, a 5-$HT_{2A}$ receptor-mediated disorder is one in which modulation of 5-$HT_{2A}$ receptors results in some effect on the underlying disorder e.g., administration of a 5-$HT_{2A}$ receptor modulator results in some improvement in at least some of the subjects being treated.

The term "5-$HT_{1A}$ receptor", as used herein, refers to a subclass of a family of receptors for the neurotransmitter and peripheral signal mediator serotonin. 5-$HT_{1A}$ receptors can mediate a plurality of central and peripheral physiologic functions of serotonin. Ligand activity at 5-$HT_{1A}$ is generally not associated with hallucination, although many hallucinogenic compounds are known to modulate 5-$HT_{1A}$ receptors to impart complex physiological responses (Inserra et al., 2020, Pharmacol Rev 73: 202).

The term "modulating 5-HT$_{1A}$ receptors", as used herein, refers to the ability of a compound disclosed herein to alter the function of 5-HT$_{1A}$ receptors. A 5-HT$_{2A}$ receptor modulator may activate the activity of a 5-HT$_{1A}$ receptor, may activate or inhibit the activity of a 5-HT$_{1A}$ receptor depending on the concentration of the compound exposed to the 5-HT$_{1A}$ receptor, or may inhibit the activity of a 5-HT$_{1A}$ receptor. Such activation or inhibition may be contingent on the occurrence of a specific event, such as activation of a signal transduction pathway, and/or maybe manifest only in particular cell types. The term "modulating 5-HT$_{1A}$ receptors," also refers to altering the function of a 5-HT$_{1A}$ receptor by increasing or decreasing the probability that a complex forms between a 5-HT$_{1A}$ receptor and a natural binding partner to form a multimer. A 5-HT$_{1A}$ receptor modulator may increase the probability that such a complex forms between the 5-HT$_{1A}$ receptor and the natural binding partner, may increase or decrease the probability that a complex forms between the 5-HT$_{2A}$ receptor and the natural binding partner depending on the concentration of the compound exposed to the 5-HT$_{1A}$ receptor, and or may decrease the probability that a complex forms between the 5-HT$_{1A}$ receptor and the natural binding partner. Furthermore, the term includes allosteric modulation of the receptor 5-HT$_{1A}$, i.e., modulation of the 5-HT$_{1A}$ receptor through interaction with the 5-HT$_{1A}$ receptor that is topographically different than the orthosteric site recognized by the cell's endogenous agonist, such modulation further including positive allosteric modulation (PAM), negative allosteric modulation (NAM) and silent allosteric modulation (SAM).

The term "5-HT$_{1A}$ receptor-mediated disorder", as used herein, refers to a disorder that is characterized by abnormal 5-HT$_{1A}$ receptor activity. A 5-HT$_{1A}$ receptor-mediated disorder may be completely or partially mediated by modulating 5-HT$_{2A}$ receptors. In particular, a 5-HT$_{1A}$ receptor-mediated disorder is one in which modulation of 5-HT$_{1A}$ receptors results in some effect on the underlying disorder e.g., administration of a 5-HT$_{1A}$ receptor modulator results in some improvement in at least some of the subjects being treated.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term "psilocybin biosynthetic enzyme complement", as used herein, refers to one or more polypeptides which alone or together are capable of facilitating the chemical conversion of a psilocybin precursor compound and form another psilocybin precursor compound, or an aminated psilocybin derivative compound. A psilocybin biosynthetic enzyme complement can include, for example, a tryptophan synthase subunit B polypeptide, a tryptophan decarboxylase and/or a N-acetyl transferase.

The term "tryptophan synthase subunit B polypeptide" as used herein, refers to any and all enzymes comprising a sequence of amino acid residues which is (i) substantially identical to the amino acid sequences constituting any tryptophan synthase subunit B polypeptide set forth herein, including, for example, SEQ. ID NO: 9, or (ii) encoded by a nucleic acid sequence capable of hybridizing under at least moderately stringent conditions to any nucleic acid sequence encoding any tryptophan synthase subunit B polypeptide set forth herein, but for the use of synonymous codons.

The term "tryptophan decarboxylase" as used herein, refers to any and all enzymes comprising a sequence of amino acid residues which is (i) substantially identical to the amino acid sequences constituting any tryptophan decarboxylase polypeptide set forth herein, including, for example, SEQ. ID NO: 12, or (ii) encoded by a nucleic acid sequence capable of hybridizing under at least moderately stringent conditions to any nucleic acid sequence encoding any tryptophan decarboxylase set forth herein, but for the use of synonymous codons.

The term "N-acetyl transferase" as used herein, refers to any and all enzymes comprising a sequence of amino acid residues which is (i) substantially identical to the amino acid sequences constituting any N-acetyl transferase polypeptide set forth herein, including, for example, SEQ. ID NO: 5, or (ii) encoded by a nucleic acid sequence capable of hybridizing under at least moderately stringent conditions to any nucleic acid sequence encoding any N-acetyl transferase set forth herein, but for the use of synonymous codons.

The term "N-methyl transferase" as used herein, refers to any and all enzymes comprising a sequence of amino acid residues which is (i) substantially identical to the amino acid sequences constituting any N-methyl transferase polypeptide set forth herein, including, for example, SEQ. ID NO: 14, or (ii) encoded by a nucleic acid sequence capable of hybridizing under at least moderately stringent conditions to any nucleic acid sequence encoding any N-methyl transferase set forth herein, but for the use of synonymous codons.

The terms "nucleic acid sequence encoding tryptophan synthase subunit B polypeptide", as may be used interchangeably herein, refer to any and all nucleic acid sequences encoding a tryptophan synthase subunit B polypeptide, including, for example, SEQ. ID NO: 8. Nucleic acid sequences encoding a tryptophan synthase subunit B polypeptide further include any and all nucleic acid sequences which (i) encode polypeptides that are substantially identical to the tryptophan synthase subunit B polypeptide sequences set forth herein; or (ii) hybridize to any tryptophan synthase subunit B polypeptide nucleic acid sequences set forth herein under at least moderately stringent hybridization conditions or which would hybridize thereto under at least moderately stringent conditions but for the use of synonymous codons.

The terms "nucleic acid sequence encoding tryptophan decarboxylase", and "nucleic acid sequence encoding a tryptophan decarboxylase polypeptide", as may be used interchangeably herein, refer to any and all nucleic acid sequences encoding a tryptophan decarboxylase, including, for example, SEQ. ID NO: 11. Nucleic acid sequences encoding a tryptophan decarboxylase polypeptide further include any and all nucleic acid sequences which (i) encode polypeptides that are substantially identical to the tryptophan decarboxylase polypeptide sequences set forth herein; or (ii) hybridize to any tryptophan decarboxylase nucleic acid sequences set forth herein under at least moderately stringent hybridization conditions or which would hybridize thereto under at least moderately stringent conditions but for the use of synonymous codons.

The terms "nucleic acid sequence encoding N-acetyl transferase", and "nucleic acid sequence encoding an N-acetyl transferase polypeptide", as may be used interchangeably herein, refer to any and all nucleic acid sequences encoding an N-acetyl transferase, including, for example, SEQ. ID NO: 4. Nucleic acid sequences encoding an N-acetyl transferase polypeptide further include any and all nucleic acid sequences which (i) encode polypeptides that are substantially identical to the N-acetyl transferase polypeptide sequences set forth herein; or (ii) hybridize to any N-acetyl transferase nucleic acid sequences set forth herein under at least moderately stringent hybridization conditions or which would hybridize thereto under at least moderately stringent conditions but for the use of synonymous codons.

The terms "nucleic acid sequence encoding an N-methyl transferase", and "nucleic acid sequence encoding an N-methyl transferase polypeptide", as may be used interchangeably herein, refer to any and all nucleic acid sequences encoding an N-methyl transferase, including, for example, SEQ. ID NO: 13. Nucleic acid sequences encoding an N-methyl transferase polypeptide further include any and all nucleic acid sequences which (i) encode polypeptides that are substantially identical to the N-methyl transferase polypeptide sequences set forth herein; or (ii) hybridize to any N-methyl transferase nucleic acid sequences set forth herein under at least moderately stringent hybridization conditions or which would hybridize thereto under at least moderately stringent conditions but for the use of synonymous codons.

The terms "nucleic acid", or "nucleic acid sequence", as used herein, refer to a sequence of nucleoside or nucleotide monomers, consisting of naturally occurring bases, sugars and intersugar (backbone) linkages. The term also includes modified or substituted sequences comprising non-naturally occurring monomers or portions thereof. The nucleic acids of the present disclosure may be deoxyribonucleic nucleic acids (DNA) or ribonucleic acids (RNA) and may include naturally occurring bases including adenine, guanine, cytosine, thymidine, and uracil. The nucleic acids may also contain modified bases. Examples of such modified bases include aza and deaza adenine, guanine, cytosine, thymidine and uracil, and xanthine and hypoxanthine. A sequence of nucleotide or nucleoside monomers may be referred to as a polynucleotide sequence, nucleic acid sequence, a nucleotide sequence, or a nucleoside sequence.

The term "polypeptide", as used herein in conjunction with a reference SEQ. ID NO, refers to any and all polypeptides comprising a sequence of amino acid residues which is (i) substantially identical to the amino acid sequence constituting the polypeptide having such reference SEQ. ID NO, or (ii) encoded by a nucleic acid sequence capable of hybridizing under at least moderately stringent conditions to any nucleic acid sequence encoding the polypeptide having such reference SEQ. ID NO, but for the use of synonymous codons. A sequence of amino acid residues may be referred to as an amino acid sequence, or polypeptide sequence.

The term "nucleic acid sequence encoding a polypeptide", as used herein in conjunction with a reference SEQ. ID NO, refers to any and all nucleic acid sequences encoding a polypeptide having such reference SEQ. ID NO. Nucleic acid sequences encoding a polypeptide, in conjunction with a reference SEQ. ID NO, further include any and all nucleic acid sequences which (i) encode polypeptides that are substantially identical to the polypeptide having such reference SEQ. ID NO; or (ii) hybridize to any nucleic acid sequences encoding polypeptides having such reference SEQ. ID NO under at least moderately stringent hybridization conditions or which would hybridize thereto under at least moderately stringent conditions but for the use of synonymous codons.

By the term "substantially identical" it is meant that two amino acid sequences preferably are at least 70% identical, and more preferably are at least 85% identical and most preferably at least 95% identical, for example 96%, 97%, 98% or 99% identical. In order to determine the percentage of identity between two amino acid sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Mol. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.-16.6 (Log 10 [Na+])+0.41(% (G+C)−600/I), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/ 0.1% SDS at 60° C. Moderately stringent hybridization conditions include a washing step in 3×SSC at 42° C. It is understood however that equivalent stringencies may be achieved using alternative buffers, salts, and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "functional variant", as used herein in reference to polynucleotides or polypeptides, refers to polynucleotides or polypeptides capable of performing the same function as a noted reference polynucleotide or polypeptide. Thus, for example, a functional variant of the polypeptide set forth in SEQ. ID NO: 2, refers to a polypeptide capable of performing the same function as the polypeptide set forth in SEQ. ID NO: 2. Functional variants include modified a polypeptide wherein, relative to a noted reference polypeptide, the modification includes a substitution, deletion, or addition of one or more amino acids. In some embodiments, substitutions are those that result in a replacement of one amino acid with an amino acid having similar characteristics. Such substitutions include, without limitation (i) glutamic acid and aspartic acid; (i) alanine, serine, and threonine; (iii) isoleucine, leucine, and valine, (iv) asparagine and glutamine, and (v) tryptophan, tyrosine, and phenylalanine. Functional variants further include polypeptides having retained or exhibiting an enhanced psilocybin biosynthetic bioactivity.

The term "chimeric", as used herein in the context of nucleic acids, refers to at least two linked nucleic acids which are not naturally linked. Chimeric nucleic acids include linked nucleic acids of different natural origins. For example, a nucleic acid constituting a microbial promoter linked to a nucleic acid encoding a plant polypeptide is considered chimeric. Chimeric nucleic acids also may comprise nucleic acids of the same natural origin, provided they are not naturally linked. For example a nucleic acid constituting a promoter obtained from a particular cell-type may be linked to a nucleic acid encoding a polypeptide obtained from that same cell-type, but not normally linked to the nucleic acid constituting the promoter. Chimeric nucleic acids also include nucleic acids comprising any naturally occurring nucleic acids linked to any non-naturally occurring nucleic acids.

The terms "substantially pure" and "isolated", as may be used interchangeably herein describe a compound, e.g., a secondary metabolite, psilocybin or a psilocybin derivative, polynucleotide, or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "recovered" as used herein in association with a chemical compound, refers to a more or less pure form of the chemical compound.

General Implementation

As hereinbefore mentioned, the present disclosure relates to psilocybin derivatives. In particular, the present disclosure provides novel aminated psilocybin derivatives. In general, the herein provided compositions exhibit functional properties which deviate from the functional properties of psilocybin. Thus, for example, the aminated psilocybin derivatives, can exhibit pharmacological properties which deviate from psilocybin. Furthermore, the aminated derivatives may psilocybin derivatives may exhibit physicochemical properties which differ from psilocybin. Thus, for example, aminated psilocybin derivatives may exhibit superior solubility in a solvent, for example, an aqueous solvent. The aminated psilocybin derivatives in this respect are useful in the formulation of pharmaceutical and recreational drug formulations. Furthermore, the aminated psilocybin compounds of the present disclosure may be used as a feedstock material for deriving further psilocybin derivatives. In one embodiment, the aminated psilocybin derivatives of the present disclosure can conveniently be synthetically produced. The practice of this method avoids the extraction of psilocybin from mushrooms and the performance of subsequent chemical reactions to achieve aminated derivatives. Furthermore, the growth of mushrooms can be avoided thus limiting the dependence on climate and weather, and potential legal and social challenges associated with the cultivation of mushrooms containing psychoactive compounds. The method can efficiently yield substantial quantities of aminated psilocybin derivatives.

In what follows selected embodiments are described with reference to the drawings.

Initially example aminated psilocybin derivatives will be described. Thereafter example methods of using and making the aminated psilocybin derivatives will be described.

Accordingly, in one aspect, the present disclosure provides derivatives of a compound known as psilocybin of which the chemical structure is shown in FIG. 1. The derivatives herein provided are, in particular, derivatives of psilocybin including an amino group or N-substituted amino group.

Thus, in one aspect, the present disclosure provides, in accordance with the teachings herein, in at least one embodiment, a chemical compound or salt thereof having formula (I):

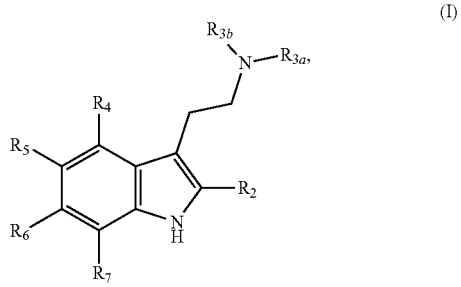
(I)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group, O-alkyl group, a hydroxy group, or a phosphate group, and wherein $R_{3A}$ and $R_{3B}$ are each independently a hydrogen atom, an alkyl group, an aryl group or an acyl group.

Thus, referring to the chemical compound having formula (I), initially it is noted that, in an aspect thereof, at least one of $R_2$, $R_4$, $R_5$, $R_6$, or $R_7$ is an amino group or N-substituted amino group.

Thus, referring to the chemical compound having the formula (I), initially it is noted that, in an aspect hereof, at least one of $R_2$, $R_5$, $R_6$, or $R_7$ is an amino group or an N-substituted amino group.

In a further aspect, at least one of $R_2$, $R_5$, $R_6$, or $R_7$ can be a N-substituted amino group, wherein one, or at least one, hydrogen atom is substituted by a group selected from an alkyl group, an aryl group, an acyl group, or a sulfonyl group. Thus, for example, in one embodiment, the N-substituted amino group can be
a chemical group having the formula (XX):

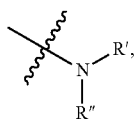
(XX)

wherein R', and R" are each independently selected from a hydrogen atom, an alkyl group, and an aryl group, provided however, that at least one of R' and R" is not a hydrogen atom.

In a further example embodiment, the N-substituted amino group can be a chemical group having the formula chemical group (XXI):

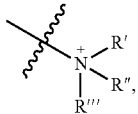
(XXI)

wherein R', R" and R'" are each independently selected from a hydrogen atom, an alkyl group and an aryl group, provided however that at least one of R', R", and R'" is not a hydrogen atom.

In a further example embodiment, the N-substituted amino group can be a chemical group having the formula (XXII) (an acyl group):

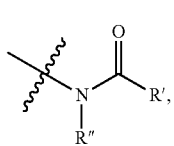
(XXII)

wherein R', and R'" are each independently selected from a hydrogen atom, an alkyl group, and an aryl group.

In a further example embodiment, the N-substituted amino group can be a chemical group having the formula (XXIII) (a sulfonyl group):

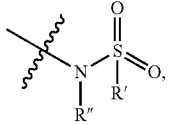
(XXIII)

wherein R' and R" are each independently selected from a hydrogen atom, an alkyl group and an aryl group.

In yet a further example embodiment, the N-substituted amino group can be a chemical group having the formula (XXIV) (a sulfo group):

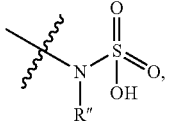
(XXIV)

wherein R" is selected from a hydrogen atom, an alkyl group, and an aryl group. The nitrogen atom of chemical groups (XXII), (XXIII) and (XXIV) can also be positively charged and be further substituted with H, or R'".

Continuing to refer to the chemical compound having formula (I), in a further aspect, $R_2$, $R_5$, $R_6$, or $R_7$ can be a N-substituted amino-group wherein two, or at least two, hydrogen atoms are substituted by a group independently selected from an alkyl group, an aryl group, an acyl group or a sulfonyl group.

In at least one embodiment, at least one of $R_2$, $R_5$, $R_6$, or $R_7$ can be a N-substituted amino-group (i.e., an ammonium group), wherein three hydrogen atoms are substituted by a group independently selected from an alkyl group, or an aryl group, wherein the nitrogen atom of the N-substituted group carries a positive charge.

Continuing to refer to the chemical compound having formula (I), in a further aspect hereof, $R_{3A}$ and $R_{3B}$ can each independently be a hydrogen atom, an alkyl group, an acyl group or an aryl group. Thus, $R_{3A}$ and $R_{3B}$ can each be a hydrogen atom, or $R_{3A}$ and $R_{3B}$ can each be an alkyl group, such as a methyl group, ethyl group, propyl group, or longer chain alkyl group, or $R_{3A}$ and $R_{3B}$ can be each be an acyl group, or $R_{3A}$ and $R_{3B}$ can each be an aryl group. Furthermore, one of $R_{3A}$ and $R_{3B}$ can be a hydrogen atom, and one of $R_{3A}$ and $R_{3B}$ can be an alkyl group. One of $R_{3A}$ and $R_{3B}$ can be a hydrogen atom, and one of $R_{3A}$ and $R_{3B}$ can be an acyl group. One of $R_{3A}$ and $R_{3B}$ can be a hydrogen atom, and one of $R_{3A}$ and $R_{3B}$ can be an aryl group. One of $R_{3A}$ and $R_{3B}$ can be an alkyl group, and one of $R_{3A}$ and $R_{3B}$ can be an aryl group. One of $R_{3A}$ and $R_{3B}$ can be an alkyl group, and one of $R_{3A}$ and $R_{3B}$ can be an acyl group. One of $R_{3A}$ and $R_{3B}$ can be an acyl group, and one of $R_{3A}$ and $R_{3B}$ can be an aryl group.

Continuing to refer to the chemical compound having formula (I), in a further aspect hereof, $R_4$, when it is not an amino group or N-substituted amino group can be is a hydrogen atom, an alkyl group, O-alkyl group, a hydroxy group, or a phosphate group.

Figure 3A:
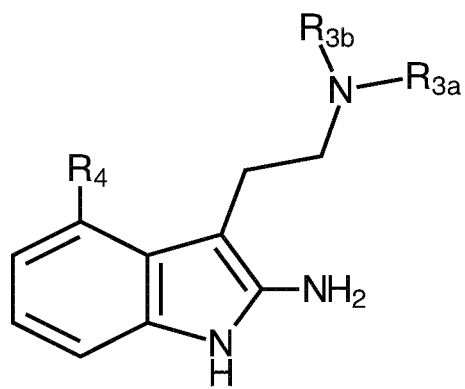
FIGS. 3A, 3B, 3C, 3D, 3E, 3F, 3G, 3H, 3I, 3J, 3K, 3L, 3M, 3N, 3O, and 3P depict the chemical structures of certain example aminated psilocybin derivatives, notably a 2-amino-psilocybin derivative (FIG. 3A), a 5-amino-psilocybin derivative (FIG. 3B), a 6-amino-psilocybin derivative (FIG. 3C), a 7-amino-psilocybin derivative (FIG. 3D), a 2-N,N-substituted-amino-psilocybin derivative (FIG. 3E), a 5-N,N-substituted-amino-psilocybin derivative (FIG. 3F), a 6-N,N-substituted-amino-psilocybin derivative (FIG. 3G), a 7-N,N-substituted amino-psilocybin derivative (FIG. 3H), a 2-amino-6-ethyl-psilocybin derivative (FIG. 3I), a 5-amino-7-methyl psilocybin derivative (FIG. 3J), a 5-O-ethyl-6-amino-psilocybin derivative (FIG. 3K), a 6-O-methyl-7-amino-psilocybin (FIG. 3L), a 2-N,N-substituted amino-7-methyl-psilocybin derivative (FIG. 3M), a 5-N,N-substituted amino-6-ethyl-psilocybin derivative (FIG. 3N), a 5-O-methyl-6-N,N-substituted amino-psilocybin derivative (FIG. 3O), and a 5-O-ethyl-7-N,N-substituted amino-psilocybin derivative (FIG. 3P).
Figure 3B:
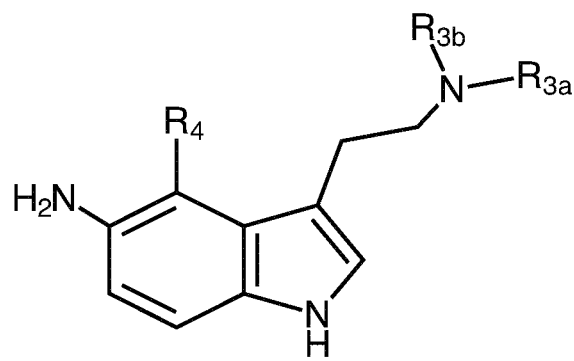
Figure 3C:
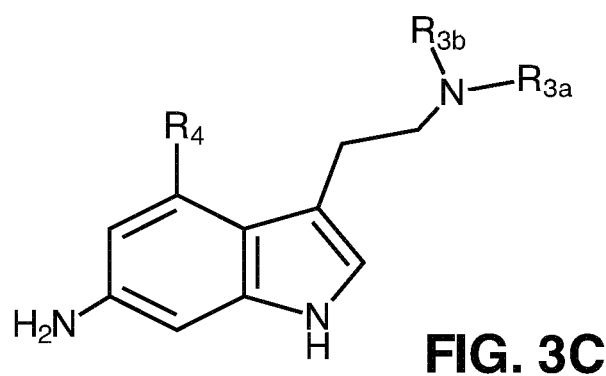
Figure 3D:
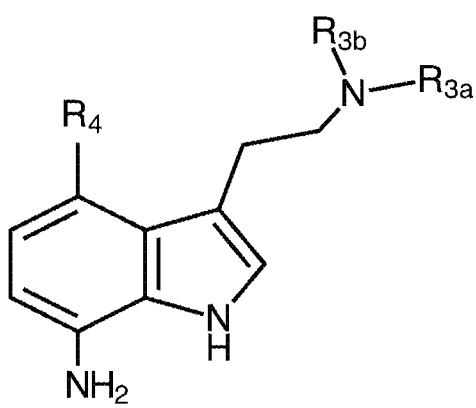
Figure 3E:
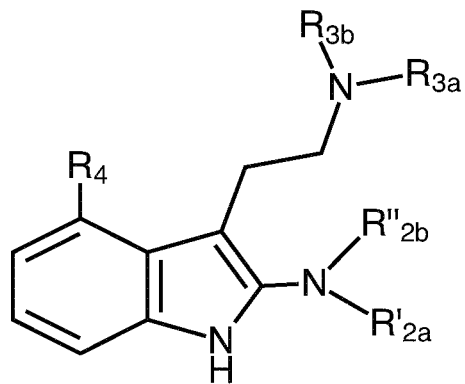
Figure 3F:
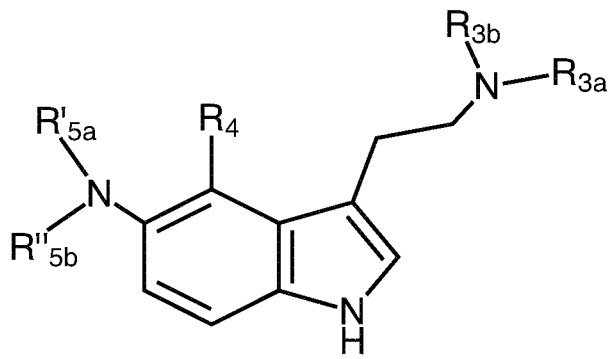
Figure 3G:
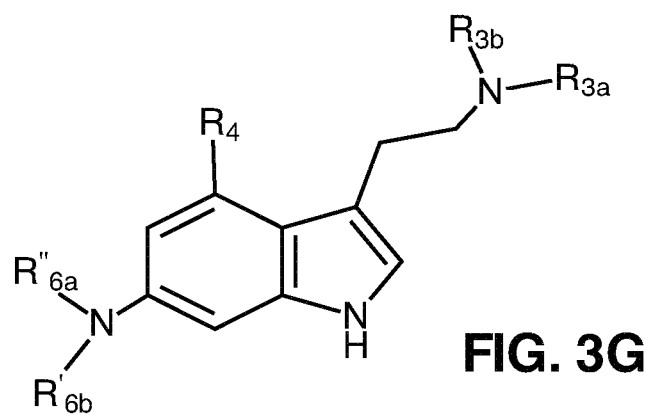
Figure 3H:
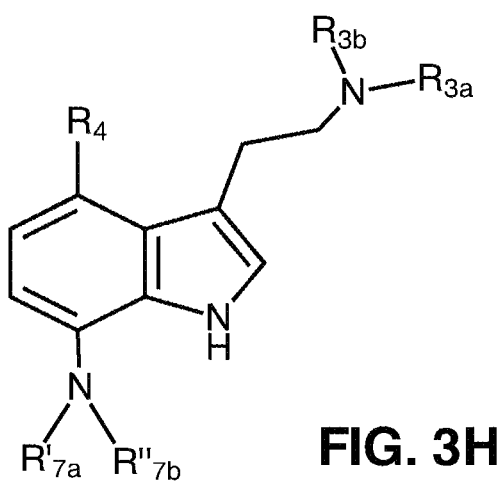
Figure 3I:
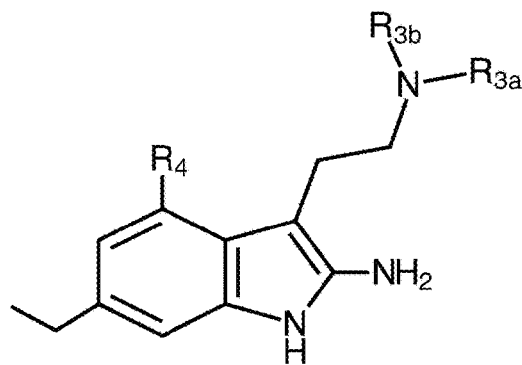
Figure 3J:
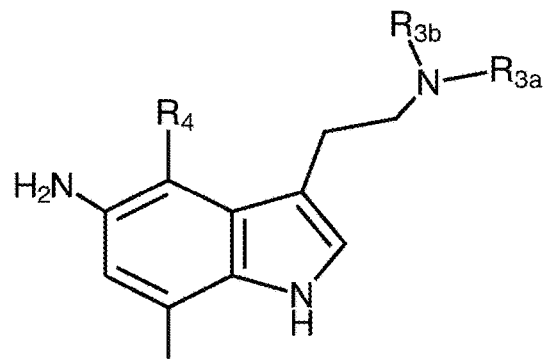
Figure 3K:
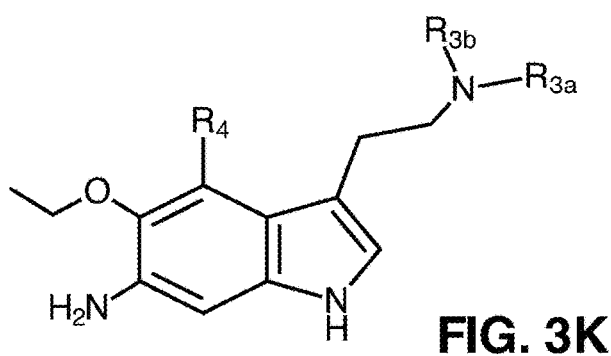
Figure 3L:
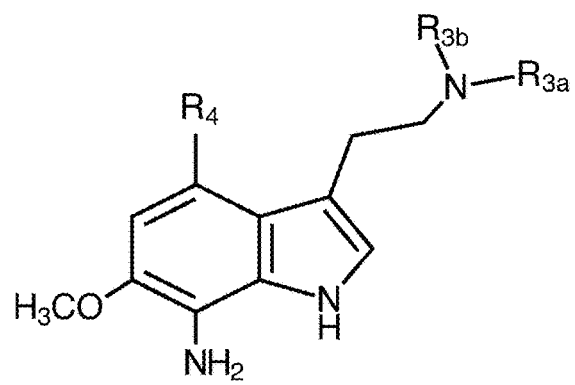

Continuing to refer to the chemical compound having formula (I), in a further aspect hereof, the non-aminated groups $R_2$, $R_5$, $R_6$, or $R_7$ can be a hydrogen atom or an alkyl or O-alkyl group. Referring now to FIGS. 3A-3D, examples of aminated psilocybin derivatives in accordance herewith, wherein one of $R_2$, $R_5$, $R_6$, or $R_7$ are aminated, and the non-aminated groups $R_2$, $R_5$, $R_6$, or $R_7$ are hydrogen atoms are: the 2-amino-psilocybin derivative compound depicted in FIG. 3A, the 5-amino-psilocybin derivative depicted in FIG. 3B, the 6-amino-psilocybin derivative depicted in FIG. 3C, the 7-amino-psilocybin derivative depicted in FIG. 3D, Referring now to FIGS. 3E-3H, examples of aminated psilocybin derivatives in accordance herewith, wherein one of $R_2$, $R_5$, $R_6$, or $R_7$ are aminated, and the non-aminated groups $R_2$, $R_5$, $R_6$, or $R_7$ are hydrogen atoms are: the 2-N,N-substituted amino-psilocybin derivative compound depicted in FIG. 3E, the 5-N,N-substituted amino-psilocybin derivative depicted in FIG. 3F, the 6-N,N-substituted amino-psilocybin derivative depicted in FIG. 3G, and the 7-N,N-substituted amino-psilocybin derivative depicted in FIG. 3H. It is noted that in FIGS. 3E-3H, $R'_{2a}$, $R''_{2b}$, $R'_{5a}$, $R''_{5b}$, $R'_{6a}$, $R''_{6b}$, $R'_{7a}$, and $R''_{7b}$ can each be independently selected from an alkyl group, an aryl group, an acyl group, a sulfonyl group, a sulfo group, or a hydrogen atom, provided however, that N-substituted amino psilocybin derivatives do not include psilocybin derivatives wherein in both $R'_{2a}$, and $R''_{2b}$, or both $R'_{5a}$, and $R''_{5b}$, or both $R'_{6a}$ and $R''_{6b}$, or both $R'_{7a}$, and $R''_{7b}$ are hydrogen atoms.

Figure 3M:
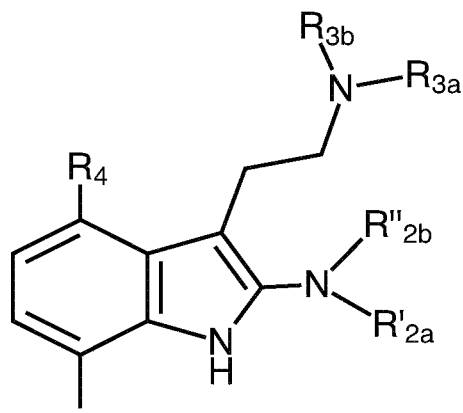
Figure 3N:
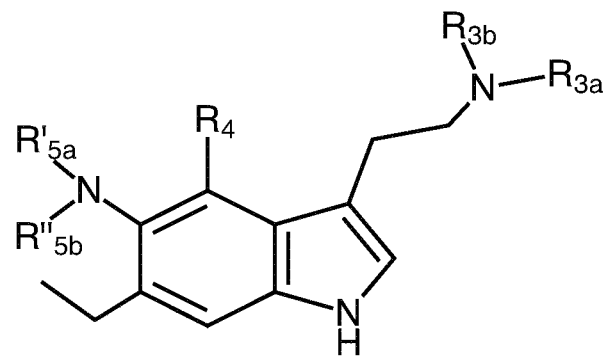
Figure 3O:
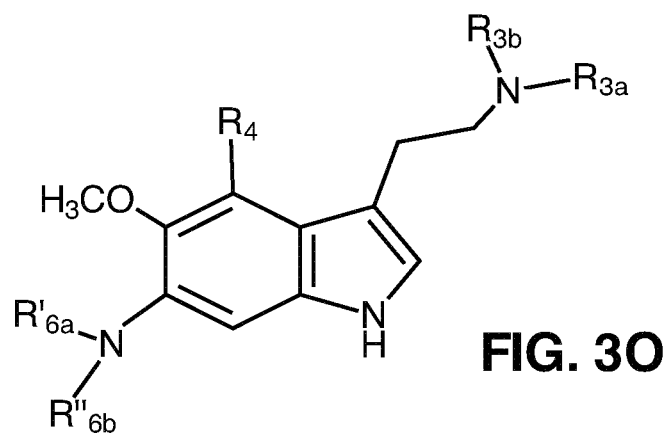
Figure 3P:
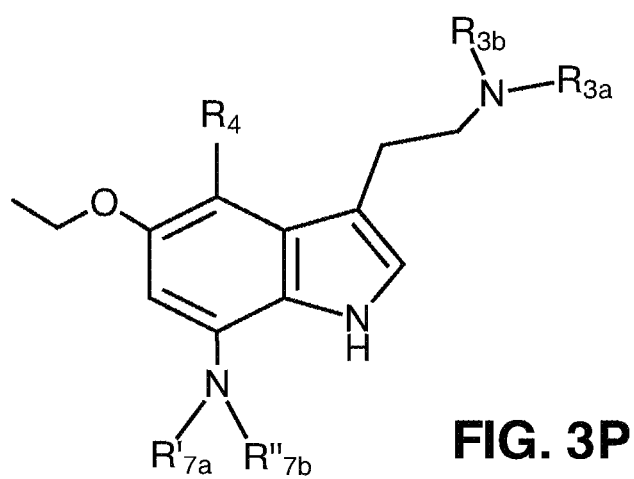

In a further aspect hereof, the non-aminated groups $R_2$, $R_5$, $R_6$, or $R_7$ can be a hydrogen atom or an alkyl or O-alkyl group. Referring now to FIGS. 3I-3L, examples of aminated psilocybin derivatives in accordance herewith, wherein one of $R_2$, $R_5$, $R_6$, or $R_7$ are aminated, and the non-aminated groups $R_2$, $R_5$, $R_6$, or $R_7$ are alkyl or O-alkyl groups are: the 2-amino-6-ethyl-psilocybin derivative compound depicted in FIG. 3I, the 5-amino-7-methyl psilocybin derivative depicted in FIG. 3J, the 5-ethoxy-6-amino-psilocybin derivative depicted in FIG. 3K, the 6-O-methyl-7-amino-psilocybin derivative depicted in FIG. 3L, Referring now to FIGS. 3M-3P, examples of aminated psilocybin derivatives in accordance herewith, wherein one of $R_2$, $R_5$, $R_6$, or $R_7$ are aminated, and the non-aminated groups $R_2$, $R_5$, $R_6$, or $R_7$ are hydrogen atoms are: the 2-N,N-substituted amino-7methyl-psilocybin derivative compound depicted in FIG. 3M, the 5-N,N-substituted amino-6-ethyl-psilocybin derivative depicted in FIG. 3N, the 5-O-methyl-6-N,N-substituted amino-psilocybin derivative depicted in FIG. 3O, and the 5-O-ethyl-7-N,N-substituted amino-psilocybin derivative depicted in FIG. 3P. It is noted that in FIGS. 3M-3P, $R'_{2a}$, $R''_{2b}$, $R'_{5a}$, $R''_{5b}$, $R'_{6a}$, $R''_{6b}$, $R'_{7a}$, and $R''_{7b}$ can each be independently selected from an alkyl group, an aryl group, an acyl group, a sulfonyl group, a sulfo group, or a hydrogen atom, provided however, that N-substituted amino psilocybin derivatives do not include psilocybin derivatives wherein in both $R'_{2a}$, and $R''_{2b}$, or both $R'_{5a}$, and $R''_{5b}$, or both $R'_{6a}$ and $R''_{6b}$, or both $R'_{7a}$, and $R''_{7b}$ are hydrogen atoms.

Figure 4A:
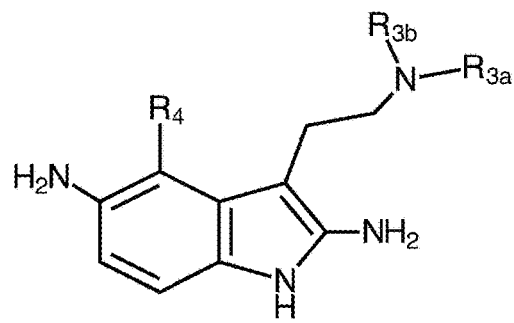
FIGS. 4A, 4B, 4C, 4D, 4E, 4F, 4G, 4H, 4I, 4J, 4K, 4L, 4M, 4N, 4O, 4P, 4Q, 4R, 4S, 4T, 4U, and 4V depict the chemical structures of certain example aminated psilocybin derivatives, notably alkylated hydroxy-containing psilocybin derivatives, notably a 2,5-di-amino-psilocybin derivative (FIG. 4A), a 2,6-di-amino-psilocybin derivative (FIG. 4B), a 2,7-di-amino-psilocybin derivative (FIG. 4C), a 5,6-di-amino-psilocybin derivative (FIG. 4D), a 5,7-di-amino-psilocybin derivative (FIG. 4E), a 6,7-di-amino-psilocybin derivative (FIG. 4F), a 2,5,6-tri-amino-psilocybin derivative (FIG. 4G), a 2,5,7-tri-amino-psilocybin derivative (FIG. 4H), a 2,6,7-tri-amino-psilocybin derivative (FIG. 4I) a 5,6,7-tri-amino-psilocybin derivative (FIG. 4J), a 2,5,6,7-tetra-amino-psilocybin derivative (FIG. 4K), a 2-N,N,5-N,N-di-substituted-amino-psilocybin derivative (FIG. 4L), a 2-N,N,6-N,N-di-substituted-amino-psilocybin derivative (FIG. 4M), a 2-N,N,7-N,N-di-substituted-amino-psilocybin derivative (FIG. 4N), a 5-N,N,6-N,N-di-substituted-amino-psilocybin derivative (FIG. 4O), a 5-N,N,7-N,N-disubstituted-amino-psilocybin derivative (FIG. 4P), a 6-N,N,7-N,N-di-substituted-amino-psilocybin derivative (FIG. 4Q), a 2-N,5-N,6-N,N-tri-substituted-amino-psilocybin derivative (FIG. 4R), a 2-N,N,5-N,N,7-N,N-tri-substituted-amino-psilocybin derivative (FIG. 4S), a 2-N,N,6-N,N,7-N,N-tri-substituted-amino-psilocybin derivative (FIG. 4T) a 5-N,N,6-N,N,7-N,N-tri-substituted-amino-psilocybin derivative (FIG. 4U), a 2-N,N,5-N,N,6-N,N,7-N,N-tetra-substituted-amino-psilocybin derivative (FIG. 4V).
Figure 4B:
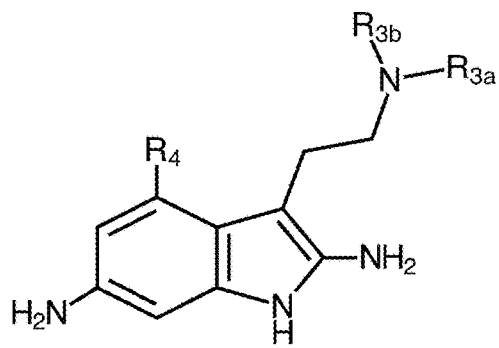
Figure 4C:
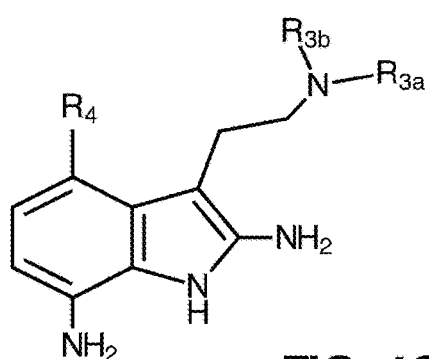
Figure 4D:
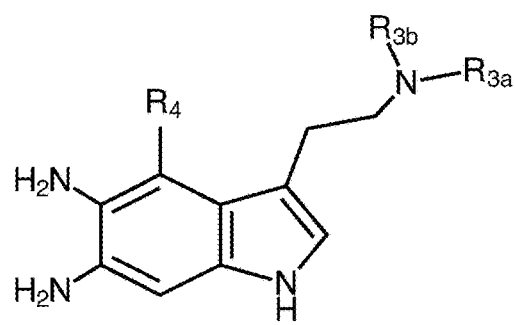
Figure 4E:
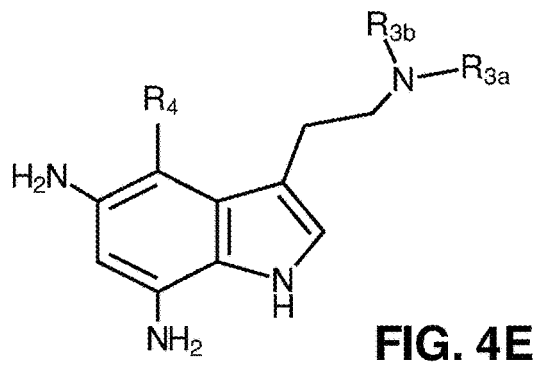
Figure 4F:
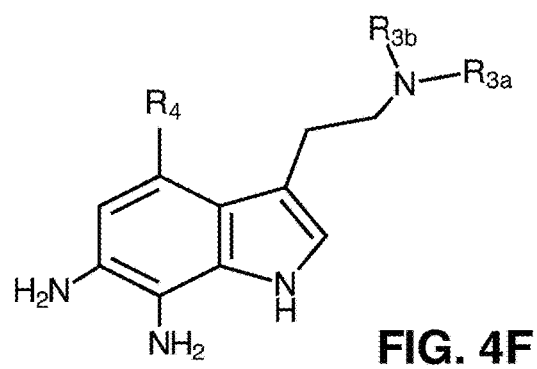

Referring now to FIGS. 4A-4F, examples of aminated psilocybin derivatives in accordance herewith, wherein two of $R_2$, $R_5$, $R_6$, or $R_7$ are aminated, and the non-aminated groups $R_2$, $R_5$, $R_6$, or $R_7$ are hydrogen atoms are: the 2,5-di-amino-psilocybin derivative compound depicted in FIG. 4A, the 2,6-di-amino-psilocybin derivative depicted in FIG. 4B, the 2,7-di-amino-psilocybin derivative depicted in FIG. 4C, the 5,6-di-amino-psilocybin derivative depicted in FIG. 4D, the 5,7-di-amino-psilocybin derivative depicted in FIG. 4E, and the 6,7-di-amino-psilocybin derivative depicted in FIG. 4F.

Figure 4G:
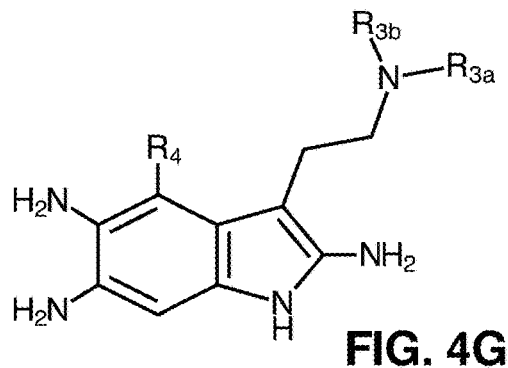
Figure 4H:
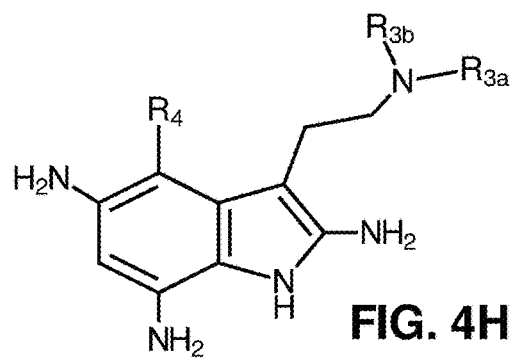
Figure 4I:
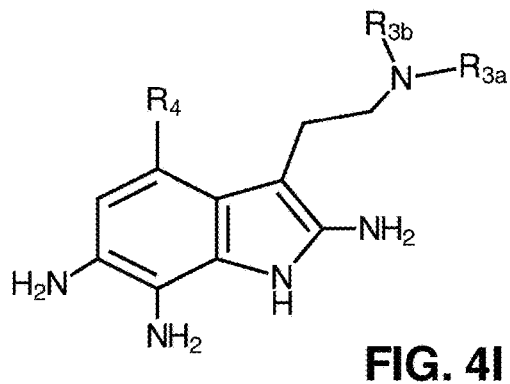
Figure 4J:
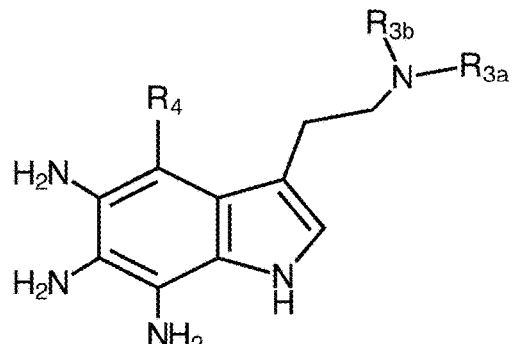

Referring now to FIGS. 4G-4J, examples of aminated psilocybin derivatives in accordance herewith, wherein three of $R_2$, $R_5$, $R_6$, or $R_7$ are aminated, and the non-aminated groups $R_2$, $R_5$, $R_6$, or $R_7$ are hydrogen atoms are: the 2,5,6-tri-amino-psilocybin derivative compound depicted in FIG. 4G, the 2,5,7-tri-amino-psilocybin derivative depicted in FIG. 4H, the 2,6,7-tri-amino-psilocybin derivative depicted in FIG. 4I, and the 5,6,7-tri-amino-psilocybin derivative depicted in FIG. 4J.

Figure 4K:
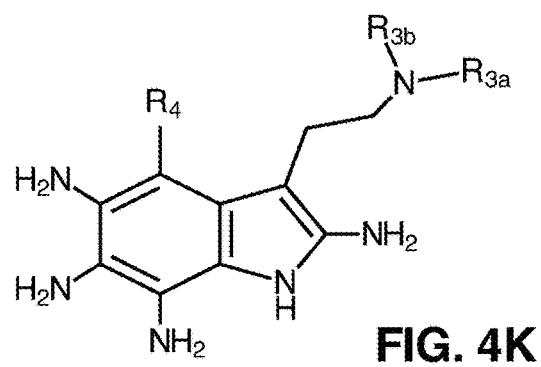

Referring now to FIG. 4K an example of a aminated psilocybin derivatives in accordance herewith, wherein all four of $R_2$, $R_5$, $R_6$, or $R_7$ are aminated is the 2,5,6,7-tetra-amino-psilocybin derivative depicted in FIG. 4K.

Figure 4L:
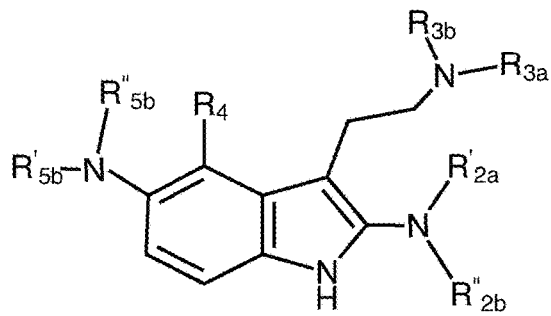
Figure 4M:
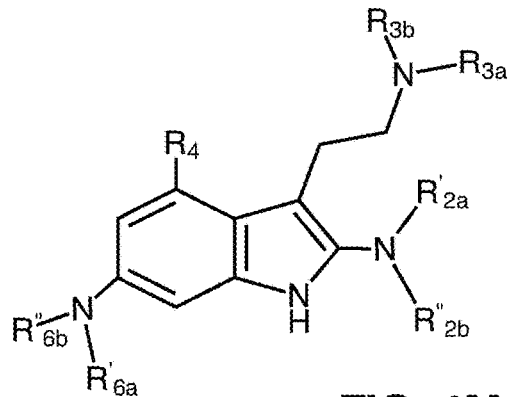
Figure 4N:
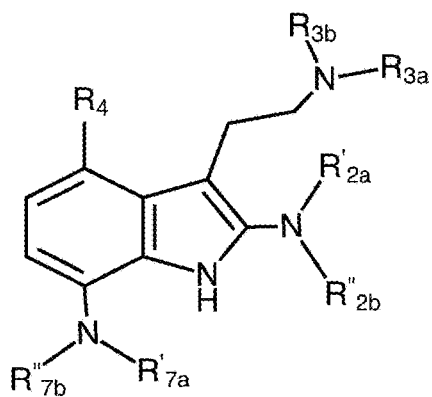
Figure 4O:
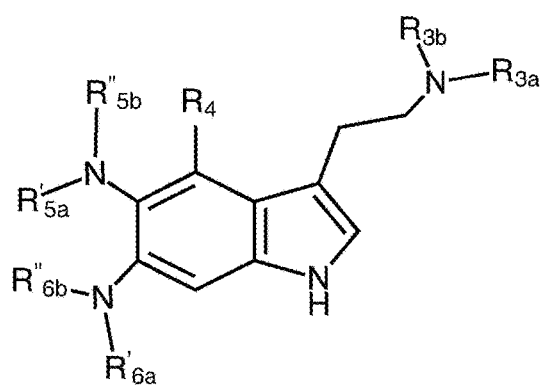
Figure 4P:
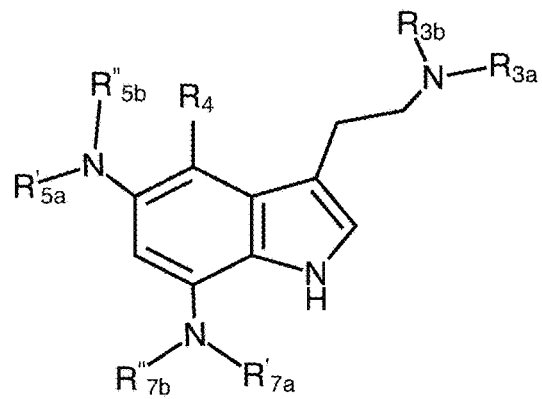
Figure 4Q:
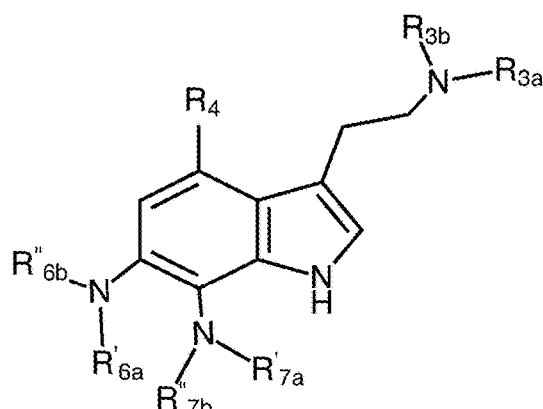

Referring now to FIGS. 4L-4Q, examples of aminated psilocybin derivatives in accordance herewith, wherein two of $R_2$, $R_5$, $R_6$, or $R_7$ are aminated, and the non-aminated groups $R_2$, $R_5$, $R_6$, or $R_7$ are hydrogen atoms are: the 2-N,5-N,N-di-substituted-amino-psilocybin derivative compound depicted in FIG. 4L, the 2-N,6-N,N-di-substituted-amino-psilocybin derivative depicted in FIG. 4M, the 2-N,7-N,N-di-substituted-amino-psilocybin derivative depicted in FIG. 4N, the 5-N,6-N,N-di-substituted-amino-psilocybin derivative depicted in FIG. 4O, the 5-N,7-N,N-di-substituted-amino-psilocybin derivative depicted in FIG. 4P, and the 6-N,N-7-N,N-di-substituted-amino-psilocybin derivative depicted in FIG. 4Q. As hereinbefore noted, the substituents may be a group selected from an alkyl group, an aryl group, an acyl group, or a sulfonyl group. Thus, by way of example only, in the 5-N,6-N,N-di-substituted-amino-psilocybin derivative depicted in FIG. 4O at least one of $R'_{5a}$, of $R''_{5b}$, and at least one of $R'_{6a}$, and $R''_{6b}$, is an alkyl group, an aryl group, an acyl group, a sulfo group, or a sulfonyl group.

Continuing to refer to FIGS. 4L-4Q, it is noted that, in other embodiments, instead of being di-substituted, only one of the aminated groups may be an N-substituted amino group while the other aminated group is an amino group. Thus, for example, referring to FIG. 4P, in such embodiments, only $R''_{7a}$ or $R'_{7b}$ may be N-substituted, while $R'_{5a}$ and $R''_{5b}$ may each be a hydrogen atom, thus forming an amino group, or conversely, only $R''_{5a}$ or $R'_{5b}$ may be N-substituted, while $R'_{7a}$ and $R''_{7b}$ may be hydrogen atoms thus forming an amino group. It is to be understood that any and all embodiments including the aminated psilocybin derivatives shown in FIGS. 4L-4Q, provided that at least one of the $R'_{2a}$, $R''_{2b}$, $R'_{5a}$, $R''_{5b}$, $R'_{6a}$, $R''_{6b}$, $R'_{7a}$, and $R''_{7b}$ is an N-substituted amino group are also included herein. As hereinbefore noted, the substituents may be a group selected from an alkyl group, an aryl group, an acyl group, a sulfo group, or a sulfonyl group.

Figure 4R:
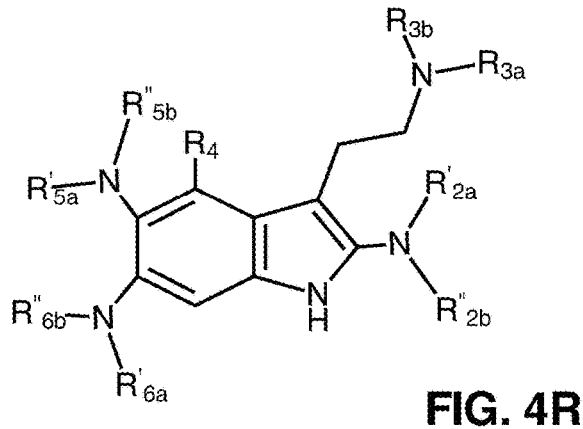
Figure 4S:
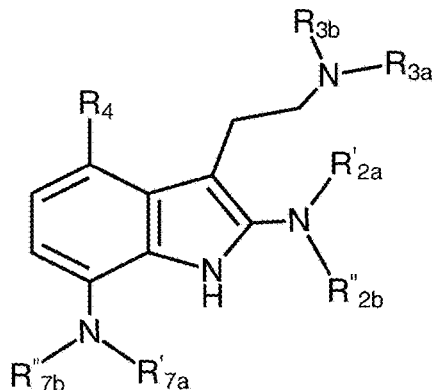
Figure 4T:
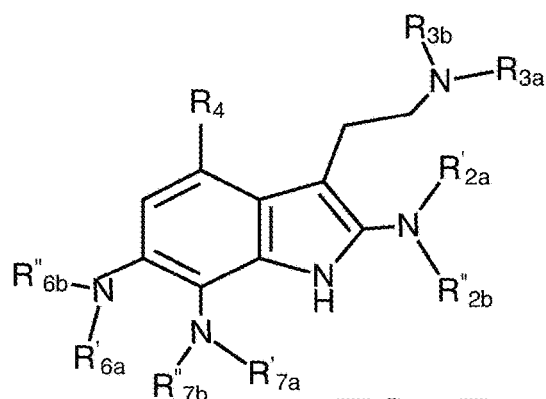
Figure 4U:
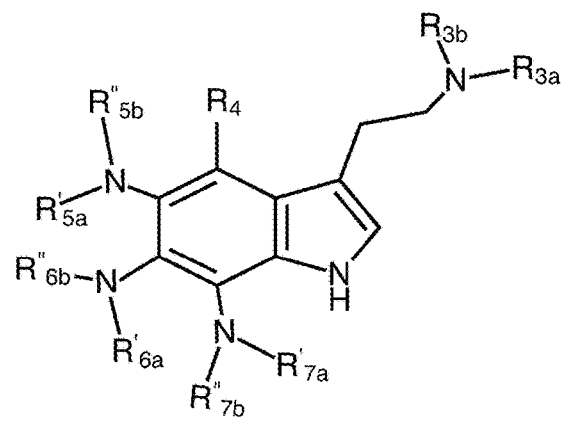

Referring now to FIGS. 4R-4U, examples of aminated psilocybin derivatives in accordance herewith, wherein three of $R_2$, $R_5$, $R_6$, or $R_7$ are aminated, and the non-aminated groups $R_2$, $R_5$, $R_6$, or $R_7$ are hydrogen atoms are: the 2-N,5-N,6-N,N-tri-substituted-amino-psilocybin derivative compound depicted in FIG. 4R, the 2-N,5-N,7-N,N-tri-substituted-amino-psilocybin derivative depicted in FIG. 4S, the 2-N,6-N,7-N,N-tri-substituted amino-psilocybin derivative depicted in FIG. 4T, and the 5-N,6-N,7-N,N-tri-substituted-amino-psilocybin derivative depicted in FIG. 4U. As hereinbefore noted, the substituents may be a group selected from an alkyl group, an aryl group, an acyl group, or a sulfonyl group. Thus, by way of example only, in the 5-N,6-N,7-N,N-tri-substituted-amino-psilocybin derivative depicted in FIG. 4U at least one of $R'_{5a}$, of $R''_{5b}$, and at least one of $R'_{6a}$, and $R''_{6b}$, and at least one of $R'_{7a}$, and $R''_{7b}$ is an alkyl group, an aryl group, an acyl group, a sulfo group, or a sulfonyl group.

Continuing to refer to FIGS. 4R-4U, it is noted that, in other embodiments, instead of being tri-substituted, only one or two of the aminated groups may be an N-substituted amino group while the other aminated groups is/are an amino group. Thus, for example, referring to FIG. 4S, in such embodiments, only $R''_{7a}$ or $R'_{7b}$ may be N-substituted, while $R'_{5a}$ and $R''_{5b}$ and $R'_{2a}$ and $R''_{2b}$ may all be a hydrogen atoms, thus forming two an amino groups, or $R''_{5a}$ or $R'_{5b}$ may be N-substituted, and $R'_{7a}$ and $R''_{7b}$ may N-substituted, but $R'_{2a}$ and $R''_{2b}$ may be hydrogen atoms thus forming an amino group. It is to be understood that any and all embodiments including aminated psilocybin derivatives shown in FIGS. 4R-4U, provided that at least one of the $R'_{2a}$, $R''_{2b}$, $R'_{5a}$, $R''_{5b}$, $R'_{6a}$, $R''_{6b}$, $R'_{7a}$, and $R''_{7b}$ is an N-substituted amino group are also included herein. As hereinbefore noted, the substituents may be a group selected from an alkyl group, an aryl group, an acyl group, a sulfo group, or a sulfonyl group.

Figure 4V:
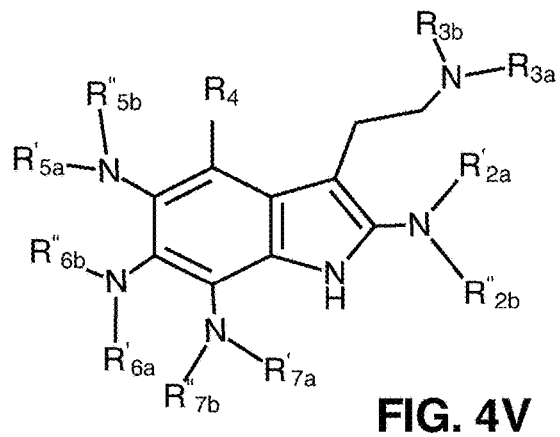

Referring now to FIG. 4V, an example of an aminated psilocybin derivatives in accordance herewith, wherein all four of $R_2$, $R_5$, $R_6$, or $R_7$ are aminated is the 2-N,5-N,6-N,7-N,N-tetra-substituted-amino-psilocybin derivative depicted in FIG. 4K. As hereinbefore noted, the substituents may be a group selected from an alkyl group, an aryl group, an acyl group, or a sulfonyl group. Thus, by way of example only, in the 2-N,N-5-N,6-N,7-N,N-tri-substituted-amino-psilocybin derivative depicted in FIG. 4V at least one of $R'_{2a}$, of $R''_{2b}$ and $R'_{5a}$, of $R''_{5b}$, at least one of $R'_{6a}$, and $R''_{6b}$, at least one of $R'_{7a}$, and $R''_{7b}$ is an alkyl group, an aryl group, an acyl group, a sulfo group, or a sulfonyl group.

Continuing to refer to FIG. 4V, it is noted that, in other embodiments, instead of being tetra-substituted, only one, two or three of the aminated groups may be an N-substituted amino group while the other aminated groups is/are an amino group. Thus, for example, referring to FIG. 4V, in such embodiments, only $R''_{7a}$ or $R'_{7b}$ may be N-substituted, while $R'_{5a}$ and $R''_{5b}$, $R'_{6a}$ and $R''_{6b}$ and $R'_{2a}$ and $R''_{2b}$ may all be a hydrogen atoms, thus forming three amino groups, or, for example $R''_{5a}$ or $R'_{5b}$ may be N-substituted, and $R'_{7a}$ and $R''_{7b}$ may N-substituted, but $R'_{2a}$ and $R''_{2b}$ and $R'_{6a}$ and $R''_{6b}$ may be hydrogen atoms thus forming two amino groups. It is to be understood that any and all embodiments including the aminated psilocybin derivatives shown in FIGS. 4V, provided that at least one of the $R'_{2a}$, $R''_{2b}$, $R'_{5a}$, $R''_{5b}$, $R'_{6a}$, $R''_{6b}$, $R'_{7a}$, and $R''_{7b}$ is an N-substituted amino group are also included herein. As hereinbefore noted, the substituents may be a group selected from an alkyl group, an aryl group, an acyl group, a sulfo group, or a sulfonyl group.

In a further aspect, $R_4$, can be an O-alkyl group. Referring now to FIGS. 5A, 5B, 6A, 6B, 7A, and 7B examples of aminated psilocybin derivatives in accordance herewith, wherein $R_5$, and/or $R_7$ are amino groups and $R_4$ is an O-alkyl group are: the 4-O-methyl-5-amino-psilocybin derivative depicted in FIG. 5A, the 4-O-ethyl-5-amino-psilocybin derivative depicted in FIG. 5B, the 4-O-methyl-7-amino-psilocybin derivative depicted in FIG. 6A, the 4-O-ethyl-7-amino-psilocybin derivative depicted in FIG. GB, the 4-O-methyl-5,7-di-amino-psilocybin derivative depicted in FIG. 7A, the 4-O-ethyl-5,7-di-amino-psilocybin derivative depicted in FIG. 7B. It is noted that in these specific examples only 5-amino, 7-amino, and 5,7-di-O-alkyl psilocybin derivatives are shown. Further examples of O-alkyl psilocybin derivatives included herein are any and all O-alkyl psilocybin derivatives which may be selected by referring to the chemical formulas shown in FIGS. 4A-4J, wherein $R_4$ is an O-alkyl group. It will thus be clearly understood that FIGS. 5A, 5B, 6A, 6B, 7A, and 7B represent examples only of aminated psilocybin derivatives having chemical formula (I) wherein non-aminated groups $R_2$, $R_5$, $R_6$, or $R_7$ are a hydrogen atom. Other aminated psilocybin derivatives wherein non-aminated groups $R_2$, $R_5$, $R_6$, or $R_7$ are a hydrogen atom can readily be selected, and thus are included in the O-alkylated aminated psilocybin derivatives compounds of the present disclosure.

It is noted that the example aminated psilocybin derivatives shown in FIGS. 5A, 5B, 6A, 6B, 7A, and 7B are aminated psilocybin derivatives compounds by virtue of their amino groups. Considering FIGS. 5A, 5B, 6A, 6B, 7A, and 7B, in conjunction with FIGS. 4L, 4N, and 4P, it is noted, and it will be clear that, in other embodiments, included herein are, further, aminated psilocybin derivatives FIGS. 5A, 5B, 6A, 6B, 7A, and 7B, wherein instead of an amino group the psilocybin derivative possesses at least on N-substituted amino group, i.e., $R'_{7a}$ or $R''_{7b}$ is substituted by a group selected from an alkyl group, an aryl group, an acyl group, a sulfo group, or a sulfonyl group.

In a further aspect, $R_4$, can be an O-acyl group. Referring now to FIGS. 5C, 5D, 6C, 6D, 7C, and 7D examples of aminated psilocybin derivatives in accordance herewith, wherein $R_5$, and/or $R_7$ are amino groups and $R_4$ is an O-acyl group are: the 4-acetyl-5-amino-psilocybin derivative depicted in FIG. 5C, the 4-propanoyl-5-amino-psilocybin derivative depicted in FIG. 5D, the 4-acetyl-7-amino-psilocybin derivative depicted in FIG. GC, the 4-propanoyl-7-amino-psilocybin derivative depicted in FIG. 6D, the 4-acetyl-5,7-di-amino-psilocybin derivative depicted in FIG. 7C, the 4-propanoyl-5,7-di-amino-psilocybin derivative depicted in FIG. 7D. It is noted that in these specific examples only 5-amino, 7-amino, and 5,7-di-O-acyl psilocybin derivatives are shown. Further examples of O-acyl psilocybin derivatives included herein are any and all O-acyl psilocybin derivatives which may be selected by referring to the chemical formulas shown in FIGS. 4A-4J, wherein $R_4$ is an O-acyl group. It will thus be clearly understood that FIGS. 5C, 5D, 6C, 6D, 7C, and 7D represent examples only of O-acylated psilocybin derivatives having chemical formula (I) wherein non-aminated groups $R_2$, $R_5$, $R_6$, or $R_7$ are a hydrogen atom. Other aminated psilocybin derivatives wherein non-aminated groups $R_2$, $R_5$, $R_6$, or $R_7$ are a hydrogen atom can readily be selected, and thus are included in the aminated O-acylated psilocybin derivatives compounds of the present disclosure.

It is noted that the example aminated psilocybin derivatives shown in FIGS. 5C, 5D, 6C, 6D, 7C, and 7D are aminated psilocybin derivatives compounds by virtue of their amino groups. Considering 5C, 5D, 6C, 6D, 7C, and 7D, in conjunction with FIGS. 4L, 4N, and 4P, it is noted, and it will be clear that, in other embodiments, included herein are, further, aminated psilocybin derivatives 5C, 5D, 6C, 6D, 7C, and 7D, wherein instead of an amino group the psilocybin derivative possesses at least on N-substituted amino group, i.e., $R'_{7a}$ or $R''_{7b}$ is substituted by a group selected from an alkyl group, an aryl group, an acyl group, a sulfo group, or a sulfonyl group.

Figure 5E:
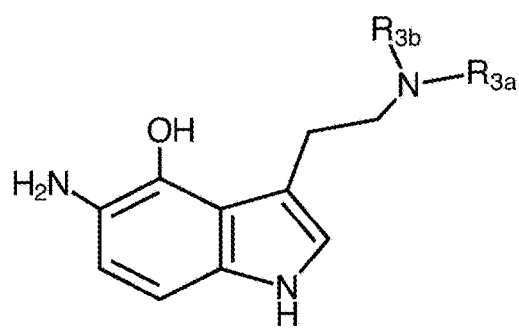

In a further aspect, $R_4$ can be a hydroxy group. Referring now to FIGS. 5E, 6E, and 7E examples of aminated psilocybin derivatives in accordance herewith, wherein $R_5$, and/or $R_7$ are amino groups and are $R_4$ is a hydroxy group are: the 4-hydroxy-5-amino-psilocybin derivative depicted in FIG. 5E, the 4-hydroxy-7-amino-psilocybin derivative depicted in FIG. 6E, and the 4-hydroxy-5,7-di-amino-psilocybin derivative depicted in FIG. 7E, It is noted that in these specific examples only 5-amino, 7-amino, and 5,7-di-hydroxy-psilocybin derivatives are shown. Further examples of hydroxy-psilocybin derivatives included herein are any and all hydroxy-psilocybin derivatives which may be selected by referring to the chemical formulas shown in FIGS. 4A-4J, wherein $R_4$ is a hydroxy group. It will thus be clearly understood that FIGS. 5E, 6E, and 7E represent examples only of hydroxy psilocybin derivatives having chemical formula (I) wherein non-aminated groups $R_2$, $R_5$, $R_6$, or $R_7$ are a hydrogen atom. Other aminated psilocybin derivatives wherein non-aminated groups $R_2$, $R_5$, $R_6$, or $R_7$ are a hydrogen atom can readily be selected, and thus are included in the aminated hydroxy psilocybin derivatives compounds of the present disclosure.

It is noted that the example aminated psilocybin derivatives shown in FIGS. 5E, 6E, and 7E are aminated psilocybin derivatives compounds by virtue of their amino groups. Considering FIGS. 5E, 6E, and 7E, in conjunction with FIGS. 4L, 4N, and 4P, it is noted, and it will be clear that, in other embodiments, included herein are, further, aminated psilocybin derivatives FIGS. 5E, 6E, and 7E, wherein instead of an amino group the psilocybin derivative possesses at least on N-substituted amino group, i.e., $R'_{7a}$ or $R''_{7b}$ is substituted by a group selected from an alkyl group, an aryl group, an acyl group, a sulfo group, or a sulfonyl group.

Figure 5F:
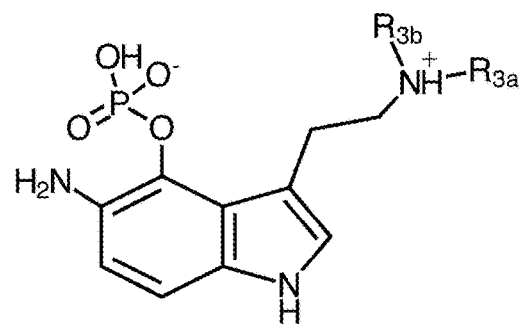

In a further aspect, $R_4$ can be a phosphate group. Referring now to FIGS. 5F, 6F, and 7F examples of aminated psilocybin derivatives in accordance herewith, wherein $R_5$, and/or $R_7$ are amino groups and are $R_4$ is a phosphate group are: the 4-phospho-5-amino-psilocybin derivative depicted in FIG. 5F, the 4-phospho-7-amino-psilocybin derivative depicted in FIG. 6F, and the 4-phosphate-5,7-amino-psilocybin derivative depicted in FIG. 7F, It is noted that in these specific examples only 5-amino, 7-amino, and 5,7-di-phospho-psilocybin derivatives are shown. Further examples of phosphate-psilocybin derivatives included herein are any and all phosphate-psilocybin derivatives which may be selected by referring to the chemical formulas shown in FIGS. 4A-4J, wherein $R_4$ is a phosphate group. It will thus be clearly understood that FIGS. 5F, 6F, and 7F represent examples only of phosphate psilocybin derivatives having chemical formula (I) wherein non-aminated groups $R_2$, $R_5$, $R_6$, or $R_7$ are a hydrogen atom. Other aminated psilocybin derivatives wherein non-aminated groups $R_2$, $R_5$, $R_6$, or $R_7$ are a hydrogen atom can readily be selected, and thus are included in the aminated phosphate psilocybin derivatives compounds of the present disclosure.

It is noted that the example aminated psilocybin derivatives shown in FIGS. 5F, 6F, and 7F are aminated psilocybin derivatives compounds by virtue of their amino groups. Considering FIGS. 5F, 6F, and 7F, in conjunction with FIGS. 4L, 4N, and 4P, it is noted, and it will be clear that, in other embodiments, included herein are, further, aminated psilocybin derivatives FIGS. 5F, 6F, and 7F, wherein instead of an amino group the psilocybin derivative possesses at least on N-substituted amino group, i.e., $R'_{7a}$ or $R''_{7b}$ is substituted by a group selected from an alkyl group, an aryl group, an acyl group, a sulfo group, or a sulfonyl group.

Figure 5G:
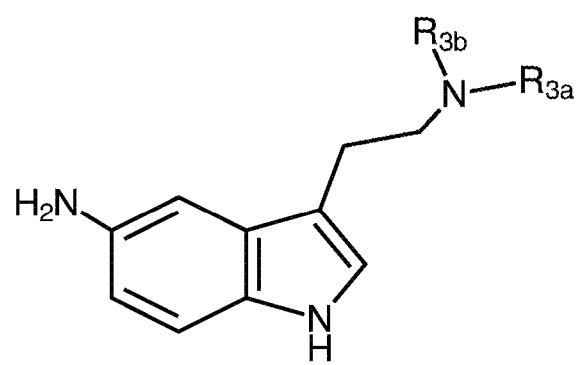

In a further aspect, $R_4$ can be a hydrogen atom. Referring now to FIGS. 5G, 6G, and 7G examples of aminated psilocybin derivatives in accordance herewith, wherein $R_5$, and/or $R_7$ are amino groups and are $R_4$ is a hydrogen atom are: the 5-amino-psilocybin derivative depicted in FIG. 5G, the 7-amino-psilocybin derivative depicted in FIG. 6G, and the 5,7-di-amino-psilocybin derivative depicted in FIG. 7G, It is noted that in these specific examples only 5-amino, 7-amino, and 5,7-di-amino-hydro-psilocybin derivatives are shown. Further examples of hydro-psilocybin derivatives included herein are any and all hydro-psilocybin derivatives which may be selected by referring to the chemical formulas shown in FIGS. 4A-4J, wherein $R_4$ is a hydrogen atom. It will thus be clearly understood that FIGS. 5G, 6G, and 7G represent examples only of hydro psilocybin derivatives having chemical formula (I) wherein non-aminated groups $R_2$, $R_5$, $R_6$, or $R_7$ are a hydrogen atom. Other aminated psilocybin derivatives wherein non-aminated groups $R_2$, $R_5$, $R_6$, or $R_7$ are a hydrogen atom can readily be selected, and thus are included in the aminated hydro psilocybin derivatives compounds of the present disclosure.

It is noted that the example aminated psilocybin derivatives shown in FIGS. 5G, 6G, and 7G are aminated psilocybin derivatives compounds by virtue of their amino groups. Considering FIGS. 5G, 6G, and 7G, in conjunction with FIGS. 4L, 4N, and 4P, it is noted, and it will be clear that, in other embodiments, included herein are, further, aminated psilocybin derivatives FIGS. 5G, 6G, and 7G, wherein instead of an amino group the psilocybin derivative possesses at least one N-substituted amino group, i.e., $R'_{7a}$ or $R''_{7b}$ is substituted by a group selected from an alkyl group, an aryl group, an acyl group, a sulfo group, or a sulfonyl group.

Furthermore, in one embodiment, an aminated psilocybin derivative according to the present disclosure can be a chemical compound having the formula (III):

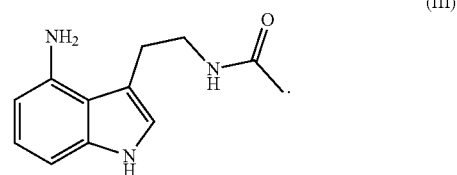

(III)

Furthermore, in one embodiment, an aminated psilocybin derivative according to the present disclosure can be a chemical compound having the formula (IV):

(IV)

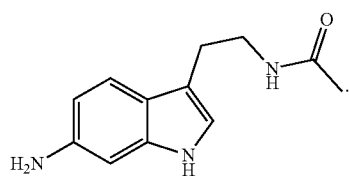

Furthermore, in one embodiment, an aminated psilocybin derivative according to the present disclosure can be a chemical compound having the formula (V):

(V)

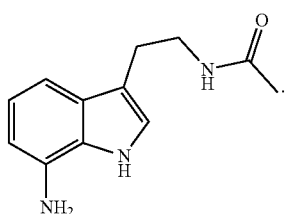

Furthermore, in one embodiment, an aminated psilocybin derivative according to the present disclosure can be a chemical compound having the formula (VI):

(VI)

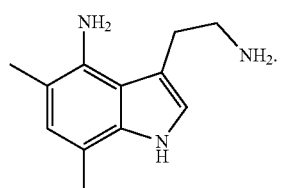

Furthermore, in one embodiment, an aminated psilocybin derivative according to the present disclosure can be a chemical compound having the formula (VII):

(VII)

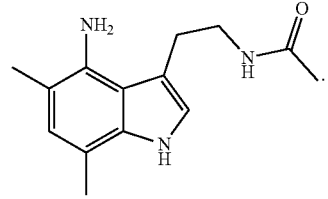

Furthermore, in one embodiment, an aminated psilocybin derivative according to the present disclosure can be a chemical compound having the formula (VIII):

(VIII)

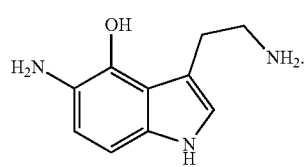

Furthermore, in one embodiment, an aminated psilocybin derivative according to the present disclosure can be a chemical compound having the formula (IX):

(IX)

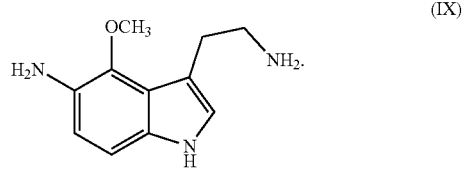 [SMILES: COc1c(N)ccc2[nH]cc(CCN)c12]

Furthermore, in one embodiment, an aminated psilocybin derivative according to the present disclosure can be a chemical compound having the formula (X):

(X)

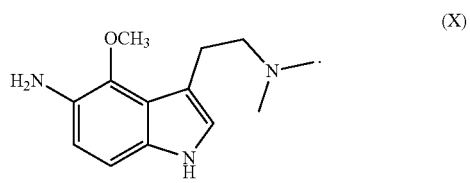 [SMILES: COc1c(N)ccc2[nH]cc(CCN(C)C)c12]

Furthermore, in one embodiment, an aminated psilocybin derivative according to the present disclosure can be a chemical compound having the formula (XI):

(XI)

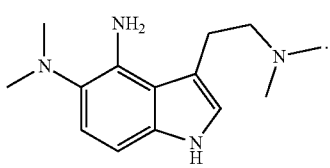

Furthermore, in one embodiment, an aminated psilocybin derivative according to the present disclosure can be a chemical compound having the formula (XII):

(XII)

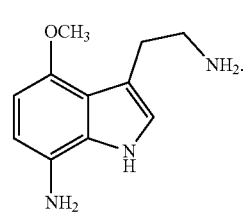

Furthermore, in one embodiment, an aminated psilocybin derivative according to the present disclosure can be a chemical compound having the formula (XIII):

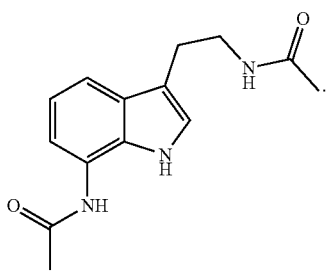
(XIII)

Furthermore, in one embodiment, an aminated psilocybin derivative according to the present disclosure can be a chemical compound having the formula (XIV):

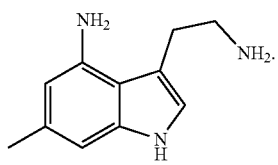
(XIV)

Furthermore, in one embodiment, an aminated psilocybin derivative according to the present disclosure can be a chemical compound having the formula (XV):

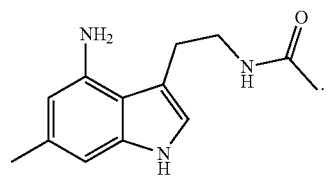
(XV)

Furthermore, in one embodiment, an aminated psilocybin derivative according to the present disclosure can be a chemical compound having the formula (XVI):

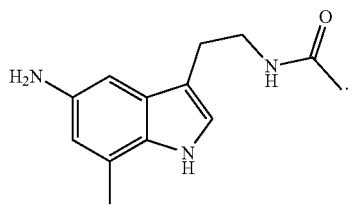
(XVI)

Furthermore, in one embodiment, an aminated psilocybin derivative according to the present disclosure can be a chemical compound having the formula (XVII):

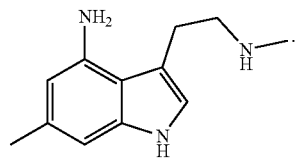
(XVII)

Furthermore, it is noted that the aminated psilocybin derivatives of the present disclosure include salts thereof, including pharmaceutically acceptable salts. Thus, the nitrogen atom of the ethyl-amino group extending in turn from the $C_3$ atom may be protonated, and the positive charge may be balanced by, for example, chloride or sulfate ions, to thereby form a chloride salt or a sulfate salt. Furthermore, in compounds wherein $R_4$ is a phosphate group, the phosphate group may be de-protonated, and the negative charge may be balanced by, for example, sodium ions or potassium ions, to thereby form a sodium salt or a potassium salt.

Furthermore, it is noted that when $R_4$ is a phosphate group, the term aminated psilocybin derivative also includes compounds having the formula (XVIII):

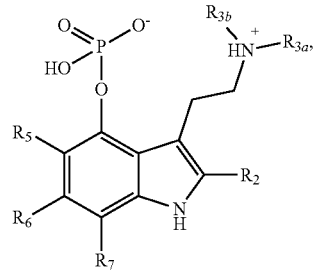
(XVIII)

wherein at least one of $R_2$, $R_5$, $R_6$, or $R_7$ is an amino group or N-substituted amino group, and wherein any $R_2$, $R_5$, $R_6$, or $R_7$ which are not an amino group or N-substituted amino group are a hydrogen atom, an alkyl group or O-alkyl group, and wherein $R_{3A}$ and $R_{3B}$ are each independently a hydrogen atom, an alkyl group, and aryl group or an acyl group. Further included are salts of aminated psilocybins having the formula (XVIII), such as a sodium salt, a potassium salt etc.

Thus, to briefly recap, the present disclosure provides aminated psilocybin derivatives. The disclosure provides, in particular, a chemical compound or salt thereof having formula (I):

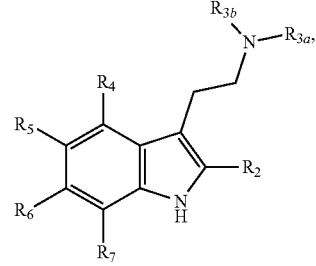
(I)

wherein in an aspect, at least one of $R_2$, $R_4$, $R_5$, $R_6$, or $R_7$ is an amino group or N-substituted amino group. In an aspect, in formula (I), each non-aminated $R_2$, $R_5$, $R_6$, or $R_7$ is a hydrogen atom, an alkyl group or O-alkyl group. In a further aspect, in formula (I), $R_4$ when it is not aminated is a hydrogen atom, an alkyl group or O-alkyl group, a hydroxy group, or a phosphate group. Yet in a further aspect, $R_{3A}$ and $R_{3B}$ are each independently a hydrogen atom, an alkyl group, an aryl group, or an acyl group.

In one embodiment of the disclosure, a chemical compound or salt thereof having formula (I) is included:

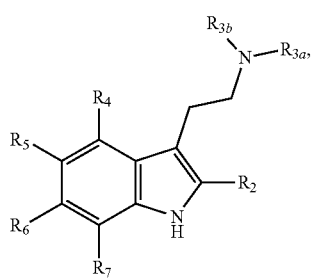

(I)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, alkyl group or O-alkyl group, a hydroxy group, or a phosphate group, and wherein $R_{3A}$ and $R_{3B}$ are each independently a hydrogen atom, an alkyl group, an aryl group, or an acyl group.

In one embodiment, at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom or a $(C_1-C_{20})$-alkyl group or $(C_1-C_{20})$—O-alkyl group. In another embodiment, each non-aminated $R_2$, $R_5$, $R_6$, or $R_7$ is a hydrogen atom, a methyl group, ethyl group, a propyl group, an O-methyl group, an O-ethyl group, or an O-propyl group.

In another embodiment, each non-aminated $R_2$, $R_5$, $R_6$, or $R_7$ is a hydrogen atom or a $(C_1-C_{10})$-alkyl group or $(C_1-C_{10})$—O-alkyl group. In another embodiment, each non-aminated $R_2$, $R_5$, $R_6$, or $R_7$ is a hydrogen atom, a methyl group, ethyl group, a propyl group, an O-methyl group, an O-ethyl group, or an O-propyl group.

In another embodiment, each non-aminated $R_2$, $R_5$, $R_6$, or $R_7$ is a hydrogen atom or a $(C_1-C_6)$-alkyl group or $(C_1-C_6)$—O-alkyl group. In another embodiment, each non-aminated $R_2$, $R_5$, $R_6$, or $R_7$ is a hydrogen atom, a methyl group, ethyl group, a propyl group, an O-methyl group, an O-ethyl group, or an O-propyl group.

In another embodiment, when $R_4$ is not aminated, $R_4$ is a hydrogen atom, a $(C_1-C_{20})$-alkyl group or $(C_1-C_{20})$—O-alkyl group, a hydroxy group, or a phosphate group. In another embodiment, when $R_4$ is not aminated, $R_4$ is a hydrogen atom, a $(C_1-C_{10})$-alkyl group or $(C_1-C_{10})$—O-alkyl group, a hydroxy group, or a phosphate group. In another embodiment, when $R_4$ is not aminated, $R_4$ is a hydrogen atom, a $(C_1-C_6)$-alkyl group or $(C_1-C_6)$—O-alkyl group, a hydroxy group, or a phosphate group. In another embodiment, when $R_4$ is not aminated, $R_4$ is a hydrogen atom, a methyl group, an ethyl group, a propyl group, a phosphate group, an O-methyl group, an O-ethyl group, or an O-propyl group.

In another embodiment, $R_{3A}$ and $R_{3B}$ are each independently a hydrogen atom, a $(C_1-C_{20})$-alkyl group, a $(C_6-C_{14})$-aryl group, or a —C(=O)($C_1-C_{20}$)-alkyl group. In another embodiment, $R_{3A}$ and $R_{3B}$ are each independently a hydrogen atom, a $(C_1-C_{10})$-alkyl group, a $(C_6-C_{10})$-aryl group, or a —C(=O)($C_1-C_{10}$)-alkyl group. In another embodiment, $R_{3A}$ and $R_{3B}$ are each independently a hydrogen atom, a $(C_1-C_6)$-alkyl group, a phenyl group, or a —C(=O)($C_1-C_6$)-alkyl group. In another embodiment, $R_{3A}$ and $R_{3B}$ are each independently a hydrogen atom, a methyl group, an ethyl group, a propyl group, a phenyl group, —C(=O)—$CH_3$, —C(=O)—$CH_2CH_3$, or —C(=O)—$CH_2CH_2CH_3$.

In one embodiment of the disclosure, a chemical compound or salt thereof having formula (I) is included:

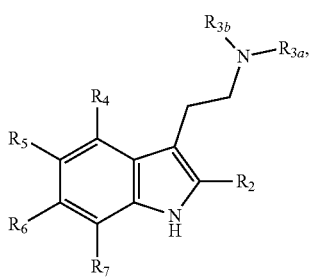

(I)

wherein $R_2$, $R_5$, $R_6$, and $R_7$ are independently or simultaneously a hydrogen atom, an alkyl group or O-alkyl group or an amino group or N-substituted amino group, $R_{3A}$ and $R_{3B}$ are each independently a hydrogen atom, an alkyl group, an aryl group, or an acyl group; and $R_4$ is hydrogen atom, alkyl group or O-alkyl group, an amino group or N-substituted amino group, a hydroxy group, or a phosphate group; wherein at least one of $R_2$, $R_4$ $R_5$, $R_6$, and $R_7$ is an amino group or N-substituted amino group.

In one embodiment, $R_2$, $R_5$, $R_6$, and $R_7$ are independently or simultaneously a hydrogen atom, $(C_1-C_{20})$-alkyl group or $(C_1-C_{20})$—O-alkyl group or an amino group or N-substituted amino group. In one embodiment, $R_2$, $R_5$, $R_6$, and $R_7$ are independently or simultaneously a hydrogen atom, $(C_1-C_{10})$-alkyl group or $(C_1-C_{10})$—O-alkyl group or an amino group or N-substituted amino group. In one embodiment, $R_2$, $R_5$, $R_6$, and $R_7$ are independently or simultaneously a hydrogen atom, $(C_1-C_6)$-alkyl group or $(C_1-C_6)$—O-alkyl group or an amino group or N-substituted amino group. In one embodiment, $R_2$, $R_5$, $R_6$, and $R_7$ are independently or simultaneously a hydrogen atom, methyl, ethyl, propyl, O-methyl, O-ethyl, O-propyl, or an amino group or N-substituted amino group.

In one embodiment, $R_4$ is a hydrogen atom, $(C_1-C_{20})$-alkyl group or $(C_1-C_{20})$—O-alkyl group, an amino group or N-substituted amino group or a phosphate group. In one embodiment, $R_4$ is a hydrogen atom, $(C_1-C_{10})$-alkyl group or $(C_1-C_{10})$—O-alkyl group, an amino group or N-substituted amino group or a phosphate group. In one embodiment, $R_4$ is a hydrogen atom, $(C_1-C_6)$-alkyl group or $(C_1-C_6)$—O-alkyl group, an amino group or N-substituted amino group, a hydroxy group, or a phosphate group. In one embodiment, $R_4$ is a hydrogen atom, methyl, ethyl, propyl, O-methyl, O-ethyl, O-propyl, an amino group or N-substituted amino group, a hydroxy group, or a phosphate group.

In another embodiment, $R_{3A}$ and $R_{3B}$ are each independently a hydrogen atom, a $(C_1-C_{20})$-alkyl group, a $(C_6-C_{14})$-aryl group, or a —C(=O)($C_1-C_{20}$)-alkyl group. In another embodiment, $R_{3A}$ and $R_{3B}$ are each independently a hydrogen atom, a $(C_1-C_{10})$-alkyl group, a $(C_6-C_{10})$-aryl group, or a —C(=O)($C_1-C_{10}$)-alkyl group or O-alkyl group. In another embodiment, $R_{3A}$ and $R_{3B}$ are each independently a hydrogen atom, a $(C_1\text{-}C_6)$-alkyl group, a phenyl group, or a $-C(=O)(C_1\text{-}C_6)$-alkyl group. In another embodiment, $R_{3A}$ and $R_{3B}$ are a hydrogen atom, a methyl group, an ethyl group, a propyl group, a phenyl group, $-C(=O)-CH_3$, $-C(=O)-CH_2CH_3$, or $-C(=O)-CH_2CH_2CH_3$.

The aminated psilocybin derivatives of the present disclosure may be used to prepare a pharmaceutical or recreational drug formulation. Thus in one embodiment, the present disclosure further provides in another aspect, pharmaceutical and recreational drug formulations comprising aminated psilocybin derivatives. Accordingly, in one aspect, the present disclosure provides in a further embodiment a pharmaceutical or recreational drug formulation comprising a chemical compound having formula (I):

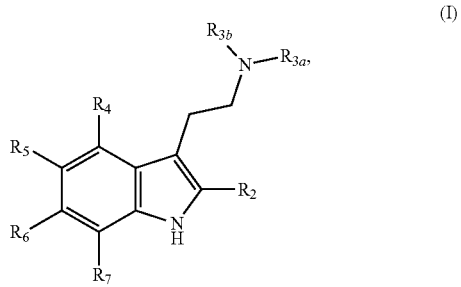

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom an alkyl group, an aryl group, or an acyl group, or a slat of the chemical compound, together with a diluent, carrier or excipient.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the aminated psilocybin compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", $22^{nd}$ Edition (Pharmaceutical Press and Philadelphia College of Pharmacy at the University of the Sciences, 2012).

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated, or prophylaxis is conducted, on the mode of delivery of the compound, or on whether further active compounds are administered in addition to the compounds of the present disclosure. Representative doses of the present disclosure include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg, or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical and drug formulations comprising the aminated psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the aminated psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the aminated psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the aminated psilocybin derivatives of the present disclosure for parenteral administration may be formulated to be immediate and/or modified release. Modified release formulations include delayed-, sustained-, pulsed-, controlled-, targeted and programmed release. Thus the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic) acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

In further embodiments, in which the aminated psilocybin compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound or salt thereof having formula (I):

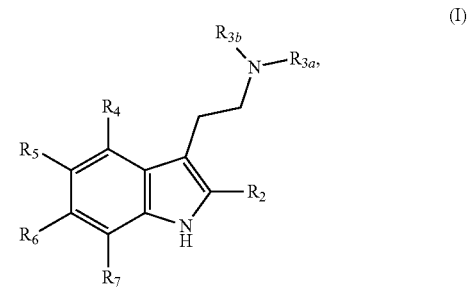

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group, together with a diluent, carrier, or excipient.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition for example, psychiatric and existential distress within life-threatening cancer situations (ACS Pharmacol Transl Sci 4: 553-562; J Psychiatr Res 137: 273); substance-related disorders, such as alcohol-related disorders, cannabis related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder.

In an aspect, the compounds of the present disclosure may be used to be contacted with a 5-$HT_{2A}$ receptor to thereby modulate the 5-$HT_{2A}$ receptor. Such contacting includes bringing a compound of the present disclosure and 5-$HT_{2A}$ receptor together under in vitro conditions, for example, by introducing the compounds in a sample containing a 5-$HT_{2A}$ receptor, for example, a sample containing purified 5-$HT_{2A}$ receptors, or a sample containing cells comprising 5-$HT_{2A}$ receptors. In vitro conditions further include the conditions described in Example 4 hereof. Contacting further includes bringing a compound of the present disclosure and 5-$HT_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5-$HT_{2A}$ receptor, the compound may activate the 5-$HT_{2A}$ receptor or inhibit the 5-$HT_{2A}$ receptor.

Thus, in a further aspect, the condition that may be treated in accordance herewith can be any 5-$HT_{2A}$ receptor mediated disorder. Such disorders include, but are not limited to schizophrenia, psychotic disorder, attention deficit hyperactivity disorder, autism, and bipolar disorder.

In an aspect, the compounds of the present disclosure may be used to be contacted with a 5-$HT_{1A}$ receptor to thereby modulate the 5-$HT_{1A}$ receptor. Such contacting includes bringing a compound of the present disclosure and 5-$HT_{1A}$ receptor together under in vitro conditions, for example, by introducing the compounds in a sample containing a 5-$HT_{1A}$ receptor, for example, a sample containing purified 5-$HT_{1A}$ receptors, or a sample containing cells comprising 5-$HT_{1A}$ receptors. In vitro conditions further include the conditions described in Example 1 hereof. Contacting further includes bringing a compound of the present disclosure and 5-$HT_{1A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5-$HT_{2A}$ receptor, the compound may activate the 5-$HT_{1A}$ receptor or inhibit the 5-$HT_{1A}$ receptor.

Thus, in a further aspect, the condition that may be treated in accordance herewith can be any 5-$HT_{1A}$ receptor mediated disorder. Such disorders include, but are not limited to schizophrenia, psychotic disorder, attention deficit hyperactivity disorder, autism, and bipolar disorder.

The chemical compounds of the present disclosure may also be used as a feedstock material for other psilocybin derivatives. Thus in one embodiment, the chemical compounds of the present disclosure may be in used manufacture of a pharmaceutical or recreational drug formulation, wherein the manufacture may comprise derivatizing a chemical compound having the formula

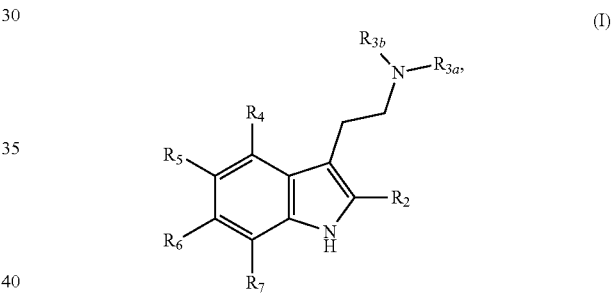

(I)

wherein at least one of $R_2$, $R_4$, $R_5$, $R_6$ or $R_7$ is an amino group or N-substituted amino group, wherein each non-aminated $R_2$, $R_5$, $R_6$, or $R_7$ is a hydrogen atom, alkyl group or O-alkyl group, wherein $R_4$ when it is not aminated is a phosphate group, a hydrogen atom, a hydroxy group, an alkyl group, or O-alkyl group, and wherein $R_{3A}$ and $R_{3B}$ are each independently a hydrogen atom, an alkyl group, an aryl group, or an acyl group, or a salt of the chemical compound.

In order to use the compound having formula (I) as a feedstock, one or more amino group or N-substituted amino groups may be substituted by any atoms or groups, for example hydrocarbon groups. Those of skill in the art will be generally familiar with methods that may be used to substitute amino group or N-substituted amino groups. In this respect, guidance may be found in Schnepel C. et al. (2017) Chem. Eur. J. 23:12064-12086; Durak L. J. et al. (2016) ACS Catal. 6: 1451; Runguphan W. et al. (2013) Org Lett 15: 2850; Corr M. J. et al. (2017) Chem. Sci. 8: 2039; and Roy A. D. et al. Chem. Comm. 4831.

Turning now to methods of making the aminated psilocybin derivatives of the present disclosure, it is initially noted that the aminated psilocybin derivatives of the present disclosure may be prepared in any suitable manner, including by any organic chemical synthesis methods, biosynthetic methods, or a combination thereof.

One suitable method of making the aminated psilocybin derivatives of the present disclosure initially involves selecting and obtaining or preparing a reactant psilocybin derivative compound, and reacting the compound under suitable conditions to form an aminated psilocybin derivative.

Suitable reactant psilocybin derivative compounds include compounds comprising an indole prototype structure (see: FIG. 2), including, for example, a chemical compound having formula (II):

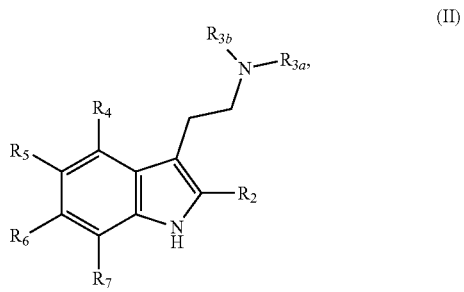

(II)

wherein at least one of $R_2$, $R_4$, $R_5$, $R_6$, or $R_7$ is a reactive group selected from a nitro group, an azido group, or a hydrogen atom, and wherein $R_2$, $R_4$, $R_5$, $R_6$, or $R_7$ which are not a reactive group, are a hydrogen atom, an alkyl of O-alkyl group, and wherein $R_{3A}$ and $R_{3B}$ are each independently a hydrogen atom, an alkyl group, and acyl group, or an aryl group. Reactant psilocybin derivative compound (II) comprises a plurality of compounds, some examples of which will next be described.

Figure 8A:
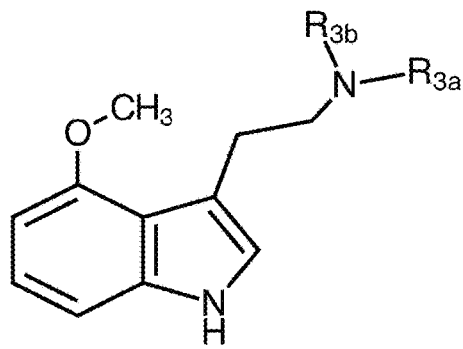
FIGS. 8A, 8B, 8C, 8D, 8E, 8F, and 8G depict the chemical structures of certain example psilocybin derivatives, notably O-alkylated psilocybin derivatives, notably a 4-O-methyl-psilocybin derivative (FIG. 8A), a 4-O-ethyl-psilocybin derivative (FIG. 8B), a 4-acetyl-psilocybin derivative (FIG. 8C), a 4-propanoyl-psilocybin derivative (FIG. 8D), a 4-hydroxy-psilocybin derivative (FIG. 8E), a 4-phospho-psilocybin derivative (FIG. 8F), and a 4-psilocybin derivative (FIG. 8G).
Figure 8B:
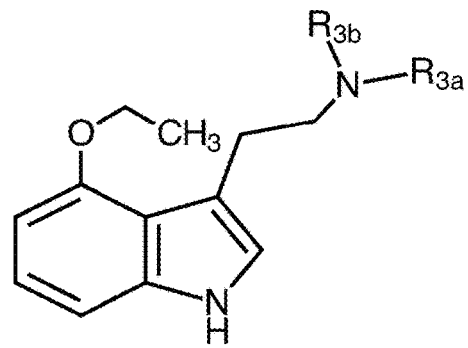

In one example embodiment, the reactant psilocybin derivative can be selected to be a chemical compound wherein $R_4$ is an O-alkyl group, $R_2$, $R_5$, $R_6$, and $R_7$ are a hydrogen atom, and $R_{3A}$ and $R_{3B}$ are each independently a hydrogen atom, an alkyl group, an acyl group, or an aryl group, such as, for example, the reactant psilocybin derivative shown in FIGS. 8A and 8B.

Figure 8C:
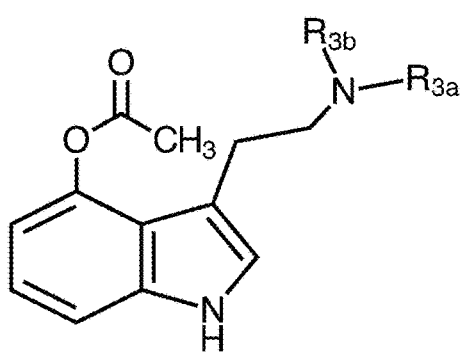
Figure 8D:
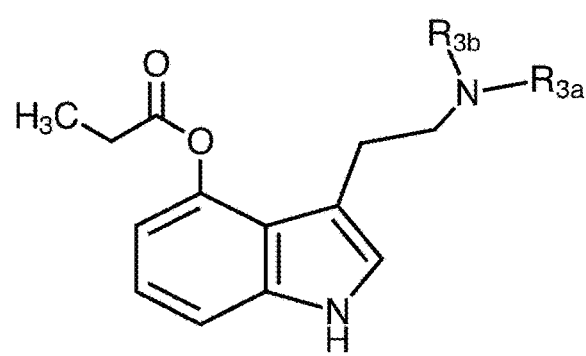

In one example embodiment, the reactant psilocybin derivative can be selected to be a chemical compound wherein $R_4$ is an O-acyl group, $R_2$, $R_5$, $R_6$, and $R_7$ are a hydrogen atom, and $R_{3A}$ and $R_{3B}$ are each independently a hydrogen atom, an alkyl group, an acyl group, or an aryl group, such as, for example, the reactant psilocybin derivative shown in FIGS. 8C and 8D.

Figure 8E:
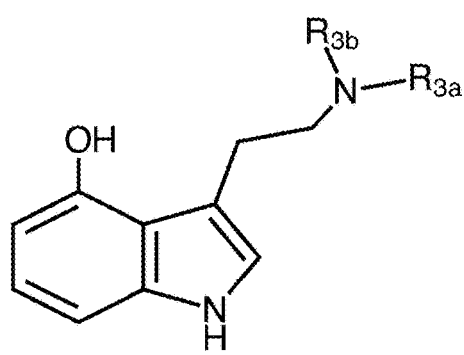

In one example embodiment, the reactant psilocybin derivative can be selected to be a chemical compound wherein $R_4$ is a hydroxyl group, $R_2$, $R_5$, $R_6$, and $R_7$ are a hydrogen atom, and $R_{3A}$ and $R_{3B}$ are each independently a hydrogen atom, an alkyl group, an acyl group, or an aryl group, such as, for example, the reactant psilocybin derivative shown in FIG. 8E.

Figure 8F:
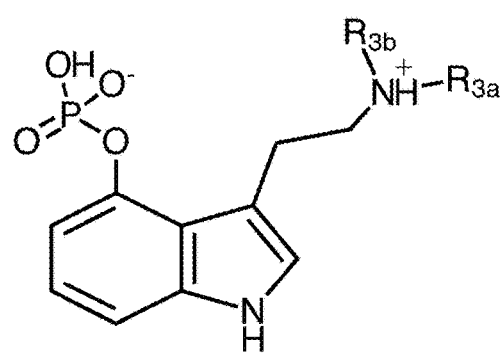

In one example embodiment, the reactant psilocybin derivative can be selected to be a chemical compound wherein $R_4$ is a phosphate group, $R_2$, $R_5$, $R_6$, and $R_7$ are a hydrogen atom, and $R_{3A}$ and $R_{3B}$ are each independently a hydrogen atom, an alkyl group, an acyl group, or an aryl group, such as, for example, the reactant psilocybin derivative shown in FIG. 8F.

Figure 8G:
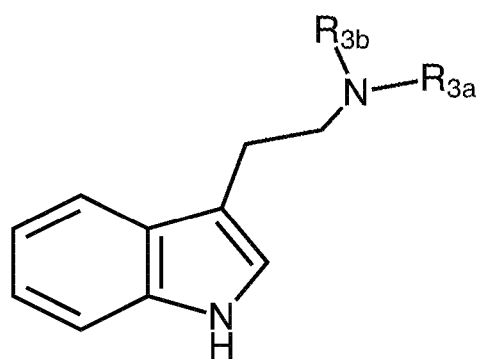

In one example embodiment, the reactant psilocybin derivative can be selected to be a chemical compound wherein $R_4$ is a hydrogen atom, $R_2$, $R_5$, $R_6$, and $R_7$ are a hydrogen atom, and $R_{3A}$ and $R_{3B}$ are each independently a hydrogen atom, an alkyl group, an acyl group, or an aryl group, such as, for example, the reactant psilocybin derivative shown in FIG. 8G.

The reactant psilocybin derivative compounds may be provided in a more or less chemically pure form, for example, in the form of a psilocybin derivative preparation having a purity of at least about 95%, at least about 96%, at least about 97%, at least about 98%, at least about 99%, or at least 99.9%. The psilocybin derivative may be chemically synthesized, or obtained from a fine chemical manufacturer.

In one example embodiment, the reactant psilocybin derivative compound, may be reacted with a nitrogenous compound with a nitrogenous compound, including, for example, a nitrogenous compound selected from nitric acid ($HNO_3$), a nitrate salt, an acyl nitrate, trifluoromethansulfonyl nitrate, nitrosonium tetrafluoroborate ($NO_2BF_4$), and trifluoracetyl nitrate to initially form a nitrated psilocybin compound which can then be reacted under reducing conditions to form an aminated psilocybin compound.

Alternatively, in order to form the aminated psilocybin derivatives of the present disclosure a nitrated or azido group containing compound reactant psilocybin compounds may be obtained and reacted under reducing conditions to form the aminated psilocybin derivatives of the present disclosure.

Figure 9A:
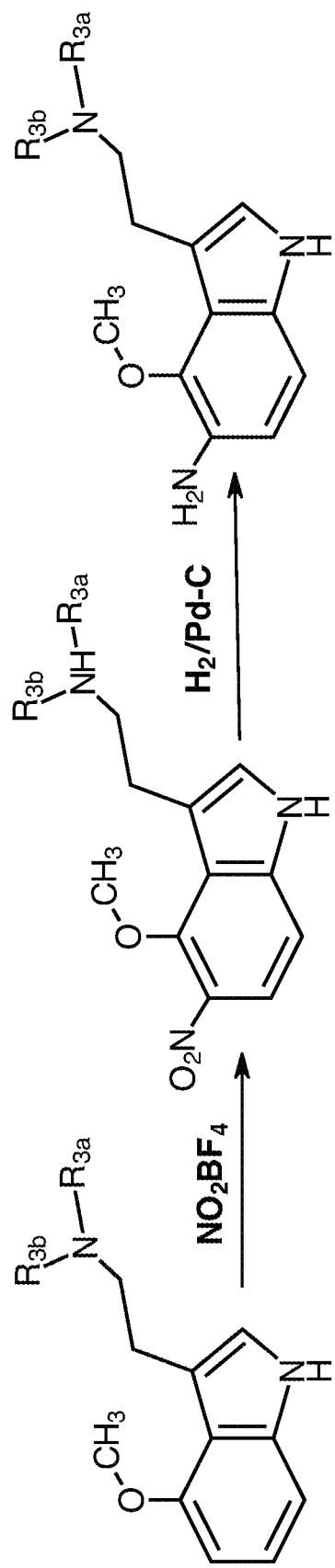
FIGS. 9A, 9B, 9C and 9D depict certain example chemical reactions for synthesizing aminated psilocybin derivatives with subsequent N-substitutions, notably a reaction wherein a 4-O-methyl-5-nitro-psilocybin derivative is reacted with hydrogen under the catalysis of palladium on charcoal to form a 4-O-methyl-5-amino-psilocybin derivative (FIG. 9A). The formed amino group at the 5-position can then be substituted with different group such as an acylation with acetic anhydride. The amino group can also be alkylated via a condensation with an aldehyde (such as acetaldehyde) followed by a reduction of the intermediate imine with borohydride (FIG. 9B).
Figure 9B:
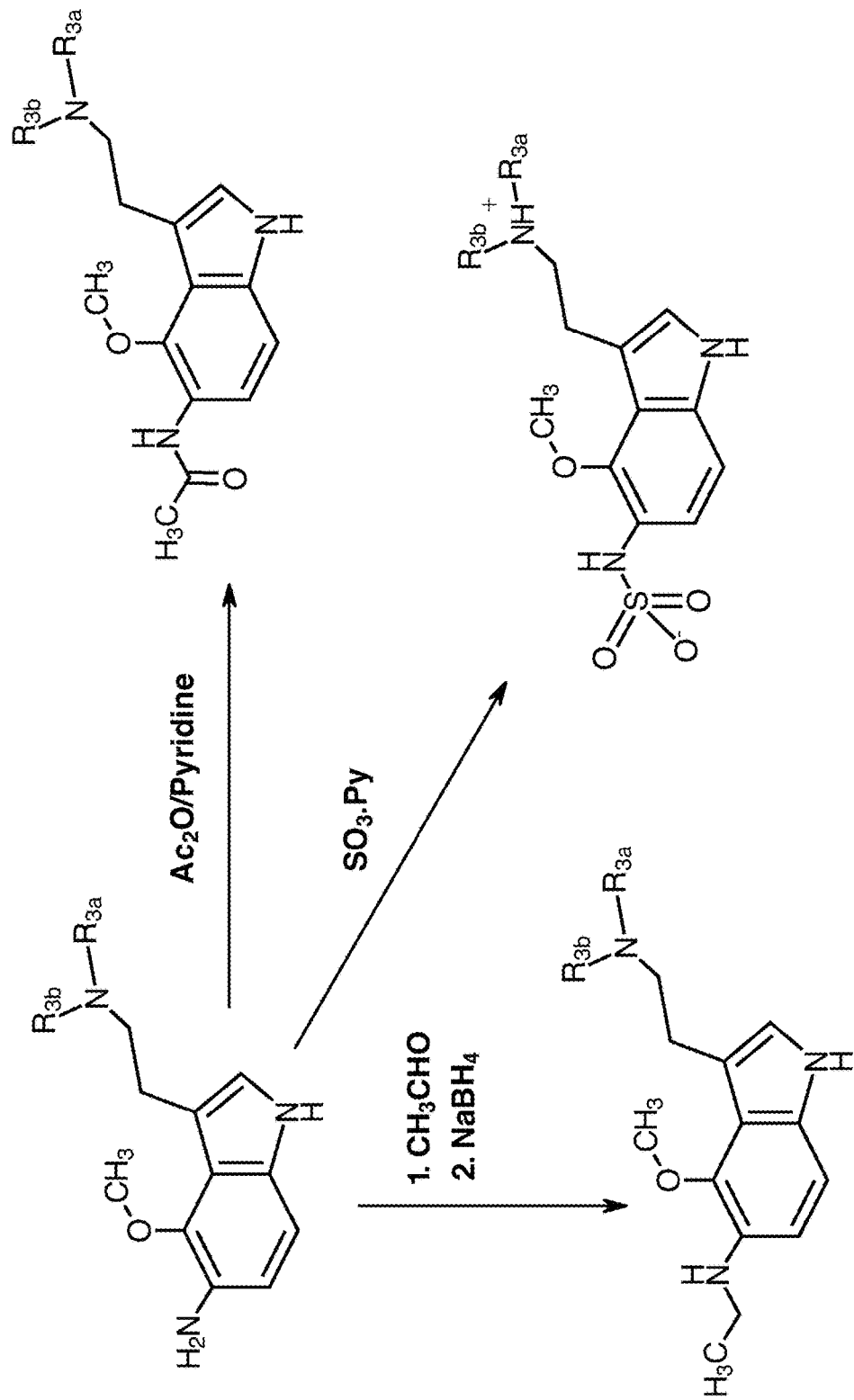

Referring now to FIGS. 9A-9B, shown therein is an example reaction wherein 5-nitro-4-O-methyl-psilocybin derivative is converted to the 5-amino-4-O-methyl-psilocybin and some example N-substituted derivatives.

Referring now to FIG. 9A, shown therein is an example chemical reaction wherein nitrosonium tetrafluoroborate ($NO_2BF_4$) is reacted with a 4-O-methyl-psilocybin derivative (FIG. 8A) in a chemical reaction which results initially in the formation of an intermediate psilocybin derivative, notably a 4-O-methyl-5-nitro-psilocybin derivative. Subsequently, in the presence of hydrogen, the nitro group of the intermediate psilocybin derivative is reduced to an amino group under the catalytic hydrogenolysis condition with the help of palladium on charcoal. This affords the 5-amino-4-O-methyl-psilocybin derivative.

Subsequent N-substitutions on the formed amino group (FIG. 9B) can be carried out using (1) N-acylations, such as N-acetylation with acetic anhydride or N-sulfonylation with sulfur trioxide-pyridine complex, (2) selective N-alkylation via a reaction with an aldehyde followed by a reduction of the intermediate imine, such as the reaction with acetaldehyde to form an intermediate imine, followed by a reduction with sodium borohydride.

Figure 9C:
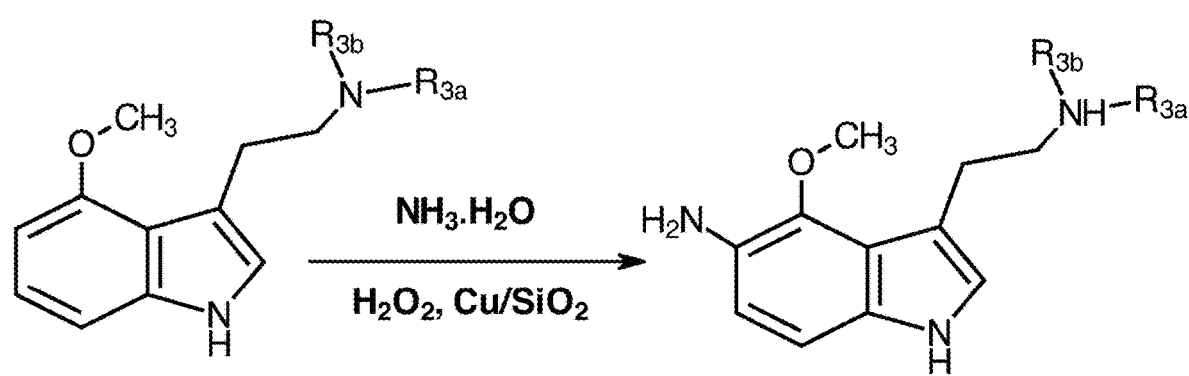
Figure 9D:
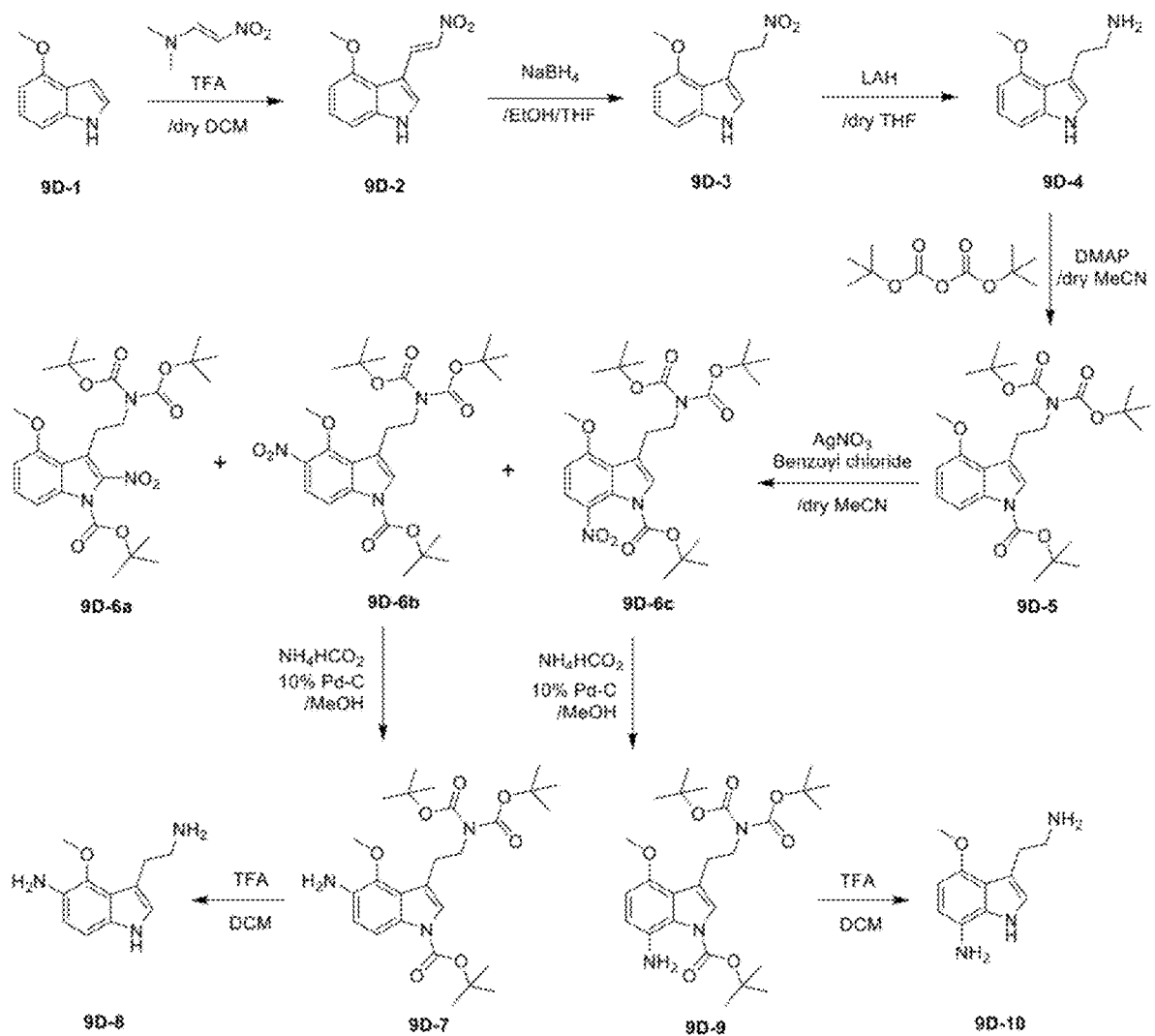

Referring now to FIG. 9D, shown therein is an example of multistep synthesis of two 4-O-methyl-psilocybin derivative respectively aminated at $C_5$ (compound 9D-8, corresponding with the compound having chemical formula (IX), set forth herein) and $C_7$ (compound 9D-10, corresponding with the compound having chemical formula (XII), set forth herein) using 4-methoxyindole (compound 9D-1) as a starting compound. Thus, starting from 9D-1, a regioselective 2-nitrovinylation can be carried out using 1-(dimethylamino)-2-nitroethylene as an electrophile in the presence of trifluoroacetic acid as a catalyst. The reaction can provide the desired (E)-3-(2-nitroethenyl)-4-methoxyindole (9D-2) which can be directly reduced using sodium borohydride in a mixture of ethanol and THF, to provide the desired 3-(2-nitroethyl)-4-methoxyindole (9D-3), for example, yielding 33% (2 steps). The nitro group of the side chain can be further reduced using lithium aluminum hydride in THF to afford the intermediate 4-O-methy-tryptamine (9D-4), for example, yielding 57%. To facilitate subsequent nitration, compound 9D-4 can be protected with an excess of di-tert-butyl decarbonate in the presence of 4-N,N-dimethylaminopyridine to provide the tri-Boc-protected 4-O-methy-tryptamine (9D-5), for example, yielding 51%. Compound 9D-5 can then be subjected to a reaction with benzoyl nitrate, generated by mixing benzoyl chloride and silver nitrate in anhydrous acetonitrile. This can provide three nitrated products respectively at $C_2$ (compound 9D-6a, e.g., 7% yield), $C_5$ (compound 9D-6b, 14% yield), and $C_7$ (compound 9D-6c, 12%). Compound 9D-6b can subsequently be subjected to a reduction using ammonium formate in the presence of 10% palladium on charcoal in methanol at room temperature to afford the 5-aminated intermediate 9D-7 (e.g., 88% yield) which can be fully deprotected subsequently by a treatment with trifluoroacetic acid to furnish the desired 5-amino-4-O-methyl-psilocybin derivative (9D-8, e.g., 56% yield, corresponding with the compound having chemical formula (IX), set forth herein). Analogously, compound 9D-6c can also subjected to a reduction using ammonium formate in the presence of 10% palladium on charcoal in methanol at room temperature to afford the 7-aminated intermediate 9D-9 (e.g., 67% yield) which can further be fully deprotected by a treatment with trifluoroacetic acid to furnish the desired 7-amino-4-O-methyl-psilocybin derivative 9D-10, (e.g., 70% yield, corresponding with the compound having chemical formula (XII), set forth herein).

Thus, referring to the reactant psilocybin derivative compound having formula (II), the conditions can comprise: (i) appropriately protecting the side-chain amino group with one or two protecting groups ($R_{3a}$, $R_{3b}$) along with or without the protection of $N_1$ using $R_1$. It is noted that the protecting groups $R_1$, $R_{3a}$, $R_{3b}$ can be, for example, an alkyl or an acyl group, such as an acetyl group or substituted acetyl group, such as trifluoroacetyl, or other groups, such as a carbamate group, e.g., fluorenylmethyloxycarbonyl (Fmoc), benzyloxycarbonyl, or tert-butyloxycarbonyl (Boc) which can, for example, be prepared by reacting with di-tert-butyl dicarbonate in the presence of 4-N,N-dimethylaminopyridine (DMAP). It is noted that the protection of $N_1$ with $R_1$ is optional depending on the nature of electrophile which is used in the nitration reaction (referring to FIG. 9D, see: e.g., reaction 9D-5 to 9D-6a, 9D-6b, 9D-6c), as well as the specific reaction conditions, e.g., pH, temperatures, solvents, catalysts; (ii) reacting the protected reactant psilocybin compound with a nitrogenous compound selected from nitric acid ($HNO_3$); a nitrate salt, such as $AgNO_3$; an acyl nitrate such as trifluoromethansulfonyl nitrate; benzoyl nitrate, nitrosonium tetrafluoroborate ($NO_2BF_4$), and trifluoracetyl nitrate to form a nitrated compound having chemical formula (XXXI):

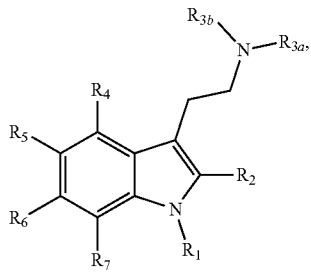

(XXXI)

wherein at least one of $R_2$, $R_4$, $R_5$, $R_6$, or $R_7$ is a nitro group, and wherein each non-nitrated $R_2$, $R_5$, $R_6$, or $R_7$ is a hydrogen atom, an alkyl group or O-alkyl group, wherein $R_4$ when it is not nitrated is a hydrogen atom, an alkyl group, O-alkyl group, a hydroxy group, or a phosphate group, and wherein $R_{3A}$ and $R_{3B}$ are a protective group, and wherein $R_1$ is a protective group or a hydrogen atom, and then (iii) reacting the nitrated compound under a reducing condition to form an aminated compound having chemical formula (XXXII):

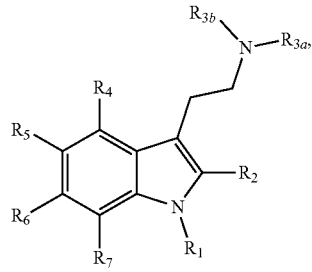

(XXXII)

wherein at least one of $R_2$, $R_4$, $R_5$, $R_6$, or $R_7$ is an amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group, O-alkyl group, a hydroxy group, or a phosphate group, and wherein $R_{3A}$ and $R_{3B}$ are a protective group, and wherein $R_1$ is a protective group or a hydrogen atom, then (iv) optionally substituting the at least one amino group at $R_2$, $R_4$, $R_5$, $R_6$, or $R_7$ group to form a N-substituted derivative, and then (v) removing the protecting groups ($R_1$, $R_{3a}$, $R_{3b}$) at $N_1$ and the side chain amino functionality, to thereby form a compound having chemical formula (I), and then (vi) optionally substituting the amino group of the side chain to form at least one N-substituted group.

Furthermore, referring now to FIG. 9C, shown therein is an alternative method for making the psilocybin derivatives of the present disclosure, notably a direct amination method using hydrogen peroxide and ammonia with the help of $Cu/SiO_2$ as a catalyst (T. Yu, R. Yang, S. Xia, G. Li, and C. Hu Catal. Sci. Technol., 2014, 4, 3159-3167). The presence of a catalyst is required in view of the fact that the reaction at practical temperatures and pressures is thermodynamically unfavorable. Such catalysts may include a platinum-containing catalyst, which may be held at high temperature, or a reducible metal oxide, for example, oxides of Fe, Ni, Co, Sn, Sb, Bi or Cu, as further described in, for example, Canadian Patent 553,988, and U.S. Pat. Nos. 2,948,755; and 4,031,106.

Similarly, referring further to FIG. 9A, having obtained the nitrated compound, the reduction reaction is preferably conducted in the presence of a catalyst capable of providing electrons, for example, a Cu, Sn, Ni or Pt containing catalyst. The reduction reaction under acidic conditions may initially lead to the formation of an intermediate psilocybin derivative possessing a cationic $NH_3^+$ group, which may be reacted with for example sodium hydroxide to form an amino group or a N-substituted amino group.

Thus, it will be clear that in one embodiment, in an aspect, in the chemical compound having formula (II), at least one of $R_2$, $R_4$, $R_5$, $R_6$, or $R_7$ in the reactant psilocybin derivative compound can be a hydrogen atom, and the reaction conditions can comprise reacting the reactant psilocybin compound with ammonia and hydrogen peroxide in the presence of a catalyst, such as $Cu/SiO_2$, to form the chemical compound having formula (I) and to then optionally substitute the at least one amino group in the chemical compound having formula (I) to form at least one N-substituted group.

Furthermore, referring to FIG. 9D, 1-3 protecting groups can be introduced to protect the selected substrate compound shown in FIG. 8A, and the protecting groups can be a group different from Boc, such as an alkyl and/or acyl group like trifluoroacetyl, trichloroacetyl, dichloroacetyl, chloroacetyl, benzyloxycarbonyl, fluorenylmethyloxycarbonyl (Fmoc) etc. It will now be clear that, in an aspect hereof, the protected reactant psilocybin derivatives disclosed herein may be reacted with a nitrogenous compound, such as, for example, nitric acid ($HNO_3$), a nitrate salt, an acyl nitrate such as trifluoromethansulfonyl nitrate, benzoyl nitrate and trifluoroacetyl nitrate, and ammonia to form the aminated psilocybin derivatives of the present disclosure. Thus, in addition to reactant psilocybin derivative shown in FIG. 8A, the example reactant psilocybin derivatives shown in FIGS. 8B-8G may also be reacted with a suitable reagent to form example aminated psilocybin derivatives of the present disclosure. The 4-O-methyl-psilocybin derivative depicted an FIG. 8A may be reacted to form, for example, the 4-O-methyl-5-amino-psilocybin derivative depicted in FIG. 5A (as already noted), the 4-O-methyl-7-amino-psilocybin derivative depicted in FIG. 6A, and the 4-O-methyl-5,7-di-amino-psilocybin depicted in FIG. 7A.

Figure 5A:
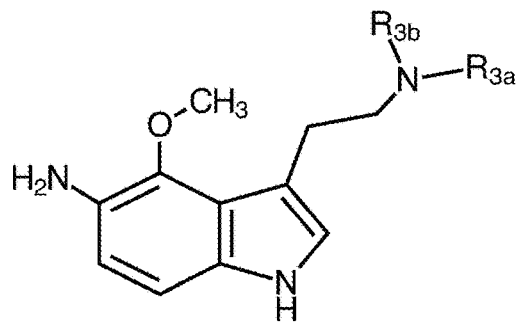
FIGS. 5A, 5B, 5C, 5D, 5E, 5F, and 5G depict the chemical structures of certain example aminated psilocybin derivatives, notably O-alkylated aminated psilocybin derivatives, notably a 4-O-methyl-5-amino-psilocybin derivative (FIG. 5A), a 4-O-ethyl-5-amino-psilocybin derivative (FIG. 5B), O-acylated aminated psilocybin derivatives, notably a 4-acetyl-5-amino-psilocybin derivative (FIG. 5C), a 4-propanoyl-5-amino-psilocybin derivative (FIG. 5D), a 4-hydroxy-5-amino-psilocybin derivative (FIG. 5E), and a 4-phospho-5-amino-psilocybin derivative (FIG. 5F), and 4- and a 5-amino-psilocybin derivative (FIG. 5G).
Figure 5B:
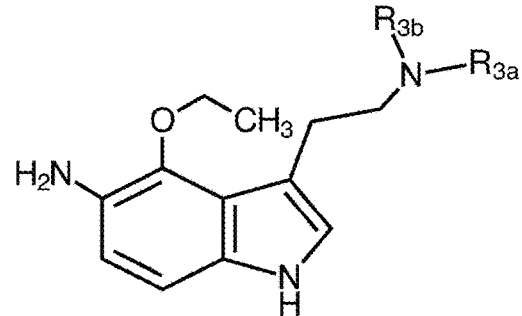
Figure 6A:
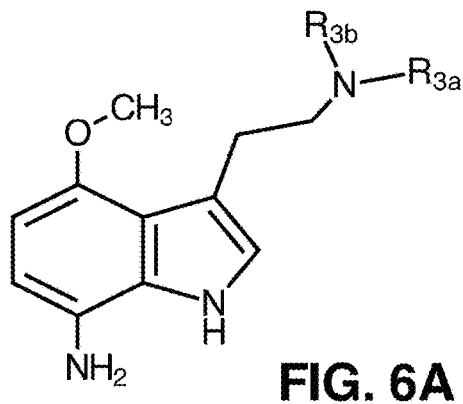
FIGS. 6A, 6B, 6C, 6D, 6E, 6F, and 6G depict the chemical structures of certain example aminated psilocybin derivatives, notably O-alkylated aminated psilocybin derivatives, notably a 4-O-methyl-7-amino-psilocybin derivative (FIG. 6A), a 4-O-ethyl-7-amino-psilocybin derivative (FIG. 6B), O-acylated aminated psilocybin derivatives, notably a 4-acetyl-7-amino-psilocybin derivative (FIG. 6C), a 4-propanoyl-7-amino-psilocybin derivative (FIG. 6D), a 4-hydroxy-7-amino-psilocybin derivative (FIG. 6E), a 4-phospho-7-amino-psilocybin derivative (FIG. 6F), and a 7-amino-psilocybin derivative (FIG. 6G).
Figure 6B:
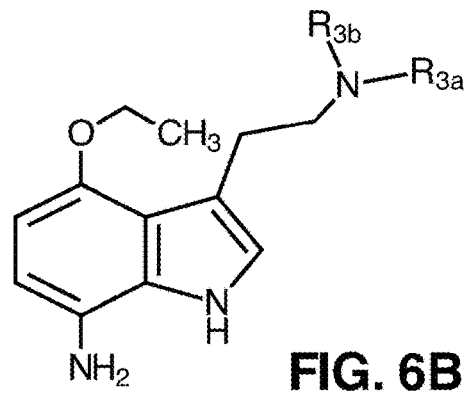
Figure 7A:
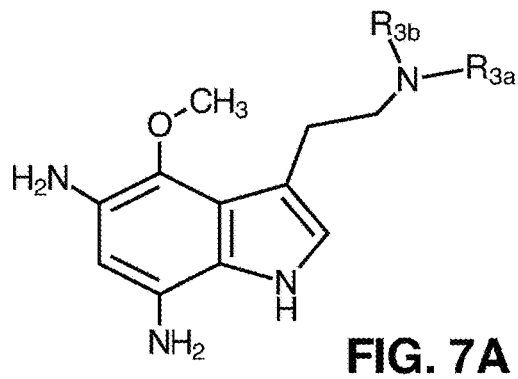
FIGS. 7A, 7B, 7C, 7D, 7E, 7F, and 7G depict the chemical structures of certain example aminated psilocybin derivatives, notably O-alkylated aminated psilocybin derivatives, notably a 4-O-methyl-5,7-di-amino-psilocybin derivative (FIG. 7A), a 4-O-ethyl-5,7-di-amino-psilocybin derivative (FIG. 78), O-acylated aminated psilocybin derivatives, notably a 4-acetyl-5,7-di-amino-psilocybin derivative (FIG. 7C), a 4-propanoyl-5,7-di-amino-psilocybin derivative (FIG. 7D), a 4-hydroxy-5,7-di-amino-psilocybin derivative (FIG. 7E), a 4-phospho-5,7-di-amino-psilocybin derivative (FIG. 7F), and a 5,7-di-amino-psilocybin derivative (FIG. 7G).
Figure 7B:
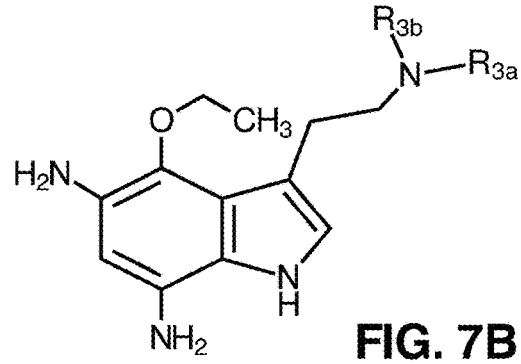

Similarly, the 4-O-ethyl-psilocybin derivative depicted an FIG. 8B may be reacted in similar reaction sequence to form, for example, the 4-O-ethyl-5-amino-psilocybin derivative depicted in FIG. 5B, the 4-O-ethyl-7-amino-psilocybin derivative depicted in FIG. 6B, and the 4-O-ethyl-5,7-di-amino-psilocybin depicted in FIG. 7B.

Figure 5C:
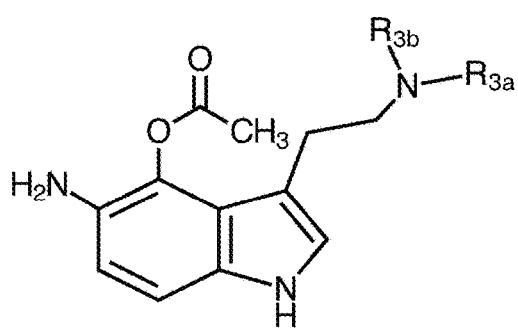
Figure 6C:
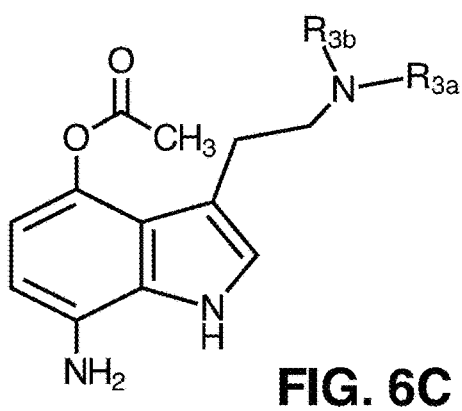
Figure 7C:
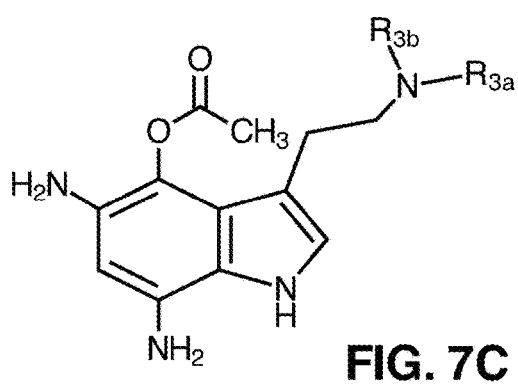

Similarly, the 4-acetyl-psilocybin derivative depicted an FIG. 8C may be reacted in similar reaction sequence to form, for example, the 4-O-acetyl-5-amino-psilocybin derivative depicted in FIG. 5C, the 4-O-acetyl-7-amino-psilocybin derivative depicted in FIG. 6C, and the 4-O-acetyl-5,7-di-amino-psilocybin depicted in FIG. 7C.

Figure 5D:
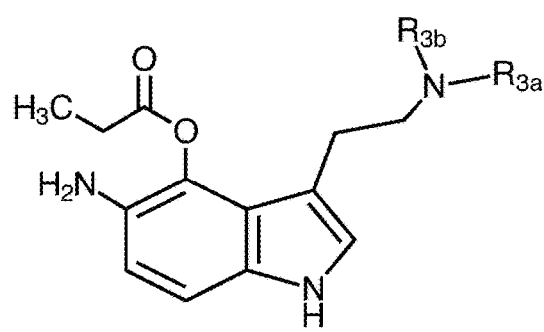
Figure 6D:
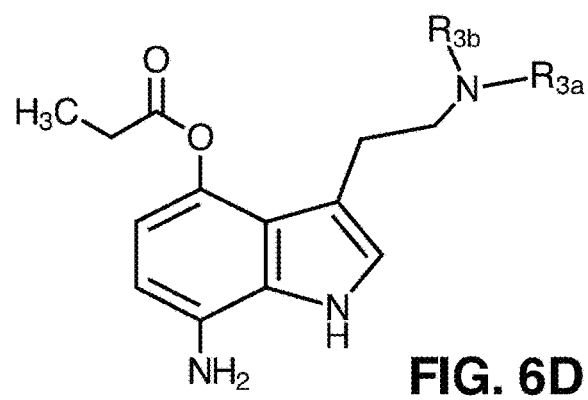
Figure 6E:
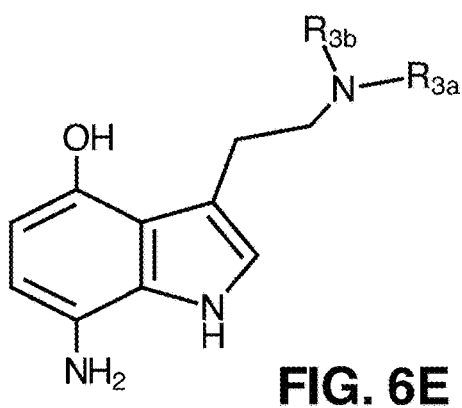
Figure 6F:
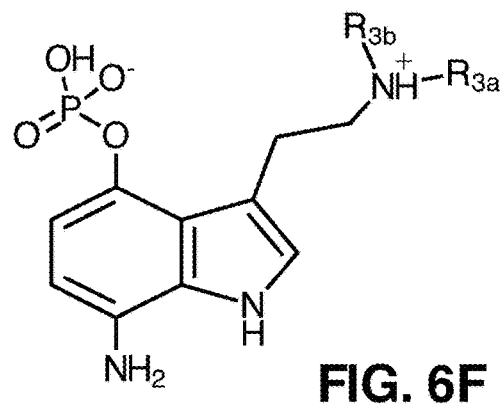
Figure 6G:
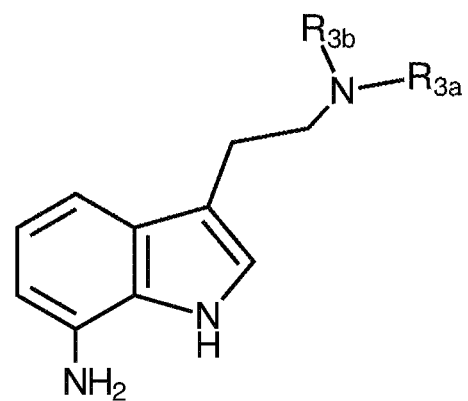
Figure 7D:
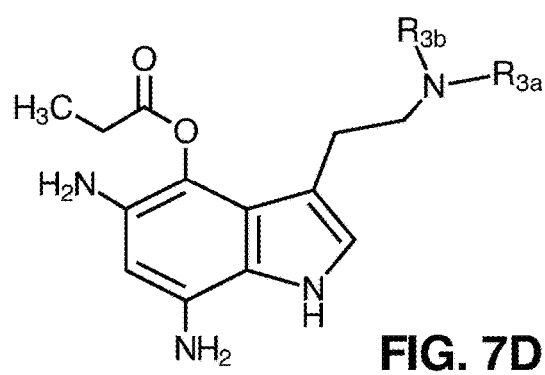
Figure 7E:
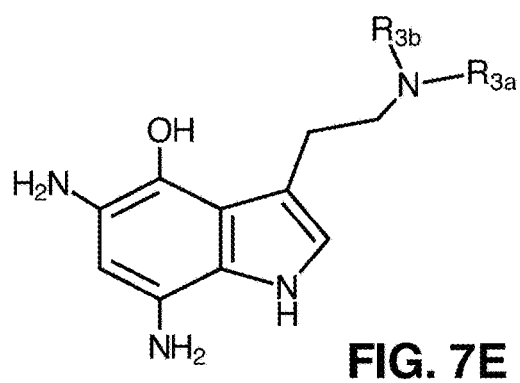
Figure 7F:
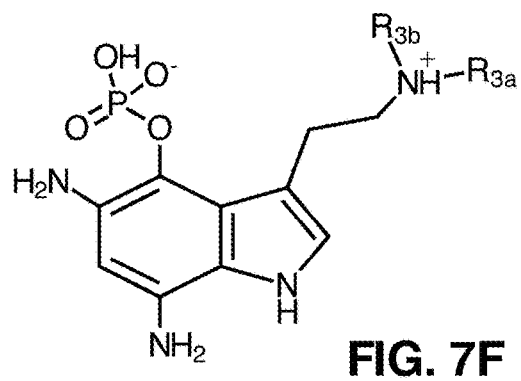
Figure 7G:
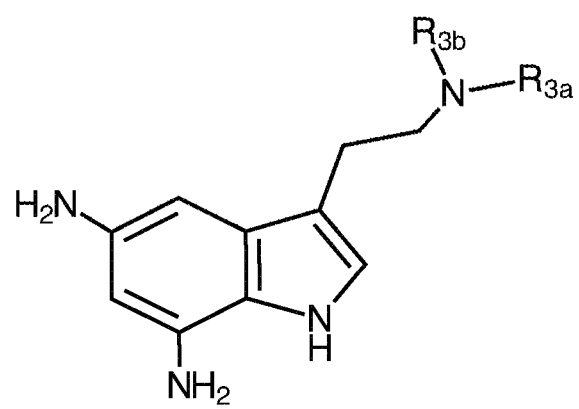

Similarly, the 4-propanoyl-psilocybin derivative depicted an FIG. 8D may be reacted in similar reaction sequence to form, for example, the 4-O-propanoyl-5-amino-psilocybin derivative depicted in FIG. 5D, the 4-O-propanoyl-7-amino-psilocybin derivative depicted in FIG. 6D, and the 4-O-propanoyl-5,7-di-amino-psilocybin depicted in FIG. 7D.

Similarly, the 4-hydroxy-psilocybin derivative depicted an FIG. 8E may be reacted in similar reaction sequence to form, for example, the 4-hydroxy-5-amino-psilocybin derivative depicted in FIG. 5E, the 4-hydroxy-7-amino-psilocybin derivative depicted in FIG. 6E, and the 4-hydroxy-5,7-di-amino-psilocybin depicted in FIG. 7E.

Similarly, the 4-phospho-psilocybin derivative depicted an FIG. 8F may be reacted in similar reaction sequence to form, for example, the 4-phosphate-5-amino-psilocybin derivative depicted in FIG. 5F, the 4-phosphate-7-amino-psilocybin derivative depicted in FIG. 6F, and the 4-phosphate-5,7-di-amino-psilocybin depicted in FIG. 7F.

Similarly, the psilocybin derivative depicted an FIG. 8G may be reacted to form, for example, the 5-amino-psilocybin derivative depicted in FIG. 5G, the 47-amino-psilocybin derivative depicted in FIG. 6G, and the 5,7-di-amino-psilocybin depicted in FIG. 7G as well as other analogs.

It is noted that the performance of the reactions, in example different embodiments, may involve amination of different carbon atoms, i.e., the $C_2$, $C_5$, $C_6$ and/or $C_7$ atom. In general, reaction conditions may be selected so that different carbon atoms or combinations thereof are aminated. Thus, for example, using either a $C_5$-nitrated or $C_5$-azido-substituted psilocybin or derivative as a starting material, the nitro or the azido group can be reduced to afford the 5-amino-psilocybin or derivative. The methods can be used to prepare any other mono-, di- or multi-aminated psilocybin derivatives from their corresponding nitrated or azido-substituted substrates (see: Kadam, H. K; Tilve, S. G. RSC Adv. 2015, 5, 83391-83407). Typical reduction conditions can be selected from a range of conventional conditions, such as catalytic hydrogenolysis with the help of heavy metal such as palladium on charcoal, palladium hydroxide on charcoal, Raney Nickel, platinum oxide; palladium on charcoal with ammonium formate; reactive metal such as zinc, iron or copper in an acidic media or with an salt, such as zinc/ammonium chloride; organic phosphine such as triphenylphosphine or trimethylphosphine (H.-C, Wu, J.-Q. Yu, J. B. Spencer, Org. Lett., 2004, 6, 4675-4678); sulfur containing reducing agent such as sodium hydrosulfite, sodium sulfide, hydrogen sulfide; tin(I) chloride; organic silanes (R. J. Rahaim, R. E. Maleczka, Jr., Org. Lett., 2005, 7, 5087-5090). The amination on the psilocybin and derivatives can also be achieved from a precursor substrate containing either an acyl azide (—$CON_3$) or amide (—$CONH_2$) functionality at any of the $C_2$, $C_5$, $C_6$, $C_7$ positions via respectively the Curtis rearrangement (Scriven, E. F. V.; Turnbull, K., Chemical Reviews. 1988, 88, 297-368) or Hoffmann rearrangement (Baumgarten, H.; Smith, H; Stakiis, A, J. Org. Chem 1975, 40 (24): 3554-3561). The obtained amines can be further substituted with N-alkylation or N-acylation or a combination of the two, and it can also be modified with a sulfur containing acylating agent such as sulfur trioxide-pyridine, sulfonyl chloride. Furthermore, the obtained amines can also be reacted with an aldehyde or ketone for form the corresponding imines that can be reduced subsequently.

The reactions may be conducted in any suitable reaction vessel (e.g., a tube, bottle). Suitable solvents that may be used are for example, water, alcohol (such as methanol, ethanol, tetrahydrofuran (THF), N,N-dimethylformamide (DMF), dimethylsulfoxide (DMSO), or a combination of solvents. Suitable temperatures may range from, for example, e.g., from about 20° C. to about 100° C. Furthermore, reaction times may be varied. As will readily be appreciated by those of skill in the art, the reaction conditions may be optimized, for example by preparing several psilocybin derivative reactants preparations and azido and reacting these in different reaction vessels under different reaction conditions, for example, at different temperatures, using different solvents, using different catalysts etc., evaluating the obtained aminated psilocybin derivative reaction product, adjusting reaction conditions, and selecting a desired reaction condition. Further general guidance regarding appropriate reaction conditions for performing amination reactions may be found in, for example Kadarn, H. K.: Tilve, S. G. RSC Adv. 2015, 5, 83391-83407.

In another aspect of the present disclosure, the aminated psilocybin compounds may be made biosynthetically. Accordingly, the present disclosure further includes, in one embodiment, a method of making an aminated psilocybin derivative the method comprising:
  (a) contacting a aminated psilocybin precursor compound with a host cell comprising a psilocybin biosynthetic enzyme complement, and
  (b) growing the host cell to produce an aminated psilocybin derivative or salts thereof having the formula (I):

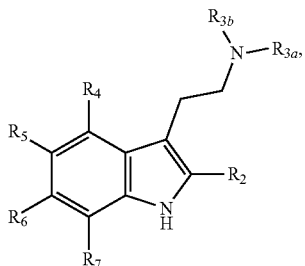

(I)

wherein at least one of $R_2$, $R_4$, $R_5$, $R_6$, or $R_7$ is an amino group or an N-amino substituted amino group, and wherein each non-aminated $R_2$, $R_5$, $R_6$, or $R_7$ is a hydrogen atom, an alkyl or O-alkyl group, wherein $R_4$ when it is not aminated is a hydrogen atom, an alkyl group or O-alkyl group, a hydroxy group, or a phosphate group, and wherein $R_{3A}$ and $R_{3B}$ are each independently a hydrogen atom, an alkyl group, an aryl group, or an acyl group.

Implementation of the foregoing example embodiment initially involves providing aminated psilocybin precursor compounds and host cells having a psilocybin biosynthetic enzyme complement. Accordingly, next, example aminated psilocybin precursor compounds and example host cells that may be selected and used in accordance with the present disclosure will be described. Thereafter, example methodologies and techniques will be described to contact and use the aminated psilocybin precursor compounds and cells to produce example aminated psilocybin compounds.

A variety of aminated psilocybin precursor compounds may be selected, prepared, and used. In some embodiments, for example, the aminated psilocybin precursor compound is a compound comprising an aminated indole prototype structure. Examples of such compounds are an aminated indole, e.g., 2-amino-indole, 4-amino-indole, 5-amino-indole, 6-amino-indole, and 7-amino-indole; and aminated tryptophan derivatives, e.g., 2-amino-tryptophan, 4-amino-tryptophan, 5-amino-tryptophan, 6-amino-tryptophan, and 7-amino-tryptophan.

Further aminated psilocybin precursor compounds that may be used include aminated indoles, having the formula (XXIX):

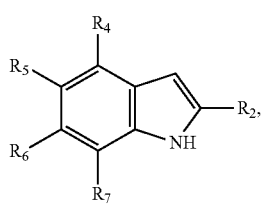

(XXIX)

wherein at least one of $R_2$, $R_4$, $R_5$, $R_6$ and $R_7$ is an amino group or N-substituted amino group, wherein $R_2$, $R_4$, $R_5$, $R_6$ and $R_7$ when they are not aminated are hydrogen atoms, an alkyl group or O-alkyl group, wherein $R_4$ when it is not aminated is a hydrogen atom, an alkyl group or O-alkyl group, a hydroxy group, or a phosphate group.

Further aminated psilocybin precursor compounds that may be used include compounds having the formula (XXVII):

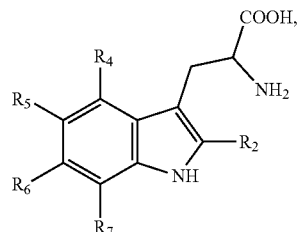

(XXVII)

wherein at least one of $R_2$, $R_4$, $R_5$, $R_6$ and $R_7$ is an amino group or an N-substituted group, wherein $R_2$, $R_4$, $R_5$, $R_6$ and $R_7$ when they are not aminated are hydrogen atoms, an alkyl group or O-alkyl group, wherein $R_4$ when it is not aminated is a hydrogen atom, an alkyl group or O-alkyl group, a hydroxy group, or a phosphate group Turning now to the host cells that can be used in accordance with the present disclosure, it is initially noted that a variety of host cells may be selected in accordance with the present disclosure, including microorganism host cells, plant host cells, and animal host cells.

In accordance herewith the host cell includes a psilocybin biosynthetic enzyme complement. Such cells can be obtained in at least two ways. First, in some embodiments, host cells may be selected in which a psilocybin biosynthetic enzyme complement is naturally present. Generally cells naturally producing psilocybin for example, cells of fungal species belonging to the genus *Psilocybe*, are suitable in this respect. Second, in some embodiments, a host cell that not naturally produces psilocybin may be modulated to produce a psilocybin biosynthetic enzyme complement. Thus, for example, a nucleic acid sequence encoding a psilocybin biosynthetic enzyme complement may be introduced into a host cell, and upon cell growth the host cells can make the psilocybin biosynthetic enzyme complement.

Typically a nucleic acid sequence encoding one or more enzymes constituting a psilocybin biosynthetic enzyme complement further includes one or more additional nucleic acid sequences, for example, a nucleic acid sequences controlling expression of the one or more enzymes, and these one or more additional nucleic acid sequences together with the nucleic acid sequence encoding the one or more enzymes can be said to form a chimeric nucleic acid sequence.

A host cell which upon cultivation expresses the chimeric nucleic acid can be selected and used in accordance with the present disclosure. Suitable host cells in this respect include, for example, microbial cells, such as bacterial cells, yeast cells, for example, and algal cells or plant cells. A variety of techniques and methodologies to manipulate host cells to introduce nucleic acid sequences in cells and attain expression exists and are well known to the skilled artisan. These methods include, for example, cation based methods, for example, lithium ion or calcium ion based methods, electroporation, biolistics, and glass beads based methods. As will be known to those of skill in the art, depending on the host cell selected, the methodology to introduce nucleic acid material in the host cell may vary, and, furthermore, methodologies may be optimized for uptake of nucleic acid material by the host cell, for example, by comparing uptake of nucleic acid material using different conditions. Detailed guidance can be found, for example, in Sambrook et al., Molecular Cloning, a Laboratory Manual, Cold Spring Harbor Laboratory Press, 2012, Fourth Ed. It is noted that the chimeric nucleic acid is a non-naturally occurring chimeric nucleic acid sequence and can be said to be heterologous to the host cell.

In some embodiments, the one or more enzymes constituting a psilocybin enzyme complement can be selected from by a nucleic acid sequence selected from the nucleic acid sequences consisting of:
  (a) SEQ. ID NO: 4, SEQ. ID NO: 8, SEQ. ID NO: 11 and SEQ. ID NO: 13;
  (b) a nucleic acid sequence that is substantially identical to any one of the nucleic acid sequences of (a);
  I a nucleic acid sequence that is substantially identical to any one of the nucleic acid sequences of (a) but for the degeneration of the genetic code;
  (d) a nucleic acid sequence that is complementary to any one of the nucleic acid sequences of (a);
  (e) a nucleic acid sequence encoding a polypeptide having any one of the amino acid sequences set forth in SEQ. ID NO: 5, SEQ. ID NO: 9, SEQ. ID NO: 12 and SEQ. ID NO: 14;
  (f) a nucleic acid sequence that encodes a functional variant of any one of the amino acid sequences set forth in SEQ. ID NO: 5, SEQ. ID NO: 9, SEQ. ID NO: 12 and SEQ. ID NO: 14; and
  (g) a nucleic acid sequence that hybridizes under stringent conditions to any one of the nucleic acid sequences set forth in (a), (b), (c), (d), (e) or (f).

Thus any of the nucleic acid sequence set forth in (a), (b), (c), (d), (e), (f) or (g) may be selected and introduced into a host cell. In particular, however the nucleic acid sequence is selected in conjunction with the selected psilocybin precursor compound, as hereinafter further discussed in reference with FIG. 10.

One example host cell that conveniently may be used is *Escherichia coli*. The preparation of the *E. coli* vectors may be accomplished using commonly known techniques such as restriction digestion, ligation, gel electrophoresis, DNA sequencing, the polymerase chain reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Suitable promoter sequences for use in *E. coli* include, for example, the T7 promoter, the T5 promoter, tryptophan (trp) promoter, lactose (lac) promoter, tryptophan/lactose (tac) promoter, lipoprotein (lpp) promoter, and A phage PL promoter. Typically, cloning vectors contain a marker, for example, an antibiotic resistance marker, such as ampicillin or kanamycin resistance marker, allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells.

Another example host cell that may be conveniently used is a yeast cell. Example yeast host cells that can be used are yeast cells belonging to the genus *Candida, Kluyveromyces, Saccharomyces, Schizosaccharomyces, Pichia, Hansenula*, and *Yarrowia*. In specific example embodiments, the yeast cell can be a *Saccharomyces cerevisiae* cell, a *Yarrowia lipolytica* cell, or *Pichia pastoris* cell.

A number of vectors exist for the expression of recombinant proteins in yeast host cells. Examples of vectors that may be used in yeast host cells include, for example, Yip type vectors, YEp type vectors, YRp type vectors, YCp type vectors, pGPD-2, pAO815, pGAPZ, pGAPZα, pHIL-D2, pHIL-S1, pPIC3.5K, pPIC9K, pPICZ, pPICZα, pPIC3K, pHWO10, pPUZZLE and 2 µm plasmids. Such vectors are known to the art and are, for example, described in Cregg et al, Mol Biotechnol. (2000) 16(1): 23-52. Suitable promoter sequences for use in yeast host cells are also known and described, for example, in Mattanovich et al., Methods Mol Biol, 2012, 824:329-58, and in Romanos et al, 1992, Yeast 8: 423-488. Examples of suitable promoters for use in yeast host cells include promoters of glycolytic enzymes, like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), *P. pastoris* glucose-6-phosphate isomerase promoter (PPGI), the 3-phosphoglycerate kinase promoter (PPGK), the glycerol aldehyde phosphate dehydrogenase promoter (PGAP), translation elongation factor promoter (PTEF), *S. cerevisiae* enolase (ENO-1), *S. cerevisiae* galactokinase (GAL1), *S. cerevisiae* alcohol dehydrogenase/glyceraldehyde-3-phosphate dehydrogenase (ADH1, ADH2/GAP), *S. cerevisiae* triose phosphate isomerase (TPI), *S. cerevisiae* metallothionein (CUP1), and *S. cerevisiae* 3-phosphoglycerate kinase (PGK), and the maltase gene promoter (MAL). Marker genes suitable for use in yeast host cells are also known to the art. Thus, antibiotic resistance markers, such as ampicillin resistance markers, can be used in yeast, as well as marker genes providing genetic functions for essential nutrients, for example, leucine (LEU2), tryptophan (TRP1 and TRP2), uracil (URA3, URA5, URA6), histidine (HIS3), and the like. Methods for introducing vectors into yeast host cells can, for example, be found in S. Kawai et al., 2010, Bioeng. Bugs 1(6): 395-403.

Further, guidance with respect to the preparation of expression vectors and introduction thereof into host cells, including in *E. coli* cells, yeast cells, and other host cells, may be found in, for example: Sambrook et al., Molecular Cloning, a Laboratory Manual, Cold Spring Harbor Laboratory Press, 2012, Fourth Ed.

Thus, to briefly recap, a host cell comprising a chimeric nucleic acid comprising (i) a nucleic acid sequence controlling expression in a host cell and (ii) a nucleic acid sequence encoding a psilocybin biosynthetic enzyme complement, can be prepared in accordance with the present disclosure.

In accordance herewith, host cells are grown to multiply and to express a chimeric nucleic acid. Expression of the chimeric nucleic acid results in the biosynthetic production in the host cell of a psilocybin biosynthetic enzyme complement. Growth media and growth conditions can vary depending on the host cell that is selected, as will be readily appreciated to those of ordinary skill in the art. Growth media typically contain a carbon source, one or several nitrogen sources, essential salts including salts of potassium, sodium, magnesium, phosphate and sulphate, trace metals, water soluble vitamins, and process aids including but not limited to antifoam agents, protease inhibitors, stabilizers, ligands, and inducers. Example carbon sources are e.g., mono- or disaccharides. Example nitrogen sources are, e.g., ammonia, urea, amino acids, yeast extract, corn steep liquor and fully or partially hydrolyzed proteins. Example trace metals are e.g., Fe, Zn, Mn, Cu, Mo and $H_3BO_3$. Example water soluble vitamins are e.g. biotin, pantothenate, niacin, thiamine, p-aminobenzoic acid, choline, pyridoxine, folic acid, riboflavin, and ascorbic acid. Further, specific example media include liquid culture media for the growth of yeast cells and bacterial cells including, Luria-Bertani (LB) broth for bacterial cell cultivation, and yeast extract peptone dextrose (YEPD or YPD), for yeast cell cultivation. Further media and growth conditions can be found in Sambrook et al., Molecular Cloning, a Laboratory Manual, Cold Spring Harbor Laboratory Press, 2012, Fourth Ed.

In order for the host cells to produce the aminated psilocybin compound, the cells are provided with a precursor compound. Thus in accordance herewith, host cells may be contacted with a psilocybin precursor compound. In some embodiments, a psilocybin precursor compound can be exogenously supplied, for example, by including a psilocybin precursor compound in the growth medium of the host cells, and growing the host cells in a medium including the psilocybin precursor compound.

Figure 10:
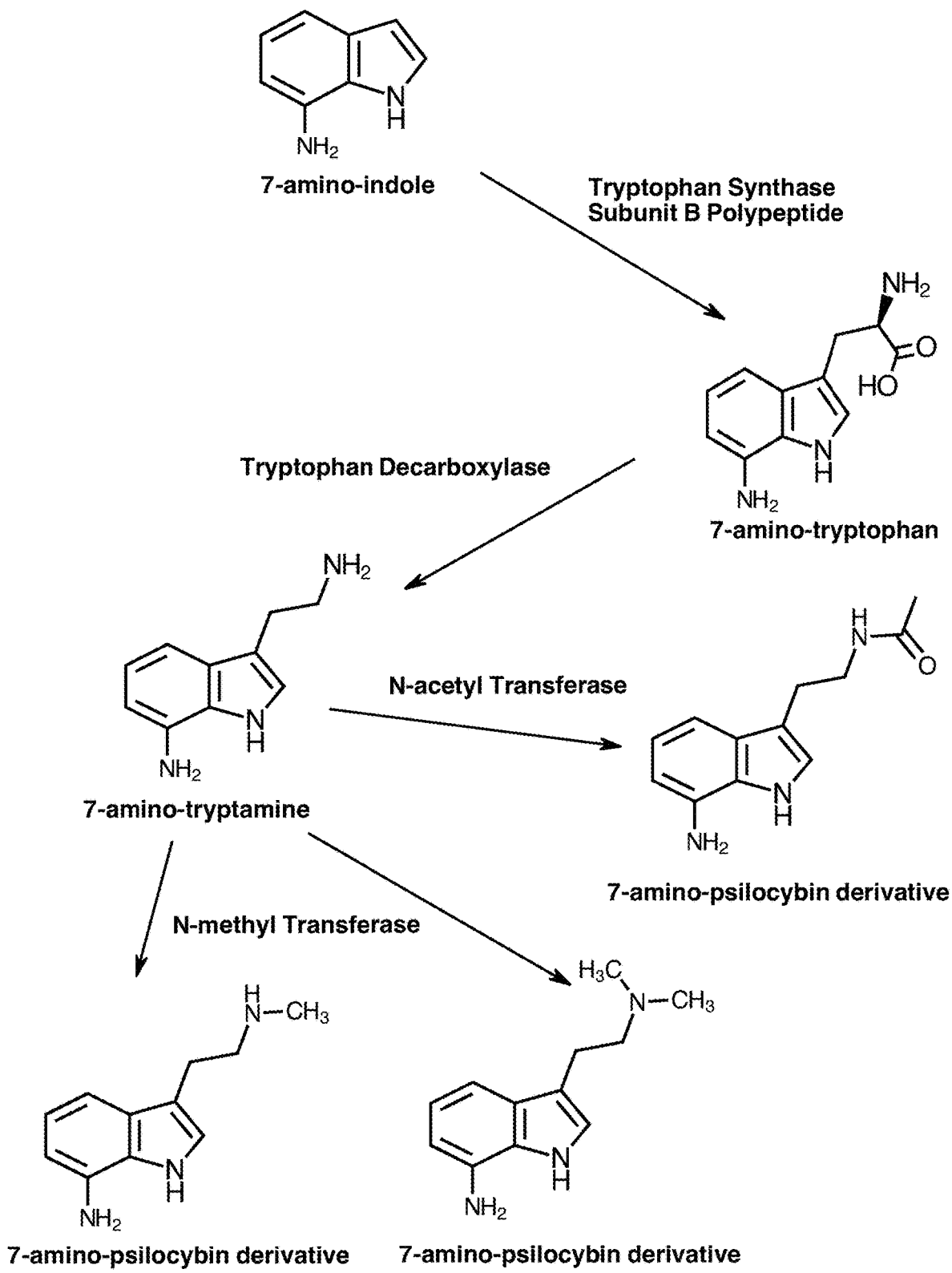

Referring next to FIG. 10, shown therein is an example biosynthetic pathway showing the conversion of example psilocybin precursor compounds to form an aminated psilocybin. Thus, as can be appreciated from FIG. 10, various psilocybin precursor compounds may be selected and prepared in aminated form, in conjunction with a psilocybin biosynthetic enzyme complement. Thus, by way of example, aminated tryptophan (e.g., 2-,5-, 6-, or 7-aminated tryptophan) may be selected and contacted with a host cell comprising a psilocybin biosynthetic enzyme complement comprising tryptophan decarboxylase and optionally N-acetyl transferase, and upon growth of the cells aminated psilocybin derivatives can be formed. By way of further example, aminated indole (e.g., 2-,5-, 6-, or 7-aminated indole) may be selected and contacted with a host cell comprising a psilocybin biosynthetic enzyme complement comprising tryptophan synthase subunit B polypeptide and tryptophan decarboxylase and optionally N-acetyl transferase, and upon growth of the cells aminated psilocybin derivatives can be formed In some embodiments, the psilocybin precursor compound can be an aminated psilocybin precursor compound which is exogenously supplied to a host cell, for example by inclusion in the host cell's growth medium. Thus, for example, referring to FIG. 10, it will be understood that in accordance herewith, for example, 7-amino-indole or 7-amino-tryptophan, may be included in the growth medium of a host cell comprising a psilocybin biosynthetic enzyme complement.

Referring to FIG. 10, in a further example embodiment, the aminated psilocybin precursor compound can be an aminated indole, having the formula (XXIX):

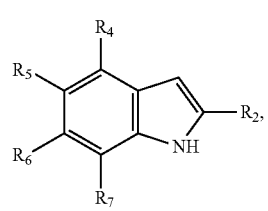

(XXIX)

wherein at least one of $R_2$, $R_4$, $R_5$, $R_6$ and $R_7$ is an amino group or N-substituted amino group, wherein $R_2$, $R_4$, $R_5$, $R_6$ and $R_7$ when they are not aminated are hydrogen atoms, an alkyl group or O-alkyl group, wherein $R_4$ when it is not aminated is a hydrogen atom, an alkyl, O-alkyl or O-aryl group, a hydroxy group, or a phosphate group, the psilocybin biosynthetic enzyme complement can comprise:

(i) a tryptophan synthase subunit B polypeptide encoded by a nucleic acid selected from:
(a) SEQ. ID NO: 8;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 9;
(f) a nucleic acid sequence that encodes a functional variant of any one of the amino acid sequences set forth in SEQ. ID NO: 9; and
(g) a nucleic acid sequence that hybridizes under stringent conditions to any one of the nucleic acid sequences set forth in (a), (b), (c), (d), (e) or (f); and (ii) a tryptophan decarboxylase encoded by a nucleic acid sequence selected from:
(a) SEQ. ID NO: 11;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 12;
(f) a nucleic acid sequence that encodes a functional variant of any one of the amino acid sequences set forth in SEQ. ID NO: 12; and
(g) a nucleic acid sequence that hybridizes under stringent conditions to any one of the nucleic acid sequences set forth in (a), (b), (c), (d), (e) or (f); and the formed aminated psilocybin derivative can be a compound having formula (XXVIII):

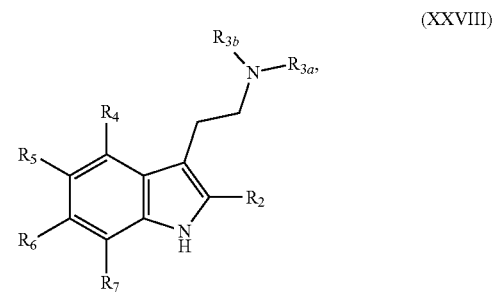

(XXVIII)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein at least one of $R_{3A}$ and $R_{3B}$ are hydrogen atom.

Referring further to FIG. 10, in another example embodiment, the aminated psilocybin precursor compound can be a compound, having the formula (XXVII):

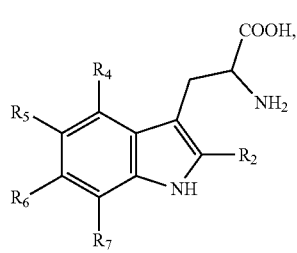

(XXVII)

wherein at least one of $R_2$, $R_4$, $R_5$, $R_6$ and $R_7$ is an amino group or an N-substituted amino group, wherein $R_2$, $R_4$, $R_5$, $R_6$ and $R_7$ when they are not aminated are hydrogen atoms, an alkyl group or O-alkyl group, wherein $R_4$ when it is not aminated is a hydrogen atom, an alkyl group or O-alkyl group, a hydroxy group, or a phosphate group;

the psilocybin biosynthetic enzyme complement can comprise:

a tryptophan decarboxylase encoded by a nucleic acid sequence selected from:
(a) SEQ. ID NO: 11;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 12;
(f) a nucleic acid sequence that encodes a functional variant of any one of the amino acid sequences set forth in SEQ. ID NO: 12; and
(g) a nucleic acid sequence that hybridizes under stringent conditions to any one of the nucleic acid sequences set forth in (a), (b), (c), (d), (e) or (f); and the formed aminated psilocybin derivative can be a compound having formula (XXVIII):

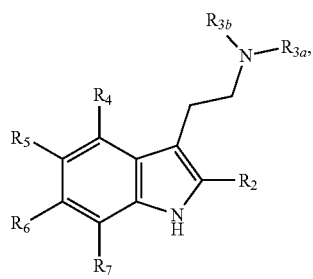

(XXVIII)

wherein at least one of $R_2$, $R_4$, $R_5$, $R_6$, or $R_7$ is an amino group or N-substituted amino group, and wherein each non-aminated $R_2$, $R_5$, $R_6$, or $R_7$ is a hydrogen atom, an alkyl group or O-alkyl group, wherein $R_4$ when it is not aminated is a hydrogen atom, an alkyl group or O-alkyl group, a hydroxy group, or a phosphate group, and wherein at least one of $R_{3A}$ and $R_{3B}$ are hydrogen atom.

In some embodiments, in formula (XXVIII) $R_{3A}$ and $R_{3B}$ are each a hydrogen atom.

Referring again to FIG. 10, the psilocybin biosynthetic enzyme complement can, in addition to the aforementioned tryptophan decarboxylase and tryptophan synthase subunit B polypeptide further comprise an N-acetyl transferase.

In at least one embodiment, in an aspect, the N-acetyl transferase can be an enzyme encoded by a nucleic acid sequence selected from:
(a) SEQ. ID NO: 4;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 5;
(f) a nucleic acid sequence that encodes a functional variant of any one of the amino acid sequences set forth in SEQ. ID NO: 5; and
(g) a nucleic acid sequence that hybridizes under stringent conditions to any one of the nucleic acid sequences set forth in (a), (b), (c), (d), (e) or (f).

In at least one embodiment, in an aspect, the formed aminated psilocybin compound can have the formula (XXX):

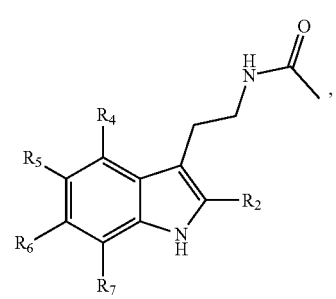

(XXX)

wherein at least one of $R_2$, $R_4$, $R_5$, $R_6$ or $R_7$ is an amino group or N-substituted amino group, wherein each non-aminated $R_2$, $R_5$, $R_6$, or $R_7$ is a hydrogen atom, an alkyl group or O-alkyl group, wherein $R_4$ when it is not aminated is a phosphate group, a hydrogen atom or an alkyl group or O-alkyl group.

Referring again to FIG. 10, the psilocybin biosynthetic enzyme complement can, in addition to the aforementioned tryptophan decarboxylase and tryptophan synthase subunit B polypeptide further comprise an N-methyl transferase.

In at least one embodiment, in an aspect, the N-methyl transferase can be an enzyme encoded by a nucleic acid sequence selected from:
(a) SEQ. ID NO: 13;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ. ID NO: 14;

(f) a nucleic acid sequence that encodes a functional variant of the amino acid sequence set forth in SEQ. ID NO: 14; and (g) a nucleic acid sequence that hybridizes under stringent conditions to any one of the nucleic acid sequences set forth in (a), (b), (c), (d), (e) or (f).

In at least one embodiment, in an aspect, the formed aminated psilocybin compound can have the chemical formula (XXXIII):

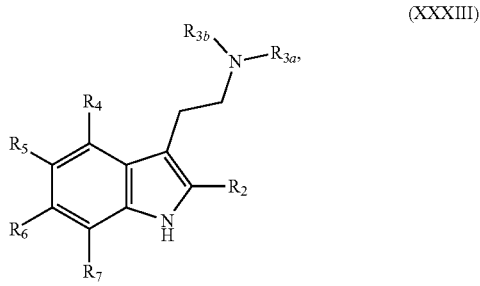

(XXXIII)

wherein at least one of $R_2$, $R_4$, $R_5$, $R_6$ or $R_7$ is an amino group or substituted amino group, wherein each non-aminated $R_2$, $R_5$, $R_6$, or $R_7$ is a hydrogen atom, or an alkyl group or O-alkyl group, wherein $R_4$ when it is not aminated is a phosphate group, a hydrogen atom or an alkyl group or O-alkyl group, and wherein at least one of $R_{3a}$ and $R_{3b}$ is an amino group, and wherein a non-aminated $R_{3a}$ and $R_{3b}$ is a hydrogen atom.

It will be clear to those of skill in the art that a significant variety of different aminated psilocybin precursor compounds may be selected. FIG. 10 in this respect provides guidance and allows a person of skill in the art to select appropriate psilocybin precursor compounds and a matching a psilocybin biosynthetic enzyme complement.

Upon production by the host cells of the aminated psilocybin compounds in accordance with the methods of the present disclosure, the aminated psilocybin compounds may be extracted from the host cell suspension, and separated from other constituents within the host cell suspension, such as media constituents and cellular debris. Separation techniques will be known to those of skill in the art and include, for example, solvent extraction (e.g., butane, chloroform, ethanol), column chromatography based techniques, high-performance liquid chromatography (HPLC), for example, and/or countercurrent separation (CCS) based systems. The recovered aminated psilocybin compounds may be obtained in a more or less pure form, for example, a preparation of aminated psilocybin compounds of at least about 60% (w/w), about 70% (w/w), about 80% (w/w), about 90% (w/w), about 95% (w/w), about 96% (w/w), about 97% (w/w), about 98% (w/w) or about 99% (w/w) purity may be obtained. Thus, in this manner, aminated psilocybin derivatives in more or less pure form may be prepared.

Similarly, other methods of making the aminated psilocybin compounds that may be used in accordance herewith may yield preparations of aminated compounds of at least about 60% (w/w), about 70% (w/w), about 80% (w/w), about 90% (w/w), about 95% (w/w), about 96% (w/w), about 97% (w/w), about 98% (w/w), or about 99% (w/w) purity.

It will now be clear form the foregoing that novel aminated psilocybin derivatives are disclosed herein. The aminated psilocybin compounds may be formulated for use as a pharmaceutical drug or recreational drug. The aminated psilocybin compounds may also be used as a feedstock to produce other psilocybin derivatives.

Hereinafter are provided examples of specific implementations for performing the methods of the present disclosure, as well as implementations representing the compositions of the present disclosure. The examples are provided for illustrative purposes only, and are not intended to limit the scope of the present disclosure in any way.

Summary of Sequences

SEQ. ID NO: 1 sets forth a nucleic acid sequence of pCDM4 vector.

SEQ. ID NO: 2 sets forth a nucleic acid sequence encoding a synthetic FLAG epitope tag polypeptide.

SEQ. ID NO: 3 sets forth deduced amino acid sequence of a synthetic FLAG epitope tag polypeptide.

SEQ. ID NO: 4 sets forth a nucleic acid sequence encoding a *Streptomyces griseofuscus* PsmF N-acetyltransferase polypeptide.

SEQ. ID NO: 5 sets forth a deduced amino acid sequence of a *Streptomyces griseofuscus* PsmF N-acetyltransferase polypeptide.

SEQ. ID NO: 6 sets forth a nucleic acid sequence encoding a synthetic V5 epitope tag polypeptide.

SEQ. ID NO: 7 sets forth deduced amino acid sequence of a synthetic V5 epitope tag polypeptide.

SEQ. ID NO: 8 sets forth a nucleic acid sequence encoding a mutated *Thermotoga maritima* TmTrpB-2F3 tryptophan synthase subunit B polypeptide.

SEQ. ID NO: 9 sets forth a deduced amino acid sequence of a mutated *Thermotoga maritima* TmTrpB-2F3 tryptophan synthase subunit B polypeptide.

SEQ. ID NO: 10 sets forth a nucleic acid sequence of pETM6-H10 vector

SEQ. ID NO: 11 sets forth a nucleic acid sequence encoding a *Bacillus atrophaeus* BaTDC tryptophan decarboxylase polypeptide.

SEQ. ID NO: 12 sets forth a deduced amino acid sequence of a *Bacillus atrophaeus* BaTDC tryptophan decarboxylase polypeptide.

SEQ. ID NO: 13 sets forth an *Escherichia coli* codon optimized nucleic acid sequence encoding a *Rhinella marina* N-methyltransferase polypeptide.

SEQ. ID NO: 14 sets forth a deduced amino acid sequence of a *Rhinella marina* N-methyltransferase polypeptide.

SEQUENCES

SEQ. ID NO: 1
GCTAACAGCGCGATTTGCTGGTGACCCAATGCGACCAGATGCTCCACGCCCAGTCGCGT
ACCGTCTTCATGGGAGAAAATAATACTGTTGATGGGTGTCTGGTCAGAGACATCAAGAA
ATAACGCCGGAACATTAGTGCAGGCAGCTTCCACAGCAATGGCATCCTGGTCATCCAGC
GGATAGTTAATGATCAGCCCACTGACGCGTTGCGCGAGAAGATTGTGCACCGCCGCTTT
ACAGGCTTCGACGCCGCTTCGTTCTACCATCGACACCACCACGCTGGCACCCAGTTGAT
CGGCGCGAGATTTAATCGCCGCGACAATTTGCGACGGCGCGTGCAGGGCCAGACTGGAG

| SEQUENCES |
|---|
| GTGGCAACGCCAATCAGCAACGACTGTTTGCCCGCCAGTTGTTGTGCCACGCGGTTGGG
AATGTAATTCAGCTCCGCCATCGCCGCTTCCACTTTTTCCCGCGTTTTCGCAGAAACGT
GGCTGGCCTGGTTCACCACGCGGGAAACGGTCTGATAAGGACCACCGGCATACTCTGCG
ACATCGTATAACGTTACTGGTTTCACATTCACCACCCTGAATTGACTCTCTTCCGGGCG
CTATCATGCCATACCGCGAAAGGTTTTGCGCCATTCGATGGTGTCCGGGATCTCGACGC
TCTCCCTTATGCGACTCCTGCATTAGGAAGCAGCCCAGTAGTAGGTTGAGGCCGTTGAG
CACCGCCGCCGCAAGGAATGGTGCATGCAAGGAGATGGCGCCCAACAGTCCCCCGGCCA
CGGGGCCTGCCACCCATACCCACGCCGAAACAAGCGCTCATGAGCCCGAAGTGGCGAGCC
CGATCTTCCCCATCGGTGATGTCGGCGATATAGGCGCCAGCAACCGCACCTGTGGCGCC
GGTGATGCCGGCCACGATGCGTCCGGCGTAGCCTAGGATCGAGATCGATCTCGATCCCG
CGAAATTAATACGACTCACTATAGGGGAATTGTGAGCGGATAACAATTCCCCTCTAGAA
ATAATTTTGTTTAACTTTAAGAAGGAGATATACATATGGCAGATCTCAATTGGATATCG
GCCGGCCACGCGATCGCTGACGTCGGTACCCTCGAGTCTGGTAAAGAAACCGCTGCTGC
GAAATTTGAACGCCAGCACATGGACTCGTCTACTAGTCGCAGCTTAATTAACCTAAACT
GCTGCCACCGCTGAGCAATAACTAGCATAACCCTTGGGGCCTCTAAACGGGTCTTGAG
GGGTTTTTTGCTAGCGAAAGGAGGAGTCGACACTGCTTCCGGTAGTCAATAAACCGGTA
AACCAGCAATAGACATAAGCGGCTATTTAACGACCCTGCCCTGAACCGACGACCGGGTC
ATCGTGGCCGGATCTTGCGGCCCCTCGGCTTGAACGAATTGTTAGACATTATTTGCCGA
CTACCTTGGTGATCTCGCCTTTCACGTAGTGGACAAATTCTTCCAACTGATCTGCGCGC
GAGGCCAAGCGATCTTCTTGTCCAAGATAAGCCTGTCTAGCTTCAAGTATGACGGG
CTGATACTGGGCCGGCAGGCGCTCCATTGCCCAGTCGGCAGCGACATCCTTCGGCGCGA
TTTTGCCGGTTACTGCGCTGTACCAAATGCGGGACAACGTAAGCACTACATTTCGCTCA
TCGCCAGCCCAGTCGGGCGGCGAGTTCCATAGCGTTAAGGTTTCATTTAGCGCCTCAAA
TAGATCCTGTTCAGGAACCGGATCAAAGAGTTCCTCCGCCGCTGGACCTACCAAGGCAA
CGCTATGTTCTCTTGCTTTTGTCAGCAAGATAGCCAGATCAATGTCGATCGTGGCTGGC
TCGAAGATACCTGCAAGAATGTCATTGCGCTGCCATTCTCCAAATTGCAGTTCGCGCTT
AGCTGGATAACGCCACGGAATGATGTCGTCGTGCACAACAATGGTGACTTCTACAGCGC
GGAGAATCTCGCTCTCTCCAGGGGAAGCCGAAGTTTCCAAAAGGTCGTTGATCAAAGCT
CGCCGCGTTGTTTCATCAAGCCTTACGGTCACCGTAACCAGCAAATCAATATCACTGTG
TGGCTTCAGGCCGCCATCCACTGCGGAGCCGTACAAATGTACGGCCAGCAACGTCGGTT
CGAGATGGCGCTCGATGACGCCAACTACCTCTGATAGTTGAGTCGATACTTCGGCGATC
ACCGCTTCCCTCATACTCTTCCTTTTTCAATATTATTGAAGCATTTATCAGGGTTATTG
TCTCATGAGCGGATACATATTTGAATGTATTTAGAAAAATAAACAAATAGCCAGCTCAC
TCGGTCGCTACGCTCCGGGCGTGAGACTGCGGCGGGCGCTGCGGACACATACAAAGTTA
CCCACAGATTCCGTGGATAAGCAGGGGACTAACATGTGAGGCAAAACAGCAGGGCCGCG
CCGGTGGCGTTTTTCCATAGGCTCCGCCCTCCTGCCAGAGTTCACATAAACAGACGCTT
TTCCGGTGCATCTGTGGGAGCCGTGAGGCTCAACCATGAATCTGACAGTACGGGCGAAA
CCCGACAGGACTTAAAGATCCCCACCGTTTCCGGCGGGTCGCTCCCTCTTGCGCTCTCC
TGTTCCGACCCTGCCGTTTACCGGATACCTGTTCCGCCTTTCTCCCTTACGGGAAGTGT
GGCGCTTTCTCATAGCTCACGCACTGGTATCTCGGCTCGGTGTAGGTCGTTCGCTCCAA
GCTGGGCTGTAAGCAAGAACTCCCCGTTCAGCCCGACTGCTGCGCCTTATCCGGTAACT
GTTCACTTGAGTCCAACCCGGAAAAGCACGGTAAAACGCCACTGGCAGCAGCCATTGGT
AACTGGGAGTTCGCAGAGGATTTGTTTAGCTAAACACGCGGTTGCTCTTGAAGTGTGCG
CCAAAGTCCGGCTACACTGGAAGGACAGATTTGGTTGCTGTGCTCTGCGAAAGCCAGTT
ACCACGGTTAAGCAGTTCCCCAACTGACTTAACCTTCGATCAAACCACCTCCCCAGGTG
GTTTTTTCGTTTACAGGGCAAAAGATTACGCGCAGAAAAAAAGGATCTCAAGAAGATCC
TTTGATCTTTTCTACTGAACCGCTCTAGATTTCAGTGCAATTTATCTCTTCAAATGTAG
CACCTGAAGTCAGCCCCATACGATATAAGTTGTAATTCTCATGTTAGTCATGCCCCGCG
CCCACCGGAAGGAGCTGACTGGGTTGAAGGCTCTCAAGGGCATCGGTCGAGATCCCGGT
GCCTAATGAGTGAGCTAACTTACATTAATTGCGTTGCGCTCACTGCCCGCTTTCCAGTC
GGGAAACCTGTCGTGCCAGCTGCATTAATGAATCGGCCAACGCGCGGGGAGAGGCGGTT
TGCGTATTGGGCGCCAGGGTGGTTTTTCTTTTCACCAGTGAGACGGGCAACAGCTGATT
GCCCTTCACCGCCTGGCCCTGAGAGAGTTGCAGCAAGCGGTCCACGCTGGTTTGCCCCA
GCAGGCGAAAATCCTGTTTGATGGTGGTTAACGGCGGGATATAACATGAGCTGTCTTCG
GTATCGTCGTATCCCACTACCGAGATGTCCGCACCAACGCGCAGCCCGGACTCGGTAAT
GGCGCGCATTGCGCCCAGCGCCATCTGATCGTTGGCAACCAGCATCGCAGTGGGAACGA
TGCCCTCATTCAGCATTTGCATGGTTTGTTGAAAACCGGACATGGCACTCCAGTCGCCT
TCCCGTTCCGCTATCGGCTGAATTTGATTGCGAGTGAGATATTTATGCCAGCCAGCCAG
ACGCAGACGCGCCGAGACAGAACTTAATGGGCCC |

SEQ. ID NO: 2
GACTACAAGGATGACGATGACAAA

SEQ. ID NO: 3
DYKDDDDK

SEQ. ID NO: 4
ATGAACACCTTCAGAACAGCCACTGCCAGAGACATACCTGATGTAGCAGCAACTCTTAC
GGAAGCCTTCGCAACTGATCCACCCACGCAGTGGGTGTTCCCCGACGGTACTGCCGCCG
TCAGCAGGTTCTTTACACATGTTGCAGATAGGGTTCACACGGCCGGTGGTATTGTTGAG
CTACTACCAGACAGAGCCGCCATGATTGCATTGCCACCACACGTGAGGCTGCCAGGAGA
AGCTGCCGACGGAAGGCAGGCGGAAATTCAGAGAAGGCTGGCAGACAGGCACCCGCTGA
CACCTCACTACTACCTGCTGTTTTACGGAGTTAGAACGGCACACCAGGGTTCGGGATTG
GGCGGAAGAATGCTGGCCAGATTAACTAGCAGAGCTGATAGGGACAGGGTGGTACATA
TACTGAGGCATCCACCTGGCGTGGCGCTAGACTGATGCTGAGACATGGATTCCATGCTA
CAAGGCCACTAAGATTGCCAGATGGACCCAGCATGTTTCCACTTTGGAGAGATCCAATC
CATGATCATTCTGATTAG

| SEQUENCES |
|---|

SEQ. ID NO: 5
```
MNTFRTATARDIPDVAATLTEAFATDPPTQWVFPDGTAAVSRFFTHVADRVHTAGGIVE
LLPDRAAMIALPPHVRLPGEAADGRQAEIQRRLADRHPLTPHYYLLFYGVRTAHQGSGL
GGRMLARLTSRADRDRVGTYTEASTWRGARLMLRHGFHATRPLRLPDGPSMFPLWRDPI
HDHSD
```

SEQ. ID NO: 6
```
GGTAAGCCAATTCCAAATCCTTTGTTGGGTTTGGACTCCACC
```

SEQ. ID NO: 7
```
GKPIPNPLLGLDST
```

SEQ. ID NO: 8
```
ATGAAAGGATATTTCGGACCATACGGTGGCCAGTACGTACCAGAAATATTAATGGGTGC
CTTAGAGGAGTTAGAGGCAGCATACGAGGAGATTATGAAGGATGAGAGCTTCTGGAAGG
AGTTCAACGATCTACTGAGGGATTACGCAGGCAGACCAACGCCATTGTACTTTGCCAGG
AGATTGTCTGAGAAGTACGGCGCCCGTGTTTACTTGAAGCGTGAGGATCTGCTGCACAC
TGGAGCACACAAGATAAATAACGCTATCGGACAGGTTTTATTGGCCAAATTAATGGGGA
AGACACGTATCATAGCCGAGACGGGAGCTGGGCAGCATGGAGTCGCTACTGCTACCGCT
GCTGCCCTGTTCGGAATGGAATGTGTGATCTACATGGGTGAAGAGGACACAATCAGACA
GAAGTTGAACGTGGAGCGTATGAAATTATTAGGGGCTAAAGTTGTCCCTGTTAAGTCTG
GCAGTAGGACCTTGAAGGATGCGATAGACGAGGCTTTGAGAGACTGGATTACTAATTTA
CAGACAACATATTATGTTATCGGATCTGTTGTTGGTCCCCACCCTTACCCAATTATCGT
AAGGAATTTCCAGAAGGTTATCGGTGAGGAGACCAAGAAGCAAATACCAGAAAGGGAAG
GTCGTTTGCCAGACTATATAGTTGCCTGCGTAGGCGGCGGTAGCAATGCCGCAGGTATA
TTTTACCCATTCATAGACTCTGGAGTAAAGCTGATAGGTGTTGAGGCAGGTGGCGAGGG
ATTGGAGACAGGTAAACACGCAGCCTCGTTATTAAAGGGTAAAATTGGCTATTTACATG
GATCGAAGACCTTTGTTCTACAAGATGACTGGGGTCAAGTCCAAGTGAGCCATTCGGTG
TCAGCTGGTCTTGACTATTCAGGAGTAGGACCTGAGCATGCTTATTGGAGAGAGACAGG
GAAGGTTCTGTACGACGCAGTGACTGACGAAGAGGCTTTGGACGCATTTATAGAGTTAT
CAAGACTAGAGGGCATTATACCCGCTTTAGAGTCATCGCATGCTCTACATATTTGAAG
AAGATAAATATAAAAGGTAAGGTTGTGGTGGTCAACCTATCAGGGAGAGGGGATAAAGA
CCTGGAGTCAGTCTTAAACCATCCATACGTGAGAGAAAGAATTAGATGA
```

SEQ. ID NO: 9
```
MKGYFGPYGGQYVPEILMGALEELEAAYEEIMKDESFWKEFNDLLRDYAGRPTPLYFAR
RLSEKYGARVYLKREDLLHTGAHKINNAIGQVLLAKLMGKTRIIAETGEGQHGVATATA
AALFGMECVIYMGEEDTIRQKLNVERMKLLGAKVVPVKSGSRTLKDAIDEALRDWITNL
QTTYYVIGSVVGPHPYPIIVRNFQKVIGEETKKQIPEKEGRLPDYIVACVGGGSNAAGI
FYPFIDSGVKLIGVEAGGEGLETGKHAASLLKGKIGYLHGSKTFVLQDDWGQVQVSHSV
SAGLDYSGVGPEHAYWRETGKVLYDAVTDEEALDAFIELSRLEGIIPALESSHALAYLK
KINIKGKVVVVNLSGRGDKDLESVLNHPYVRERIR
```

SEQ. ID NO: 10
```
GAAGAATTGTGAGCGGATAACAATTCCCCTCTAGAAATAATTTTGTTTAACTTTAAGAA
GGAGATATACATATGGCAGATCTCAATTGGATATCGGCCGGCCACGCGATCGCTGACGT
CGGTACCCTCGAGTCTGGTAAAGAAACCGCTGCTGCGAAATTTGAACGCCAGCACATGG
ACTCGTCTACTAGTCGCAGCTTAATTAACCTAAACTGCTGCCACCGCTGAGCAATAACT
AGCATAACCCCTTGGGGCCTCTAAACGGGTCTTGAGGGGTTTTTGCTAGCGAAAGGAG
GAGTCGACTATATCCGGATTGGCGAATGGGACGCGCCCTGTAGCGGCGCATTAAGCGCG
GCGGGTGTGGTGGTTACGCGCAGCGTGACCGCTACACTTGCCAGCGCCCTAGCGCCCGC
TCCTTTCGCTTTCTTCCCTTCCTTTCTCGCCACGTTCGCCGGCTTTCCCCGTCAAGCTC
TAAATCGGGGGCTCCCTTTAGGGTTCCGATTTAGTGCTTTACGGCACCTCGACCCCAAA
AAACTTGATTAGGGTGATGGTTCACGTAGTGGGCCATCGCCCTGATAGACGGTTTTTCG
CCCTTTGACGTTGGAGTCCACGTTCTTTAATAGTGGACTCTTGTTCCAAACTGGAACAA
CACTCAACCCTATCTCGGTCTATTCTTTTGATTTATAAGGGATTTTGCCGATTTCGGCC
TATTGGTTAAAAAATGAGCTGATTTAACAAAAATTTAACGCGAATTTTAACAAAATATT
AACGTTTACAATTTCTGGCGGCACGATGGCATGAGATTATCAAAAAGGATCTTCACCTA
GATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTT
ACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTA
TCCGCCTCCATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACGCTCGTCGT
TTGGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAGTT
GGCCGCAGTGTTATCACTCATGGTTATGGCAGCACTGCATAATTCTCTTACTGTCATGC
CATCCGTAAGATGCTTTTCTGTGACTGGTGAGTACTCAACCAAGTCATTCTGAGAATAG
TGTATGCGGCGACCGAGTTGCTCTTGCCCGGCGTCAATACGGGATAATACCGCGCCACA
TAGCAGAACTTTAAAAGTGCTCATCATTGGAAAACGTTCTTCGGGGCGAAAACTCTCAA
GGATCTTACCGCTGTTGAGATCCAGTTCGATGTAACCCACTCGTGCACCCAACTGATCT
TCAGCATCTTTTACTTTCACCAGCGTTTCTGGGTGAGCAAAAACAGGAAGGCAAAATGC
CGCAAAAAAGGGAATAAGGGCGACACGGAAATGTTGAATACTCATACTCTTCCTTTTTC
AATCATGATTGAAGCATTTATCAGGGTTATTGTCTCATGAGCGGATACATATTTGAATG
TATTTAGAAAAATAAACAAATAGGTCATGACCAAAATCCCTTAACGTGAGTTTTCGTTC
```

| SEQUENCES |
|---|
| CACTGAGCGTCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGC
ACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGG
ACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCG
ATTTTTGTGATGCTCGTCAGGGGGCGGAGCCTATGGAAAAACGCCAGCAACGCGGCCT
TTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCCTGATGCGGT
ATTTTCTCCTTACGCATCTGTGCGGTATTTCACACCGCATATATGGTGCACTCTCAGTA
CAATCTGCTCTGATGCCGCATAGTTAAGCCAGTATACACTCCGCTATCGCTACGTGACT
GGGTCATGGCTGCGCCCCGACACCCGCCAACACCCGCTGACGCGCCCTGACGGGCTTGT
CTGCTCCCGGCATCCGCTTACAGACAAGCTGTGACCGTCTCCGGGAGCTGCATGTGTCA
GAGGTTTTCACCGTCATCACCGAAACGCGCGAGGCAGCTGCGGTAAAGCTCATCAGCGT
GGTCGTGAAGCGATTCACAGATGTCTGCCTGTTCATCCGCGTCCAGCTCGTTGAGTTTC
TCCAGAAGCGTTAATGTCTGGCTTCTGATAAAGCGGGCCATGTTAAGGGCGGTTTTTTC
CTGTTTGGTCACTGATGCCTCCGTGTAAGGGGGATTTCTGTTCATGGGGGTAATGATAC
CGATGAAACGAGAGAGGATGCTCACGATACGGGTTACTGATGATGAACATGCCCGGTTA
CTGGAACGTTGTGAGGGTAAACAACTGGCGGTATGGATGCGGCGGGACCAGAGAAAAT
CACTCAGGGTCAATGCCAGCGCTTCGTTAATACAGATGTAGGTGTTCCACAGGGTAGCC
AGCAGCATCCTGCGATGCAGATCCGGAACATAATGGTGCAGGGCGCTGACTTCCGCGTT
TCCAGACTTTACGAAACACGGAAACCGAAGACCATTCATGTTGTTGCTCAGGTCGCAGA
CGTTTTGCAGCAGCAGTCGCTTCACGTTCGCTCGCGTATCGTGATTCATTCTGCTAAC
CAGTAAGGCAACCCCGCCAGCCTAGCCGGGTCCTCAACGACAGGAGCACGATCATGCTA
GTCATGCCCGCGCCCACCGGAAGGAGCTGACTGGGTTGAAGGCTCTCAAGGGCATCGG
TCGAGATCCCGGTGCCTAATGAGTGAGCTAACTTACATTAATTGCGTTGCGCTCACTGC
CCGCTTTCCAGTCGGGAAACCTGTCGTGCCAGCTGCATTAATGAATCGGCCAACGCGCG
GGGAGAGGCGGTTTGCGTATTGGGCGCCAGGGTGGTTTTTCTTTTCACCAGTGAGACGG
GCAACAGCTGATTGCCCTTCACCGCCTGGCCCTGAGAGAGTTGCAGCAAGCGGTCCACG
CTGGTTTGCCCCAGCAGGCGAAAATCCTGTTTGATGGTGGTTAACGGCGGGATATAACA
TGAGCTGTCTTCGGTATCGTCGTATCCCACTACCGAGATGTCCGCACCAACGCGCAGCC
CGGACTCGGTAATGGCGCGCATTGCGCCCAGCGCCATCTGATCGTTGGCAACCAGCATC
GCAGTGGGAACGATGCCCTCATTCAGCATTTGCATGGTTTGTTGAAAACCGGACATGGC
ACTCCAGTCGCCTTCCCGTTCCGCTATCGGCTGAATTTGATTGCGAGTGAGATATTTAT
GCCAGCCAGCCAGACGCAGACGCGCCGAGACAGAACTTAATGGGCCCGCTAACAGCGCG
ATTTGCTGGTGACCCAATGCGACCAGATGCTCCACGCCCAGTCGCGTACCGTCTTCATG
GGAGAAAATAATACTGTTGATGGGTGTCTGGTCAGAGACATCAAGAAATAACGCCGGAA
CATTAGTGCAGGCAGCTTCCACAGCAATGGCATCCTGGTCATCCAGCGGATAGTTAATG
ATCAGCCCACTGACGCGTTGCGCGAGAAGATTGTGCACCGCCGCTTTACAGGCTTCGAC
GCCGCTTCGTTCTACCATCGACACCACCACGCTGGCACCCAGTTGATCGGCGCGAGATT
TAATCGCCGCGACAATTTGCGACGGCGCGTGCAGGGCCAGACTGGAGGTGGCAACGCCA
ATCAGCAACGACTGTTTGCCCGCCAGTTGTTGTGCCACGCGGTTGGGAATGTAATTCAG
CTCCGCCATCGCCGCTTCCACTTTTTCCCGCGTTTTCGCAGAAACGTGGCTGGCCTGGT
TCACCACGCGGGAAACGGTCTGATAAGAGACACCGGCATACTCTGCGACATCGTATAAC
GTTACTGGTTTCACATTCACCACCCTGAATTGACTCTCTTCCGGGCGCTATCATGCCAT
ACCGCGAAAGGTTTTGCGCCATTCGATGGTGTCCGGGATCTCGACGCTCTCCCTTATGC
GACTCCTGCATTAGGAAGCAGCCCAGTAGTAGGTTGAGGCCGTTGAGCACCGCCGCCGC
AAGGAATGGTGCATGCAAGGAGATGGCGCCCAACAGTCCCCGGCCACGGGGCCTGCCA
CCATACCCACGCCGAAACAAGCGCTCATGAGCCCGAAGTGGCGAGCCCGATCTTCCCCA
TCGGTGATGTCGGCGATATAGGCGCCAGCAACCGCACCTGTGGCGCCGGTGATGCCGGC
CACGATGCGTCCGGCGTAGCCTAGGATCGAGATCGATCTCGATCCCGCGAAATTAATAC
GACTCACTACG |

SEQ. ID NO: 11
ATGATGTCTGAAAATTTGCAATTGTCAGCTGAAGAAATGAGACAATTGGGTTACCAAGC
AGTTGATTTGATCATCGATCACATGAACCATTTGAAGTCTAAGCCAGTTTCAGAAACAA
TCGATTCTGATATCTTGAGAAATAAGTTGACTGAATCTATCCCAGAAAATGGTTCAGAT
CCAAAGGAATTGTTGCATTTCTTGAACAGAAACGTTTTTAATCAAATTACACATGTTGA
TCATCCACATTTCTTGGCTTTTGTTCCAGGTCCAAATAATTACGTTGGTGTTGTTGCAG
ATTTCTTGGCTTCTGGTTTTAATGTTTTTCCAACTGCATGGATTGCTGGTGCAGGTGCT
GAACAAATCGAATTGACTACAATTAATTGGTTGAAATCTATGTTGGGTTTTCCAGATTC
AGCTGAAGGTTTATTTGTTTCTGGTGGTTCAATGGCAAATTTGACAGCTTTGACTGTTG
CAAGACAGGCTAAGTTGAACAACGATATCGAAATGCTGTTGTTTACTTCTCTGATCAA
ACACATTTCTCAGTTGATAGAGCATTGAAGGTTTTAGGTTTTAAACATCATCAAATCTG
TAGAATCGAAACAGATGAACATTTGAGAATCTCTGTTTCAGCTTTGAAGAAACAAATTA
AAGAAGATAGAACTAAGGGTAAAAAGCCATTCTGTGTTATTGCAAATGCTGGTACTACA
AATTGTGGTGCTGTTGATTCTTTGAACGAATTAGCAGATTTGTGTAACGATGAAGATGT
TTGGTTGCATGCTGATGGTTCTTATGGTGCTCCAGCTATCTTGTCTGAAAAGGGTTCAG
CTATGTTGCAAGGTATTCATAGAGCAGATTCTTTGACTTTAGATCCACATAAGTGGTTG
TTCCAACCATACGATGTGGTTGTGTTTTGATCAGAAACTCTCAATATTGTCAAAGAC
TTTTAGAATGATGCCAGAATACATCAAGGATTCAGAAACTAACGTTGAAGGTGAAATTA
ATTTCGGTGAATGTGGTATCGAATTGTCAAGAAGATTCAGAGCTTTGAAGGTTTGGTTG

| SEQUENCES |
|---|
| TCTTTTAAAGTTTTCGGTGTTGCTGCTTTTAGACAAGCAATCGATCATGGTATCATGTT<br>AGCAGAACAAGTTGAAGCATTTTTGGGTAAAGCAAAAGATTGGGAAGTTGTTACACCAG<br>CTCAATTGGGTATCGTTACTTTTAGATACATTCCATCTGAATTGGCATCAACAGATACT<br>ATTAATGAAATTAATAAGAAATTGGTTAAGGAAATCACACATAGAGGTTTCGCTATGTT<br>ATCTACTACAGAATTGAAGGAAAAGGTTGTTATTAGATTGTGTTCAATTAATCCAAGAA<br>CTACAACTGAAGAAATGTTGCAAATCATGATGAAGATTAAAGCATTGGCTGAAGAAGTT<br>TCTATTTCATACCCATGTGTTGCTGAATAA |
| SEQ. ID NO: 12 |
| MMSENLQLSAEEMRQLGYQAVDLIIDHMNHLKSKPVSETIDSDILRNKLTESIPENGSD<br>PKELLHFLNRNVFNQITHVDHPHFLAFVPGPNNYVGVVADFLASGFNVFPTAWIAGAGA<br>EQIELTTINWLKSMLGFPDSAEGLFVSGGSMANLTALTVARQAKLNNDIENAVVYFSDQ<br>THFSVDRALKVLGFKHHQICRIETDEHLRISVSALKKQIKEDRTKGKKPFCVIANAGTT<br>NCGAVDSLNELADLCNDEDVWLHADGSYGAPAILSEKGSAMLQGIHRADSLTLDPHKWL<br>FQPYDVGCVLIRNSQYLSKTFRMMPEYIKDSETNVEGEINFGECGIELSRRFRALKVWL<br>SFKVFGVAAFRQAIDHGIMLAEQVEAFLGKAKDWEVVTPAQLGIVTFRYIPSELASTDT<br>INEINKKLVKEITHRGFAMLSTTELKEKVVIRLCSINPRTTTEEMLQIMMKIKALAEEV<br>SISYPCVAE |
| SEQ. ID NO: 13 |
| ATGTTTGGTGTACAAGACACCCCGCAACATATATGCTACGAGCCTCAGCAGCGTAAGGT<br>CAGTGAGAGAACATCACGTAACAGATCTCGTTCTAAATCACTGGACCCGGACAGCTTGC<br>GCGAGAAAGGAAAGAAGACGCAACACCGTGAGGCGGATTGTTTCTTCGGTGAAGACAAC<br>CGGATGCGAAAACTCCTACTCTGCGCAAATGTACATTGACGAGTTCGACCCTGTACACTA<br>TTACCAAACCTATTATTCCTCAGGGAAGGGCGGCATTGCTCGTGAGTGGACAGATTTTG<br>CTTTGCAAAACTTGCATGAAACGTTCGGGCCTGGCGGGGTTAAAGGTGACATTCTTATT<br>GACTTCGGTGCTGGGCCGACAATATATCAGCTTCTGAGCGCATGTGAGGTTTTCAATAG<br>CATTATTACATCCGACTTTCTTGAGCAAAACCGCGAGCAACTTGAGAAATGGCTTCGAA<br>AGGACCCGGACGCCCTTGACTGGTCCCATTTCACGAAGTACGTTTGCGAGCTCGAAGGC<br>AACCGGGACAACTGGGAAAAGAAAGAGGAAACCCTGCGCCGAAAGGTTACCAAGGTGCT<br>TAAATGTGACGCACTGGCCGAGAAGCCTTTCGACGACGTGCCAATGCCAGAGGCTGACT<br>GTCTGATCTCATGCCTGTGTTTAGAGAACCCTTGTCAAGACCAGGAGGCTTACATTAAC<br>ATATTGAAGAAGTTAAAAGAGCTCTTGAAACCGGGCGGCCACATCATTATACAGTCCAT<br>ATTGAACTGCTCGTATTACCATATTGGCAATAGCTGCTTCTCACATTTGTCGTTAAGCA<br>AGGACGACGTGGAGAAATCGTTTAAGGAAGCTGGCTACGAAATCGTCAAATTGAAGGTT<br>CTTCCACGCTCAGTTATGTCGGAAATGGAAATCAGCGACTCAAATGGCTACTACTTCAT<br>CCACGCTCGGAAACCGCAAAAGGAGTAA |
| SEQ. ID NO: 14 |
| MFGVQDTPQHICYEPQQRKVSERTSRNRSRSKSLDPDSLREKGKKTQHREADCFFGEDN<br>RMENSYSAQMYIDEFDPVHYYQTYYSSGKGGIAREWTDFALQNLHETFGPGGVKGDILI<br>DFGAGPTIYQLLSACEVFNSIITSDFLEQNREQLEKWLRKDPDALDWSHFTKYVCELEG<br>NRDNWEKKEETLRRKVTKVLKCDALAEKPFDDVPMPEADCLISCLCLENPCQDQEAYIN<br>ILKKLKELLKPGGHIIIQSILNCSYYHIGNSCFSHLSLSKDDVEKSFKEAGYEIVKLKV<br>LPRSVMSEMEISDSNGYYFIHARKPQKE |

EXAMPLES

Example 1—Chemical Synthesis of a First, a Second and a Third Aminated Psilocybin Derivative Referring to FIG. 9D, shown therein is a 7-step synthesis for two 4-O-methyl-psilocybin derivatives respectively aminated at $C_5$ and $C_7$ from 4-methoxyindole.

The first step involved the regioselective 3-nitrovinylation of 4-methoxyindole (9D-1). Under argon, 4-methoxy indole (9D-1) (4000 mg, 27.18 mmol, 1.00 eq) and 1-(dimethylamino)-2-nitroethylene (3472 mg, 29.90 mmol, 1.10 eq) were dissolved in trifluoroacetic acid (20.8 mL, 272 mmol, 10.0 eq) and allowed to stir at room temperature for 3 hours until complete as determined by TLC (1:1 ethyl acetate-hexanes). The dark red solution was diluted with ethyl acetate (100 mL) and carefully poured over saturated sodium bicarbonate solution (200 mL). This biphasic mixture was then separated, and the aqueous phase extracted with ethyl acetate (4×100 mL). The combined organic extracts were washed with brine, dried with $MgSO_4$, and concentrated under reduced pressure to yield the crude product 9D-2 (5600 mg) that was used directly without any further purification.

The second step involved the conjugated reduction of the alkene functionality of compound 9D-2. To a solution of crude compound 9D-2 (5600 mg) in ethanol (50 mL) and THF (50 mL) under ambient air was added sodium borohydride (5141 mg, 136 mmol) in small portions, waiting for effervescence to decrease between additions. This mixture was allowed to stir at room temperature for 18 hours at which point reaction was complete as determined by TLC (1:1 ethyl acetate-hexanes). The reaction was quenched by pouring over ice-water (200 ml) and extracted with DCM (4×100 mL). The combined organic extracts were dried with $MgSO_4$ and concentrated under reduced pressure to yield the crude product as a brown solid. Purification by column chromatography on silica gel using a 10% to 50% ethyl acetate-hexanes gradient to yield compound 9D-3 as a white solid (1950 mg, 8.94 mg, 33% over 2 steps). $^1$H NMR (400 MHz, $CDCl_3$): δ (ppm)=8.02 (s, 1H), 7.15 (t, J=8.0 Hz, 1H), 7.00 (dd, J=8.3, 0.7 Hz, 1H), 6.94 (dd, J=2.5, 1.0 Hz, 1H), 6.55 (dd, J=7.8, 0.7 Hz, 1H), 4.76 (t, J=7.2 Hz, 2H), 3.97 (s, 3H), 3.57 (td, J=7.2, 0.8 Hz, 2H).

The third step involved the reduction of the nitro functionality of compound 3. Under argon in a flame-dried flask compound 9D-3 (800 mg, 3.63 mmol, 1.00 eq) was dissolved in anhydrous THF (20 mL) and cooled to 0° C. To this solution was added 1 M lithium aluminum hydride in THF (18.2 mL, 18.2 mmol, 5.00 eq), causing a colour change to yellow. The reaction mixture was heated to reflux for 2.5 hours, yielding a milky-white solution. After cooling to 0° C., the reaction was quenched with 10% water-THF (15 mL) and allowed to stir for 10 minutes. The precipitated white solids were filtered off and the filter-cake rinsed with THF (10 mL), dichloromethane (10 mL) and methanol (10 mL). The organic filtrate was dried with MgSO$_4$ and concentrated under reduced pressure to yield compound 9D-4 as an off-white solid (395 mg, 2.08 mmol, 57%). $^1$H NMR (400 MHz, CDCl$_3$): δ (ppm)=8.12 (s, 1H), 7.09 (t, J=7.9 Hz, 1H), 6.97 (d, J=8.1 Hz, 1H), 6.89 (d, J=2.2 Hz, 1H), 6.50 (d, J=7.8 Hz, 1H), 3.92 (s, 3H), 3.02 (s, 4H).

The fourth step involved the full protection of the side-chain amino group and the N1 of compound 9D-4. Under argon in a flame-dried flask, compound 9D-4 (245 mg, 1.29 mmol, 1.00 eq) was dissolved in anhydrous acetonitrile (10 mL). To this solution, di-tert-butyl dicarbonate (2811 mg, 12.9 mmol, 10.0 eq) and 4-dimethylaminopyridine (157 mg, 1.29 mmol, 1.00 eq) was added, and the reaction mixture allowed to stir at room temperature for 20 hours. Water (20 mL) was added, and the mixture was extracted with dichloromethane (4×30 mL). The combined organic extracts were washed with brine (25 mL), dried with MgSO$_4$, and concentrated under vacuum to yield the crude product as a dark red oil. Purification by column chromatography on silica gel using an 8% to 15% ethyl acetate-hexanes gradient yielded compound 9D-5 as an oily white solid (325 mg, 0.663 mmol, 51%). $^1$H NMR (400 MHz, CDCl$_3$): δ (ppm)=7.74 (d, J=8.4 Hz, 1H), 7.23-7.13 (m, 2H), 6.63 (d, J=7.9 Hz, 1H), 3.91 (m, 5H), 3.08 (ddd, J=7.5, 6.3, 1.0 Hz, 2H), 1.63 (s, 9H), 1.38 (s, 18H).

The fifth step involved the regioselective nitration of compound 9D-5. A flame-dried round-bottom flask was charged with compound 9D-5 (325 mg, 0.662 mmol, 1.00 eq), silver nitrate (124 mg, 0.729 mmol, 1.10 eq), and dry acetonitrile (2.5 mL), then cooled to 0° C. under argon atmosphere. Benzoyl chloride (102 mg, 0.729 mmol, 1.10 eq) was diluted with dry acetonitrile (0.5 mL) and added dropwise to the reaction mixture, which was then allowed to stir at 0° C. for 3 hours. The reaction mixture was diluted with ethyl acetate (10 mL) and the precipitated salts were removed via vacuum filtration and washed with ethyl acetate (5 mL). The organic filtrate was washed with water (3×20 mL) and saturated Na$_2$CO$_3$ (20 mL), then dried with MgSO$_4$ and solvent removed in vacuo. The crude mixture was purified by column chromatography on silica gel using a gradient of 5 to 15% ethyl acetate-hexanes to afford compounds 9D-6a (25 mg, 0.047 mmol, 7%), 9D-6b (48 mg, 0.090 mmol, 14%), and 9D-6c (45 mg, 0.078 mmol, 12%) in order of elution as yellow solids. Compound 9D-6a: $^1$H NMR (400 MHz, CDCl$_3$): δ (ppm)=7.62 (dd, J=8.5, 0.7 Hz, 1H), 7.41 (t, J=8.3 Hz, 1H), 7.41 (s, 1H), 6.70 (dd, J=8.1, 0.7 Hz, 1H), 4.07-4.02 (m, 2H), 3.94 (s, 3H), 3.37-3.31 (m, 2H), 1.55 (s, 9H), 1.33 (s, 18H). Compound 9D-9D-6b: $^1$H NMR (400 MHz, CDCl$_3$): δ (ppm)=8.00-7.94 (m, 1H), 7.87 (d, J=9.0 Hz, 1H), 7.38 (s, 1H), 4.01 (s, 3H), 3.94 (t, J=7.6 Hz, 2H), 3.10 (t, J=7.6 Hz, 2H), 1.65 (s, 9H), 1.41 (s, 18H). Compound 9D-6c: $^1$H NMR (400 MHz, CDCl$_3$): δ (ppm)= 7.82 (d, J=8.8 Hz, 1H), 6.64 (d, J=8.8 Hz, 1H), 4.02 (s, 3H), 3.91 (dd, J=7.4, 6.4 Hz, 2H), 3.08 (td, J=6.8, 6.4, 1.0 Hz, 2H), 1.57 (s, 9H), 1.40 (s, 18H).

The sixth step involved the reduction of the nitro group. To a vigorously stirring solution of compound 9D-6b (27 mg, 0.050 mmol, 1.0 eq) in methanol (2 mL) was added 10% palladium on activated charcoal (23 mg, 0.021 mmol, 0.50 eq) followed by ammonium formate (46 mg, 0.70 mmol, 17 eq). The reaction mixture was allowed to stir at room temperature for 2 hours until complete as determined by TLC (1:4 ethyl acetate-hexanes). The catalyst was removed and methanol was removed under vacuum. The residue was taken up in dichloromethane (10 mL), washed with brine (10 mL), the organic phase dried with MgSO$_4$ and concentrated under reduced pressure to yield compound 9D-7 as a colourless film (22 mg, 0.044 mmol, 88%). $^1$H NMR (400 MHz, CDCl$_3$): δ (ppm)=7.72 (s, 1H), 7.26-7.18 (m, 1H), 6.76 (d, J=8.7 Hz, 1H), 3.96-3.91 (m, 2H), 3.84 (s, 3H), 3.09-3.00 (m, 2H), 1.62 (s, 9H), 1.43 (s, 18H).

Similarly, the nitro group of compound 9D-6c can also be reduced in an analogous manner. To a vigorously stirring solution of compound 9D-6c (22 mg, 0.041 mmol, 1.0 eq) in methanol (2 mL) was added 10% palladium on activated charcoal (22 mg, 0.021 mmol, 0.50 eq) followed by ammonium formate (44 mg, 0.70 mmol, 17 eq). The reaction mixture was allowed to stir at room temperature for 2 hours and monitored by TLC (1:4 ethyl acetate-hexanes). The catalyst was removed and methanol was removed under vacuum. The residue was taken up in dichloromethane (10 mL), washed with brine (10 mL), the organic phase dried with MgSO$_4$ and concentrated under reduced pressure to yield compound 9D-9 as a brown film (14 mg, 0.028 mmol, 67%). $^1$H NMR (600 MHz, CDCl$_3$): δ (ppm)=7.13 (s, 1H), 6.69 (d, J=8.3 Hz, 1H), 6.57 (dt, J=8.5, 1.0 Hz, 1H), 3.93-3.87 (m, 2H), 3.85 (s, 3H), 3.04 (t, J=6.9 Hz, 2H), 1.61 (s, 9H), 1.40 (s, 18H).

The seventh step involved the removal of all protecting group. To a solution of 9D-7 (22 mg, 0.044 mmol, 1.0 eq) in dichloromethane (1.0 mL) and methanol (0.1 mL) was added trifluoroacetic acid (0.15 mL, 1.5 mmol, 35 eq) dropwise. The reaction mixture was heated to 40° C. for 2 hours, then allowed to stir at room temperature for 18 hours. As the reaction was incomplete, the reaction was heated for a further 20 hours at 40° C. The reaction mixture was concentrated under reduced pressure to yield compound 9D-8 (5 mg, 0.2 mmol, 56%). $^1$H NMR (600 MHz, D$_2$O): δ (ppm)=7.24 (d, J=8.5 Hz, 1H), 7.22 (s, 1H), 7.03 (d, J=8.5 Hz, 1H), 3.81 (s, 3H), 3.23 (t, J=7.0 Hz, 2H), 3.10 (t, J=7.0 Hz, 2H).

It is noted that compound 9D-8 corresponds with an example compound having chemical formula (IX):

(IX)

set forth herein.

Similarly, compound 9D-9 can also be deprotected in an analogous manner. To a solution of 9D-9 (14 mg, 0.028 mmol, 1.0 eq) in dichloromethane (1.0 mL) and methanol (0.1 mL) was added trifluoroacetic acid (0.064 mL, 0.83 mmol, 30 eq). The reaction mixture was heated to 40° C. for 20 hours. The reaction mixture was concentrated under reduced pressure to yield compound 9D-10 (4 mg, 0.2 mmol, 70%). $^1$H NMR (600 MHz, D$_2$O): δ (ppm)=7.25 (s, 1H), 7.18 (d, J=8.3 Hz, 1H), 6.66 (d, J=8.3 Hz, 1H), 3.96 (s, 3H), 3.30 (t, J=6.8 Hz, 2H), 3.21 (t, J=6.9 Hz, 2H).

It is noted that compound 9D-10 corresponds with an example compound having chemical formula (XII):

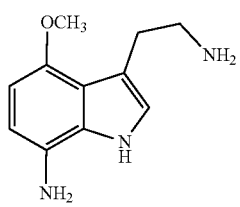

(XII)

set forth herein.

Assessment of Cell Viability Upon Treatment of Aminated Psilocybin Derivatives

Figure 11A:
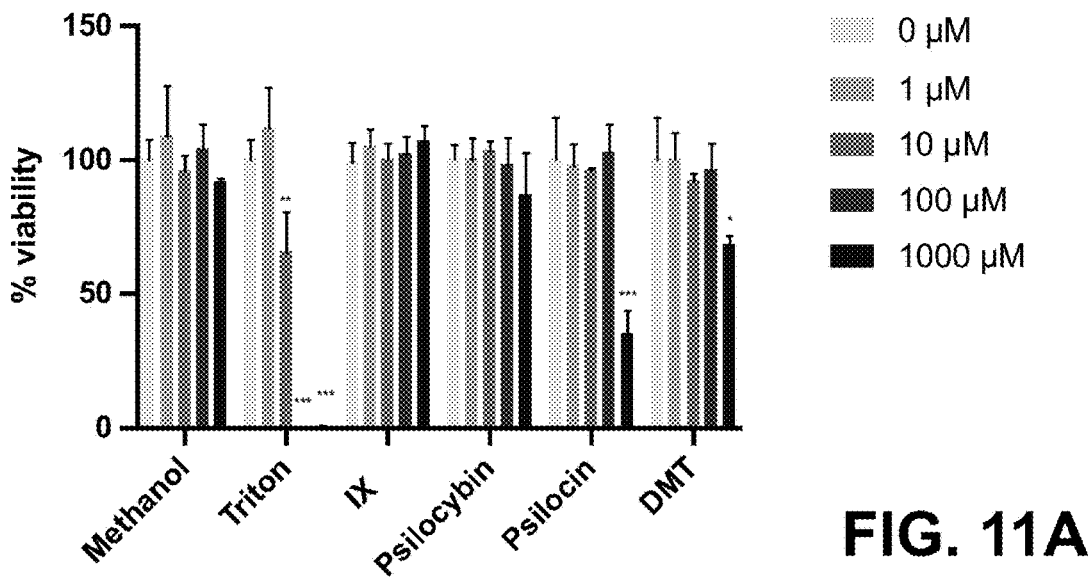
Figure 11B:
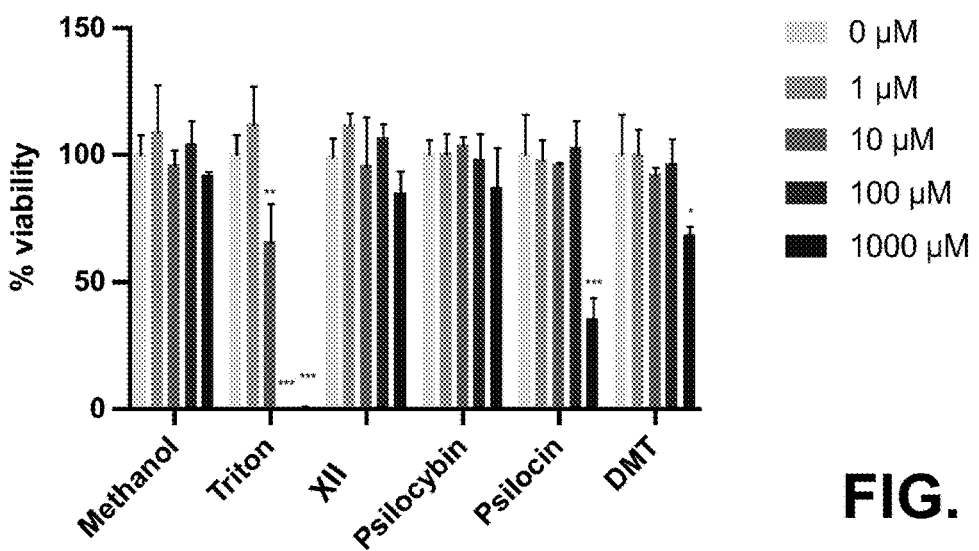

To establish suitable ligand concentrations for competitive binding assays, PrestoBlue assays were first performed. The PrestoBlue assay measures cell metabolic activity based on tetrazolium salt formation, and is a preferred method for routine cell viability assays (Terrasso et al., 2017, J Pharmacol Toxicol Methods 83: 72). Results of these assays were conducted using both control ligands (e.g., psilocybin, psilocin, DMT) and novel derivatives, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Drug-induced changes in cell health within simple in vitro systems such as the HepG2 cell line are commonly adopted as first-line screening approaches in the pharmaceutical industry (Weaver et al, 2017, Expert Opin Drug Metab Toxicol 13: 767). HepG2 is a human hepatoma that is most commonly used in drug metabolism and hepatotoxicity studies (Donato et al., 2015, Methods Mol Biol 1250: 77). Herein, HepG2 cells were cultured using standard procedures using the manufacture's protocols (ATCC, HB-8065). Briefly, cells were cultured in Eagle's minimum essential medium supplemented with 10% fetal bovine serum and grown at 37° C. in the presence of 5% $CO_2$. To test the various compounds with the cell line, cells were seeded in a clear 96-well culture plate at 20,000 cells per well. After allowing cells to attach and grow for 24 hours, compounds were added at 1 µM, 10 µM, 100 µM, and 1 mM. Methanol was used as vehicle, at concentrations 0.001, 0.01, 0.1, and 1%. As a positive control for toxicity, TritonX concentrations used were 0.0001, 0.001, 0.01 and 0.1%. Cells were incubated with compounds for 48 hours before accessing cell viability with the PrestoBlue assay following the manufacture's protocol (ThermoFisher Scientific, P50200). PrestoBlue reagent was added to cells and allowed to incubate for 1 hour before reading. Absorbance readings were performed at 570 nm with the reference at 600 nm on a SpectraMax iD3 plate reader. Non-treated cells were assigned 100% viability. Bar graphs show the mean +/−SD, n=3. Significance was determined by 2-way ANOVA followed by Dunnett's multiple comparison test and is indicated by * ($P<0.0001$),  ($P<0.001$), * ($P<0.005$). Data acquired for the derivative having chemical formula (IX) is displayed as "IX" on the x-axis of FIG. 11A.). Data acquired for the derivative having chemical formula (XII) is displayed as "XII" on the x-axis of FIG. 11B.

Radioligand Receptor Binding Assays.

Figure 11C:
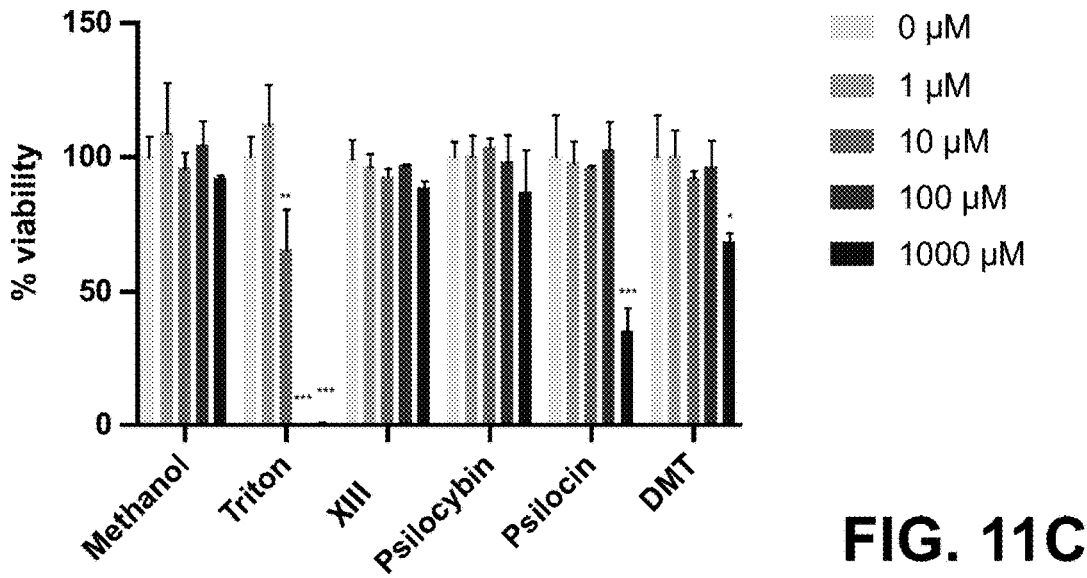
Figure 11D:
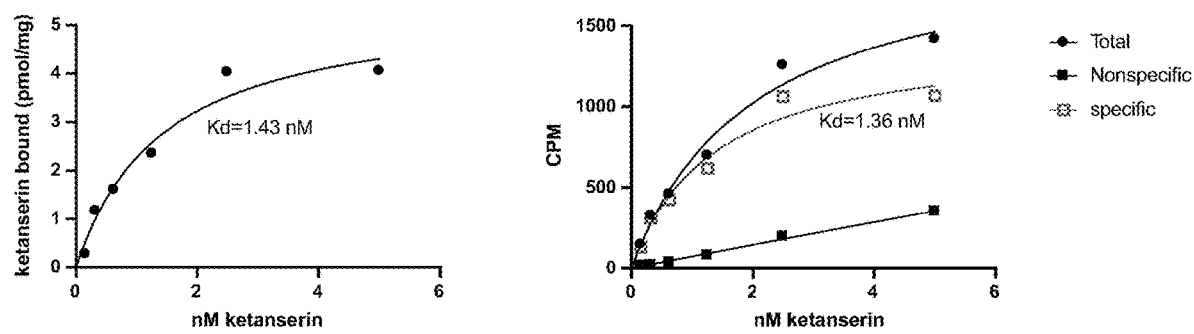
Figure 11E:
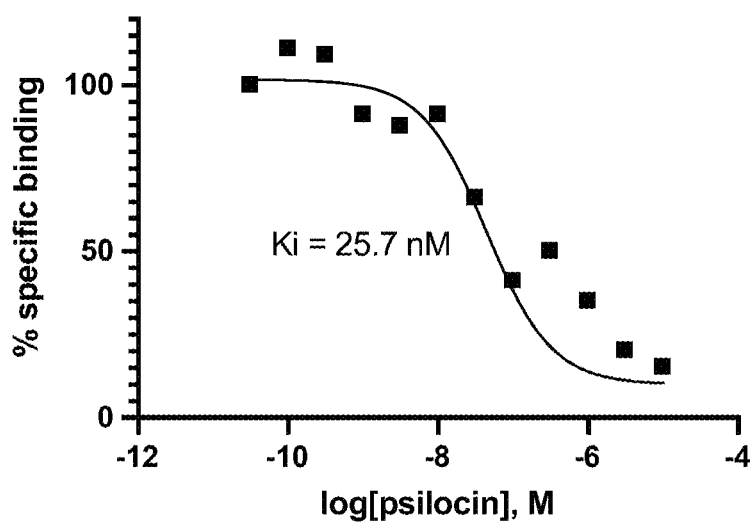
Figure 11E:
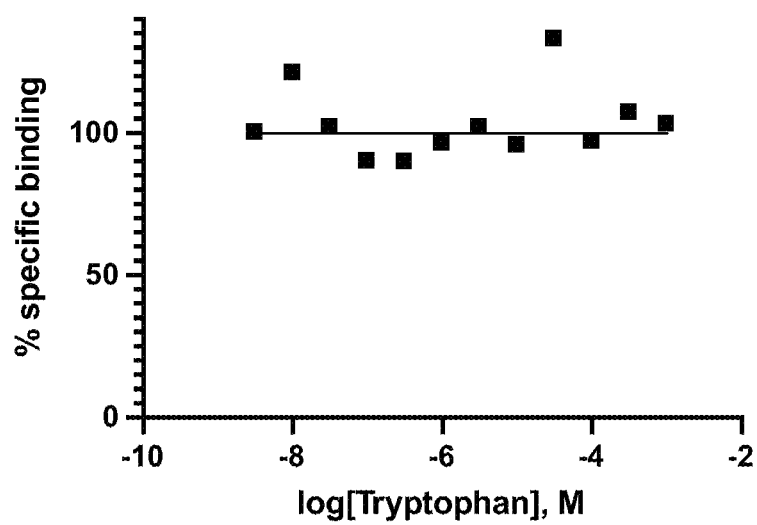
Figure 11F:
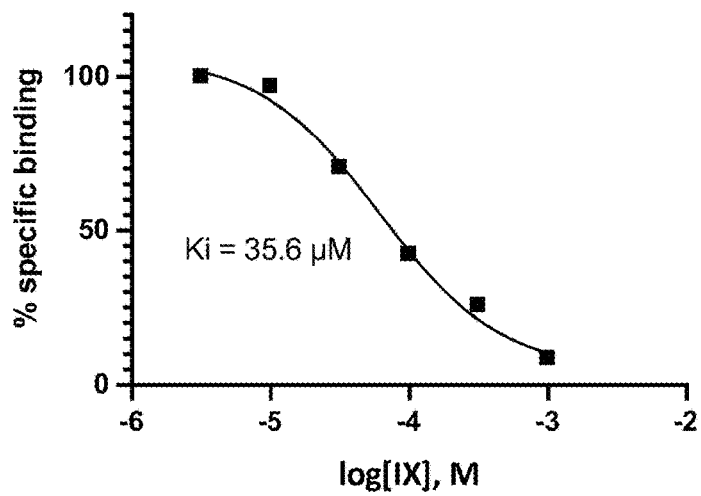
Figure 11G:
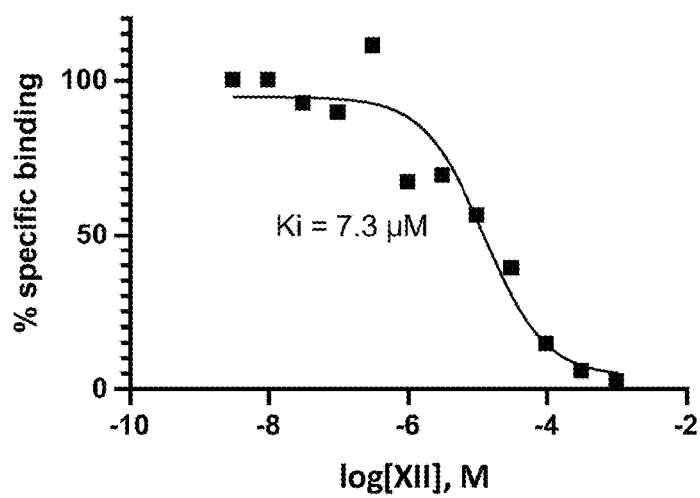

Evaluation of drug binding is an essential step to characterization of all drug-target interactions (Fang 2012, Exp Opin Drug Discov 7:969). The binding affinity of a drug to a target is traditionally viewed as an acceptable surrogate of its in vivo efficacy (NGAez et al., 2012, Drug Disc Today 17: 10). Competition assays, also called displacement or modulation binding assays, are a common approach to measure activity of a ligand at a target receptor (Flanagan 2016, Methods Cell Biol 132: 191). In these assays, standard radioligands acting either as agonists or antagonists are ascribed to specific receptors. In the case of G protein-coupled receptor 5-$HT_{2A}$, [$^3$H]ketanserin is a well-established antagonist used routinely in competition assays to evaluate competitive activity of novel drug candidates at the 5-$HT_{2A}$ receptor (Maguire et al., 2012, Methods Mol Biol 897: 31). Thus, to evaluate activity of novel psilocybin derivatives at the 5-$HT_{2A}$ receptor, competition assays using [$^3$H]ketanserin were employed as follows. SPA beads (RPNQ0010), [$^3$H] ketanserin (NET1233025UC), membranes containing 5-$HT_{2A}$ (ES-313-M400UA), and isoplate-96 microplate (6005040) were all purchased from PerkinElmer. Radioactive binding assays were carried out using Scintillation Proximity Assay (SPA). For saturation binding assays, mixtures of 10 ug of membrane containing 5-$HT_{2A}$ receptor was pre-coupled to 1 mg of SPA beads at room temperature in a tube rotator for 1 hour in binding buffer (50 mM Tris-HCl pH7.4, 4 mM $CaCl_2$, 1 mM ascorbic acid, 10 µM pargyline HCl). After pre-coupling, the beads and membrane were aliquoted in an isoplate-96 microplate with increasing amounts of [$^3$H]ketanserin (0.1525 nM to 5 nM) and incubated for two hours at room temperature in the dark with shaking. After incubation, the samples were read on a MicroBeta 2 Microplate Counter (Perkin Elmer). Determination of non-specific binding was carried out in the presence of 20 µM of spiperone (S7395-250MG, Sigma). Equilibrium binding constants for ketanserin ($K_d$) were determined from saturation binding curves using the 'one-site saturation binding analysis' method of GraphPad PRISM software (Version 9.2.0). Competition binding assays were performed using fixed (1 nM) [$^3$H]ketanserin and different concentrations of tryptophan (3 nM to 1 mM), psilocin (30 pM to 10 µM) or unlabeled test compound (3 nM to 1 mM) similar to the saturation binding assay. $K_i$ values were calculated from the competition displacement data using the competitive binding analysis from GraphPad PRISM software. Tryptophan was included as a negative control as it has no activity at the 5-$HT_{2A}$ receptor. In contrast, psilocin was used as a positive control since it has established binding activity at the 5-$HT_{2A}$ receptor (Kim et al., 2020, Cell 182: 1574). FIG. 11D depicts the saturation binding curves for [$^3$H]ketanserin at the 5-$HT_{2A}$ receptor. Panel 1 shows the specific saturation ligand binding of [$^3$H]ketanserin (from 0.1525 nM to 5 nM) to membranes containing 5-$HT_{2A}$ receptor, which was obtained after subtracting non-specific binding values (shown in Panel 2). Specific binding in counts per minute (cpm) was calculated by subtracting non-specific binding from total binding. Specific binding (pmol/mg) was calculated from pmol of [$^3$H]ketanserin bound per mg of protein in the assay. The $K_d$ was calculated by fitting the data with the one-site binding model of PRISM software (version 9.2.0). FIG. 11E (top panel) shows the competition binding curve for psilocin as a positive control (binding). FIG. 11E (bottom panel) shows the competition binding curve for tryptophan as a negative control (no binding). FIG. 11F shows competition binding curve for compound with formula (IX), designated "IX" in the figure. FIG. 11G shows competition binding curve for compound with formula (XII), designated "XII" in the figure.

Cell Lines and Control Ligands Used to Assess Activity at 5-$HT_{1A}$.

CHO-K1/Gα$_{15}$ (GenScript, M00257) (−5-$HT_{1A}$) and CHO-K1/5-$HT_{1A}$/Gα$_{15}$ (GenScript, M00330) (+5-$HT_{1A}$)

cells lines were used. Briefly, CHO-K1/Gα$_{15}$ is a control cell line that constitutively expresses Gα$_{15}$ which is a promiscuous G$_q$ protein. This control cell line lacks any transgene encoding 5-HT$_{1A}$ receptors, but still responds to forskolin; thus, cAMP response to forskolin should be the same regardless of whether or not 5-HT$_{1A}$ agonists are present. Conversely, CHO-K1/5-HT$_{1A}$/Gα$_{15}$ cells stably express 5-HT$_{1A}$ receptor in the CHO-K1 host background. Notably, Gα$_{15}$ is a promiscuous G protein known to induce calcium flux response, present in both control and 5-HT$_{1A}$ cell lines. In +5-HT$_{1A}$ cells, Gα$_{15}$ may be recruited in place of G$_{αi/o}$, which could theoretically dampen cAMP response (Rojas and Fiedler 2016, Front Cell Neurosci 10: 272). Thus, we included two known 5-HT$_{1A}$ agonists, DMT (Cameron and Olson 2018, ACS Chem Neurosci 9: 2344) and serotonin (Rojas and Fiedler 2016, Front Cell Neurosci 10: 272) as positive controls to ensure sufficient cAMP response was observed, thereby indicating measurable recruitment of G$_{αi/o}$ protein to activated 5-HT$_{1A}$ receptors. In contrast, tryptophan is not known to activate, or modulate in any way, 5-HT$_{1A}$ receptors, and was thus used as a negative control. Cells were maintained in complete growth media as recommended by supplier (GenScript) which is constituted as follows: Ham's F12 Nutrient mix (HAM's F12, GIBCO #11765-047) with 10% fetal bovine serum (FBS) (Thermo Scientific #12483020), 200 µg/ml zeocin (Thermo Scientific #R25005) and/or 100 µg/ml hygromycin (Thermo Scientific #10687010). The cells were cultured in a humidified incubator with 37° C. and 5% CO$_2$. Cells maintenance was carried out as recommended by the cell supplier. Briefly, vials with cells were removed from the liquid nitrogen and thawed quickly in 37° C. water bath. Just before the cells were completely thawed the vial's outside was decontaminated by 70% ethanol spray. The cell suspension was then retrieved from the vial and added to warm (37° C.) complete growth media, and centrifuged at 1,000 rpm for 5 minutes. The supernatant was discarded, and the cell pellet was then resuspended in another 10 ml of complete growth media, and added to the 10 cm cell culture dish (Greiner Bio-One #664160). The media was changed every third day until the cells were about 90% confluent. The ~90% confluent cells were then split 10:1 for maintenance or used for experiment.

Evaluation of 5-HT$_{1A}$ Receptor Modulation

Figure 11H:
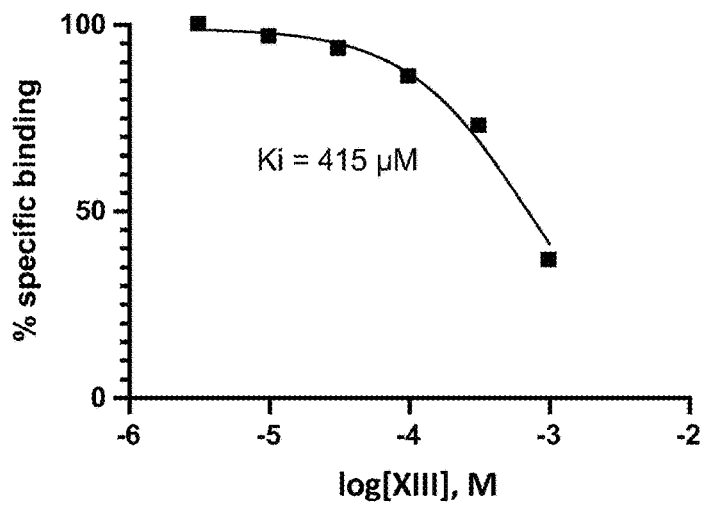
Figure 11I:
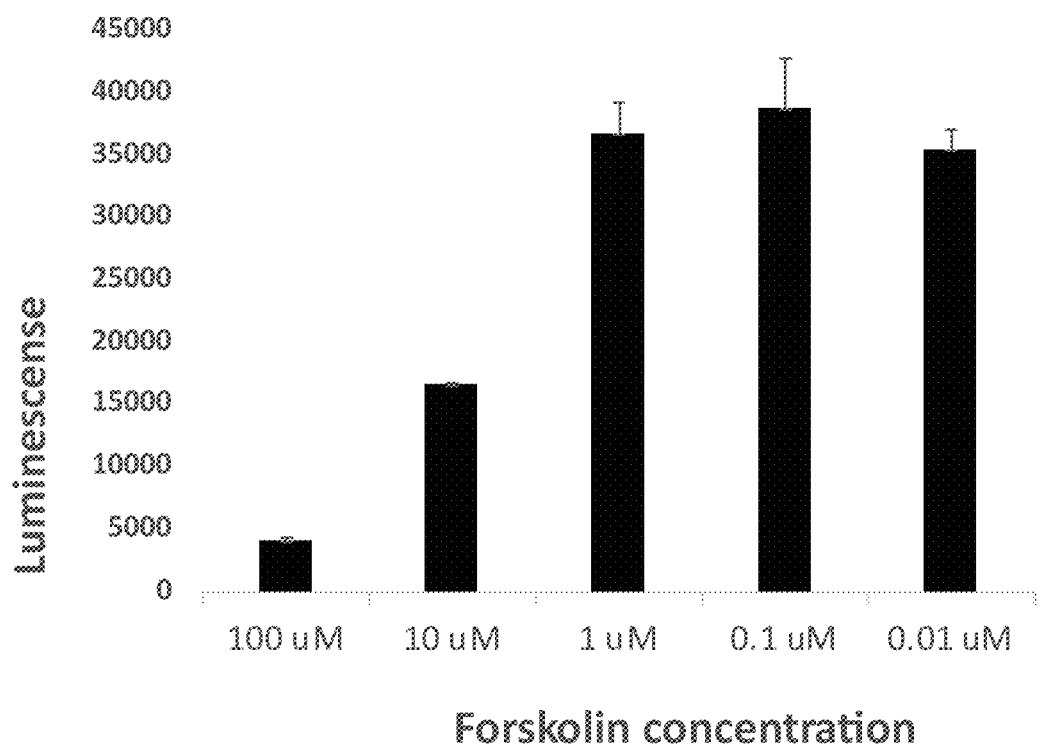
Figure 11J:
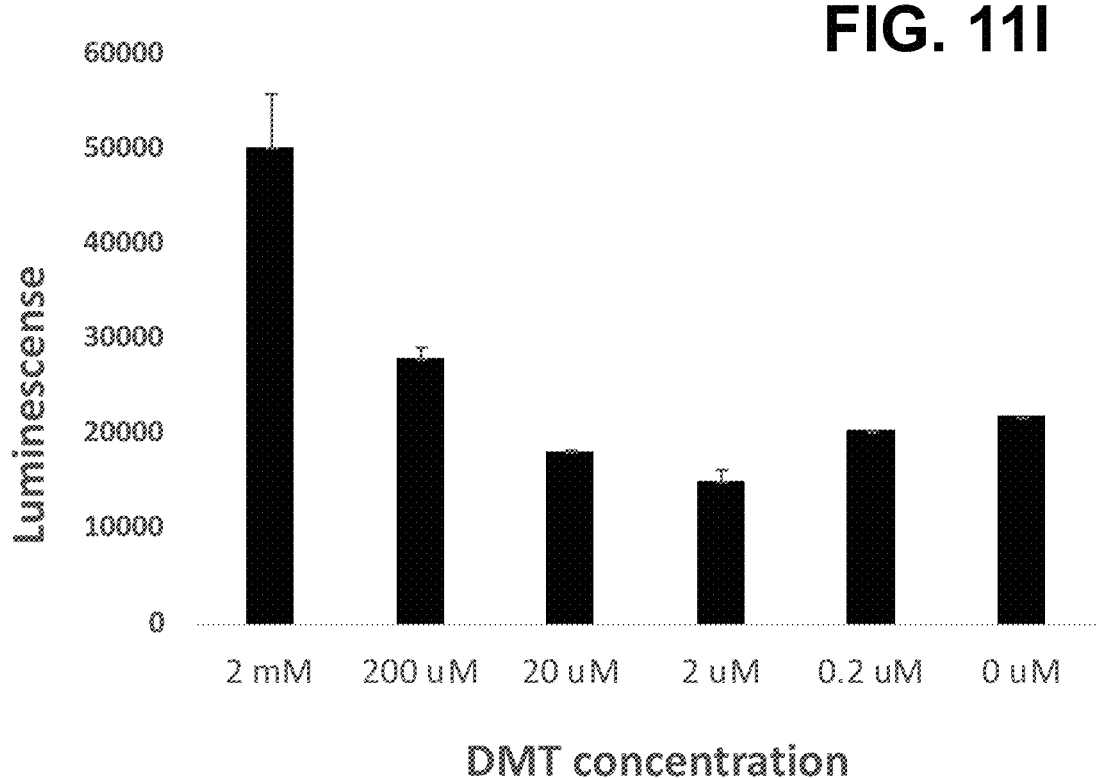
Figure 11K:
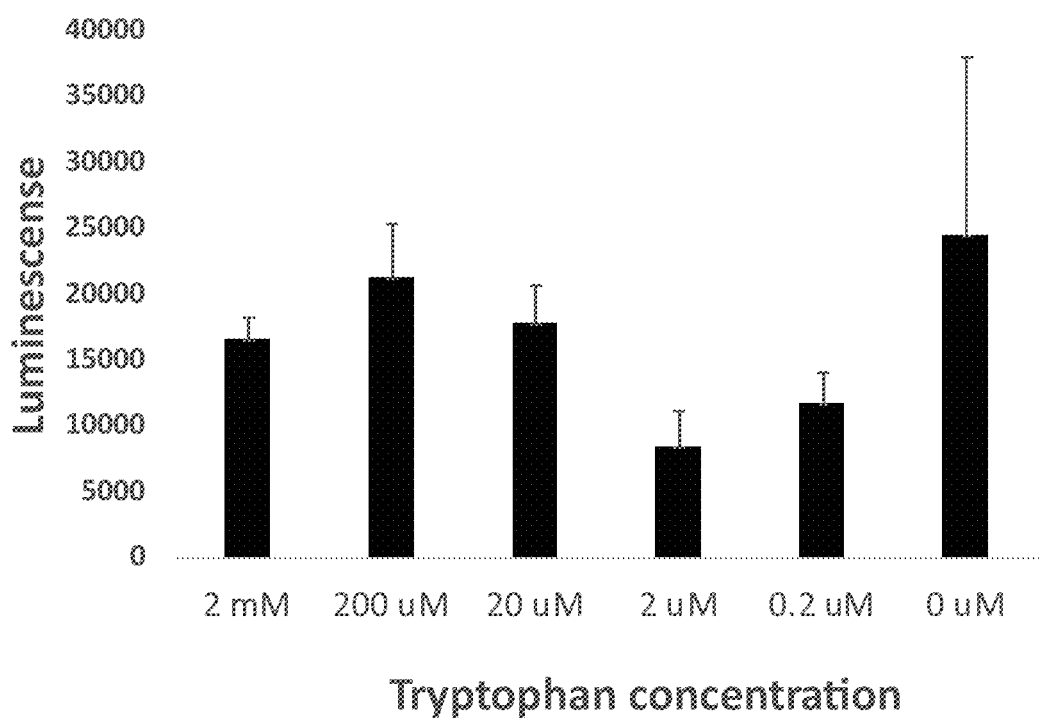
Figure 11L:
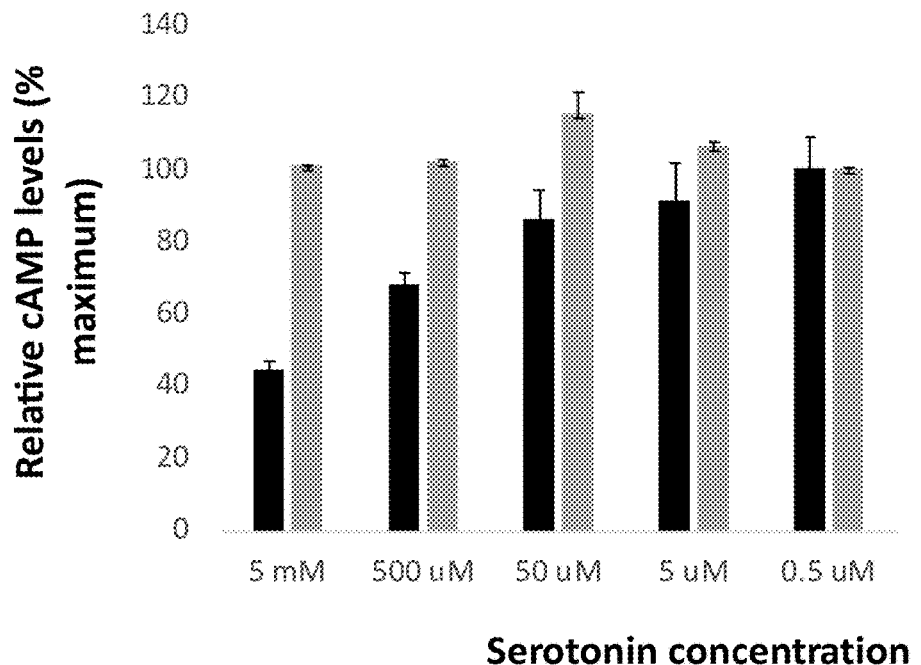

As 5-HT$_{1A}$ activation inhibits cAMP formation, the ability of test molecules to modulate 5-HT$_{1A}$ response was measured via changes in the levels of cAMP produced due to application of 4 µM forskolin. The change in intracellular cAMP levels due to the treatment of novel molecules was measured using cAMP-Glo Assay kit (Promega #V1501). Briefly, +5-HT$_{1A}$ cells were seeded on 1-6 columns and base −5-HT$_{1A}$ cells were seeded on columns 7-12 of the white walled clear bottom 96-well plate (Corning, #3903). Both cells were seeded at the density of 30,000 cells/well in 100 µl complete growth media and cultured 24 hrs in humidified incubator at 37° C. and 5% CO$_2$. On the experiment day, the media of cells was replaced with serum/antibiotic free culture media. Then the cells were treated for 20 minutes with test molecules dissolved in induction medium (serum/antibiotic free culture media containing 4 µM forskolin, 500 µM IBMX (isobutyl-1-methylxanthine, Sigma-Aldrich, Cat. #17018) and 100 µM (RO 20-1724, Sigma-Aldrich, Cat. #B8279)). Forskolin induced cAMP formation whereas IBMX and RO 20-1724 inhibited the degradation of cAMP. PKA was added to the lysate, mixed, and subsequently the substrate of the PKA was added. PKA was activated by cAMP, and the amount of ATP consumed due to PKA phosphorylation directly corresponded to cAMP levels in the lysate. Reduced ATP caused reduced conversion of luciferin to oxyluciferin, conferring diminished luminescence as the result of 5-HT$_{1A}$ activation. Conversely, enhanced luminescence was expected in cases where 5-HT$_{1A}$ receptor modulation—imparted by a test molecule—caused downstream increases in ATP, thus imparting enhanced conversion of luciferin to oxyluciferin. FIG. 11I shows increased luminescence resulting from decreased dosages of forskolin (and decreased cAMP) in +5HT$_{1A}$ cell culture. FIG. 11J illustrates reduced luminescence (i.e., increased cAMP) in the presence of fixed (4 µM) forskolin as dosages of DMT decrease, revealing 5-HT$_{1A}$ activity of DMT. FIG. 11K illustrates no trend in luminescence (i.e., no trend in cAMP levels) in the presence of fixed (4 µM) forskolin, as dosages of tryptophan decrease, revealing a lack of 5-HT$_{1A}$ modulation for tryptophan. FIG. 11L illustrates increased % cAMP levels in the presence of fixed (4 µM) forskolin as dosages of serotonin decrease, revealing 5-HT$_{1A}$ binding activity of serotonin in +5HT$_{1A}$ cell cultures. Conversely, this trend of increasing % cAMP levels with decreasing serotonin is not observed in −5HT$_{1A}$ cell cultures.

Figure 11M:
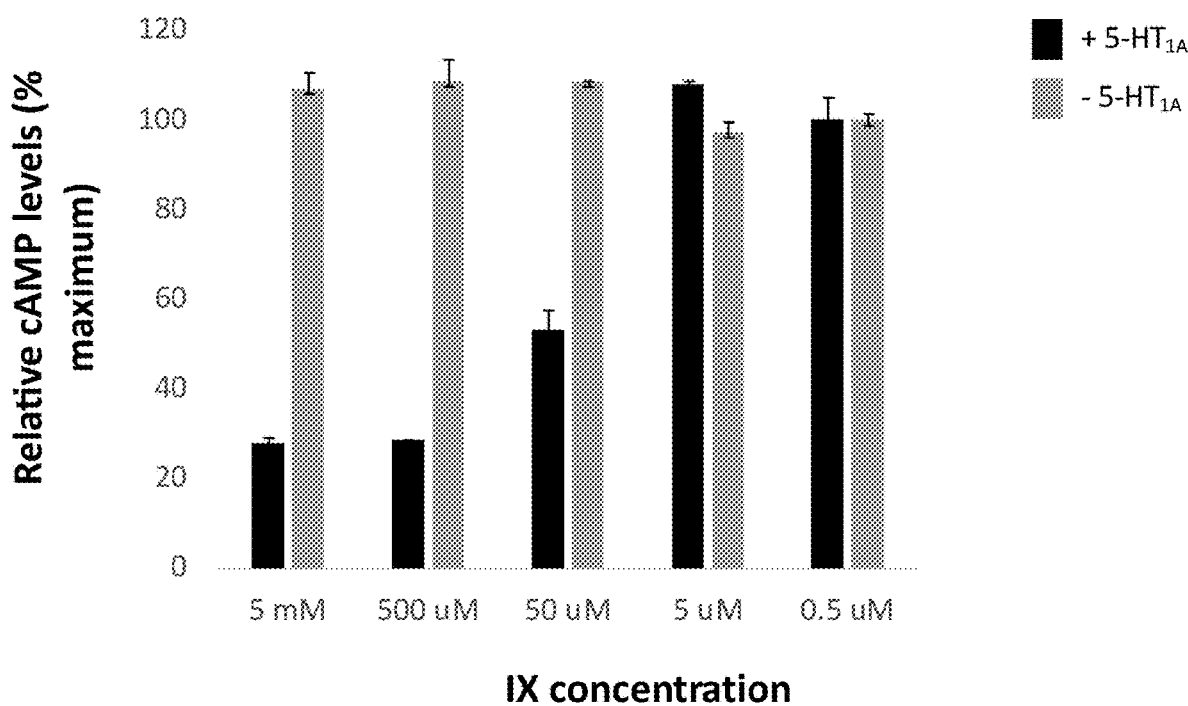

FIG. 11M illustrates increased % cAMP levels in the presence of fixed (4 µM) forskolin as dosages of compound (IX) decrease, revealing 5-HT$_{1A}$ binding activity of compound (IX) in +5HT$_{1A}$ cell cultures. Conversely, this trend of increasing % cAMP levels with decreasing compound (IX) is not observed in −5HT$_{1A}$ cell cultures. Note that compound (IX) is shown simply as (IX) along the x-axis. For FIGS. 11I-11M, error bars represent results of three experiments (n=3).

Example 2—Biochemical Synthesis of a Fourth Aminated Psilocybin Derivative

E. coli strain Ec-1 was constructed as follows. For plasmid cloning, Top10 or XL1-blue strains were used depending on antibiotic markers. Standard LB media was used for culturing. For gene expression and feeding experiments, the parent host strain employed was BL21 (DE3). The plasmid pETM6-H10-TmTrpB-2F3-V5-BaTDC-FLAG was created by first cloning the in-frame, C-terminally V5-tagged (SEQ. ID NO: 6, SEQ. ID NO: 7) TmTrpB-2F3 (SEQ. ID NO: 8, SEQ. ID NO: 9) into the NdeI/XhoI site of pETM6-H10 (SEQ. ID NO: 10) to create pETM6-H$_{10}$-TmTrpB-2F3-V5. This intermediate plasmid was digested with SpeI and SalI, and in-frame, C-terminally FLAG tagged (SEQ. ID NO: 2, SEQ. ID NO: 3) BaTDC (SEQ. ID NO: 11, SEQ. ID NO: 12) was cloned into the site with XbaI and SalI, nullifying the SpeI restriction site. In this setup, the T7 polymerase was able to drive the expression of the polycistronic DNA containing both TmTrpB-2F3 and BaTDC. The target plasmid pETM6-H$_{10}$-TmTrpB-2F3-V5-BaTDC-FLAG was transformed into BL21 (DE3) cells, and ampicillin was used to select for the correct clones containing the plasmid. Scaled-up culturing of engineered E. coli was conducted as follows: seed cultures were inoculated in AMM (Jones et al. 2015, Sci Rep. 5: 11301) medium overnight. The overnight culture was then divided into two flasks containing 500 mL each of AMM medium additionally containing 0.5% (w/v) serine, 1M IPTG, 50 ug/L ampicillin, and 100 mg/L aminated indole feedstock (5,7-dimethyl-1H-indol-4-ylamine; 1clickchemistry, www.1clickchemistry.com) for conversion by Ec-1. Cultures were grown for 24 h. Cultures were then centrifuged (10,000 g×5 minutes) to remove cellular content, and culture broth containing secreted derivative was stored at −80° C. until further processing.

Analysis and Purification,

Analysis was carried out using high-resolution LC-HESI-LTQ-Orbitrap-XL MS (Thermo Fisher Scientific), employing a modified version of a method described previously (Chang et al., 2015, Plant Physiol. 169: 1127-1140), with the exception that liquid chromatography was carried out using an UltiMate 3000 HPLC (Thermo Fisher Scientific) equipped with a Poroshell 120 SB-C18 column (Agilent Technologies) instead of an Accela HPLC system (Thermo Fisher Scientific) equipped with a Zorbax C18 column (Agilent Technologies). Briefly, 100 microliters of culture media were dried and resuspended in 100 microliters of DMSO. One tenth (10 microliters) of this suspension was injected at a flow rate of 0.5 mL/min and a gradient of solvent A (water with 0.1% of formic acid) and solvent B (ACN with 0.1% formic acid) as follows: 100% to 0% (v/v) solvent A over 5 min; isocratic at 0% (v/v) for 1 min; 0% to 100% (v/v) over 0.1 min; and isocratic at 100% (v/v) for 1.9 min. Total run time was 8 minutes. Heated ESI source and interface conditions were operated in positive ion mode as follows: vaporizer temperature, 400° C.; source voltage, 3 kV; sheath gas, 60 au, auxiliary gas, 20 au; capillary temperature, 380° C.; capillary voltage, 6 V; tube lens, 45 V. Instrumentation was performed as a single, HR scan event using Orbitrap detection of m/z in the range of 100-500 m/z. Ion injection time was 300 ms with scan time of 1 s. External and internal calibration procedures ensured <2 ppm error to facilitate elemental formulae predictions. Singly protonated product with exact m/z and expected elemental formula matching the singly protonated form of 3-(2-aminoethyl)-5,7-dimethyl-1H-indol-4-amine, having chemical formula (VI):

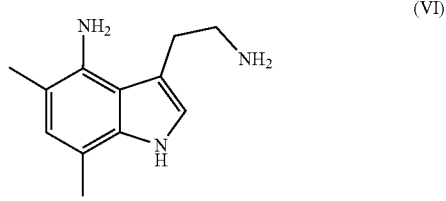

Figure 12A:
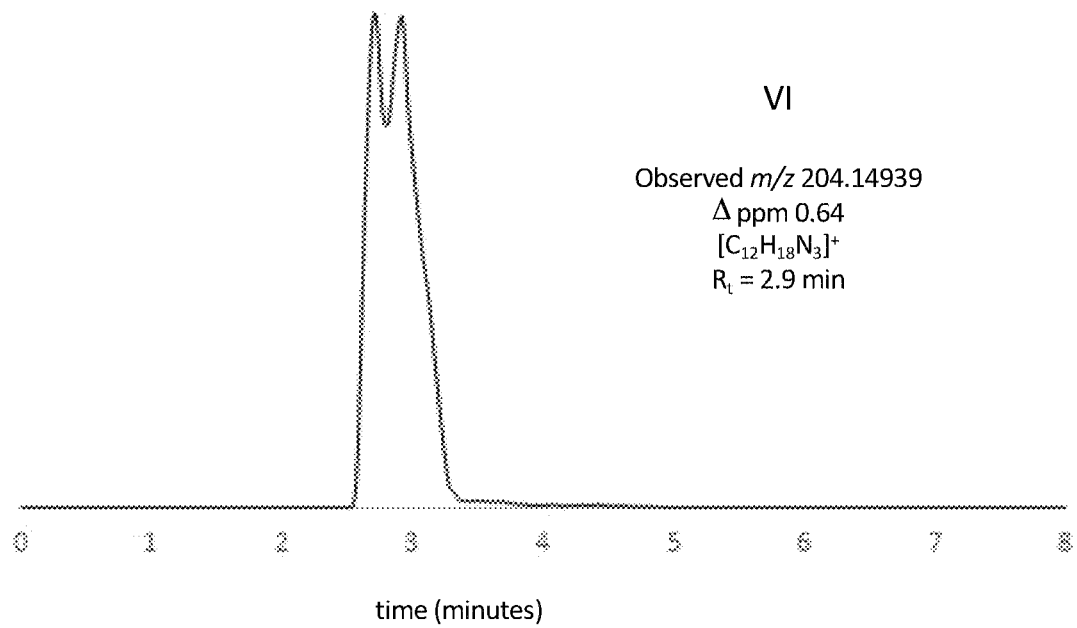

(VI)

eluted at 2.9 minutes (EIC, see: FIG. 12A). Although peak splitting can be minimized through the use of DMSO as injection solvent (Kaufman and Jegle 2005, Agilent Technologies Technical Bulletin 5989-2485EN), this phenomenon persisted owing to ion pairing effects between matrix components (Tarafder et al. 2010, J Chromatogr A 1217: 7065-7073).

Figure 12B:
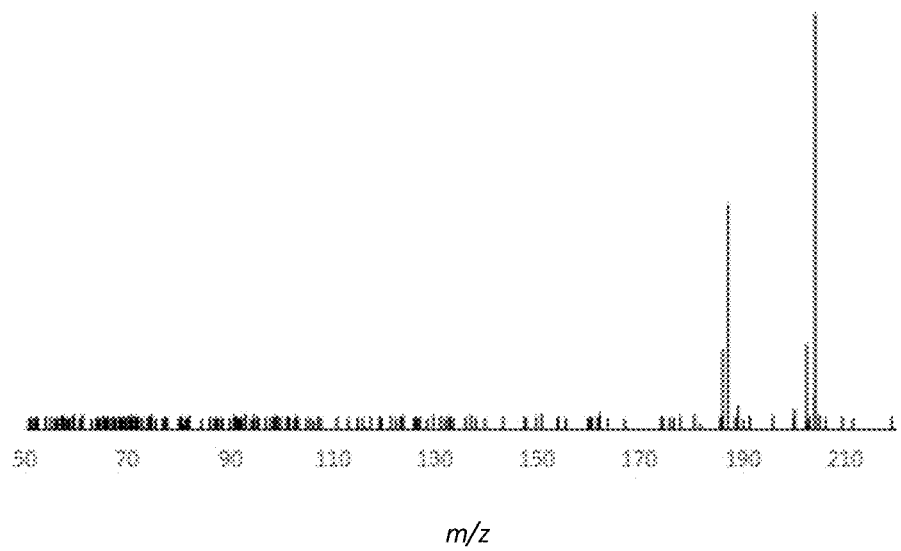

As per standard procedures (Menéndez-Perdomo et al. 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted aminated psilocybin derivative with formula (VI) as follows (FIG. 12B, Table 1) (Servillo L et al., 2013, J. Agric. Chem. 61: 5156-5162).

TABLE I

| m/z | % Relative abundance | Ionic species | Empirical formula |
|---|---|---|---|
| 204.1131 | 100 | [M + H]⁺ | $C_{12}H_{15}N_3$ |
| 187.1229 | 55 | [M + H − NH₂]⁺ | $C_{12}H_{16}N_2$ |
| 202.4920 | 21 | | |

TABLE I-continued

| m/z | % Relative abundance | Ionic species | Empirical formula |
|---|---|---|---|
| 186.1106 | 19 | | |
| 189.0976 | 6.0 | | |
| 200.0973 | 5.0 | | |
| 162.1027 | 4.1 | | |
| 150.6854 | 3.8 | | |
| 92.8785 | 3.8 | | |
| 61.0962 | 3.8 | | |

Example 3—Biochemical Synthesis of a Fifth Aminated Psilocybin Derivative

*Escherichia coli* strain Ec-1 was used to biosynthesize aminated psilocybin derivative with formula (XIV) from aminated indole feedstock. The construction of Ec-1 is described in Example 2. Scaled-up culturing and material storage of engineered *E. coli* was conducted as described in Example 2, except that 6-methyl-1H-indol-4-ylamine (Combi-Blocks, www.combi-blocks.com) was used in place of 5,7-dimethyl-1H-indol-4-ylamine. To assess product, high-resolution LC-HESI-LTQ-Orbitrap-XL MS analysis was conducted as described in Example 2. Singly protonated product with exact m/z and expected elemental formula matching the singly protonated form of 3-(2-aminoethyl)-6-methyl-1H-indol-4-amine having chemical formula (XIV):

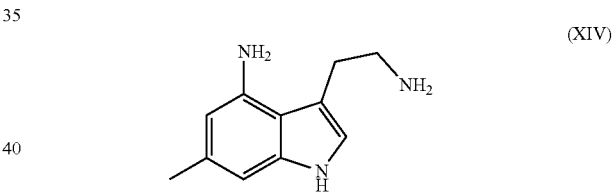

Figure 13A:
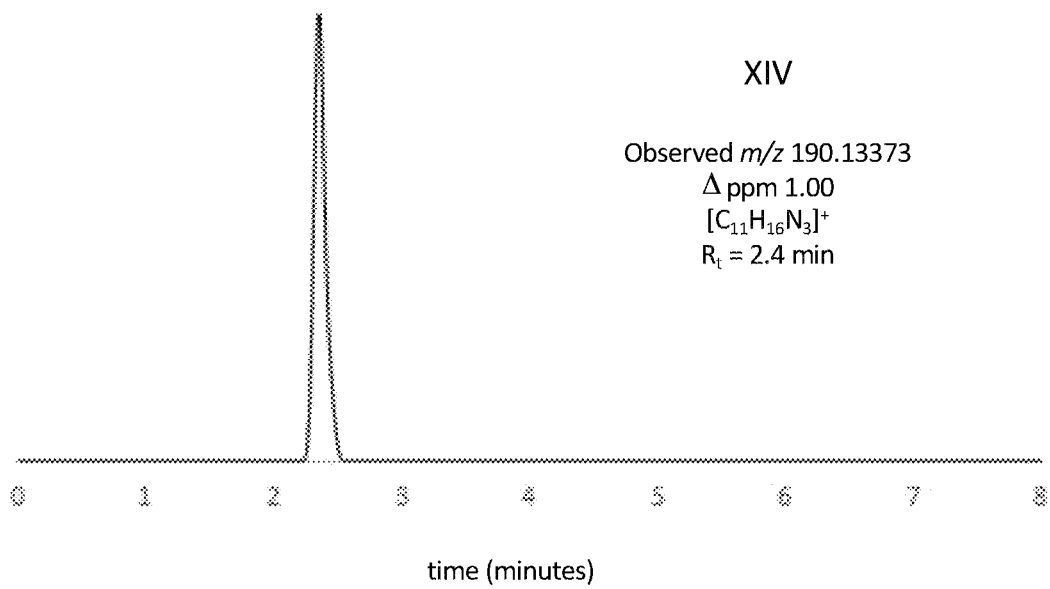
Figure 13B:
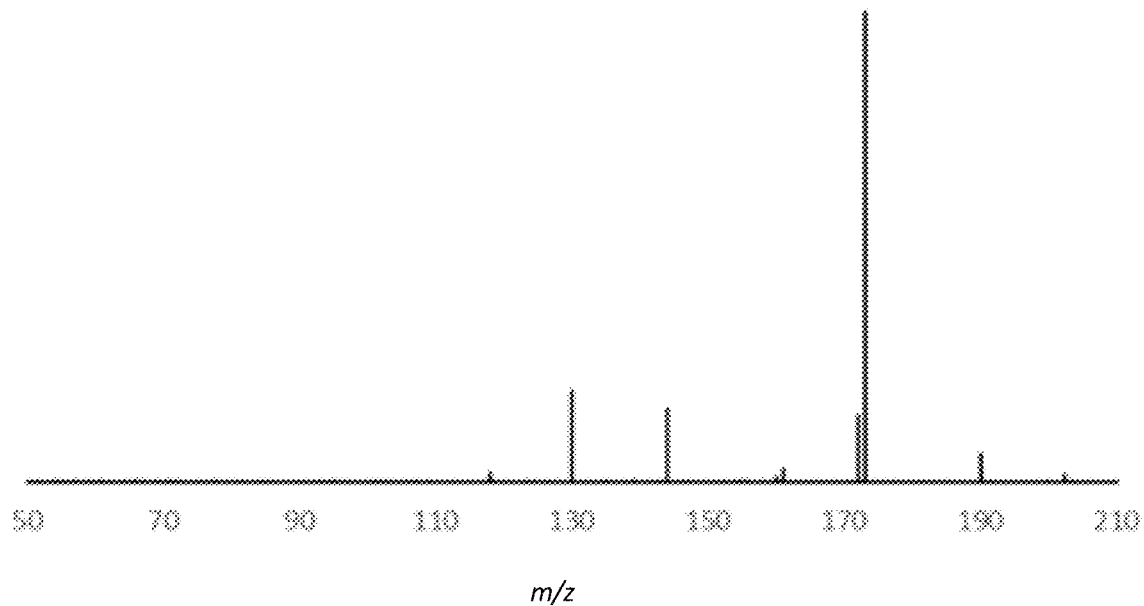

(XIV)

eluted at 2.4 minutes (EIC, see: FIG. 13A). As per standard procedures (Menéndez-Perdomo et al. 2021, Mass Spectrom 56: 34683) high energy collisions (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (XIV), as follows (FIG. 13B, Table II) (Servillo L. et al., 2013, J. Agric. Chem. 61: 5156-5162),

TABLE II

| m/z | % Relative abundance | Ionic species | Δ ppm |
|---|---|---|---|
| 173.10707 | 100 | [M + H − NH₂]⁺ | 1.44 |
| 130.06489 | 20 | | |
| 144.08057 | 16 | | |
| 190.13373 | 2.7 | [M + H]⁺ | 1.00 |
| 161.10715 | 2.6 | | |
| 118.06485 | 1.9 | | |
| 202.35010 | 1.5 | | |
| 160.07551 | 1.0 | | |

Example 4—Biochemical Synthesis of a Sixth Aminated Psilocybin Derivative

*Escherichia coli* strain Ec-2 was used to biosynthesize aminated psilocybin derivative, where the amino group terminating the 2-carbon aliphatic side chain was conjugated to an acetyl group. Ec-2 was constructed using the same method as for Ec-1 (see: Example 2), except that an additional plasmid was assembled and transformed into cells along with pETM6-H$_{10}$-TmTrpB-2F3-V5-BaTDC-FLAG. This additional plasmid encoded a promiscuous and efficient *Streptomyces griseofuscus* N-acetyltransferase enzyme named PsmF (SEQ. ID NO: 5). This additional plasmid was assembled as follows: from plasmid pCDM4 (SEQ. ID NO: 1), the plasmid pCDM4-PsmF-FLAG was created by inserting an in-frame, C-terminally FLAG-tagged (SEQ. ID NO: 2, SEQ. ID NO: 3) PsmF gene (SEQ. ID NO: 4, SEQ. ID NO: 5) into the NdeI/XhoI site of pCDM4. The two target plasmids pCDM4-PsmF-FLAG and pETM6-H10-TmTrpB-2F3-V5-BaTDC-FLAG were transformed into BL21 (DE3) cells, and antibiotics ampicillin plus streptomycin were used to select for the correct clones containing both plasmids. Scaled up culturing, analysis, purification, toxicology, and pharmacological testing were performed as described in Example 2, except that 1H-indol-7-ylamine (Combi-Blocks, www.combi-blocks.com) was used in place of 5,7-dimethyl-1H-indol-4-ylamine. Purification of the target product was achieved as follows: to 0.75 L of *E. coli* culture, 10M NaOH solution was added until the pH reached ~7. The culture was then extracted by ethyl acetate (4×500 ml). The organic layer was dried over Na$_2$SO$_4$, followed by concentration under reduced pressure. The residue was purified by flash chromatography on silica gel methanol-dichloromethane (2->4%) as eluent, to give the compound as light yellow solid (15 mg). NMR and HRMS data were as follows: $^1$H NMR (400 MHz, CD$_3$OD): δ=1.91 (s, 3H), 2.22 (s, 3H), 2.93 (t, J=6.9 Hz, 2H), 3.46 (t, J=7.2 Hz, 2H), 6.99 (t, J=7.8 Hz, 1H), 7.10 (m, 2H), 7.44 (dd, J=7.9, 1.0 Hz, 1H). Selective $^{13}$C NMR (100 MHz, CD$_3$OD): δ=21.2, 21.8, 24.7, 40.0, 112.5, 115.2, 115.8, 118.3, 122.1, 122.3, 129.4, 170.5, 171.8. HRMS (ESI) m/z: calcd. for C$_{14}$H$_{17}$N$_3$O$_2$ [M+H]$^+$ 260.1394, found 260.1392. Purity was assessed at 95%. This characterization confirmed a structure corresponding to compound (XIII):

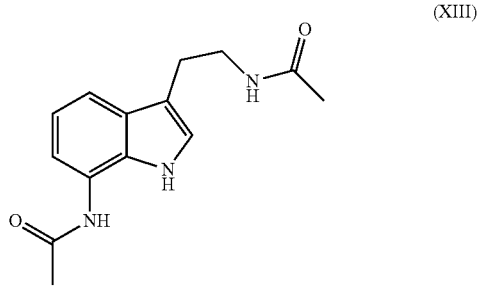 [SMILES: CC(=O)NCCc1c[nH]c2c(NC(C)=O)cccc12]

(XIII)

Assessment of Cell Viability Upon Treatment of Aldehyde Psilocybin Derivative

Cell viability was assessed as described for Example 1, except the compound with formula (XIII) was evaluated in place of the compounds with formulae (IX) and (XII). FIG. 11C shows PrestoBlue assay results for compound with formula (XIII), depicted on the x-axis as "XIII".

Radioligand Receptor Binding Assays.

Activity at 5-HT$_{2A}$ receptor was assessed as described for Example 1, except the compound with formula (XIII) was evaluated in place of the compounds with formulae (IX) and (XII). FIG. 11H shows radioligand competition assay results for compound with formula (XIII), depicted on the x-axis simply as "XIII".

Example 5—Biochemical Synthesis of a Seventh Aminated Psilocybin Derivative

*Escherichia coli* strain Ec-2 was used to biosynthesize aminated psilocybin derivative with formula (VII) from aminated indole feedstock. The construction of Ec-2 is described in Example 4. Scaled-up culturing and material storage of engineered *E. coli* was conducted as described in Example 2. To assess product, high-resolution LC-HESI-LTQ-Orbitrap-XL MS analysis was conducted as described in Example 2. Singly protonated product with exact m/z and expected elemental formula matching the singly protonated form of N-[2-(4-amino-5,7-dimethyl-1H-indol-3-yl)ethyl] acetamide having chemical formula (VII):

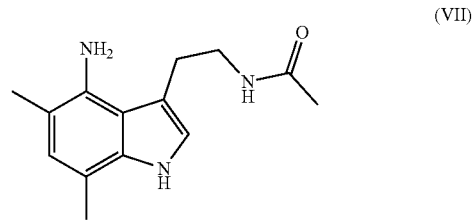 [SMILES: CC(=O)NCCc1c[nH]c2c(C)cc(C)c(N)c12]

Figure 14A:
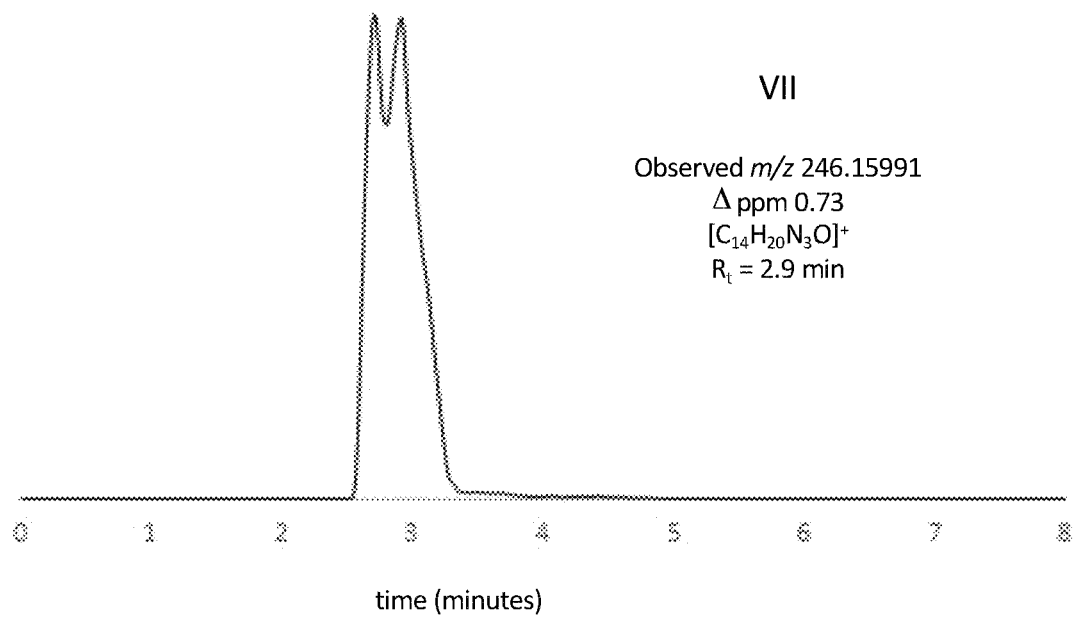

(VII)

eluted at 2.9 minutes (EIC, see: FIG. 14A). Although peak splitting can be minimized through the use of DMSO as injection solvent (Kaufman and Jegle 2005, Agilent Technologies Technical Bulletin 5989-2485EN), this phenomenon persisted owing to ion pairing effects between matrix components (Tarafder et al 2010, J Chromatogr A 1217: 7065-7073).

Figure 14B:
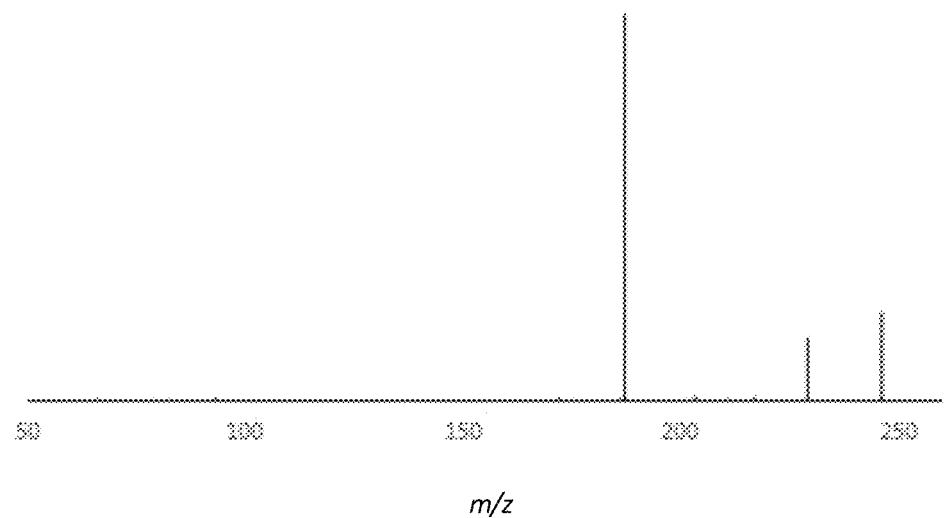

As per standard procedures (Menéndez-Perdomo et al. 2021, Mass Spectrom 56: 34683) high energy collisions (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (VII), as follows (FIG. 14B, Table 111) (Servillo L. et al, 2013, J. Agric. Chen. 61: 5156-5162).

TABLE III

| m/z | % Relative Abundance | Ionic species | Empirical formula |
|---|---|---|---|
| 187.1228 | 100 | [M + H − N-acetyl]$^+$ | C$_{12}$H$_{15}$N$_2$ |
| 246.1601 | 23 | [M + H]$^+$ | C$_{14}$H$_{20}$N$_3$O |
| 229.1335 | 16 | [M + H − NH$_2$]$^+$ | C$_{14}$H$_{17}$N$_2$O |
| 187.1257 | 1.2 | | |
| 203.2231 | 1.0 | | |
| 217.1334 | 0.9 | | |
| 187.1191 | 0.6 | | |
| 93.0529 | 0.6 | | |
| 66.1240 | 0.6 | | |

Example 6—Biochemical Synthesis of an Eighth Aminated Psilocybin Derivative

*Escherichia coli* strain Ec-2 was used to biosynthesize aminated psilocybin derivative with formula (IV) from aminated indole feedstock. The construction of Ec-2 is described in Example 4. Scaled-up culturing and material storage of engineered E. coli was conducted as described in Example 2, except that 1H-indol-6-ylamine was used in place of 5,7-dimethyl-1H-indol-4-ylamine. To assess product, high-resolution LC-HESI-LTQ-Orbitrap-XL MS analysis was conducted as described in Example 2. Singly protonated product with exact m/z and expected elemental formula matching the singly protonated form of N-[2-(6-amino-1H-indol-3-yl)ethyl]acetamide having chemical formula (IV):

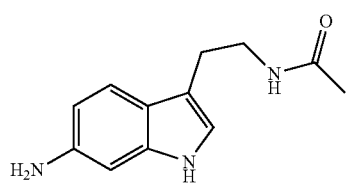

Figure 15A:
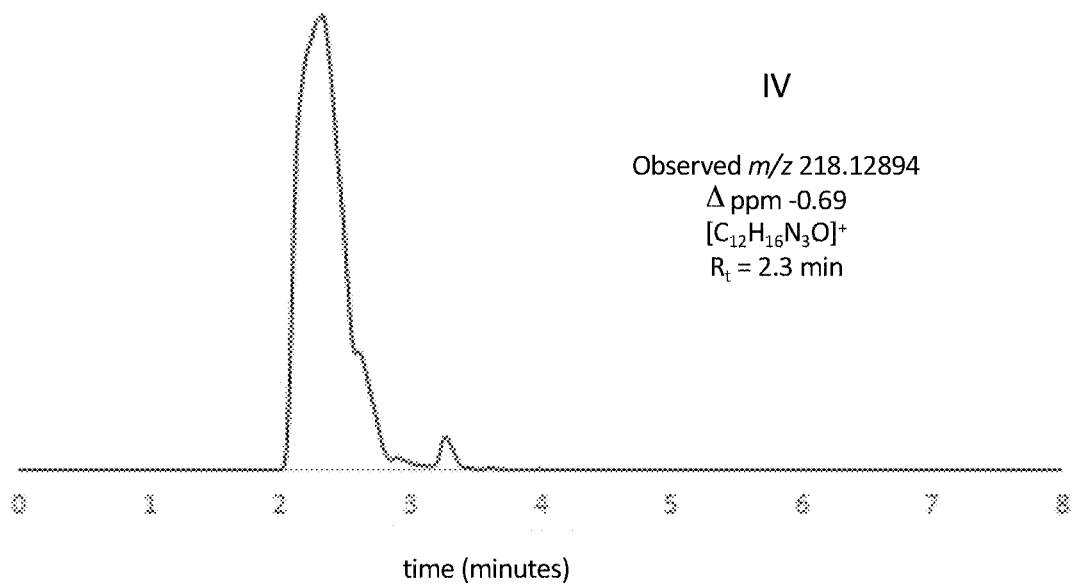

(IV)

eluted at 2.3 minutes (EIC, see: FIG. 15A).

Figure 15B:
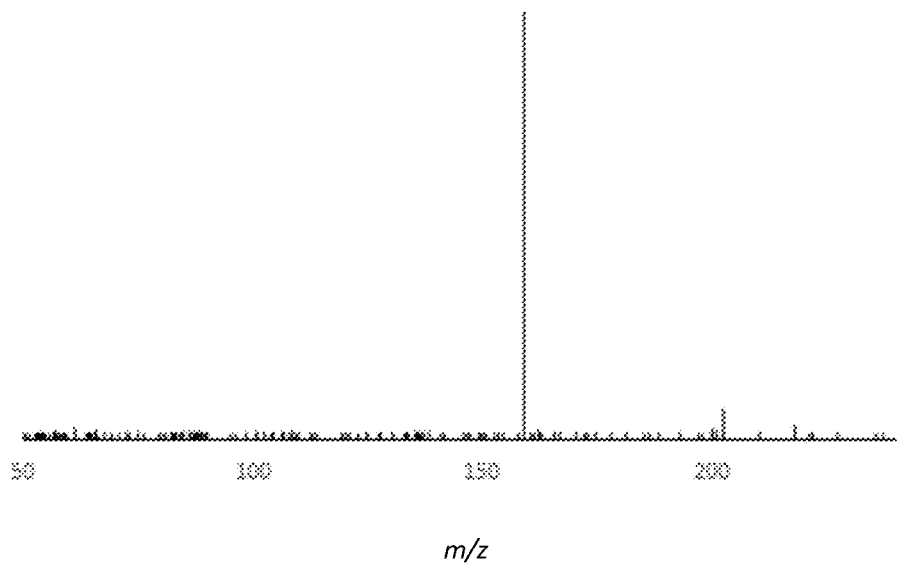

As per standard procedures (Menéndez-Perdomo et al. 2021, Mass Spectrom 56: 34683) high energy collisions (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (IV), as follows (FIG. 15B, Table IV) (Servillo L. et al., 2013, J. Agric. Chem. 61: 5156-5162).

TABLE IV

| m/z | % Relative Abundance | Ionic Species | Empirical Formula |
| --- | --- | --- | --- |
| 159.0916 | 100 | [M + H − NH$_2$—C$_2$H$_3$O]$^+$ | C$_{10}$H$_{11}$N$_2$ |
| 201.1022 | 12 | [M + H − NH$_2$]$^+$ | C$_{12}$H$_{13}$N$_2$O |
| 218.1288 | 5.1 | [M + H]$^+$ | C$_{12}$H$_{16}$N$_3$O |
| 202.4931 | 1.2 | | |
| 159.0946 | 1.1 | | |
| 160.4383 | 0.5 | | |
| 167.4664 | 0.3 | | |
| 83.3505 | 0.3 | | |
| 56.9868 | 0.3 | | |

Example 7—Biochemical Synthesis of a Ninth Aminated Psilocybin Derivative

*Escherichia coli* strain Ec-2 was used to biosynthesize aminated psilocybin derivative with formula (III) from aminated indole feedstock. The construction of Ec-2 is described in Example 4. Scaled-up culturing and material storage of engineered E. coli was conducted as described in Example 2, except that 1H-indol-4-ylamine (Combi-Blocks; www.combi-blocks.com) was used in place of 5,7-dimethyl-1H-indol-4-ylamine. To assess product, high-resolution LC-HESI-LTQ-Orbitrap-XL MS analysis was conducted as described in Example 2. Singly protonated product with exact m/z and expected elemental formula matching the singly protonated form of N-[2-(4-amino-1H-indol-3-yl)ethyl]acetamide having chemical formula (III):

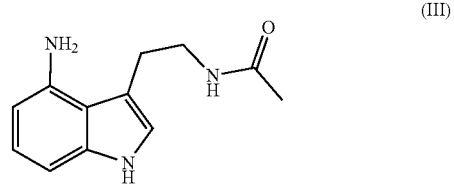 [SMILES: CC(=O)NCCc1c[nH]c2cccc(N)c12]

Figure 16A:
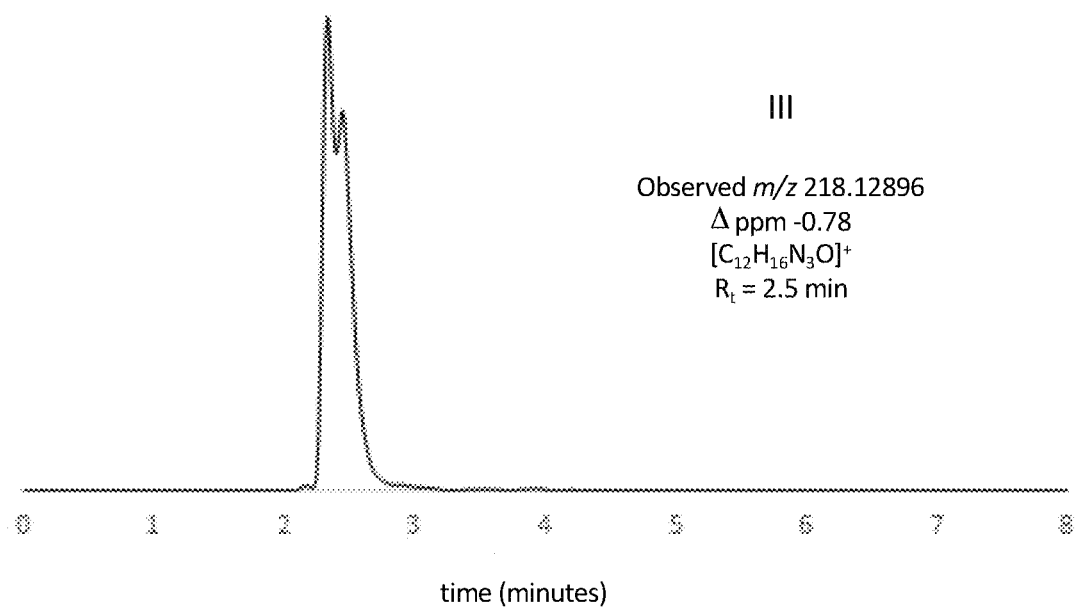

(III)

eluted at 2.5 minutes (EIC, see: FIG. 16A). Although peak splitting can be minimized through the use of DMSO as injection solvent (Kaufman and Jegle 2005, Agilent Technologies Technical Bulletin 5989-2485EN), this phenomenon persisted owing to ion pairing effects between matrix components (Tarafder et al. 2010, J Chromatogr A 1217: 7065-7073).

Figure 16B:
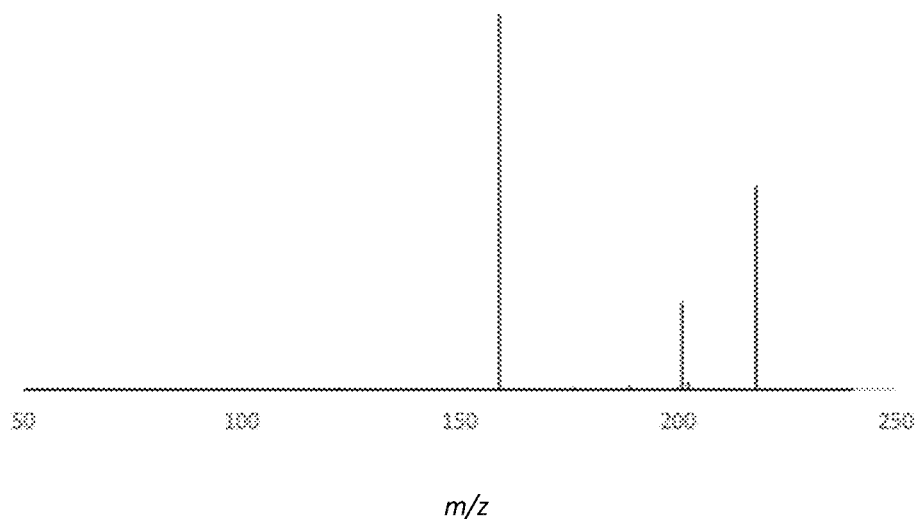
Figure 17A:
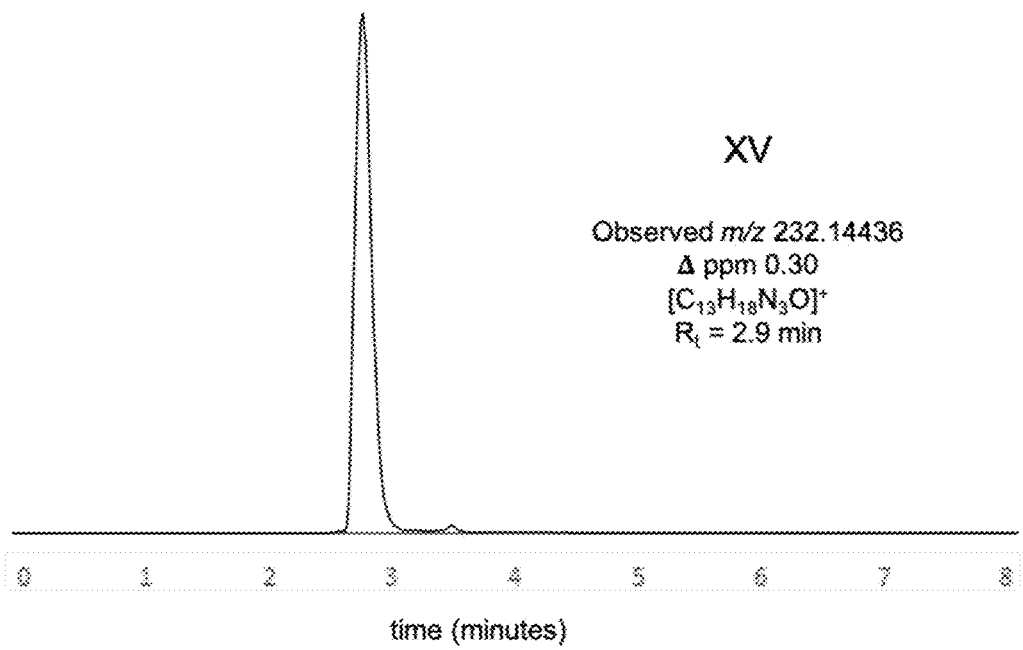
Figure 17B:
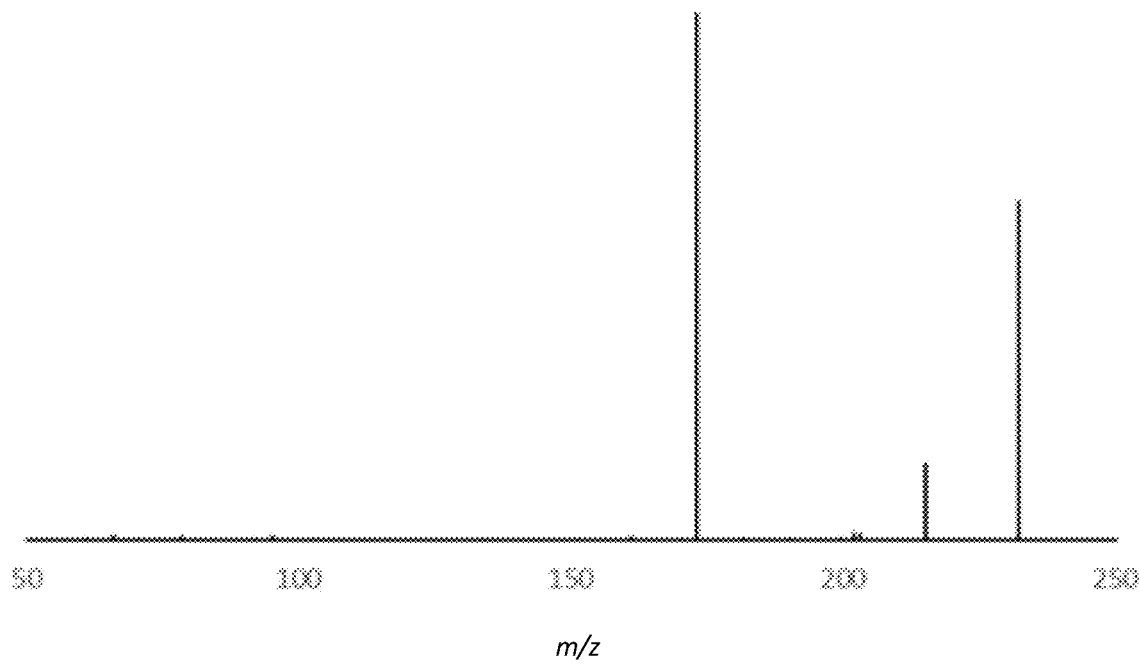

As per standard procedures (Menéndez-Perdomo et al. 2021, Mass Spectrom 56: 34683) high energy collisions (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (III), as follows (FIG. 16B, Table V) (Servillo L. et al., 2013, J. Agric. Chem. 61: 5156-5162).

TABLE V

| m/z | % Relative Abundance | Ionic Species | Empirical Formula |
| --- | --- | --- | --- |
| 159.0915 | 100 | | |
| 218.1288 | 56 | [M + H]$^+$ | C$_{12}$H$_{16}$N$_3$O |
| 201.1022 | 23 | | C$_{12}$H$_{13}$N$_2$O |
| 202.4901 | 2.1 | | |
| 189.1022 | 1.0 | | C$_{11}$H$_{13}$N$_2$O |
| 176.1182 | 0.6 | | C$_{10}$H$_{14}$N$_3$ |
| 200.1049 | 0.6 | | |
| 122.0354 | 0.5 | | |
| 183.0916 | 0.4 | | |
| 61.0965 | 0.4 | | |

Example 8—Biochemical Synthesis of a Tenth Aminated Psilocybin Derivative

*Escherichia coli* strain Ec-2 was used to biosynthesize aminated psilocybin derivative with formula (XV) from aminated indole feedstock. The construction of Ec-2 is described in Example 4. Scaled-up culturing and material storage of engineered E. coli was conducted as described in Example 2, except that 6-methyl-1H-indol-4-ylamine (BLDPharm; www.bldpharm.com) was used in place of 5,7-dimethyl-1H-indol-4-ylamine. To assess product, high-resolution LC-HESI-LTQ-Orbitrap-XL MS analysis was conducted as described in Example 2. Singly protonated product with exact m/z and expected elemental formula matching the singly protonated form of N-[2-(4-amino-6-methyl-1H-indol-3-yl)ethyl]acetamide having chemical formula (XV):

(XV)

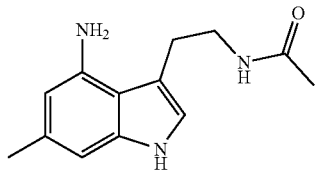

eluted at 2.9 minutes (EIC, see: 17A). As per standard procedures (Menéndez-Perdomo et al. 2021, Mass Spectrom 56: 34683) high energy collisions (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (XV), as follows (17B, Table VI) (Servillo L. et al., 2013, J. Agric. Chem. 61: 5156-5162).

TABLE VI

| m/z | % Relative abundance | Ionic species | Δ ppm |
|---|---|---|---|
| 173.10712 | 100 | [M + H − C$_2$H$_5$NO]$^+$ | 1.55 |
| 232.14436 | 64 | [M + H]$^+$ | 0.30 |
| 215.11772 | 14 | | |
| 201.98703 | 1.3 | | |
| 203.11772 | 1.1 | | |
| 66.12433 | 0.8 | | |
| 95.31106 | 0.8 | | |
| 78.58906 | 0.7 | | |

Example 9—Biochemical Synthesis of an Eleventh Aminated Psilocybin Derivative

*Escherichia coli* strain Ec-2 was used to biosynthesize aminated psilocybin derivative with formula (XVI) from aminated indole feedstock. The construction of Ec-2 is described in Example 4. Scaled-up culturing and material storage of engineered *E. coli* was conducted as described in Example 2, except that 7-methyl-1H-indol-5-ylamine (BLDPharm; www.bldpharm.com) was used in place of 5,7-dimethyl-1H-indol-4-ylamine. To assess product, high-resolution LC-HESI-LTQ-Orbitrap-XL MS analysis was conducted as described in Example 2. Singly protonated product with exact m/z and expected elemental formula matching the singly protonated form of N-[2-(5-amino-7-methyl-1H-indol-3-yl)ethyl]acetamide having chemical formula (XVI):

(XVI)

Figure 18A:
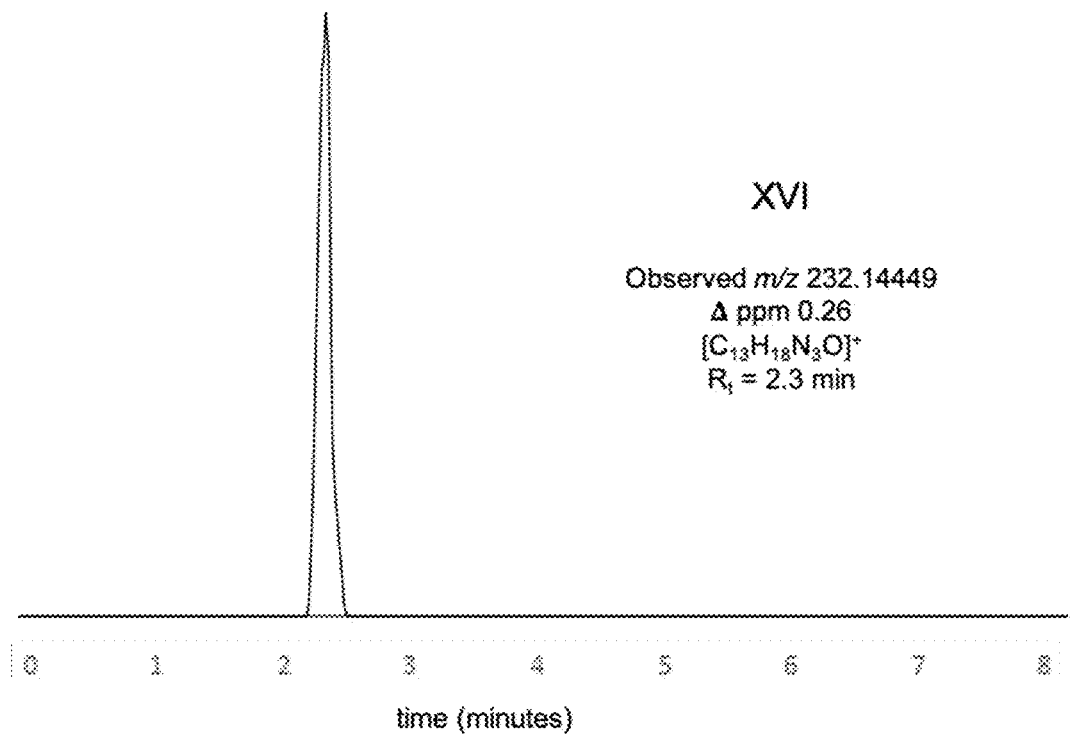

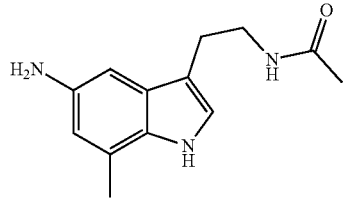

eluted at 2.3 minutes (EIC, see: FIG. 18A). Although peak splitting can be minimized through the use of DMSO as injection solvent (Kaufman and Jegle 2005, Agilent Technologies Technical Bulletin 5989-2485EN), this phenomenon persisted owing to ion pairing effects between matrix components (Tarafder et al. 2010, J Chromatogr A 1217: 7065-7073).

Figure 18B:
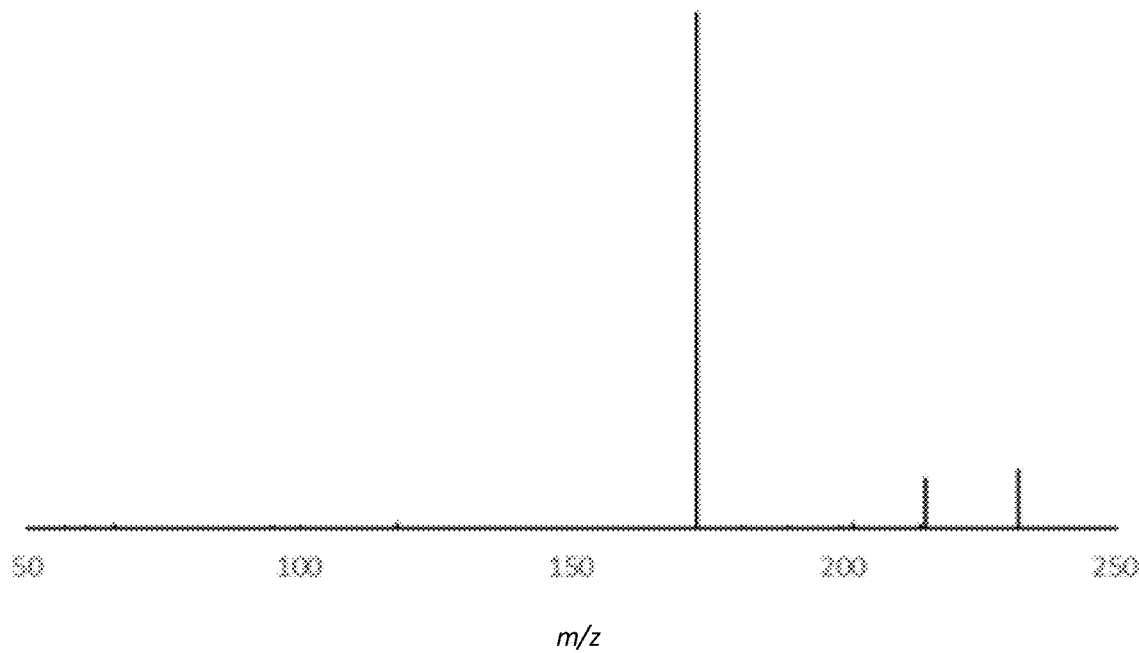

As per standard procedures (Menéndez-Perdomo et al. 2021, Mass Spectrom 56: 34683) high energy collisions (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (XVI), as follows (FIG. 18B, Table VII) (Servillo L. et al., 2013, J. Agric. Chem. 61: 5156-5162).

TABLE VII

| m/z | % Relative Abundance | Ionic Fragment | Δ ppm |
|---|---|---|---|
| 173.10714 | 100.00 | [M + H − C$_2$H$_5$NO]$^+$ | 1.04 |
| 232.14449 | 11.17 | [M + H]$^+$ | 0.26 |
| 215.11788 | 9.63 | | |
| 117.99882 | 0.95 | | |
| 201.97239 | 0.95 | | |
| 214.13376 | 0.63 | | |

Example 10—Biochemical Synthesis of a Twelfth Aminated Psilocybin Derivative

*Escherichia coli* strain Ec-3 was used to biosynthesize aminated psilocybin derivative, where the amino group terminating the 2-carbon aliphatic side chain was singly methylated. Ec-3 was constructed using the same method as for Ec-1 (see: Example 2), except that an additional plasmid was assembled and transformed into cells along with pETM6-H10-TmTrpB-2F3-V5-BaTDC-FLAG. This additional plasmid encoded a promiscuous and efficient *Rhinella marina* N-methyltransferase enzyme named RmNMT (SEQ. ID NO: 14). This additional plasmid was assembled as follows: from plasmid pCDM4 (SEQ. ID NO: 1), the plasmid pCDM4-RmNMT-FLAG was created by inserting an in-frame, C-terminally FLAG-tagged (SEQ. ID NO: 2, SEQ. ID NO: 3) RmNMT gene (SEQ. ID NO: 13) into the NdeI/XhoI site of pCDM4. The two target plasmids pCDM4-RmNMT-FLAG and pETM6-H$_{10}$-TmTrpB-2F3-V5-BaTDC-FLAG were transformed into BL21 (DE3) cells, and antibiotics ampicillin plus streptomycin were used to select for the correct clones containing both plasmids. Scaled up culturing and analysis were performed as described in Example 2, except that 6-methyl-1H-indol-4-ylamine (BLDPharm, www.bldpharm.com) was used in place of 5,7-dimethyl-1H-indol-4-ylamine. To assess product, high-resolution LC-HESI-LTQ-Orbitrap-XL MS analysis was conducted as described in Example 2. Singly protonated product with exact m/z and expected elemental formula matching the singly protonated form of 6-methyl-3-[2-(methylamino)ethyl]-1H-indol-4-amine having chemical formula (XVII):

(XVII)

Figure 19:
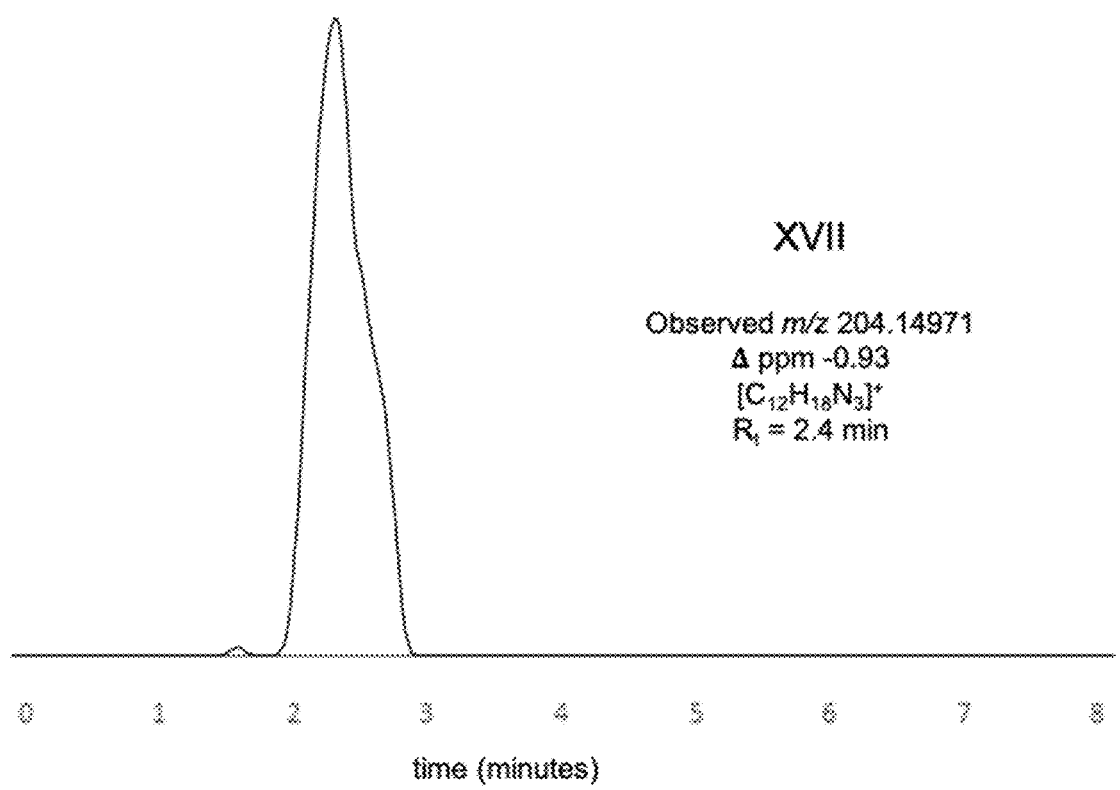

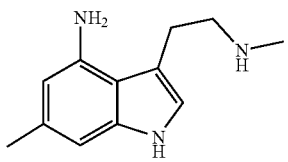

eluted at 2.4 minutes (EIC, see: FIG. 19). Although peak splitting and poor peak shape can be minimized through the use of DMSO as injection solvent (Kaufman and Jegle 2005, Agilent Technologies Technical Bulletin 5989-2485EN), this phenomenon persisted owing to ion pairing effects between matrix components (Tarafder et al. 2010, J Chromatogr A 1217:7065-7073).

The invention claimed is:

1. A chemical compound or salt thereof having formula (I):

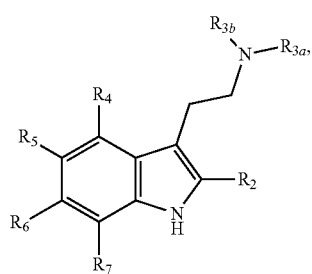

(I)

wherein (i) $R_5$ is an amino group, wherein $R_2$, $R_6$ and $R_7$ are a hydrogen atom, and wherein $R_4$ is an O-alkyl group or (ii) $R_7$ is an amino group or N-substituted amino group, wherein $R_4$ is a hydrogen atom, an O-alkyl group or a hydroxy group, and wherein $R_2$, $R_5$ and $R_6$ each are a hydrogen atom, and wherein $R_{3a}$ and $R_{3b}$ are each independently a hydrogen atom, an alkyl group, an aryl group, or an acyl group.

2. A chemical compound or salt thereof according to claim 1, wherein in (i) $R_4$ is a $(C_1-C_6)$—O-alkyl group.

3. A chemical compound or salt thereof according to claim 1, wherein in (i) $R_4$ is a $(C_1-C_3)$—O-alkyl group.

4. A chemical compound or salt thereof according to claim 1, wherein in (i) $R_4$ is a methoxy group.

5. A chemical compound or salt thereof according to claim 1, wherein in (i) $R_{3a}$ and $R_{3b}$ are each independently a hydrogen atom or an acyl group.

6. A chemical compound or salt thereof according to claim 1, wherein in (i) $R_{3a}$ and $R_{3b}$ are each a hydrogen atom.

7. A chemical compound or salt thereof according to claim 1, wherein in (ii) $R_7$ is an amino group.

8. A chemical compound or salt thereof according to claim 1, wherein in (ii) $R_7$ is an amino group, and $R_4$ is an O-alkyl group.

9. A chemical compound or salt thereof according to claim 1, wherein in (ii) $R_7$ is an amino group and $R_4$ is a $(C_1-C_6)$—O-alkyl group.

10. A chemical compound or salt thereof according to claim 1, wherein $R_7$ in (ii) is an amino group and $R_4$ is a $(C_1-C_3)$—O-alkyl group.

11. A chemical compound or salt thereof according to claim 1, wherein $R_7$ in (ii) is an amino group and $R_4$ is a methoxy group.

12. A chemical compound or salt thereof according to claim 8, wherein $R_{3a}$ and $R_{3b}$ are each independently a hydrogen atom or an acyl group.

13. A chemical compound or salt thereof according to claim 8, wherein $R_{3a}$ and $R_{3b}$ are each a hydrogen atom.

14. A chemical compound or salt thereof according to claim 1, wherein $R_7$ in (ii) is a N-substituted amino group.

15. A chemical compound or salt thereof according to claim 1, wherein $R_7$ in (ii) is an N-substituted amino group, wherein the N-substituted group has the formula:

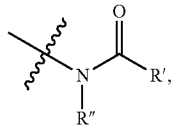

(XXII)

wherein R' and R" are each independently selected from a hydrogen atom, an alkyl group, and an aryl group.

16. A chemical compound or salt thereof according to claim 15, wherein R' and R" are each independently selected from a hydrogen atom, and an alkyl group.

17. A chemical compound or salt thereof according to claim 15, wherein R' is a hydrogen atom and R" is an alkyl group.

18. A chemical compound or salt thereof according to claim 15, wherein R' is a hydrogen atom and R" is a $(C_1-C_3)$-alkyl group.

19. A chemical compound or salt thereof according to claim 1, wherein $R_7$ is a N-substituted amino group, and $R_4$, $R_5$ and $R_6$ each are a hydrogen atom.

20. A chemical compound or salt thereof according to claim 19, wherein $R_{3a}$ and $R_{3b}$ are each independently a hydrogen atom or an acyl group.

21. A chemical compound or salt thereof according to claim 19, wherein $R_{3a}$ and $R_{3b}$ are each a hydrogen atom.

22. A chemical compound or salt thereof according to claim 1, wherein the chemical compound is selected from the group consisting of compounds having formulas (IX); (X); (XII); and (XIII):

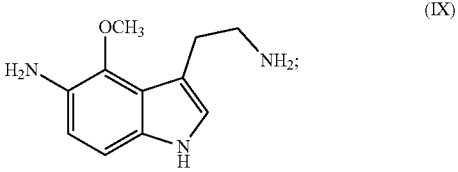

(IX)

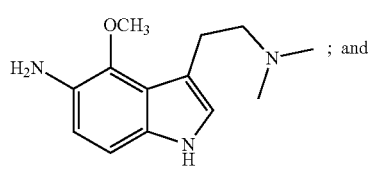

(X)

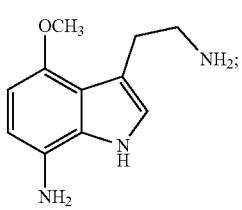

(XII)

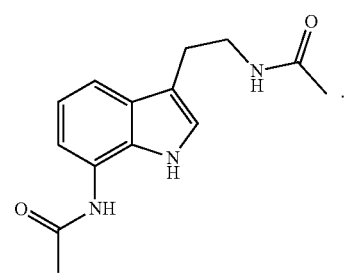

(XIII)

23. A chemical compound or salt thereof according to claim 1, wherein the chemical compound is at least about 95% (w/w) pure.

24. A pharmaceutical or recreational drug formulation comprising an effective amount of a chemical compound or salt thereof according to claim 1, together with a pharmaceutically acceptable excipient, diluent, or carrier.

25. A method for treating a psychiatric disorder, the method comprising administering to a subject in need thereof a pharmaceutical formulation comprising a chemical compound or salt thereof according to claim 1, wherein the pharmaceutical formulation is administered in an effective amount to treat the psychiatric disorder in the subject.

26. A chemical compound or salt thereof according to claim 22, wherein the chemical compound is at least about 95% (w/w) pure.

27. A pharmaceutical or recreational drug formulation comprising an effective amount of a chemical compound or salt thereof according to claim 22, together with a pharmaceutically acceptable excipient, diluent, or carrier.

28. A method for treating a psychiatric disorder, the method comprising administering to a subject in need thereof a pharmaceutical formulation comprising a chemical compound or salt thereof according to claim 22, wherein the pharmaceutical formulation is administered in an effective amount to treat the psychiatric disorder in the subject.

* * * * *

SEQUENCE LISTING

```
Sequence total quantity: 14
SEQ ID NO: 1              moltype = DNA   length = 3810
FEATURE                   Location/Qualifiers
misc_feature              1..3810
                          note = pCDM4 vector
source                    1..3810
                          mol_type = other DNA
                          organism = synthetic construct
SEQUENCE: 1
gctaacagcg cgatttgctg gtgacccaat gcgaccagat gctccacgcc cagtcgcgta   60
ccgtcttcat gggagaaaat aatactgttg atgggtgtct ggtcagagac atcaagaaat  120
aacgccggaa cattagtgca ggcagcttcc acagcaatgg catcctggtc atccagcgga  180
tagttaatga tcagcccact gacgcgttgc gcgagaagat tgtgcaccgc cgctttacag  240
gcttcgacgc cgcttcgttc taccatcgac accaccacgc tggcacccag ttgatcggcg  300
cgagatttaa tcgccgcgac aatttgcgac ggcgcgtgca ggcagact ggaggtggca  360
acgccaatca gcaacgactg tttgcccgcc agttgttgtg ccacgcggtt gggaatgtaa  420
ttcagctccg ccatcgccgc ttccactttt tcccgcgttt tcgcagaaac gtggctggcc  480
tggttcacca cgcgggaaac ggtctgataa gagacaccgg catactctgc gacatcgtat  540
aacgttactg gtttcacatt caccaccctg aattgactct cttccgggcg ctatcatgcc  600
ataccgcgaa aggttttgcg ccattcgatg gtgtccggga tctcgacgct ctcccttatg  660
cgactcctgc attaggaagc agcccagtag taggttgagg ccgttgagca ccgccgccgc  720
aaggaatggt gcatgcaagg agatggcgcc caacagtccc ccggccacgg ggcctgccac  780
cataccacg ccgaaacaag cgctcatgag cccgaagtgg caggcccgat cttcccatc  840
ggtgatgtcg gcgatatagg cgccagcaac cgcacctgtg gcgccggtga tgccggccac  900
gatgcgtccg gcgtagccta ggatcgagat cgatctcgat cccgcgaaat taatacgact  960
cactataggg gaattgtgag cggataacaa ttcccctcta gaaataattt tgtttaactt 1020
taagaaggag atatacatat ggcagatctc aattggataa cggccggcca cgcgatcgct 1080
gacgtcggta ccctcgagtc tggtaaagaa accgctgctg cgaaatttga acgccagcac 1140
atggactcgt ctactagtcg cagcttaatt aacctaaact gctgccaccg ctgagcaata 1200
actagcataa ccccttgggg cctctaaacg ggtcttgagg ggttttttgc tagcgaaagg 1260
aggagtcgac actgcttccg gtagtcaata aaccggtaaa ccagcaatag acataagcgg 1320
ctatttaacg accctgccct gaaccgacga ccgggtcatc gtggccggat cttgcggccc 1380
ctcggcttga acgaattgtt agacatatt tgccgactac cttggtgatc tgcctttca 1440
cgtagtggac aaattcttcc aactgatctg cgcgcgaggc caagcgatct tcttcttgtc 1500
caagataagc ctgtctagct tcaagtatga cgggctgata ctgggccggc aggcgctcca 1560
ttgcccagtc ggcagcgaca tccttcggcg cgattttgcc ggttactgcg cgtgtaccaaa 1620
tgcgggacaa cgtaagcact acatttcgct catccgcagc ccagtcgggc ggcgagttcc 1680
atagcgttaa ggtttcattt agcgcctcaa atagatcctg ttcaggaacc ggatcaaaga 1740
gttcctccgc cgctggacct accaaggcaa cgctatgttc tcttgctttt gtcagcaaga 1800
tagccagatc aatgtcgatc gtggctggct cgaagataac ttcaagaagt tcattgcgct 1860
gccattctcc aaattgcagt tcgcgcttag ctggataacg ccacggaatg atgtcgtcgt 1920
gcacaacaat ggtgacttct acagcgcgga gaatctcgct ctctccaggg gaagccgaag 1980
tttccaaaag gtcgttgatc aaagctcgcc gcgttgtttc atcaagcctt acggtcaccg 2040
taaccagcaa atcaatatca ctgtgtggct tcaggccgcc atccactgcg gagccgtaca 2100
aatgtacggc cagcaacgtc ggttcgagat ggcgctcgat gacgccaact acctctgata 2160
gttgagtcga tacttcggcg atcaccgctt ccctcatact cttccttttt caatattatt 2220
gaagcattta tcagggttat tgtctcatga gcggatacat atttgaatgt atttagaaaa 2280
ataaacaaat agcagctca ctcggtcgct acgctccggg cgtgagactg cggcgggcgc 2340
tgcggacaca tacaaagtta cccacagatt ccgtggataa gcaggggact aacatgtgag 2400
gcaaaacagc agggccgcgc cggtggcgtt tttccatagg ctccgccctc ctgccagagt 2460
tcacataaac agacgctttt ccggtgcatc tgtgggagcc gtgaggctca accatgaatc 2520
tgacagtacg ggcgaaaccc gacaggactt aaagatcccc accgtttccg gcgggtcgct 2580
ccctcttgcg ctctcctgtt ccgaccctgc cgtttaccgg atacctgttc cgcctttctc 2640
ccttacggga agtgtggcgc tttctcatag ctcacacact ggtatctcgg ctcggtgtag 2700
gtcgttcgct ccaagctggg ctgtaagcaa gaactcccg ttcagcccga ctgctgcgcc 2760
ttatccggta actgttcact tgagtccaac ccggaaaagc acggtaaaac gccactggca 2820
gcagccattg gtaactggga gttcgcagag gatttgttta gctaaacacg cggttgctct 2880
tgaagtgtgc gccaaagtcc ggctacactg gaaggacaga tttggttgct gtgctctgcg 2940
aaagccagtt accacggtta agcagttccc caactgactt aacctcgat caaaccacct 3000
ccccaggtgg ttttttcgtt tacagggcaa aagattacgc gcagaaaaaa aggatctcaa 3060
gaagatcctt tgatctttc tactgaaccg ctctagattt cagtgcaatt tatctcttca 3120
aatgtagcac ctgaagtcag ccccatacga tataagttgt aattctcatg ttagtcatgc 3180
cccgcgccca ccggaaggag ctgactgggt tgaaggctct caagggcatc ggtcgagatc 3240
ccggtgccta atgagtgagc taacttacat taattgcgtt gcgctcactg cccgctttcc 3300
agtcgggaaa cctgtcgtgc cagctgcatt aatgaatcgg ccaacgcgcg gggagaggcg 3360
gtttgcgtat tgggcgccag ggtggttttt cttttcacca gtgagacggg caacagctga 3420
ttgcccttca ccgcctggcc ctgagagagt tgcagcaagc ggtccacgct ggtttgcccc 3480
agcaggcgaa aatcctgttt gatggtggtt aacggcggga tataacatga gctgtcttcg 3540
gtatcgtcgt atcccactac cgagatgtcc gcaccaacgc gcagcccgga ctcggtaatg 3600
gcgcgcattg cgcccagcgc catctgatcg ttggcaacca gcatcgcagt gggaacgatg 3660
ccctcattca gcatttgcat ggtttgttga aaaccggaca tggcactcca gtcgccttcc 3720
cgttccgcta tcggctgaat ttgattgcga gtgagatatt tatgccagcc agccagacgc 3780
agacgcgccg agacagaact taatgggccc                                 3810

SEQ ID NO: 2              moltype = DNA   length = 24
FEATURE                   Location/Qualifiers
misc_feature              1..24
                          note = Synthetic FLAG epitope tag polypeptide
```

```
source                   1..24
                         mol_type = other DNA
                         organism = synthetic construct
SEQUENCE: 2
gactacaagg atgacgatga caaa                                          24

SEQ ID NO: 3             moltype = AA  length = 8
FEATURE                  Location/Qualifiers
REGION                   1..8
                         note = Synthetic FLAG epitope tag polypeptide
source                   1..8
                         mol_type = protein
                         organism = synthetic construct
SEQUENCE: 3
DYKDDDDK                                                             8

SEQ ID NO: 4             moltype = DNA  length = 549
FEATURE                  Location/Qualifiers
source                   1..549
                         mol_type = other DNA
                         organism = Streptomyces griseofuscus
SEQUENCE: 4
atgaacacct tcagaacagc cactgccaga gacatacctg atgtagcagc aactcttacg    60
gaagccttcg caactgatcc acccacgcag tgggtgttcc ccgacggtac tgccgccgtc   120
agcaggttct ttacacatgt tgcagatagg gttcacacgg ccgtggtat tgttgagcta   180
ctaccagaca gagccgccat gattgcattg ccaccagtca tgaggctgcc aggagaagct   240
gccgacggaa ggcaggcgga aattcagaga aggctggcag acaggcaccc gctgacacct   300
cactactacc tgctgtttta cggagttaga acggcacacc agggttcggg attgggcgga   360
agaatgctgg ccagattaac tagcagagct gatagggaca gggtgggtac atatactgag   420
gcatccacct ggcgtggcgc tagactgatg ctgagacatg gattccatgc tacaaggcca   480
ctaagattgc cagatggacc cagcatgttt ccactttgga gagatccaat ccatgatcat   540
tctgattag                                                           549

SEQ ID NO: 5             moltype = AA  length = 182
FEATURE                  Location/Qualifiers
source                   1..182
                         mol_type = protein
                         organism = Streptomyces griseofuscus
SEQUENCE: 5
MNTFRTATAR DIPDVAATLT EAFATDPPTQ WVFPDGTAAV SRFFTHVADR VHTAGGIVEL    60
LPDRAAMIAL PPHVRLPGEA ADGRQAEIQR RLADRHPLTP HYYLLFYGVR TAHQGSGLGG   120
RMLARLTSRA DRDRVGTYTE ASTWRGARLM LRHGFHATRP LRLPDGPSMF PLWRDPIHDH   180
SD                                                                  182

SEQ ID NO: 6             moltype = DNA  length = 42
FEATURE                  Location/Qualifiers
misc_feature             1..42
                         note = Synthetic V5 epitope tag polypeptide
source                   1..42
                         mol_type = other DNA
                         organism = synthetic construct
SEQUENCE: 6
ggtaagccaa ttccaaatcc tttgttgggt ttggactcca cc                       42

SEQ ID NO: 7             moltype = AA  length = 14
FEATURE                  Location/Qualifiers
REGION                   1..14
                         note = Synthetic V5 epitope tag polypeptide
source                   1..14
                         mol_type = protein
                         organism = synthetic construct
SEQUENCE: 7
GKPIPNPLLG LDST                                                      14

SEQ ID NO: 8             moltype = DNA  length = 1170
FEATURE                  Location/Qualifiers
source                   1..1170
                         mol_type = other DNA
                         organism = Thermotoga maritima
SEQUENCE: 8
atgaaaggat atttcggacc atacggtggc cagtacgtac cagaaatatt aatgggtgcc    60
ttagaggagt tagaggcagc atacgaggag attatgaagg atgagagctt ctggaaggag   120
ttcaacgatc tactgaggga ttcgcaggc agaccaacgc cattgtactt tgccaggaga   180
ttgtctgaga agtacgcgc ccgtgtttac ttgaagcgtg aggatctgct gcacactgga   240
gcacacaaga taataacgc tatcggacga gttttattgg ccaaattaat ggggaagaca   300
cgtatccatag ccgagacggg agctgggcag catggagtcg ctactgctac cgctgctgcc   360
ctgttcggaa tggaatgtgt gatctacatg ggtgaagagg acacaatcag acagaagttg   420
aacgtggagc gtatgaaatt attaggggct aaagttgtcc ctgttaagtc tggcagtagg   480
acctgaagg atgcgataga cgaggctttg agagactgga ttactaattt acagacaaca   540
```

```
tattatgtta tcggatctgt tgttggtccc cacccttacc caattatcgt aaggaatttc    600
cagaaggtta tcggtgagga gaccaagaag caaataccag aaaaggaagg tcgtttgcca    660
gactatatag ttgcctgcgt aggcggcggt agcaatgccg caggtatatt ttacccattc    720
atagactctg gagtaaagct gataggtgtt gaggcaggtg cgagggatt ggagacaggt     780
aaacacgcag cctcgttatt aaaggtaaa attggcatt tacatggatc gaagacctt       840
gttctacaag atgactgggg tcaagtccaa gtgagccatt cggtgtcagc tggtcttgac    900
tattcaggag taggacctga gcatgcttat tggagagaga cagggaaggt tctgtacgac    960
gcagtgactg acgaagaggc tttggacgca tttatagagt tatcaagact agagggcatt   1020
atacccgctt tagagtcatc gcatgctcta gcatatttga agaagataaa tataaaaggt   1080
aaggttgtgg tggtcaacct atcagggaga ggggataaag acctggagtc agtcttaaac   1140
catccatacg tgagagaaag aattagatga                                    1170

SEQ ID NO: 9            moltype = AA   length = 389
FEATURE                 Location/Qualifiers
source                  1..389
                        mol_type = protein
                        organism = Thermotoga maritima
SEQUENCE: 9
MKGYFGPYGG QYVPEILMGA LEELEAAYEE IMKDESFWKE FNDLLRDYAG RPTPLYFARR     60
LSEKYGARVY LKREDLLHTG AHKINNAIGQ VLLAKLMGKT RIIAETGAGQ HGVATATAAA    120
LFGMECVIYM GEEDTIRQKL NVERMKLLGA KVVPVKSGSR TLKDAIDEAL RDWITNLQTT    180
YVIGSVVGP HPYPIIVRNF QKVIGEETKK QIPEKEGRLP DYIVACVGGG SNAAGIFYPF     240
IDSGVKLIGV EAGGEGLETG KHAASLLKGK IGYLHGSKTF VLQDDWGVQ VSHSVSAGLD     300
YSGVGPEHAY WRETGKVLYD AVTDEEALDA FIELSRLEGI IPALESSHAL AYLKKINIKG    360
KVVVVNLSGR GDKDLESVLN HPYVRERIR                                     389

SEQ ID NO: 10           moltype = DNA   length = 5203
FEATURE                 Location/Qualifiers
misc_feature            1..5203
                        note = pETM6-H10 vector
source                  1..5203
                        mol_type = other DNA
                        organism = synthetic construct
SEQUENCE: 10
gaagaattgt gagcggataa caattcccct ctagaaataa ttttgtttaa ctttaagaag     60
gagatataca tatggcagat ctcaattgga tatcggccgg ccacgcgatc gctgacgtcg    120
gtaccctcga gtctggtaaa gaaaccgctg ctgcgaaatt tgaacgccag cacatggact    180
cgtctactag tcgcagctta attaacctaa actgctgcca ccgctgagca ataactagca    240
taaccccttg gggcctctaa acgggtcttg aggggttttt tgctagcgaa aggaggagtc    300
gactatatcc ggattggcga atgggacgcg ccctgtagcg gcgcattaag cgcggcgggt    360
gtggtggtta cgcgcagcgt gaccgctaca cttgccagcg ccctagcgcc cgtcctttc    420
gctttcttcc cttcctttct cgccacgttc gccggctttc ccgtcaagc tctaaatcgg     480
gggctccctt taggttccg atttagtgct ttacggcacc tcgaccccaa aaaacttgat    540
tagggtgatg gttcacgtag tgggccatcg ccctgataga cggtttttcg ccctttgacg    600
ttggagtcca cgttctttaa tagtggactc ttgttccaaa ctgaacaac actcaaccct     660
atctcggtct attcttttga tttataaggg attttgccga tttcggccta ttggttaaaa    720
aatgagctga tttaacaaaa atttaacgcg aattttaaca aaatattaac gtttacaatt    780
tctggcggca cgatggcatg agattatcaa aaaggatctt cacctagatc cttttaaatt    840
aaaaatgaag ttttaaatca atctaaagta tatatgagta aacttggtct gacagttacc    900
aatgcttaat cagtgaggca cctatctcag cgatctgtct atttcgttca tccatagttg    960
cctgactccc cgtcgtgtag ataactacga tacgggaggg cttaccatct ggccccagtg   1020
ctgcaatgat accgcgagac ccacgctcac cggctccaga tttatcagca ataaaccagc   1080
cagccggaag ggccgagcgc agaagtggtc ctgcaacttt atccgcctcc atccagtcta   1140
ttaattgttg ccgggaagct agagtaagta gttcgccagt taatagtttg cgcaacgttg   1200
ttgccattgc tacaggcatc gtggtgtcac gctcgtcgtt tggtatggct tcattcagct   1260
ccggttccca acgatcaagg cgagttacat gatcccccat gttgtgcaaa aaagcggtta   1320
gctccttcgg tcctccgatc gttgtcagaa gtaagttggc cgcagtgtta tcactcatgg   1380
ttatggcagc actgcataat tctcttactg tcatgccatc cgtaagatgc ttttctgtga   1440
ctggtgagta ctcaaccaag tcattctgag aatagtgtat gcggcgaccg agttgctctt   1500
gcccggcgtc aatacgggat aataccgcgc cacatagcag aactttaaaa gtgctcatca   1560
ttggaaaacg ttcttcgggg cgaaaactct caaggatctt accgctgttg atccagtt    1620
cgatgtaacc cactcgtgca cccaactgat cttcagcatc ttttactttc accagcgttt   1680
ctgggtgagc aaaaacagga aggcaaaatg ccgcaaaaaa gggaataagg gcgacacgga   1740
aatgttgaat actcatactc ttccttttc aatcattatt gaagcattta tcagggttta   1800
tgtctcatga gcggatacat atttgaatgt atttagaaaa ataaacaaat aggtcatgac   1860
caaaatccct taacgtgagt tttcgttcca ctgagcgtca ccccgtag aaaagatcaa     1920
aggatcttct tgagatcctt ttttttctgcg cgtaatctgc tgcttgcaaa caaaaaaacc   1980
accgctacca gcggtggttt gtttgccgga tcaagagcta ccaactcttt ttccgaaggt   2040
aactggcttc agcagagcgc agataccaaa tactgtcctt ctagtgtagc cgtagttagg   2100
ccaccacttc aagaactctg tagcaccgcc tacatacctc gctctgctaa tcctgttacc   2160
agtggctgct gccagtggcg ataagtcgtg tcttaccggg ttggactcaa gacgatagtt   2220
accggataag gcgcagcggt cgggctgaac ggggggttcg tgcacacagc ccagcttgga   2280
gcgaacgacc tacaccgaac tgagatacct acagcgtgag ctatgagaaa gcgccacgct   2340
tcccgaaggg agaaaggcgg acaggtatcc ggtaagcggc agggtcggaa caggagagcg   2400
cacgagggag cttccagggg gaaacgcctg gtatctttat agtcctgtcg ggtttcgcca   2460
cctctgactt gagcgtcgat ttttgtgatg ctcgtcaggg gggcggagcc tatgaaaaa    2520
cgccagcaac gcggcctttt tacgttcct ggccttttgc tggccttttg ctcacatgtt    2580
ctttcctgcg ttatccctg attctgtgga taaccgtatt accgcctttg agtgagctga    2640
taccgctcgc cgcagccgaa cgaccgagcg cagcgagtca gtgagcgagg aagcggaaga    2700
```

```
gcgcctgatg cggtattttc tccttacgca tctgtgcggt atttcacacc gcatatatgg   2760
tgcactctca gtacaatctg ctctgatgcc gcatagttaa gccagtatac actccgctat   2820
cgctacgtga ctgggtcatg gctgcgcccc gacacccgcc aacacccgct gacgcgccct   2880
gacgggcttg tctgctcccg gcatccgctt acagacaagc tgtgaccgtc tccgggagct   2940
gcatgtgtca gaggttttca ccgtcatcac cgaaacgcgc gaggcagctg cggtaaagct   3000
catcagcgtg gtcgtgaagc gattcacaga tgtctgcctg ttcatccgcg tccagctcgt   3060
tgagtttctc cagaagcgtt aatgtctggc ttctgataaa gcgggccatg ttaagggcgg   3120
ttttttcctg tttggtcact gatgcctccg tgtaaggggg atttctgttc atggggtaa    3180
tgataccgat gaaacgagag aggatgctca cgatacgggt tactgatgat gaacatgccc   3240
ggttactgga acgttgtgag ggtaaacaac tggcggtatg gatgcggcgg gaccagagaa   3300
aaatcactca gggtcaatgc cagcgcttcg ttaatacaga tgtaggtgtt ccacagggta   3360
gccagcagca tcctgcgatg cagatccgga acataatggt gcagggcgct gacttccgcg   3420
tttccagact ttacgaaaca cggaaaccga agaccattca tgttgttgct caggtcgcag   3480
acgttttgca gcagcagtcg cttcacgttc gctcgcgtat cggtgattca ttctgctaac   3540
cagtaaggca accccgccag cctagccggg tcctcaacga caggagcacg atcatgctag   3600
tcatgccccg cgcccaccgg aaggagctga ctggggttgaa ggctctcaag ggcatcggtc   3660
gagatcccgt gcctaatga gtgagctaac ttacattaat tgcgttgcgc tcactgcccg   3720
ctttccagtc gggaaacctg tcgtgccagc tgcattaatg aatcggccaa tgccgcgggga 3780
gaggcggttt gcgtattggg cgccagggtg ttttttcttt tcaccagtga gacgggcaac   3840
agctgattgc ccttcaccgc ctggccctga gagagttgca gcaagcggtc cacgctggtt   3900
tgccccagca ggcgaaaatc ctgtttgatg gtggttaacg gcgggatata acatgagctg   3960
tcttcggtat cgtcgtatcc cactaccgag atgtccgcac gttccggactcg              4020
gtaatggcgc gcattgcgcc cagcgccatc tgatcgttgg caaccagcat cgcagtggga   4080
acgatgccct cattcagcat ttgcatggtt tgttgaaaac cggacatggc actccagtcg   4140
ccttcccgtt ccgctatcgg ctgaatttga ttgcgagtga atatttatg ccagccagcc    4200
agacgcagac gcgccgagac agaacttaat gggcccgcta acagcgcgat ttgctggtga   4260
cccaatgcga ccagatgctc cacgcccagt cgcgtaccgt cttcatggga gaaaataata   4320
ctgttgatgg gtgtctggtc agagacatca agaaataacg ccggaacatt agtgcaggca   4380
gcttccacag caatggcatc ctggtcatcc agcggatagt taatgatcag cccactgacg   4440
cgttgcggcg gaagattgtg caccgccgct ttacaggctt cgacgccgct tcgttctacc   4500
atcgacacca ccacgctggc acccagttga tcgcgcgag atttaatcgc cgcgacaatt   4560
tgcgacggcg cgtgcagggc cagactgag gtggcaacgc caatcagcaa cgactgtttg    4620
cccgccagtg gttgtgccac gcggttggga atgtaattca gctccgccat cgccgcttcc   4680
acttttccc gcgttttcgc agaaacgtgg ctggcctggt tcaccacgcg ggaaacggtt    4740
tgataagaga caccggcata tctgcgaca tcgtataacg ttactggttt cacattcacc    4800
accctgaatt gactctcttc cgggcgctat catgccatac cgcgaaaggt tttgcgccat   4860
tcgatggtgt ccgggatctc gacgctctcc cttatgcgac tcctgcatta ggaagcagcc   4920
cagtagtagg ttgaggccgt tgagcaccgc cgccgcaagg aatggtgcat gcaaggagat   4980
ggcgcccaac agtcccccgg ccacggggcc tgccaccata cccacgccga aacaagcgct   5040
catgagcccg aagtggcgag cccgatcttc cccatcggtg atgtcggcga tataggcgcc   5100
agcaaccgca cctgtggcgc cggtgatgcc ggccacgatg cgtccggcgt agcctaggat   5160
cgagatcgat ctcgatcccg cgaaattaat acgactcact acg                     5203

SEQ ID NO: 11           moltype = DNA   length = 1446
FEATURE                 Location/Qualifiers
source                  1..1446
                        mol_type = other DNA
                        organism = Bacillus atrophaeus
SEQUENCE: 11
atgatgtctg aaaatttgca attgtcagct gaagaaatga gacaattggg ttaccaagca     60
gttgatttga tcatcgatca catgaaccat ttgaagtcta agccagtttc agaaacatgg    120
gattctgata tcttgagaaa taagttgact gaatctatcc cagaaaatgg ttcagatcca    180
aaggaattgt tgcatttctt gaacagaaac gtttttaatc aaattacaca tgttgatcat    240
ccacatttct tggcttttgt tccaggtcca ataattacg ttggtgttgt tgcagatttc     300
ttggcttctg gttttaatgt ttttccaact gcatggattg ctggtcgaca tgctgaacaa    360
atcgaattga ctacaattaa ttggttgaaa tctatgttga gttttccaga ttcagctgaa    420
ggtttatttg tttctggtgg ttcaatggca aatttgacag ctttgactgt tgcaagacag    480
gctaagttga caacgatat cgaaaatgct gttgttact tctctgatca aacacatttc      540
tcagttgata gagcattgaa ggttttaggt tttaaacatc atcaaatctg taagaatcgaa   600
acagatgaac atttgagaat ctctgtttca gctttgaaga aacaaattaa agaagatga    660
actaagggta aaagccatt ctgtgttatt gcaaatgctg gtactacaaa ttgtggtgct    720
gttgattctt tgaacgaatt agcagatttg tgtaacgatg aagatgtttg ttgcatgct    780
gatggttctt atggtgctcc agctatcttg tctgaaaagg gttcagctat gttgcaaggt    840
attcatagag cagattcttt gactttagat ccacactagt ggtgttcca accatacgat    900
gttggttgtg ttttgatcag aaactctcaa tatttgtcaa agactttag aatgatgcca    960
gaatacatca aggattcaga aactaacgtt gaaggtgaaa ttaatttcgg tgaatgtggt   1020
atcgaattgt caagaagatt cagagctttg aaggttttg tgtctttaa agttttcggt     1080
gttgctgctt ttagacaagc aatcgatcat ggtatcatgt tagcagaaca agttgaagca   1140
tttttgggta aagcaaaaga ttgggaagtt gttacaccag ctcaattggg tatcgttact   1200
ttagatacaa ttccatctga attggcatca acagatacta ttaatgaaat taataagaaa   1260
ttggttaagg aaatcacaca tagaggtttc gctatgttat ctactacaga attgaaggaa   1320
aaggttgtta ttagattgtg ttcaattaat ccaagaacta caactgaaga aatgttgcaa   1380
atcatgatga agattaaagc attggctgaa gaagtttcta tttcataccc atgtgttgct   1440
gaataa                                                              1446

SEQ ID NO: 12           moltype = AA    length = 481
FEATURE                 Location/Qualifiers
source                  1..481
                        mol_type = protein
```

```
                        organism = Bacillus atrophaeus
SEQUENCE: 12
MMSENLQLSA  EEMRQLGYQA  VDLIIDHMNH  LKSKPVSETI  DSDILRNKLT  ESIPENGSDP    60
KELLHFLNRN  VFNQITHVDH  PHFLAFVPGP  NNYVGVVADF  LASGFNVFPT  AWIAGAGAEQ   120
IELTTINWLK  SMLGFPDSAE  GLFVSGGSMA  NLTALTVARQ  AKLNNDIENA  VVYFSDQTHF   180
SVDRALKVLG  FKHHQICRIE  TDEHLRISVS  ALKKQIKEDR  TKGKKPFCVI  ANAGTTNCGA   240
VDSLNELADL  CNDEDVWLHA  DGSYGAPAIL  SEKGSAMLQG  IHRADSLTLD  PHKWLFQPYD   300
VGCVLIRNSQ  YLSKTFRMMP  EYIKDSETNV  EGEINFGECG  IELSRRFRAL  KVWLSFKVFG   360
VAAFRQAIDH  GIMLAEQVEA  FLGKAKDWEV  VTPAQLGIVT  FRYIPSELAS  TDTINEINKK   420
LVKEITHRGF  AMLSTTELKE  KVVIRLCSIN  PRTTTEEMLQ  IMMKIKALAE  EVSISYPCVA   480
E                                                                       481

SEQ ID NO: 13           moltype = DNA  length = 972
FEATURE                 Location/Qualifiers
source                  1..972
                        mol_type = other DNA
                        organism = Rhinella marina
SEQUENCE: 13
atgtttggtg  tacaagacac  cccgcaacat  atatgctacg  agcctcagca  gcgtaaggtc    60
agtgagagaa  catcacgtaa  cagatctcgt  tctaaatcac  tggacccgga  cagcttgcgc   120
gagaaaggaa  agaagacgca  acaccgtgag  gcggattgtt  tcttcggtga  agacaaccgg   180
atggaaaact  cctactctgc  gcaaatgtac  attgacgagt  cgtacccctgt acactattac   240
caaacctatt  attcctcagg  gaagggcggc  attgctcgtg  agtggacaga  ttttgctttg   300
caaaacttgc  atgaaacgtt  cgggcctggc  ggggttaaag  gtgacattct  tattgacttc   360
ggtgctgggc  cgacaatata  tcagcttctg  agcgcatgtg  aggttttcaa  tagcattatt   420
acatccgact  ttcttgagca  aaaccgcgag  caacttgaga  atggcttcg   aaaggacccg   480
gacgcccttg  actggtccca  tttcacgaag  tacgtttgcg  agctcgaagg  caaccgggac   540
aactgggaaa  agaaagagga  aaccctgcgc  cgaaaggtta  ccaaggtgct  aaatgtgac    600
gcactggccg  agaagccttt  cgacgacgtg  ccaatgccag  aggctgactg  tctgatctca   660
tgcctgtgtt  tagagaaccc  ttgtcaagac  caggaagctt  acattaacat  attgaagaag   720
ttaaaagagc  tcttgaaacc  gggcggccac  atcattatac  agtccatatt  gaactgctcg   780
tattaccata  ttggcaatag  ctgcttctca  catttgtcgt  taagcaagga  cgacgtggag   840
aaatcgttta  aggaagctgg  ctacgaaatc  gtcaaattga  aggttcttcc  acgctcagtt   900
atgtcggaaa  tggaaatcag  cgactcaaat  ggctactact  tcatccacgc  tcggaaaccg   960
caaaaggagt  aa                                                          972

SEQ ID NO: 14           moltype = AA  length = 323
FEATURE                 Location/Qualifiers
source                  1..323
                        mol_type = protein
                        organism = Rhinella marina
SEQUENCE: 14
MFGVQDTPQH  ICYEPQQRKV  SERTSRNRSR  SKSLDPDSLR  EKGKKTQHRE  ADCFFGEDNR    60
MENSYSAQMY  IDEFDPVHYY  QTYYSSGKGG  IAREWTDFAL  QNLHETFGPG  GVKGDILIDF   120
GAGPTIYQLL  SACEVFNSII  TSDFLEQNRE  QLEKWLRKDP  DALDWSHFTK  YVCELEGNRD   180
NWEKKEETLR  RKVTKVLKCD  ALAEKPFDDV  PMPEADCLIS  CLCLENPCQD  QEAYINILKK   240
LKELLKPGGH  IIIQSILNCS  YYHIGNSCFS  HLSLSKDDVE  KSFKEAGYEI  VKLKVLPRSV   300
MSEMEISDSN  GYYFIHARKP  QKE                                             323
```